United States Patent
Giordanetto et al.

(10) Patent No.: US 11,629,145 B2
(45) Date of Patent: Apr. 18, 2023

(54) SHP2 PHOSPHATASE INHIBITORS AND METHODS OF USE THEREOF

(71) Applicants: Relay Therapeutics, Inc., Cambridge, MA (US); D. E. Shaw Research, LLC, New York, NY (US)

(72) Inventors: Fabrizio Giordanetto, New York, NY (US); Jack Benjamin Greisman, New York, NY (US); Paul Maragakis, New York, NY (US); Alexander M. Taylor, Cambridge, MA (US); Lucian V. Dipietro, Gloucester, MA (US); Elizabeth H. Kelley, Cambridge, MA (US); André Lescarbeau, Somerville, MA (US); Mark Andrew Murcko, Holliston, MA (US); Levi Charles Thomas Pierce, Somerville, MA (US); Kelley C. Shortsleeves, Maynard, MA (US); W. Patrick Walters, Westborough, MA (US); Sathesh Bhat, Jersey City, NJ (US); Eric Therrien, Bronx, NY (US); Markus Kristofer Dahlgren, Shelton, CT (US)

(73) Assignees: D. E. Shaw Research, LLC, New York, NY (US); Relay Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/344,061

(22) PCT Filed: Oct. 24, 2017

(86) PCT No.: PCT/US2017/058048
§ 371 (c)(1),
(2) Date: Apr. 23, 2019

(87) PCT Pub. No.: WO2018/081091
PCT Pub. Date: May 3, 2018

(65) Prior Publication Data
US 2020/0062760 A1 Feb. 27, 2020

Related U.S. Application Data

(60) Provisional application No. 62/519,360, filed on Jun. 14, 2017, provisional application No. 62/511,583, filed on May 26, 2017, provisional application No. 62/425,301, filed on Nov. 22, 2016, provisional application No. 62/411,972, filed on Oct. 24, 2016.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
None
See application file for complete search history.

(56) References Cited

U.S. PATENT DOCUMENTS

| | | |
|---|---|---|
| 10,280,171 B2 | 5/2019 | Jones et al. |
| 10,934,302 B1 | 3/2021 | Taylor et al. |
| 2011/0130396 A1 | 6/2011 | Hoelzemann et al. |
| 2017/0001975 A1 | 1/2017 | Chen et al. |
| 2017/0015680 A1 | 1/2017 | Chen et al. |
| 2017/0204080 A1 | 7/2017 | Chen et al. |
| 2017/0342078 A1 | 11/2017 | Jones et al. |
| 2018/0186770 A1 | 7/2018 | Chen et al. |
| 2018/0251471 A1 | 9/2018 | Chen et al. |
| 2019/0077792 A1 | 3/2019 | Volkmann et al. |
| 2019/0127378 A1 | 5/2019 | Ma et al. |
| 2019/0185475 A1 | 6/2019 | Bagdanoff et al. |
| 2019/0210977 A1 | 7/2019 | Jogalekar et al. |
| 2019/0270746 A1* | 9/2019 | Jones .................. A61P 35/00 |
| 2019/0290649 A1 | 9/2019 | Xie et al. |
| 2019/0307745 A1 | 10/2019 | Albrecht et al. |
| 2019/0389867 A1 | 12/2019 | Jones et al. |
| 2020/0002330 A1 | 1/2020 | Chen et al. |
| 2020/0017511 A1 | 1/2020 | Blank et al. |
| 2020/0017517 A1 | 1/2020 | Gill et al. |
| 2020/0048249 A1 | 2/2020 | Jones et al. |
| 2020/0108071 A1 | 4/2020 | Chin et al. |
| 2020/0115389 A1 | 4/2020 | Fu et al. |
| 2020/0172546 A1 | 6/2020 | Taylor et al. |
| 2020/0253969 A1 | 8/2020 | Taylor et al. |
| 2020/0392161 A1 | 12/2020 | Walters et al. |

(Continued)

FOREIGN PATENT DOCUMENTS

| | | |
|---|---|---|
| CN | 107286150 A | 10/2017 |
| CN | 110143949 A | 8/2019 |

(Continued)

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Hellmuth et al., Specific inhibitors of the protein tyrosine phosphatase Shp2 identified by high-throughput docking. PNAS, 2008, 105, 7275-7280.*

(Continued)

*Primary Examiner* — Po-Chih Chen
(74) *Attorney, Agent, or Firm* — Alston & Bird LLP

(57) ABSTRACT

The present invention relates to novel compounds and pharmaceutical compositions thereof, and methods for inhibiting the activity of SHP2 phosphatase with the compounds and compositions of the invention. The present invention further relates to, but is not limited to, methods for treating disorders associated with SHP2 deregulation with the compounds ad compositions of the invention.

18 Claims, No Drawings

(56) References Cited

U.S. PATENT DOCUMENTS

| | | | |
|---|---|---|---|
| 2021/0069188 A1 | 3/2021 | Taylor et al. | |
| 2021/0085677 A1 | 3/2021 | Taylor et al. | |

FOREIGN PATENT DOCUMENTS

| | | |
|---|---|---|
| CN | 111153899 | 5/2020 |
| TW | 201925186 A | 7/2019 |
| WO | WO-2004/111060 A1 | 12/2004 |
| WO | WO-2010/011666 A2 | 1/2010 |
| WO | WO-2010/097798 A1 | 9/2010 |
| WO | WO-2010/121212 A2 | 10/2010 |
| WO | WO-2011/130396 A1 | 10/2011 |
| WO | WO 2015/107493 A1 | 7/2015 |
| WO | WO-2015/107494 A1 | 7/2015 |
| WO | WO-2015/107495 A1 | 7/2015 |
| WO | WO-2016/203404 A1 | 12/2016 |
| WO | WO-2016/203406 A1 | 12/2016 |
| WO | WO-2017156397 A1 | 9/2017 |
| WO | WO-2017/210134 A1 | 12/2017 |
| WO | WO-2017/211303 A1 | 12/2017 |
| WO | WO-2018/013597 A1 | 1/2018 |
| WO | WO-2018/057884 A1 | 3/2018 |
| WO | WO 2018/081091 A1 | 5/2018 |
| WO | WO-2018/172984 A1 | 9/2018 |
| WO | WO-2018/218133 A1 | 11/2018 |
| WO | WO 2019/051084 A1 | 3/2019 |
| WO | WO-2019/067843 A1 | 4/2019 |
| WO | WO 2019/075265 A1 | 4/2019 |
| WO | WO 20197118909 A1 | 6/2019 |
| WO | WO 2019/158019 A1 | 8/2019 |
| WO | WO-2019/165073 A1 | 8/2019 |
| WO | WO 2019/167000 A1 | 9/2019 |
| WO | WO-2019/183364 A1 | 9/2019 |
| WO | WO-2019/183367 A1 | 9/2019 |
| WO | WO 2019/199792 A1 | 10/2019 |
| WO | WO 2019/233810 A1 | 12/2019 |
| WO | WO 2020/022323 A1 | 1/2020 |
| WO | WO 2020/063760 A1 | 4/2020 |
| WO | WO 2020/065452 A1 | 4/2020 |
| WO | WO 2020/065453 A1 | 4/2020 |
| WO | WO 2020/073945 A1 | 4/2020 |
| WO | WO 2020/073949 A1 | 4/2020 |
| WO | WO 2020/076723 A1 | 4/2020 |
| WO | WO 2020/081848 A1 | 4/2020 |
| WO | WO 2020/094018 A1 | 5/2020 |
| WO | WO 2020/094104 A1 | 5/2020 |

OTHER PUBLICATIONS

Chloe, Copin et al. "Snar Versus Buchwald-Hartwig Amination/Amidation in the Imidazo[2,1-b] [1,3,4]thiadiazole Series," European Journal of Organic Chemistry, vol. 2015, No. 31, Sep. 29, 2015, pp. 6932-6942.

Larochelle, Jonathan et al. "Identification of An Allosteric Benzothiazolopyrimidone Inhibitor of the Oncogenic Protein Tyrosine Phosphatase SHP2," Bioorganic & Medicinal Chemistry, vol. 25, No. 24, Oct. 20, 2017, pp. 6479-6485.

Temple, Kayla et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11 Oct. 11, 2016, pp. 5481-5486.

Yokoi, Taiyo et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, Oct. 13, 2017, pp. 5305-5309.

Saifidin, Safarov et al. "Preparation of 5-Bromo-6-phenylimidazo(2,l-b)(l,3,4)thiadiazol-2-ylamines," Journal of Heterocyclic Chemistry, Wiley-Blackwell Publishing, Inc, Us, vol. 45, No. 1, Jan. 1, 2008, pp. 299-302.

Krasavin M et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Shen, Jiayi et al. "3-Aminopyrazolopyrazine Derivatives as Spleen Tyrosine Kinase Inhibitors," Hemical Biology & Drug Design, vol. 88, No. 5, 2016, pp. 690-698.

Jorge, Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

U.S. Appl. No. 16/616,361, filed Nov. 22, 2019.

Bollu et al., "Molecular Pathways: Targeting Protein Tyrosine Phosphatases in Cancer," Clin Cancer Res. 23(9): 2136-2142, (May 1, 2017).

Lazo et al., "New Approaches to Difficult Drug Targets: the Phosphatase Story," SLAS Discovery, vol. 22(9), 1071-1083, (2017).

U.S. Appl. No. 16/335,933, Non-Final Office Action dated Jan. 8, 2020.

U.S. Appl. No. 16/616,361, Requirement for Restriction/Election dated Oct. 30, 2020.

U.S. Appl. No. 16/886,105, Notice of Allowance dated Sep. 9, 2020.

U.S. Appl. No. 16/886,105, Notice of Allowance dated Nov. 4, 2020.

U.S. Appl. No. 16/335,933, Final Office Action dated Aug. 26, 2020.

WIPO Application No. PCT/US2017/052950, PCT International Preliminary Report on Patentability dated Mar. 26, 2019.

WIPO Application No. PCT/US2017/052950, PCT International Search Report and Written Opinion of the International Searching Authority dated Mar. 29, 2018.

WIPO Application No. PCT/US2017/058048, PCT International Preliminary Report on Patentability dated Apr. 30, 2019.

WIPO Application No. PCT/US2017/058048, PCT International Search Report and Written Opinion of the International Searching Authority dated May 3, 2018.

WIPO Application No. PCT/US2018/034614, PCT International Preliminary Report on Patentability dated Nov. 26, 2019.

WIPO Application No. PCT/US2018/034614, PCT International Search Report and Written Opinion of the International Searching Authority dated Nov. 29, 2018.

WIPO Application No. PCT/US2018/053322, PCT International Preliminary Report on Patentability dated Mar. 31, 2020.

WIPO Application No. PCT/US2018/053322, PCT International Search Report and Written Opinion of the International Searching Authority dated Apr. 4, 2019.

WIPO Application No. PCT/US2019/023389, PCT International Search Report and Written Opinion of the International Searching Authority dated May 10, 2019.

WIPO Application No. PCT/US2019/023389, PCT International Preliminary Report on Patentability dated Sep. 22, 2020.

WIPO Application No. PCT/US2020/052118, PCT International Search Report and Written Opinion of the International Searching Authority dated Dec. 14, 2020.

Aceto, N. et al., "Tyrosine phosphatase SHP2 promotes breast cancer progression and maintains tumor-initiating cells via activation of key transcription factors and a positive feedback signaling loop," Nature Medicine, 18(4):529-538, (2012).

Bentires-Alj, M. et al., "Activating Mutations of the Noonan Syndrome-Associated SHP2/PTPN11 Gene in Human Solid Tumors and Adult Acute Myelogenous Leukemia," Cancer Res., 64:8816-8820, (2004).

Berge, et al., "Pharmaceutical Salts," J. Pharm. Sci., 66(1):1, (1977).

Cai, P. et al., "Expression and clinical significance of tyrosine phosphatase SHP-2 in colon cancer," Biomedicine & Pharmacotherapy, 68:285-290, (2014).

Chen, Y.-N.P. et al., "Allosteric inhibition of SHP2 phosphatase inhibits cancers driven by receptor tyrosine kinases," Nature, 535:158-152, (2016).

Furcht, C.M. et al., "Diminished functional role and altered localization of SHP2 in non-small cell lung cancer cells with EGFR-activating mutations," Oncogene, 32:2346-2355, (2013).

Gould, P.L., "Salt selection for basic drugs," Int J. Pharmaceutics, 33:201-217, (1986).

Grossman, K.S. et al., "The tyrosine phosphatase Shp2 in development and cancer," Adv. Cancer Res., 106:53-89, (2010).

(56) References Cited

OTHER PUBLICATIONS

Hackam, et al., "Translation of Research Evidence from Animals to Humans," JAMA, 296(14):1731-1732, (2006).
Jordan, V.C., "Tamoxifen: A Most Unlikely Pioneering Medicine," Nature Reviews: Drug Discovery, 2:205-213, (2003).
Schneeberger, V.E. et al., "Inhibition of Shp2 suppresses mutant EGFR-induced lung tumors in transgenic mouse model of lung adenocarcinoma," Oncotarget, 6:6191-6202, (2015).
Wang, J. et al., "Inhibition of SHP2 ameliorates the pathogenesis of systemic lupus erythematosus," The Journal of Clinical Invest. 126:2077-2092, (2016).
U.S. Appl. No. 16/616,361, Non-Final Office Action dated May 13, 2021.
U.S. Appl. No. 16/651,733, Non-Final Office Action dated Jul. 23, 2021.

\* cited by examiner

SHP2 PHOSPHATASE INHIBITORS AND METHODS OF USE THEREOF

CROSS REFERENCE TO RELATED APPLICATIONS

This application is a national stage filing under 35 U.S.C. § 371 of PCT/US2017/058048, filed Oct. 24, 2017, which claims the benefit of, and priority to, U.S. Provisional Patent Application No. 62/519,360, filed Jun. 14, 2017; U.S. Provisional Patent Application No. 62/511,583, filed May 26, 2017; U.S. Provisional Patent Application No. 62/425,301, filed Nov. 22, 2016; and U.S. Provisional Patent Application No. 62/411,972, filed Oct. 24, 2016; the contents of each of which are hereby incorporated by reference in their entirety.

FIELD OF THE INVENTION

The present invention relates to novel compounds and pharmaceutical compositions thereof, and methods for inhibiting the activity of SHP2 phosphatase with the compounds and compositions of the invention.

BACKGROUND OF THE INVENTION

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g., K. S. Grossman et al., *Adv. Cancer Res.* 2010, 106, 53-89; and references cited therein.)

In the basal state, SHP2 is normally auto-inhibited due to intramolecular interactions between its N-terminal SH2 (N—SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N—SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

SUMMARY

It is understood that any of the embodiments described below can be combined in any desired way, and that any embodiment or combination of embodiments can be applied to each of the aspects described below, unless the context indicates otherwise.

In one aspect, the invention provides a compound of Formula (I), or a pharmaceutically acceptable salt thereof,

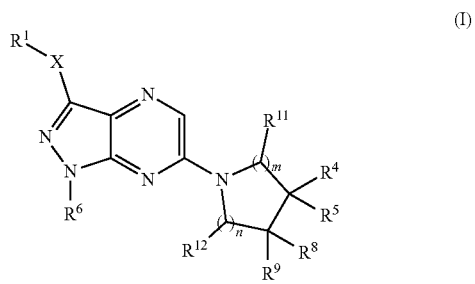

wherein
X is N—$R^{66}$, O, S, S(O), $SO_2$, $CR^{13}R^{14}$, —O—C($R^{13}R^{14}$)—, —C($R^{13}R^{14}$)O—, C(O), or C=C($R^{13}R^{14}$);
$R^1$ is selected from the group consisting of a 5-10 membered monocyclic or bicyclic aryl or heteroaryl, and a 4-7 membered heterocycle, wherein $R^1$ is optionally substituted with one or more substituents each independently selected from the group consisting of —$R^{10}$, —$OR^{10}$, —S(O)$_w R^{10}$ (wherein w is 0, 1 or 2), —N($R^{10}$)$_2$, —OS(O)$_w$—$R^{10}$ (wherein w is 0, 1, or 2), —S(O)$_w$—N($R^{10}$)$_2$ (wherein w is 0, 1 or 2), —S(O)(NH)$R^{10}$, —P(O)($R^{10}$)$_2$, —C(O)$R^{10}$, —C(O)N($R^{10}$)$_2$, oxo, halogen and nitrile; wherein each $R^{10}$ is independently selected from the group consisting of H, —($C_1$-$C_6$)alkyl, —($C_1$-$C_6$)haloalkyl, —($C_3$-$C_6$)cycloalkyl, heterocycloalkyl, aryl, and heteroaryl, where $R^{10}$ in turn may be substituted one or more substituents each selected from the group consisting of halo, C(O)$R^{20}$, $C_{1-6}$alkyl and $C_{1-6}$haloalkyl; where $R^{20}$ is —OH, halo, or —($C_1$-$C_6$)alkyl;
$R^4$ and $R^5$ are each independently, selected from the group consisting of H, —OH, —($C_1$-$C_6$)alkyl, —O($C_1$-$C_6$)alkyl, —($C_1$-$C_6$)alkyl-O—$R^6$, —C(O)N($R^6$)$_2$, —N($R^6$)$_2$, halogen, —($C_1$-$C_6$)alkyl-N($R^6$)$_2$, or nitrile, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —$NH_2$, oxo, and halogen,
or $R^4$ and $R^5$, taken together with the atoms to which they are attached, form a
3-7 membered carbocyclic or heterocyclic saturated or partially unsaturated ring, which ring is optionally substituted with —OH, —($C_1$-$C_6$)alkyl, —O($C_1$-$C_6$)alkyl, —N($R^6$)$_2$, halogen, oxo, or nitrile;
or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;
or $R^4$ is absent, and $R^4$ and $R^8$, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;
$R^6$ is independently for each occurrence selected from the group consisting of H, —($C_1$-$C_6$)alkyl and phenyl;
$R^{66}$ is selected from the group consisting of H, —($C_1$-$C_6$) alkyl and phenyl, or together with $R^1$ and the nitrogen to which they are attached form a nitrogen ring moiety selected from the group consisting of 5-7 membered monocyclic heteroaryl, a 8-12 membered bicyclic moiety with one saturated ring and one aromatic or heteroaromatic ring, a 8-12 membered bicyclic heteroaryl, and a 4-7 membered heterocycle, wherein the nitrogen ring moiety is optionally substituted with one, two or more substituents each independently selected from the group consisting of $R^{10}$, —$OR^{10}$, —$S(O)_wR^{10}$ (wherein w is 0, 1 or 2), —$N(R^{10})_2$, —$OS(O)_w$—$R^{10}$ (wherein w is 0, 1 or 2), —$S(O)_w$—$N(R^{10})_2$ (wherein w is 0, 1 or 2), —$S(O)(NH)R^{10}$, —$P(O)(R^{10})_2$, —$C(O)R^{10}$, —$C(O)N(R^{10})_2$, oxo, halogen, nitrile, phenyl (optionally substituted with one, two or three halo, $C_{1-3}$alkyl or $C_{1-3}$haloalkyl), $C_{1-3}$alkyl, $C_{1-3}$haloalkyl, and heteroaryl (optionally substituted with one, two or three halo, $C_{1-3}$alkyl or $C_{1-3}$haloalkyl);

$R^{11}$ and $R^{12}$ are, each independently selected from the group consisting of, H, —OH, —$(C_1-C_6)$alkyl, —$O(C_1-C_6)$alkyl, —$(C_1-C_6)$alkyl-O—$R^6$, aryl, arylalkylene, heteroaryl, heteroarylalkylene, —$C(O)N(R^6)_2$, —$N(R^6)_2$, halogen, —$(C_1-C_6)$alkyl-$N(R^6)_2$, —$CO_2H$, or nitrile, wherein said —$(C_1-C_6)$alkyl, —$O(C_1-C_6)$alkyl, —$(C_1-C_6)$alkyl-O—$R^6$, aryl, arylalkylene, heteroaryl, heteroarylalkylene, or —$(C_1-C_6)$alkyl-$N(R^6)_2$ is optionally substituted with one or more substituents selected from the group consisting of —OH, —$N(H)_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

$R^8$ and $R^9$ are each independently selected from the group consisting of H, —$(C_1-C_6)$alkyl, —$(C_1-C_6)$alkyl-$N(R^6)_2$, —$OR^6$, —$(C_1-C_6)$alkyl-O—$R^6$, —$C(O)NH_2$, —$N(R^6)_2$, halogen, or nitrile;

$R^{13}$ and $R^{14}$ for each occurrence, are independently selected from the group consisting of H, —OH, —$(C_1-C_6)$alkyl, —$O(C_1-C_6)$alkyl, —$C(O)N(R^6)_2$, —$N(R^6)_2$, halogen, —$(C_1-C_6)$alkyl-$N(R^6)_2$, or $R^{13}$ and $R^{14}$ taken together with the carbon to which they are attached form a $C_{3-4}$cycloalkyl, or $R^1$ and $R^{13}$, together with the carbon to which they are attached, form a carbon ring moiety selected from the group consisting of phenyl, a 5-7 membered monocyclic heteroaryl, a 8-10 membered bicyclic heteroaryl, and an 5-7 membered heterocycle, wherein the carbon ring moiety is optionally substituted with one, two or more substituents each independently selected from the group consisting of —$R^{10}$, —$N(R^6)_2$, —$C(O)N(R^6)_2$, oxo, halogen, and nitrile, where $R^{14}$ is H or is absent;

$R^{15}$ and $R^{16}$ for each occurrence, are independently selected from the group consisting of H, —OH, —$(C_1-C_6)$alkyl, —$O(C_1-C_6)$alkyl, —$C(O)N(R^6)_2$, —$N(R^6)_2$, halogen, —$(C_1-C_6)$alkyl-$N(R^6)_2$, or $R^{15}$ and $R^{16}$ taken together with the carbon to which they are attached may form a $C_{3-4}$cycloalkyl;

and each of m and n is, independently, 0, 1, 2, or 3, with m+n being at least 2 and no more than 4.

The invention also provides pharmaceutical compositions containing the compounds described herein. Further, the invention provides a method of inhibiting SHP2 phosphatase activity in a subject by administering a therapeutically effective amount of a compound or composition described herein, to a subject, e.g., a human, in need. The method may include additionally administering a therapeutically effective amount of an antibody, an antibody-drug conjugate, an immunomodulator, or a histone deacetylase inhibitor.

The invention further provides a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present invention is based, in part, on certain discoveries which are described more fully in the Examples section of the present application. For example, the present invention is based, in part, on the discovery of compounds of Formula (I) and the SHP2 phosphatase inhibition exhibited by such compounds.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION

Activating SHP2 mutations have been detected in juvenile myelomonocytic leukemia (e.g., Q506P), chronic myelomonocytic leukemia (e.g., Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in *Cancer Res.* 2004, 64, 8816-8820; and references cited therein.

SHP2 phosphatase inhibitors are disclosed, e.g., in WO 2015/107493; WO 2015/107494; WO 2015/107495; and J. G. Fortanet et al., in *J. Med. Chem.* 2016, DOI: 10.1021/acs.jmedchem.6b00680; and references cited therein. The effects of SHP2 phsophatase inhibition are described, e.g., Y.-N. P. Chen et al., in *Nature,* 2016, doi:10.1038/nature18621; J. Wang et al., in *J. Clin. Invest.* 2016, 126, 2077-2092; and references cited therein.

The compounds and/or compositions of the invention, alone or in combination with other treatments, may be effective in treating, reducing, and/or suppressing disorders related to SHP2 phosphatase activity such as, e.g., Noonan syndrome, Leopard Syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), neutropenia (Kostmann's syndrome), and systemic lupus erythematosus. See, e.g, N. Aceto et al. *Nature Medicine,* 2012, 28, 529-538; C. M. Furcht et al. *Oncogene,* 2013, 32, 2346-2355; V. E.

Schneeberger et al. *Oncotarget,* 2015, 6, 6191-6202; P. Cai et al., *Biomedicine & Pharmacotherapy* 2014, 68, 285-290; and references cited therein.

Abbreviations and Definitions

The term "compound of the invention" as used herein means a compound of Formula (I) or Formula (II). The term is also intended to encompass salts, hydrates, tautomers, stereoisomers, and isotopic substitutions thereof.

The term "composition(s) of the invention" as used herein means compositions comprising a compound of the invention, and salts thereof. The compositions of the invention may further comprise other agents such as, e.g., excipients, stabilants, lubricants, solvents, and the like.

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this invention.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2$H (also represented as D) and $^3$H. Examples of the isotope of a carbon atom include $^{13}$C and $^{14}$C. Examples of the isotope of an oxygen atom include $^{18}$O.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, wherein the one or more substituents are independently $C_1$-$C_{10}$ alkyl. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, and the like.

The terms "heteroaryl" or "heteroaromatic group" as used herein refers to a monocyclic aromatic 5-7 membered ring system containing one or more heteroatoms, for example one to three heteroatoms, such as nitrogen, oxygen, and sulfur, or a 8-12 membered bicyclic unsaturated or partially unsaturated ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, tetrahydroquinoline, etc.

The terms "heterocyclyl" or "heterocyclic group" are art-recognized and refer to saturated 4-10 membered monocyclic and bicyclic ring structures, including bridged or fused rings, and whose ring structures include one to three heteroatoms, such as nitrogen, oxygen, and sulfur. Where possible, heterocyclyl rings may be linked to the adjacent radical through carbon or nitrogen.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217; (each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the invention.

In some embodiments, SHP2 phosphatase inhibitors described herein encompass compounds of Formula (I) or pharmaceutically acceptable salts thereof,

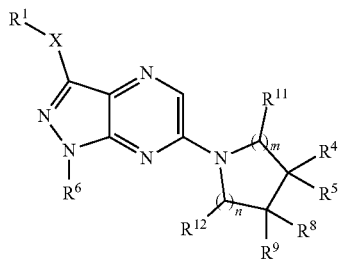
(I)

wherein

X is N—$R^{66}$, O, S, S(O), $SO_2$, $CR^{13}R^{14}$, —O—C($R^{13}R^{14}$)—, —C($R^{13}R^{14}$)O—, C(O), or C═C($R^{13}R^{14}$);

$R^1$ is selected from the group consisting of a 5-10 membered monocyclic or bicyclic aryl or heteroaryl, and a 4-7 membered heterocycle, wherein $R^1$ is optionally substituted with one or more substituents each independently selected from the group consisting of —$R^{10}$, —$OR^{10}$, —S(O)$_w$$R^{10}$ (wherein w is 0, 1 or 2), —N($R^{10}$)$_2$, —OS(O)$_w$—$R^{10}$ (wherein w is 0, 1, or 2), —S(O)$_w$—N($R^{10}$)$_2$ (wherein w is 0, 1 or 2), —S(O)(NH)$R^{10}$, —P(O)($R^{10}$)$_2$, —C(O)$R^{10}$, —C(O)N($R^{10}$)$_2$, oxo, halogen and nitrile; wherein each $R^{10}$ is independently selected from the group consisting of H, —($C_1$-$C_6$)alkyl, —($C_1$-$C_6$)haloalkyl, ($C_3$-$C_6$)cycloalkyl, heterocycloalkyl, aryl, and heteroaryl, where $R^{10}$ in turn may be substituted one or more substituents each selected from the group consisting of halo, C(O)$R^{20}$, $C_{1-6}$alkyl and $C_{1-6}$haloalkyl; wherein $R^{20}$ is —OH, halo, or —($C_1$-$C_6$)alkyl;

$R^4$ and $R^5$ are each independently, selected from the group consisting of H, —OH, —($C_1$-$C_6$)alkyl, —O($C_1$-$C_6$)alkyl, —($C_1$-$C_6$)alkyl-O—$R^6$, —C(O)N($R^6$)$_2$, —N($R^6$)$_2$, halogen, —($C_1$-$C_6$)alkyl-N($R^6$)$_2$, or nitrile, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —$NH_2$, oxo, and halogen, or $R^4$ and $R^5$, taken together with the atoms to which they are attached, form a 3-7 membered carbocyclic or heterocyclic saturated or partially unsaturated ring, which ring is optionally substituted with —OH, —($C_1$-$C_6$)alkyl, —O($C_1$-$C_6$)alkyl, —N($R^6$)$_2$, halogen, oxo, or nitrile;

or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;

or $R^4$ is absent, and $R^4$ and $R^8$, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or nitrile;

$R^6$ is independently for each occurrence selected from the group consisting of H, —($C_1$-$C_6$)alkyl and phenyl;

$R^{66}$ is selected from the group consisting of H, —($C_1$-$C_6$)alkyl and phenyl, or together with $R^1$ and the nitrogen to which they are attached form a nitrogen ring moiety selected from the group consisting of 5-7 membered monocyclic heteroaryl, a 8-12 membered bicyclic moiety with one saturated ring and one aromatic or heteroaromatic ring, a 8-12 membered bicyclic heteroaryl, and a 4-7 membered heterocycle, wherein the nitrogen ring moiety is optionally substituted with one, two or more substituents each independently selected from the group consisting of $R^{10}$, —$OR^{10}$, —S(O)$_w$$R^{10}$ (wherein w is 0, 1 or 2), —N($R^{10}$)$_2$, —OS(O)$_w$—$R^{10}$ (wherein w is 0, 1, or 2), —S(O)$_w$—N($R^{10}$)$_2$ (wherein w is 0, 1 or 2), —S(O)(NH)$R^{10}$, —P(O)($R^{10}$)$_2$, —C(O)$R^{10}$, —C(O)N($R^{10}$)$_2$, oxo, halogen, nitrile, phenyl (optionally substituted with one, two or three halo, $C_{1-3}$alkyl or $C_{1-3}$haloalkyl), $C_{1-3}$alkyl, $C_{1-3}$haloalkyl, and heteroaryl (optionally substituted with one, two or three halo, $C_{1-3}$alkyl or $C_{1-3}$haloalkyl);

$R^{11}$ and $R^{12}$ are, each independently selected from the group consisting of, H, —OH, —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, —C(O)N($R^6$)$_2$, —N($R^6$)$_2$, halogen, —($C_1$-$C_6$)alkyl-N($R^6$)$_2$, —$CO_2$H, or nitrile, wherein said —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, or —($C_1$-$C_6$)alkyl-N($R^6$)$_2$ is optionally substituted with one or more substituents selected from the group consisting of —OH, —N(H)$_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

$R^8$ and $R^9$ are each independently selected from the group consisting of H, —($C_1$-$C_6$)alkyl, —($C_1$-$C_6$)alkyl-N($R^6$)$_2$, —$OR^6$, —($C_1$-$C_6$)alkyl-O—$R^6$, —C(O)$NH_2$, —N($R^6$)$_2$, halogen, or nitrile;

$R^{13}$ and $R^{14}$ for each occurrence, are independently selected from the group consisting of H, —OH, —($C_1$-$C_6$)alkyl, —O($C_1$-$C_6$)alkyl, —C(O)N($R^6$)$_2$, —N($R^6$)$_2$, halogen, —($C_1$-$C_6$)alkyl-N($R^6$)$_2$, or $R^{13}$ and $R^{14}$ taken together with the carbon to which they are attached form a $C_{3-4}$cycloalkyl, or $R^1$ and $R^{13}$, together with the carbon to which they are attached, form a carbon ring moiety selected from the group consisting of phenyl, a 5-7 membered monocyclic heteroaryl, a 8-10 membered bicyclic heteroaryl, and an 5-7 membered heterocycle, wherein the carbon ring moiety is optionally substituted with one, two or more substituents each independently selected from the group consisting of —$R^{10}$, —N($R^6$)$_2$, —C(O)N($R^6$)$_2$, oxo, halogen, and nitrile, where $R^{14}$ is H or is absent;

$R^{15}$ and $R^{16}$ for each occurrence, are independently selected from the group consisting of H, —OH, —($C_1$-$C_6$)alkyl, —O($C_1$-$C_6$)alkyl, —C(O)N($R^6$)$_2$, —N($R^6$)$_2$, halogen, —($C_1$-$C_6$)alkyl-N($R^6$)$_2$, or $R^{15}$ and $R^{16}$ taken together with the carbon to which they are attached may form a $C_{3-4}$cycloalkyl;

and each of m and n is, independently, 0, 1, 2, or 3, with m+n being at least 2 and no more than 4.

In some embodiments, X is N—R$^{66}$, O, S, S(O), SO$_2$, CR$^{13}$R$^{14}$, C(O), or C=C(R$^{15}$R$^{16}$); R$^1$ is phenyl, pyridyl, or imidazolyl, which is optionally substituted with one or more substituents selected from the group consisting of R$^{10}$, —N(R$^{10}$)$_2$, —C(O)N(R$^{10}$)$_2$, halogen, or nitrile, wherein each R$^{10}$ is, independently, H, —(C$_1$-C$_6$)alkyl, or —(C$_1$-C$_6$)haloalkyl; wherein each R$^6$ is independently H or —(C$_1$-C$_6$)alkyl; and the moiety

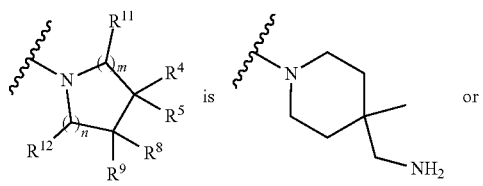

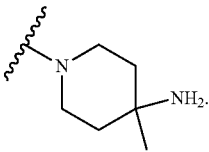

In some embodiments, X is N—R$^{66}$, O, S, S(O), or SO$_2$; R$^1$ is phenyl, pyridyl, or imidazolyl, which is optionally substituted with one or more substituents selected from the group consisting of —R$^{10}$, —N(R$^{10}$)$_2$, —C(O)N(R$^{10}$)$_2$, halogen, or nitrile, wherein each R$^{10}$ is, independently, H, —(C$_1$-C$_6$)alkyl, or —(C$_1$-C$_6$)haloalkyl; wherein each R$^6$ is independently H or —(C$_1$-C$_6$)alkyl; and the moiety

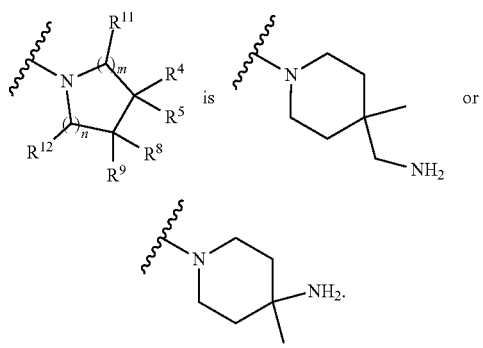

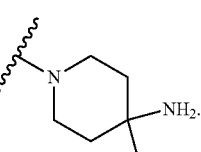

In some embodiments, X is N—R$^{66}$, O, or S; R$^1$ is phenyl, pyridyl, or imidazolyl, which is optionally substituted with one or more substituents selected from the group consisting of —R$^{10}$, —N(R$^{10}$)$_2$, —C(O)N(R$^{10}$)$_2$, halogen, or nitrile, wherein each R$^{10}$ is, independently, H, —(C$_1$-C$_6$)alkyl, or —(C$_1$-C$_6$)haloalkyl; wherein each R$^6$ is independently H or —(C$_1$-C$_6$)alkyl; and the moiety

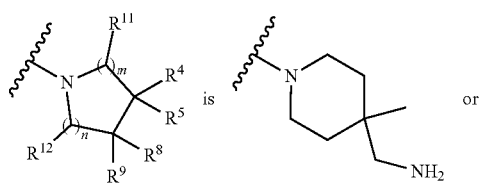

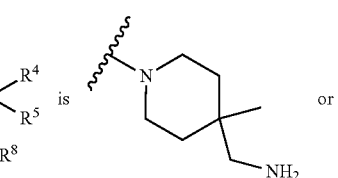

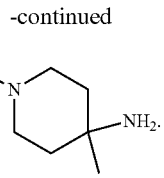

In some embodiments, X is CR$^{13}$R$^{14}$, C(O), or C=C(R$^{15}$R$^{16}$); R$^1$ is phenyl, pyridyl, or imidazolyl, which is optionally substituted with one or more substituents selected from the group consisting of —R$^{10}$, —N(R$^{10}$)$_2$, —C(O)N(R$^{10}$)$_2$, halogen, or nitrile, wherein each R$^{10}$ is, independently, H, —(C$_1$-C$_6$)alkyl, or —(C$_1$-C$_6$)haloalkyl; wherein each R$^6$ is independently H or —(C$_1$-C$_6$)alkyl; and the moiety

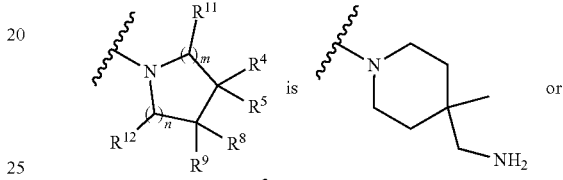

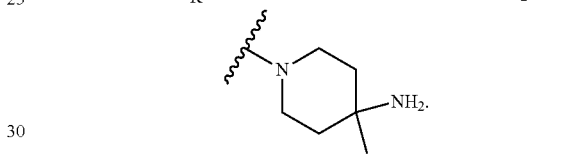

In some embodiments, X is N—R$^{66}$, O, S, S(O), SO$_2$, CR$^{13}$R$^{14}$, C(O), or C=C(R$^{15}$R$^{16}$). In some embodiments, X is N—R$^{66}$, O, S, S(O), or SO$_2$. In some embodiments, X is N—R$^{66}$, O, or S. In some embodiments, X is CR$^{13}$R$^{14}$, C(O), or C=C(R$^{15}$R$^{16}$). In some embodiments, X is N—R$^{66}$ or O. In some embodiments, X is N—R$^{66}$ or S. In some embodiments, X is O or S. In some embodiments, X is S(O) or SO$_2$. In some embodiments, X is N—R$^{66}$. In some embodiments, X is O. In some embodiments, X is S. In some embodiments, X is S(O). In some embodiments, X is SO$_2$. In some embodiments, X is CR$^{13}$R$^{14}$ or C=C(R$^{13}$R$^{14}$). In some embodiments, X is CR$^{13}$R$^{14}$ or C(O). In some embodiments, X is C(O) or C=C(R$^{15}$R$^{16}$). In some embodiments, X is CR$^{13}$R$^{14}$. In some embodiments, X is C(O). In some embodiments, X is C=C(R$^{15}$R$^{16}$). In some embodiments, X is C=CH$_2$. In some embodiments, X is C(H)(CH$_3$). In some embodiments, X is C(OH)(CH$_3$). In some embodiments, X is CH$_2$.

In some embodiments, R$^1$ is phenyl, pyridyl, or indolyl, wherein said phenyl, pyridyl, or indolyl is optionally substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile.

In some embodiments, X and R$^1$ together are a bicyclic ring system containing a nitrogen-containing 5-7 membered ring fused to an aryl or heteroaryl ring, a 8-12 membered bicyclic moiety with one saturated ring and one aromatic or heteroaromatic ring, or a nitrogen-containing 5-7 membered ring. In some embodiments, R$^{66}$ together with R$^1$ and the nitrogen to which they are attached form a tetrahydroquinoline moiety.

In some embodiments, R$^1$ is phenyl, pyridyl, indolyl, or indolinyl, wherein said phenyl, pyridyl, indolyl or indolinyl is optionally substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile. In some embodiments, R$^1$ is H, phenyl, pyridyl, imidazolyl, indolyl, naphthyl, quinolinyl, isoquinolinyl, benzimidazolyl, indazolyl, benzotriazolyl, benzothiazolyl, benzofuranyl, pyrazolopyridyl, quinazolinyl, quinoxalinyl, or cinnolinyl.

In some embodiments, $R^1$ is phenyl. In some embodiments, $R^1$ is pyridyl. In some embodiments, $R^1$ is 2-pyridyl. In some embodiments, $R^1$ is 3-pyridyl. In some embodiments, $R^1$ is 4-pyridyl. In some embodiments, $R^1$ is naphthyl. In some embodiments, $R^1$ is 1-naphthyl. In some embodiments, $R^1$ is 2-naphthyl. In some embodiments, $R^1$ is quinolinyl. In some embodiments, $R^1$ is 2-quinolinyl. In some embodiments, $R^1$ is 3-quinolinyl. In some embodiments, $R^1$ is 4-quinolinyl. In some embodiments, $R^1$ is 5-quinolinyl. In some embodiments, $R^1$ is 6-quinolinyl. In some embodiments, $R^1$ is 7-quinolinyl. In some embodiments, $R^1$ is 8-quinolinyl. In some embodiments, $R^1$ is isoquinolinyl. In some embodiments, $R^1$ is 1-isoquinolinyl. In some embodiments, $R^1$ is 3-isoquinolinyl. In some embodiments, $R^1$ is 4-isoquinolinyl. In some embodiments, $R^1$ is 5-isoquinolinyl. In some embodiments, $R^1$ is 6-isoquinolinyl. In some embodiments, $R^1$ is 7-isoquinolinyl. In some embodiments, $R^1$ is 8-isoquinolinyl. In some embodiments, $R^1$ is indolyl. In some embodiments, $R^1$ is 2-indolyl. In some embodiments, $R^1$ is 3-indolyl. In some embodiments, $R^1$ is 4-indolyl. In some embodiments, $R^1$ is 5-indolyl. In some embodiments, $R^1$ is 6-indolyl. In some embodiments, $R^1$ is 7-indolyl. In some embodiments, $R^1$ is aryl. In some embodiments, $R^1$ is bicyclic aryl. In some embodiments, $R^1$ is heteroaryl. In some embodiments, $R^1$ is fused bicyclic heteroaryl.

In some embodiments, $R^1$ is phenyl, pyridyl, or indolyl, wherein said phenyl, pyridyl, or indolyl is optionally substituted with —$OR^{10}$, halogen, or nitrile.

In some embodiments, $R^1$ is phenyl, wherein said phenyl is optionally substituted with —$OR^{10}$, halogen, or nitrile.

In some embodiments, $R^1$ is pyridyl, wherein said pyridyl is optionally substituted with —$OR^{10}$, halogen, or nitrile.

In some embodiments, $R^1$ is indolyl, wherein said indolyl is optionally substituted with —$OR^{10}$, halogen, or nitrile.

In some embodiments, $R^1$ is phenyl, pyridyl, or indolyl, wherein said phenyl, pyridyl, or indolyl is optionally substituted with —$OR^{10}$ or halogen.

In some embodiments, $R^1$ is phenyl, pyridyl, or indolyl, wherein said phenyl, pyridyl, or indolyl is optionally substituted with halogen.

In some embodiments, $R^1$ is phenyl substituted with —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile. In some embodiments, $R^1$ is phenyl substituted with —$R^{10}$. In some embodiments, $R^1$ is phenyl substituted with —$OR^{10}$. In some embodiments, $R^1$ is phenyl substituted with —$SR^{10}$. In some embodiments, $R^1$ is phenyl substituted with —$N(R^{10})_2$. In some embodiments, $R^1$ is phenyl substituted with —$OSO_2R^{10}$. In some embodiments, $R^1$ is phenyl substituted with —$SO_2R^{10}$. In some embodiments, $R^1$ is phenyl substituted with —$C(O)N(R^{10})_2$. In some embodiments, $R^1$ is phenyl substituted with halogen. In some embodiments, $R^1$ is phenyl substituted with nitrile.

In some embodiments, $R^1$ is pyridyl substituted with —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile. In some embodiments, $R^1$ is pyridyl substituted with —$R^{10}$. In some embodiments, $R^1$ is pyridyl substituted with —$OR^{10}$. In some embodiments, $R^1$ is pyridyl substituted with —$SR^{10}$. In some embodiments, $R^1$ is pyridyl substituted with —$N(R^{10})_2$. In some embodiments, $R^1$ is pyridyl substituted with —$OSO_2R^{10}$. In some embodiments, $R^1$ is pyridyl substituted with —$SO_2R^{10}$. In some embodiments, $R^1$ is pyridyl substituted with —$C(O)N(R^{10})_2$. In some embodiments, $R^1$ is pyridyl substituted with halogen. In some embodiments, $R^1$ is pyridyl substituted with nitrile.

In some embodiments, $R^1$ is 3-pyridyl substituted with —$OR^{10}$. In some embodiments, $R^1$ is 3-pyridyl substituted with —$OCH_3$. In some embodiments, $R^1$ is 6-methoxypyrid-3-yl. In some embodiments, $R^1$ is 3-pyridyl substituted with halogen. In some embodiments, $R^1$ is 3-pyridyl substituted with Cl. In some embodiments, $R^1$ is 4-chloropyrid-3-yl. In some embodiments, $R^1$ is 2,3-dichloropyrid-4-yl. In some embodiments, $R^1$ is 3-chloropyrid-2-yl.

In some embodiments, $R^1$ is naphthyl substituted with —$R^{10}$, —$OR^{10}$, —$SR^{10}$, —$N(R^{10})_2$, —$OSO_2R^{10}$, —$SO_R^{10}$, —$C(O)N(R^{10})_2$, halogen, or nitrile. In some embodiments, $R^1$ is naphthyl substituted with —$R^{10}$. In some embodiments, $R^1$ is naphthyl substituted with —$OR^{10}$. In some embodiments, $R^1$ is naphthyl substituted with —$SR^{10}$. In some embodiments, $R^1$ is naphthyl substituted with —$N(R^{10})_2$. In some embodiments, $R^1$ is naphthyl substituted with —$OSO_2R^{10}$. In some embodiments, $R^1$ is naphthyl substituted with —$SO_2R^{10}$. In some embodiments, $R^1$ is naphthyl substituted with —$C(O)N(R^{10})_2$. In some embodiments, $R^1$ is naphthyl substituted with halogen. In some embodiments, $R^1$ is naphthyl substituted with nitrile.

In some embodiments, $R^1$ is quinolinyl substituted with —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile. In some embodiments, $R^1$ is quinolinyl substituted with —$R^{10}$. In some embodiments, $R^1$ is quinolinyl substituted with —$OR^{10}$. In some embodiments, $R^1$ is quinolinyl substituted with —$SR^{10}$. In some embodiments, $R^1$ is quinolinyl substituted with —$N(R^{10})_2$. In some embodiments, $R^1$ is quinolinyl substituted with —$OSO_2R^{10}$. In some embodiments, $R^1$ is quinolinyl substituted with —$SO_2R^{10}$. In some embodiments, $R^1$ is quinolinyl substituted with —$C(O)N(R^{10})_2$. In some embodiments, $R^1$ is quinolinyl substituted with halogen. In some embodiments, $R^1$ is quinolinyl substituted with nitrile.

In some embodiments, $R^1$ is isoquinolinyl substituted with —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile. In some embodiments, $R^1$ is isoquinolinyl substituted with —$R^{10}$. In some embodiments, $R^1$ is isoquinolinyl substituted with —$OR^{10}$. In some embodiments, $R^1$ is isoquinolinyl substituted with —$SR^{10}$. In some embodiments, $R^1$ is isoquinolinyl substituted with —$N(R^{10})_2$. In some embodiments, $R^1$ is isoquinolinyl substituted with —$OSO_2R^{10}$. In some embodiments, $R^1$ is isoquinolinyl substituted with —$SO_2R^{10}$. In some embodiments, $R^1$ is isoquinolinyl substituted with —$C(O)N(R^{10})_2$. In some embodiments, $R^1$ is isoquinolinyl substituted with halogen. In some embodiments, $R^1$ is isoquinolinyl substituted with nitrile.

In some embodiments, $R^1$ is indolyl substituted with —$R^{10}$, —$OR^{10}$, —$SR^{10}$, —$N(R^{10})_2$, —$OSO_2R^{10}$, —$SO_2R^{10}$, —$C(O)N(R^{10})_2$, halogen, or nitrile. In some embodiments, $R^1$ is indolyl substituted with —$R^{10}$. In some embodiments, $R^1$ is indolyl substituted with —$OR^{10}$. In some embodiments, $R^1$ is indolyl substituted with —$SR^{10}$. In some embodiments, $R^1$ is indolyl substituted with —$N(R^{10})_2$. In some embodiments, $R^1$ is indolyl substituted with —$OSO_2R^{10}$. In some embodiments, $R^1$ is indolyl substituted with —$SO_2R^{10}$. In some embodiments, $R^1$ is indolyl substituted with —$C(O)N(R^{10})_2$. In some embodiments, $R^1$ is indolyl substituted with halogen. In some embodiments, $R^1$ is indolyl substituted with nitrile.

In some embodiments, $R^1$ is 1-methyl-1H-indol-4-yl. In some embodiments, $R^1$ is 1-methyl-1H-indol-3-yl.

In some embodiments, $R^1$ is imidazol-2-yl. In some embodiments, $R^1$ is 1-methyl-imidazol-2-yl.

In some embodiments, $R^{66}$ together with $R^1$ and the nitrogen to which they are attached form a nitrogen ring moiety selected from the group consisting of 1,2,3,4-tetrahydroquinoline; 1,2,3,4-tetrahydro-1,5,napthyridine, dihydropyridopyrazine, benzoimidazole, benzoazepine, and dihydropyridooxazine, wherein the nitrogen ring moiety is optionally substituted with one or two substituents each independently selected from halo, $CF_3$, phenyl (optionally substituted with one, two or three halo, $C_{1-3}$alkyl or $C_{1-3}$haloalkyl), $C_{1-3}$alkyl, $C_{1-3}$haloalkyl, and heteroaryl (optionally substituted with one, two or three halo, $C_{1-3}$alkyl or $C_{1-3}$haloalkyl).

In some embodiments, $R^4$ and $R^5$ are independently H, —OH, —($C_1$-$C_6$)alkyl, —O($C_1$-$C_6$)alkyl, —($C_1$-$C_6$)alkyl-O—$R^6$, —C(O)NH$_2$, —N($R^6$)$_2$, halogen, —($C_1$-$C_6$)alkyl-N($R^6$)$_2$, or nitrile.

In some embodiments, $R^4$ and $R^5$ are independently H, —OH, —($C_1$-$C_3$)alkyl, —O($C_1$-$C_3$)alkyl, —($C_1$-$C_3$)alkyl-O—$R^6$, —C(O)NH$_2$, —N($R^6$)$_2$, halogen, —($C_1$-$C_3$)alkyl-N($R^6$)$_2$, or nitrile.

In some embodiments, $R^4$ and $R^5$ are independently H, —($C_1$-$C_6$)alkyl, or —($C_1$-$C_6$)alkyl-N($R^6$)$_2$. In some embodiments, $R^4$ and $R^5$ are independently H, —($C_1$-$C_6$)alkyl, or —($C_1$-$C_4$)alkyl-N($R^6$)$_2$. In some embodiments, $R^4$ and $R^5$ are independently H, —($C_1$-$C_2$)alkyl, or —($C_1$-$C_4$)alkyl-N($R^6$)$_2$. In some embodiments, $R^4$ and $R^5$ are independently H, —CH$_3$, or —($C_1$-$C_4$)alkyl-NH$_2$. In some embodiments, $R^4$ and $R^5$ are independently H, —CH$_3$, or —($C_1$-$C_2$)alkyl-NH$_2$. In some embodiments, $R^4$ and $R^5$ are independently H, —CH$_3$, or —CH$_2$—NH$_2$. In some embodiments, $R^4$ and $R^5$ are independently —CH$_3$ or —($C_1$-$C_4$)alkyl-NH$_2$. In some embodiments, $R^4$ and $R^5$ are independently —CH$_3$ or —($C_1$-$C_2$)alkyl-NH$_2$. In some embodiments, $R^4$ and $R^5$ are independently —CH$_3$ or —CH$_2$—NH$_2$. In some embodiments, $R^4$ and $R^5$ are independently —CH$_3$ or —CH$_2$CH$_2$—NH$_2$. In some embodiments, $R^4$ and $R^5$ are independently H or —CH$_2$—NH$_2$.

In some embodiments, $R^4$ and $R^5$ are independently H, —($C_1$-$C_6$)alkyl, or —N($R^6$)$_2$. In some embodiments, $R^4$ and $R^5$ are independently —($C_1$-$C_6$)alkyl or —N($R^6$)$_2$. In some embodiments, $R^4$ and $R^5$ are independently —($C_1$-$C_4$)alkyl or —N($R^6$)$_2$. In some embodiments, $R^4$ and $R^5$ are independently —($C_1$-$C_2$)alkyl or —N($R^6$)$_2$. In some embodiments, $R^4$ and $R^5$ are independently —CH$_3$ or —N($R^6$)$_2$. In some embodiments, $R^4$ and $R^5$ are independently —CH$_3$ or —NH$_2$. In some embodiments, $R^4$ and $R^5$ are independently —CH$_3$ or —NHCH$_3$.

In some embodiments, $R^4$ and $R^5$ are independently H, —OH, or —($C_1$-$C_6$)alkyl-N($R^6$)$_2$. In some embodiments, $R^4$ and $R^5$ are independently H, OH, or —($C_1$-$C_4$)alkyl-N($R^6$)$_2$. In some embodiments, $R^4$ and $R^5$ are independently H, OH, or —($C_1$-$C_4$)alkyl-NH$_2$. In some embodiments, $R^4$ and $R^5$ are independently H, OH, or —($C_1$-$C_2$)alkyl-NH$_2$. In some embodiments, $R^4$ and $R^5$ are independently H, OH, or —CH$_2$—NH$_2$. In some embodiments, $R^4$ and $R^5$ are independently OH or —($C_1$-$C_4$)alkyl-NH$_2$. In some embodiments, $R^4$ and $R^5$ are independently OH or —($C_1$-$C_2$)alkyl-NH$_2$. In some embodiments, $R^4$ and $R^5$ are independently OH or —CH$_2$—NH$_2$. In some embodiments, $R^4$ and $R^5$ are independently OH or —CH$_2$CH$_2$—NH$_2$.

In some embodiments, $R^4$ and $R^5$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —N($R^6$)$_2$, C(O), and halogen. In some embodiments, $R^4$ and $R^5$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —NH$_2$, and fluoro. In some embodiments, $R^4$ and $R^5$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH and fluoro. In some embodiments, $R^4$ and $R^5$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —NH$_2$ and fluoro.

In some embodiments, $R^4$ and $R^5$, taken together with the atoms to which they are attached, form a 3-7 membered carbocyclic or heterocyclic ring. In some embodiments, the 3-7 membered carbocyclic or heterocyclic ring is optionally substituted with —OH, —($C_1$-$C_6$)alkyl, —O($C_1$-$C_6$)alkyl, —N($R^6$)$_2$, halogen, oxo, or nitrile.

In some embodiments, $R^4$ and $R^8$, taken together with the atoms to which they are attached, form a 4-7 membered carbocyclic or heterocyclic ring. In some embodiments, the 4-7 membered carbocyclic or heterocyclic ring is optionally substituted with —OH, —($C_1$-$C_6$)alkyl, —O($C_1$-$C_6$)alkyl, —N($R^6$)$_2$, halogen, oxo, or nitrile.

In some embodiments, $R^4$ is a bond, and $R^4$ and $R^8$, taken together with the atoms to which they are attached, form a 3-membered carbocyclic or heterocyclic ring. In some embodiments, the 3-membered carbocyclic or heterocyclic ring is optionally substituted with —OH, —($C_1$-$C_6$)alkyl, —O($C_1$-$C_6$)alkyl, —N($R^6$)$_2$, halogen, oxo, or nitrile.

In some embodiments, $R^{11}$ and $R^{12}$ are independently H, —OH, —($C_1$-$C_6$)alkyl, —O($C_1$-$C_6$)alkyl, —($C_1$-$C_6$)alkyl-O—$R^6$, —C(O)NH$_2$, —N($R^6$)$_2$, halogen, —($C_1$-$C_6$)alkyl-N($R^6$)$_2$, —CO$_2$H, or nitrile. In some embodiments, $R^{11}$ and $R^{12}$ are independently H or —($C_1$-$C_6$)alkyl. In some embodiments, $R^{11}$ and $R^{12}$ are independently H or —($C_1$-$C_4$)alkyl. In some embodiments, $R^{11}$ and $R^{12}$ are independently H or —($C_1$-$C_2$)alkyl. In some embodiments, $R^{11}$ and $R^{12}$ are independently H or —CH$_3$.

In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH, —N($R^6$)$_2$, and halogen. In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, or —($C_1$-$C_6$)alkyl-N($R^6$)$_2$ is optionally substituted with one or more substituents selected from the group consisting of —OH, —NH$_2$, and fluoro. In some embodiments, $R^{11}$ and $R^{12}$ are independently —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$, wherein said —($C_1$-$C_6$)alkyl, —O($C_1$-$C_6$)alkyl, —($C_1$-$C_6$)alkyl-O—$R^6$, or —($C_1$-$C_6$)alkyl-N($R^6$)$_2$ is optionally substituted with one or more substituents selected from the group consisting of —OH and fluoro. In some embodiments, $R^{11}$ and $R^{12}$ are independently —$(C_1$-$C_6)$alkyl, —O$(C_1$-$C_6)$alkyl, —$(C_1$-$C_6)$alkyl-O—$R^6$, or —$(C_1$-$C_6)$alkyl-N$(R^6)_2$, wherein said —$(C_1$-$C_6)$alkyl, —O$(C_1$-$C_6)$alkyl, —$(C_1$-$C_6)$alkyl-O—$R^6$, or —$(C_1$-$C_6)$alkyl-N$(R^6)_2$ is optionally substituted with one or more substituents selected from the group consisting of —$NH_2$ and fluoro.

In some embodiments, each $R^6$ is independently H or —$(C_1$-$C_6)$alkyl. In some embodiments, each $R^6$ is independently H or —$(C_1$-$C_4)$alkyl. In some embodiments, each $R^6$ is independently H or —$(C_1$-$C_3)$alkyl. In some embodiments, each $R^6$ is independently H or —$(C_1$-$C_2)$alkyl. In some embodiments, each $R^6$ is independently H or —$CH_3$. In some embodiments, each $R^6$ is independently —$(C_1$-$C_6)$alkyl. In some embodiments, each $R^6$ is independently —$(C_1$-$C_4)$alkyl. In some embodiments, each $R^6$ is independently —$(C_1$-$C_2)$alkyl. In some embodiments, each $R^6$ is independently —$CH_3$. In some embodiments, each $R^6$ is independently H, —$CH_3$, or —$CH_2CH_3$. In some embodiments, each $R^6$ is independently —$CH_3$ or —$CH_2CH_3$.

In some embodiments, $R^8$ and $R^9$ are independently H, —$(C_1$-$C_6)$alkyl, —$(C_1$-$C_6)$alkyl-N$(R^6)_2$, —$OR^6$, —$(C_1$-$C_6)$alkyl-O—$R^6$, —$C(O)NH_2$, —$N(R^6)_2$, halogen, or nitrile. In some embodiments, $R^8$ and $R^9$ are independently H, —$(C_1$-$C_6)$alkyl, or —$(C_1$-$C_6)$alkyl-N$(R^6)_2$. In some embodiments, $R^8$ and $R^9$ are independently H, —$(C_1$-$C_6)$alkyl, or —$(C_1$-$C_4)$alkyl-N$(R^6)_2$. In some embodiments, $R^8$ and $R^9$ are independently H, —$(C_1$-$C_2)$alkyl, or —$(C_1$-$C_4)$alkyl-N$(R^6)_2$. In some embodiments, $R^8$ and $R^9$ are independently H, —$CH_3$, or —$(C_1$-$C_4)$alkyl-$NH_2$. In some embodiments, $R^8$ and $R^9$ are independently H, —$CH_3$, or —$(C_1$-$C_2)$alkyl-$NH_2$. In some embodiments, $R^8$ and $R^9$ are independently H, —$CH_3$, or —$CH_2$—$NH_2$. In some embodiments, $R^8$ and $R^9$ are independently —$CH_3$ or —$(C_1$-$C_4)$alkyl-$NH_2$. In some embodiments, $R^8$ and $R^9$ are independently —$CH_3$ or —$(C_1$-$C_2)$alkyl-$NH_2$. In some embodiments, $R^8$ and $R^9$ are independently —$CH_3$ or —$CH_2$—$NH_2$. In some embodiments, $R^8$ and $R^9$ are independently —$CH_3$ or —$CH_2$—$CH_2$—$NH_2$. In some embodiments, $R^8$ and $R^9$ are independently H or —$CH_2$—$NH_2$.

In some embodiments, each $R^{10}$ is independently H, —$(C_1$-$C_{10})$alkyl, —$(C_1$-$C_{10})$heteroalkyl, or —$(C_1$-$C_6)$heterocycloalkyl. In some embodiments, each $R^{10}$ is independently H, —$(C_1$-$C_{10})$alkyl, or —$(C_1$-$C_{10})$heteroalkyl. In some embodiments, each $R^{10}$ is independently H or —$(C_1$-$C_4)$alkyl. In some embodiments, each $R^{10}$ is independently H or —$(C_1$-$C_2)$alkyl. In some embodiments, each $R^{10}$ is independently H or —$CH_3$. In some embodiments, each $R^{10}$ is independently —$(C_1$-$C_{10})$alkyl. In some embodiments, each $R^{10}$ is independently —$(C_1$-$C_8)$alkyl. In some embodiments, each $R^{10}$ is independently —$(C_1$-$C_6)$alkyl. In some embodiments, each $R^{10}$ is independently —$(C_1$-$C_4)$alkyl. In some embodiments, each $R^{10}$ is independently —$(C_1$-$C_2)$alkyl. In some embodiments, each $R^{10}$ is independently —$CH_3$. In some embodiments, each $R^{10}$ is independently H, —$CH_3$, or —$CH_2CH_3$. In some embodiments, each $R^{10}$ is independently —$CH_3$ or —$CH_2CH_3$.

In some embodiments, each $R^{10}$ is —$(C_1$-$C_{10})$alkyl or —$(C_1$-$C_{10})$heteroalkyl independently substituted with one or more substituents selected from the group consisting of —$OR^6$, —$N(R^6)_2$, —$C(O)$, and halogen. In some embodiments, each $R^{10}$ is —$(C_1$-$C_{10})$alkyl or —$(C_1$-$C_{10})$heteroalkyl independently substituted with one or more substituents selected from the group consisting of —$OR^6$, —$N(R^6)_2$, halogen. In some embodiments, each $R^{10}$ is —$(C_1$-$C_{10})$alkyl or —$(C_1$-$C_{10})$heteroalkyl independently substituted with one or more substituents selected from the group consisting of —$C(O)$, and halogen. In some embodiments, each $R^{10}$ is —$(C_1$-$C_{10})$alkyl or —$(C_1$-$C_{10})$heteroalkyl independently substituted with one or more substituents selected from the group consisting of —$N(R^6)_2$ and —$C(O)$. In some embodiments, each $R^{10}$ is —$(C_1$-$C_{10})$alkyl or —$(C_1$-$C_{10})$heteroalkyl independently substituted with one or more substituents selected from the group consisting of —$OH$, —$NH_2$, —$C(O)$, and halogen. In some embodiments, each $R^{10}$ is —$(C_1$-$C_{10})$alkyl or —$(C_1$-$C_{10})$heteroalkyl independently substituted with one or more substituents selected from the group consisting of —$OH$, —$NH_2$, and halogen. In some embodiments, each $R^{10}$ is —$(C_1$-$C_{10})$alkyl or —$(C_1$-$C_{10})$heteroalkyl independently substituted with one or more substituents selected from the group consisting of —$OH$ and —$NH_2$.

In some embodiments, each $R^{10}$ is independently substituted with one or more substituents selected from the group consisting of —$OR^6$, —$N(R^6)_2$, —$C(O)$, and halogen. In some embodiments, each $R^{10}$ is independently substituted with one or more substituents selected from the group consisting of —$OR^6$, —$N(R^6)_2$, halogen. In some embodiments, each $R^{10}$ is independently substituted with one or more substituents selected from the group consisting of —$OR^6$ and —$N(R^6)_2$. In some embodiments, each $R^{10}$ is independently substituted with one or more substituents selected from the group consisting of —$C(O)$, and halogen. In some embodiments, each $R^{10}$ is independently substituted with one or more substituents selected from the group consisting of —$N(R^6)_2$ and —$C(O)$. In some embodiments, each $R^{10}$ is independently substituted with one or more substituents selected from the group consisting of —$OH$, —$NH_2$, —$C(O)$, and halogen. In some embodiments, each $R^{10}$ is independently substituted with one or more substituents selected from the group consisting of —$OH$, —$NH_2$, and halogen. In some embodiments, each $R^{10}$ is independently substituted with one or more substituents selected from the group consisting of —$OH$ and —$NH_2$.

In some embodiments, each $R^{10}$, taken together with the atoms to which they are attached, form a 3-7 membered carbocyclic or heterocyclic ring.

In some embodiments, each $R^{13}$ and $R^{14}$ is, independently, H, —$OH$, —$(C_1$-$C_6)$alkyl, —$O(C_1$-$C_6)$alkyl, —$(C_1$-$C_6)$alkyl-O—$R^6$, —$C(O)NH_2$, —$N(R^6)_2$, halogen, —$(C_1$-$C_6)$alkyl-N$(R^6)_2$, —$CO_2H$, or nitrile. In some embodiments, each $R^{13}$ and $R^{14}$ is, independently, H, —$OH$, or —$(C_1$-$C_6)$alkyl. In some embodiments, each $R^{13}$ and $R^{14}$ is, independently, H or —$OH$. In some embodiments, each $R^{13}$ and $R^{14}$ is, independently, H or —$(C_1$-$C_6)$alkyl. In some embodiments, each $R^{13}$ and $R^{14}$ is, independently, —$OH$ or —$(C_1$-$C_6)$alkyl. In some embodiments, each $R^{13}$ and $R^{14}$ is H. In some embodiments, each $R^{13}$ and $R^{14}$ is —$OH$. In some embodiments, each $R^{13}$ and $R^{14}$ is —$(C_1$-$C_6)$alkyl.

In some embodiments, $R^1$ is selected from the group consisting of

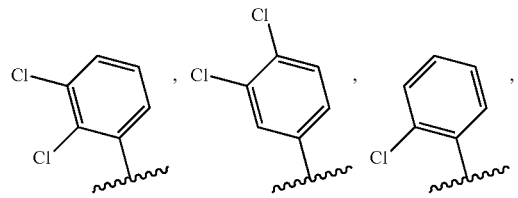

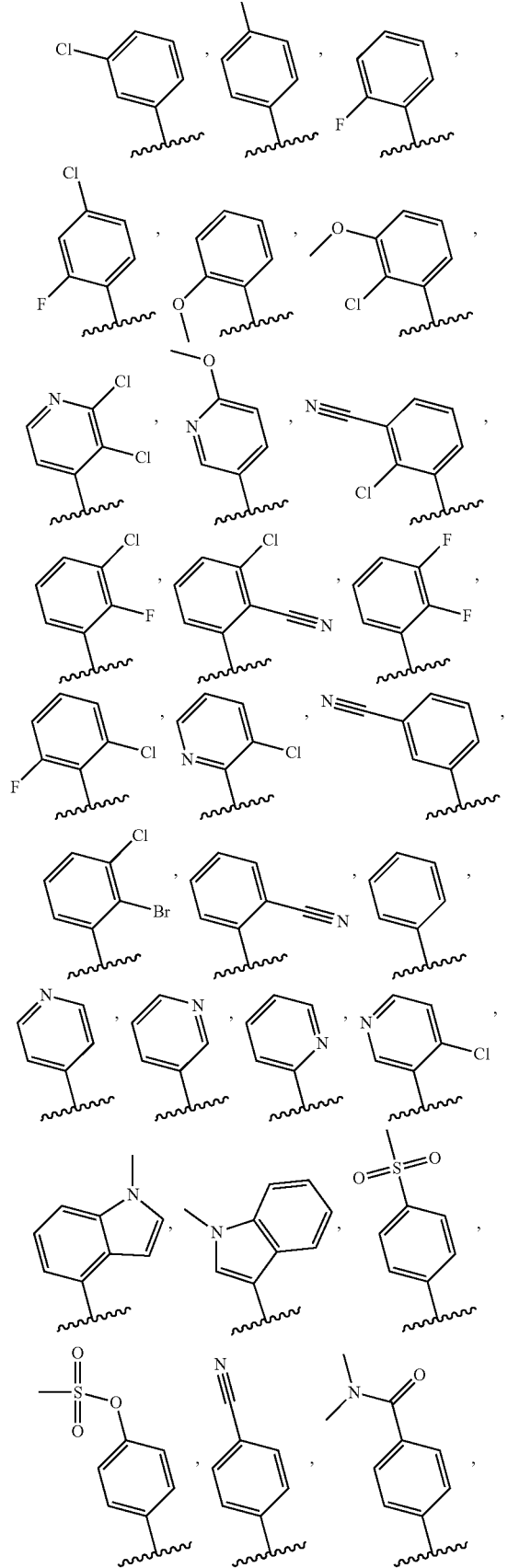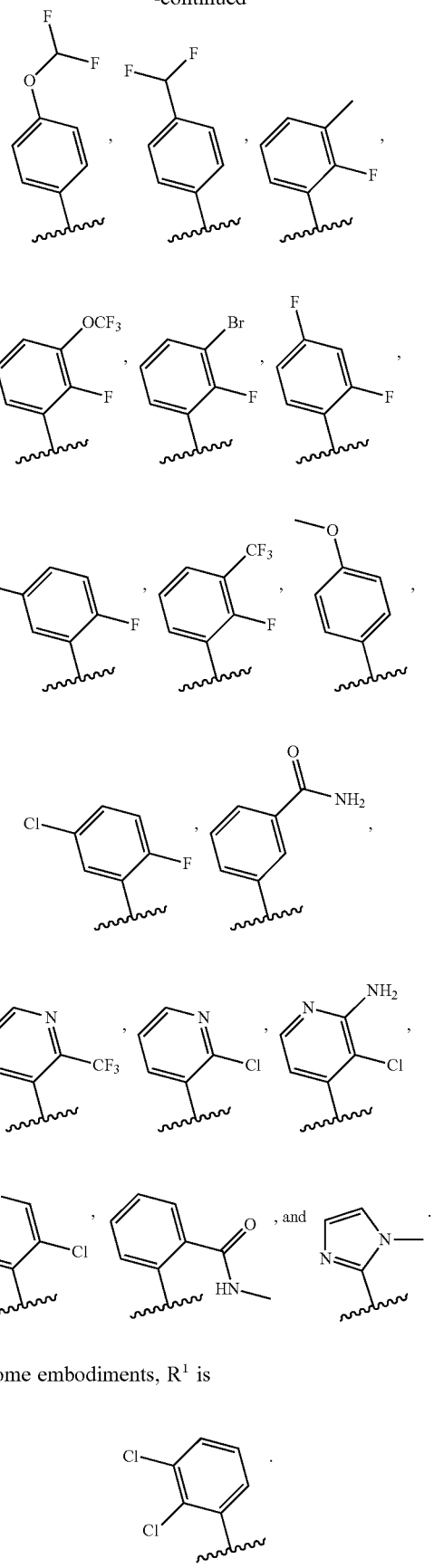
In some embodiments, $R^1$ is
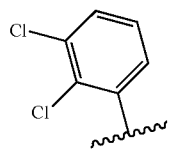

In some embodiments, R¹ is
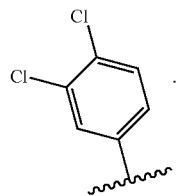
In some embodiments, R¹ is
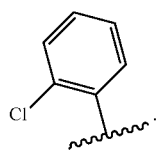 [SMILES: *c1ccccc1Cl]
In some embodiments, R¹ is
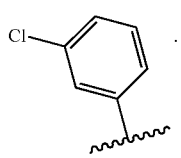
In some embodiments, R¹ is
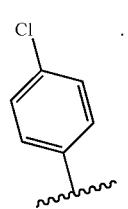 [SMILES: *c1ccc(Cl)cc1]
In some embodiments, R¹ is
In some embodiments, R¹ is
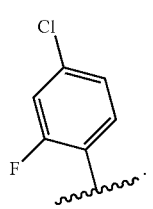
In some embodiments, R¹ is
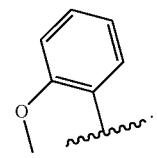
In some embodiments, R¹ is
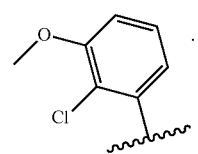 [SMILES: *c1cccc(OC)c1Cl]
In some embodiments, R¹ is
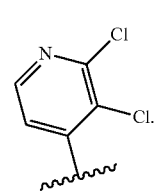 [SMILES: *c1ccnc(Cl)c1Cl]
In some embodiments, R¹ is
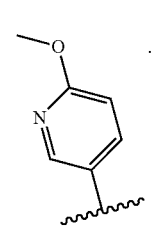 [SMILES: *c1ccc(OC)nc1]
In some embodiments, R¹ is
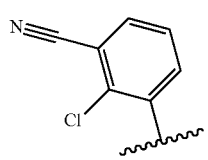
In some embodiments, R¹ is
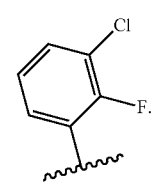

In some embodiments, R¹ is
In some embodiments, R¹ is
In some embodiments, R¹ is
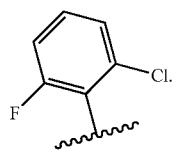
In some embodiments, R¹ is
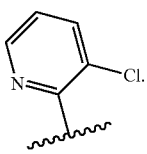 [SMILES: *c1ncccc1Cl]
In some embodiments, R¹ is
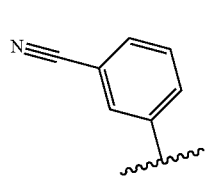
In some embodiments, R¹ is
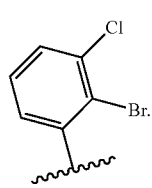 [SMILES: *c1cccc(Cl)c1Br]
In some embodiments, R¹ is
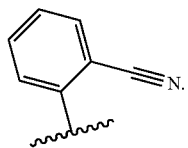 [SMILES: *c1ccccc1C#N]
In some embodiments, R¹ is
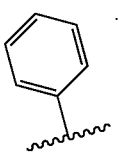 [SMILES: *c1ccccc1]
In some embodiments, R¹ is
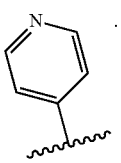 [SMILES: *c1ccncc1]
In some embodiments, R¹ is
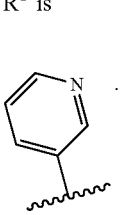
In some embodiments, R¹ is
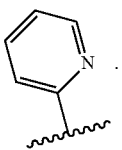
In some embodiments, R¹ is
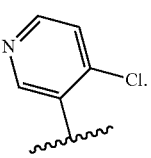

In some embodiments, R¹ is
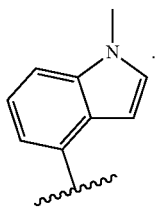 [SMILES: *c1cccc2c1ccn2C]
In some embodiments, R¹ is
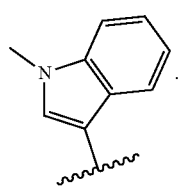 [SMILES: *c1cn(C)c2ccccc12]
In some embodiments, R¹ is
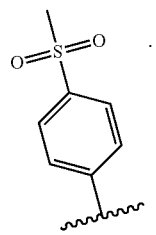
In some embodiments, R¹ is
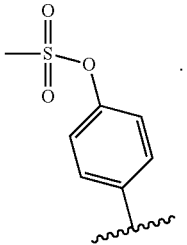 [SMILES: *c1ccc(OS(C)(=O)=O)cc1]
In some embodiments, R¹ is
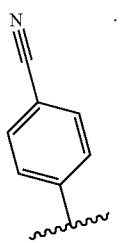 [SMILES: *c1ccc(C#N)cc1 ; "."]
In some embodiments, R¹ is
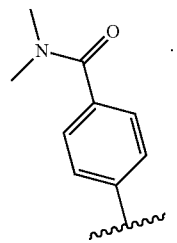 [SMILES: *c1ccc(C(=O)N(C)C)cc1 ; "."]
In some embodiments, R¹ is
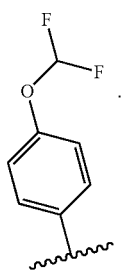 [SMILES: *c1ccc(OC(F)F)cc1 ; "."]
In some embodiments, R¹ is
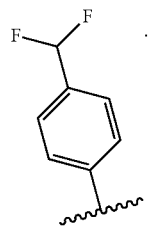 [SMILES: *c1ccc(C(F)F)cc1 ; "."]
In some embodiments, R¹ is
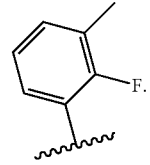
In some embodiments, R¹ is
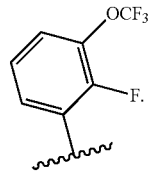 [SMILES: *c1cccc(OC(F)(F)F)c1F]

In some embodiments, R¹ is
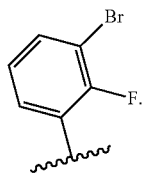
In some embodiments, R¹ is
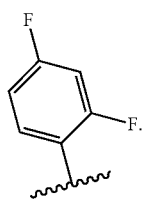
In some embodiments, R¹ is
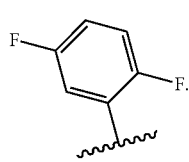
In some embodiments, R¹ is
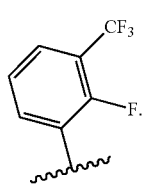
In some embodiments, R¹ is
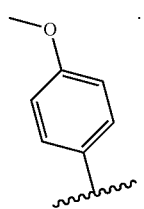 [SMILES: *c1ccc(OC)cc1 ; "."]
In some embodiments, R¹ is. In some embodiments, R¹ is
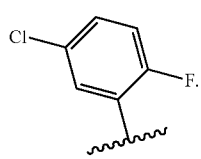 [SMILES: *c1cc(Cl)ccc1F]
In some embodiments, R¹ is
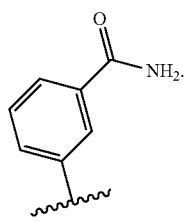 [SMILES: *c1cccc(C(N)=O)c1]
In some embodiments, R¹ is
In some embodiments, R¹ is
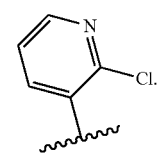 [SMILES: *c1cccnc1Cl]
In some embodiments, R¹ is
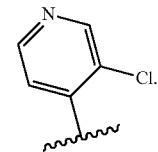 [SMILES: *c1ccncc1Cl]
In some embodiments, R¹ is
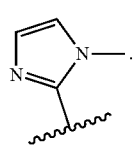
In some embodiments, R¹ is
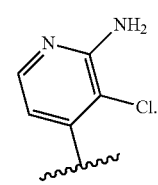 [SMILES: *c1ccnc(N)c1Cl]

In some embodiments, R[1] is
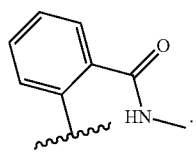
In some embodiments, the moiety
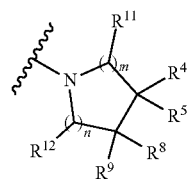
is selected from the group consisting of
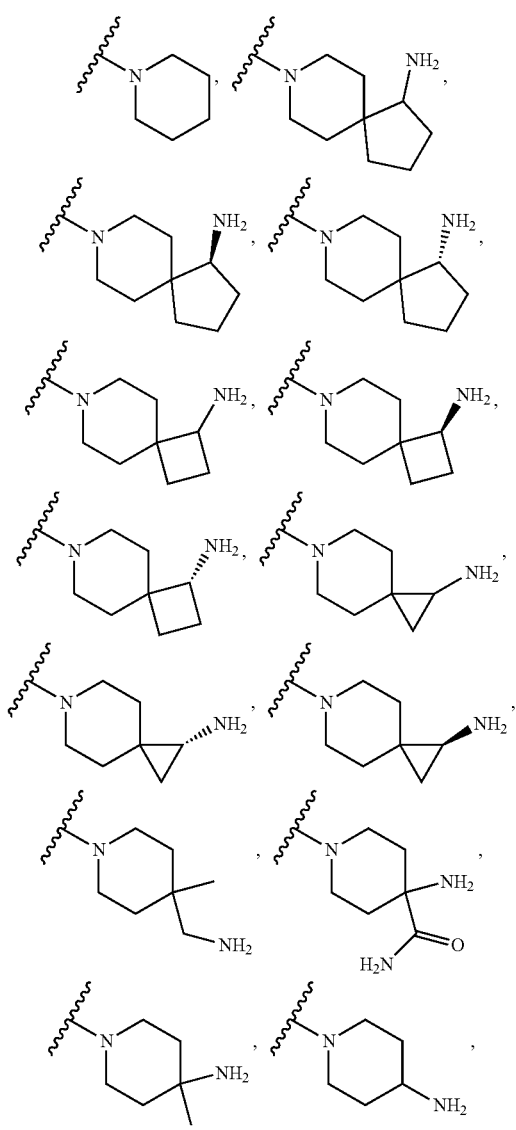
-continued
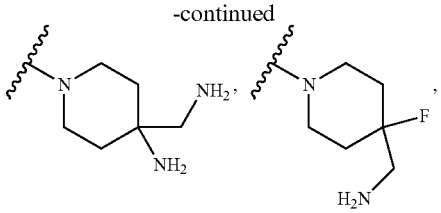
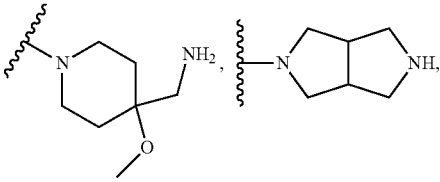
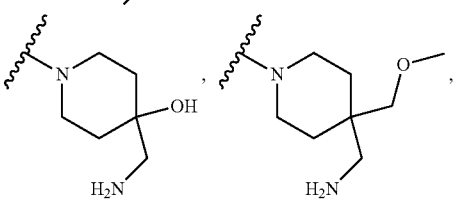
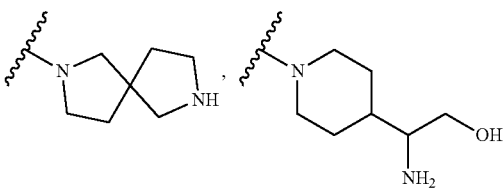
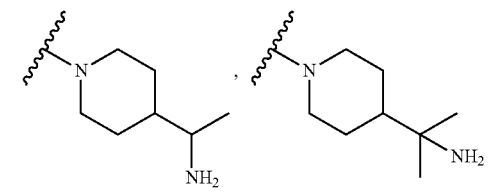
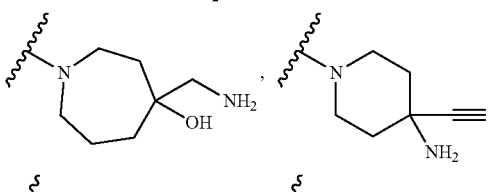
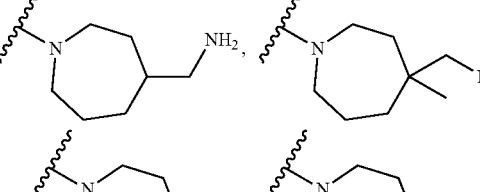
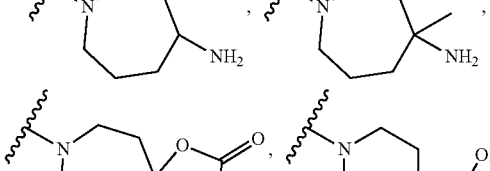
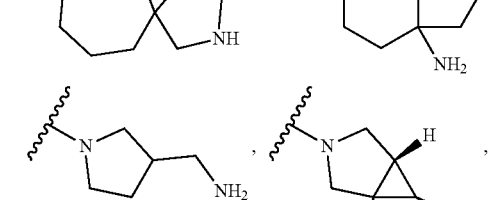

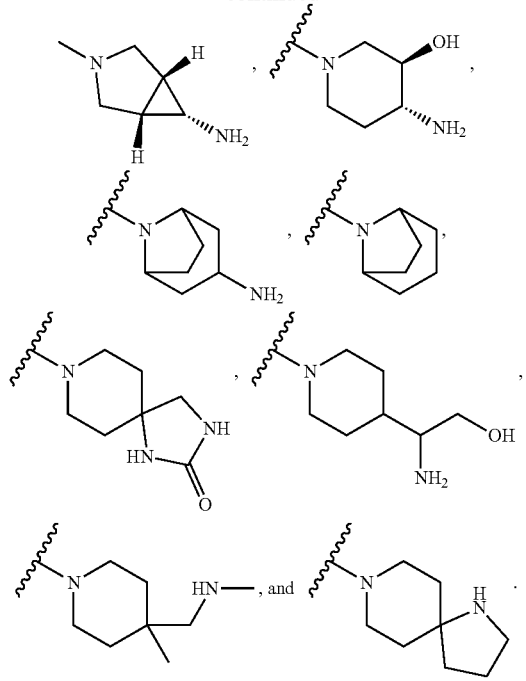
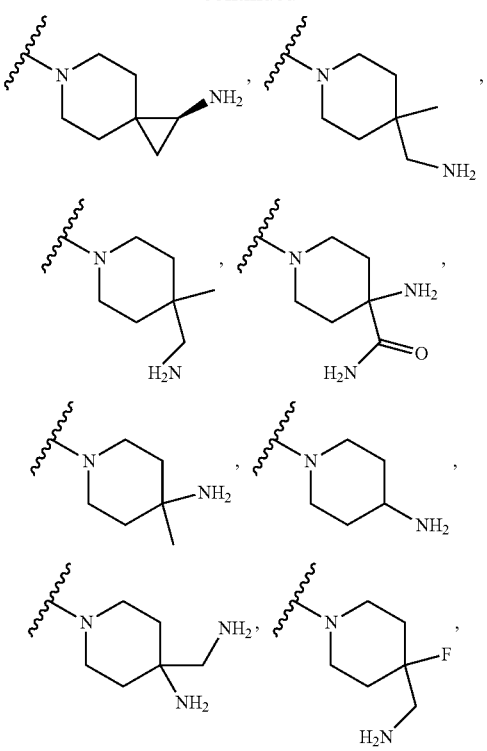
In some embodiments, the moiety
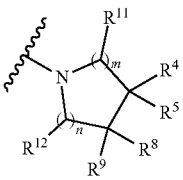
is selected from the group consisting of
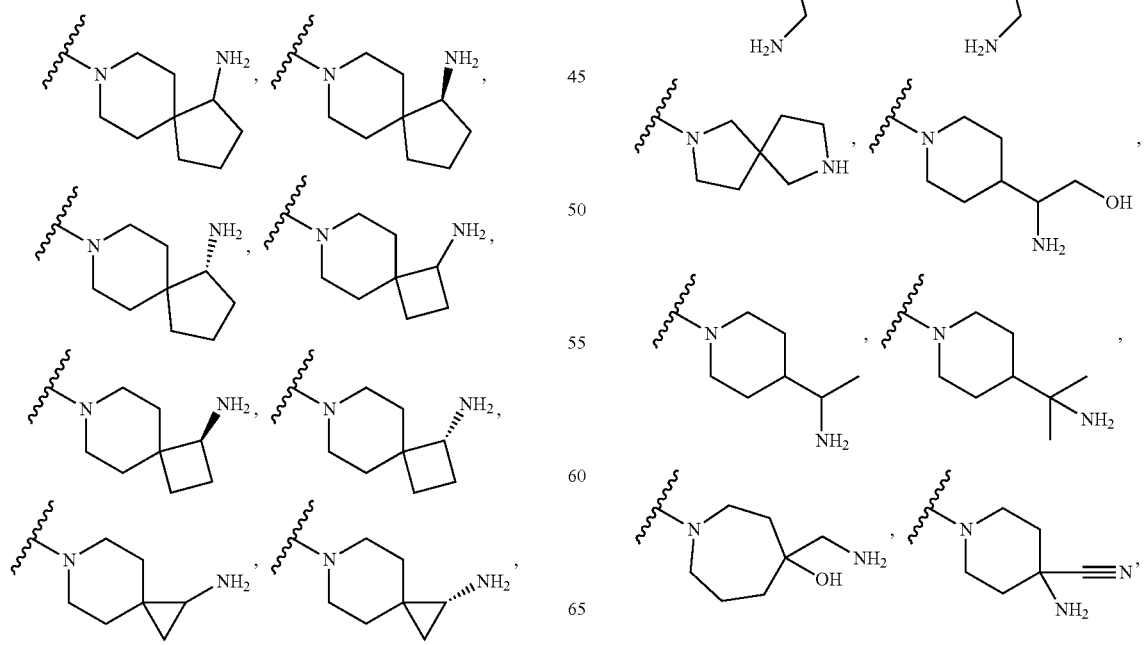

-continued
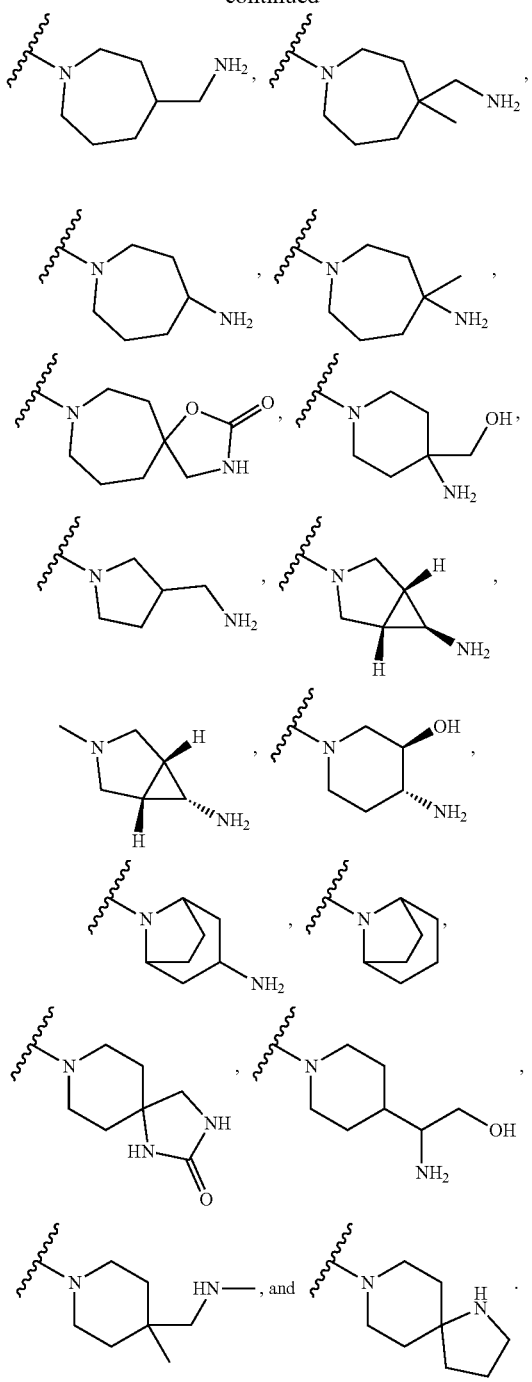
In some embodiments, the moiety shown below is referred to as R².
In some embodiments, R² is
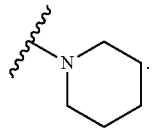 [SMILES: *N1CCCCC1 ; "."]
In some embodiments, R² is
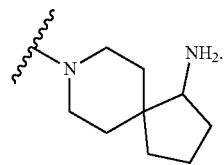 [SMILES: *N1CCC2(CCCC2N)CC1]
In some embodiments, R² is
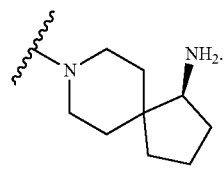 [SMILES: *N1CCC2(CCC[C@@H]2N)CC1]
In some embodiments, R² is
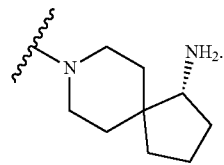 [SMILES: *N1CCC2(CCC[C@H]2N)CC1]
In some embodiments, R² is
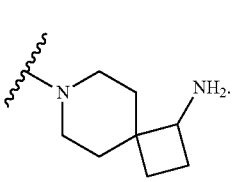 [SMILES: *N1CCC2(CCC2N)CC1]
In some embodiments, R² is
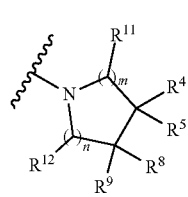
In some embodiments, R² is
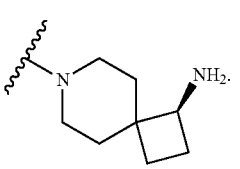 [SMILES: *N1CCC2(CC[C@@H]2N)CC1]

In some embodiments, R² is
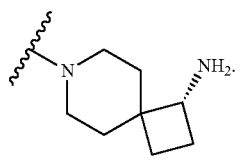 [SMILES: *N1CCC2(CC[C@H]2N)CC1]
In some embodiments, R² is
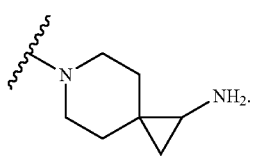 [SMILES: *N1CCC2(CC1)CC2N]
In some embodiments, R² is
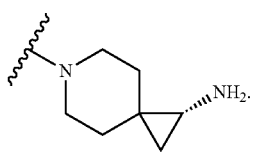 [SMILES: *N1CCC2(CC1)C[C@H]2N]
In some embodiments, R² is
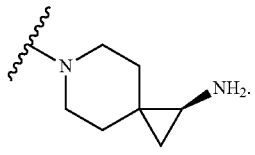 [SMILES: *N1CCC2(CC1)C[C@@H]2N]
In some embodiments, R² is
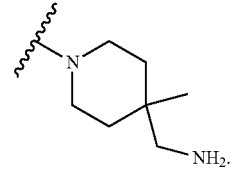
In some embodiments, R² is
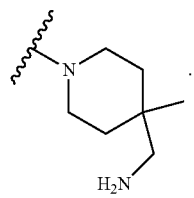 [SMILES: *N1CCC(C)(CN)CC1 ; "."]
In some embodiments, R² is
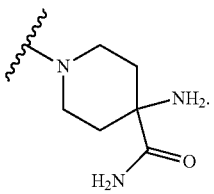
In some embodiments, R² is
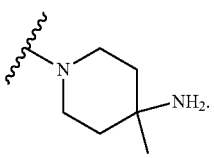 [SMILES: *N1CCC(C)(N)CC1]
In some embodiments, R² is
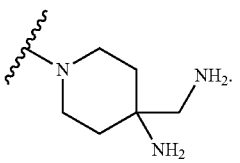
In some embodiments, R² is
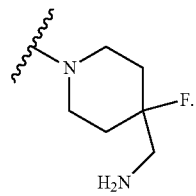 [SMILES: *N1CCC(F)(CN)CC1]
In some embodiments, R² is
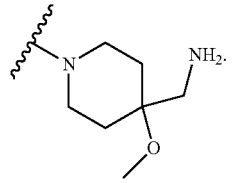 [SMILES: *N1CCC(CN)(OC)CC1]
In some embodiments, R² is
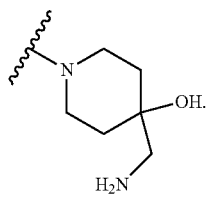 [SMILES: *N1CCC(O)(CN)CC1]

In some embodiments, R² is
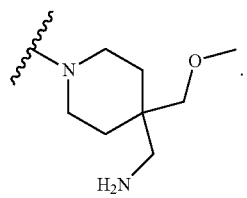 [SMILES: *N1CCC(CN)(COC)CC1 ; "."]
In some embodiments, R² is
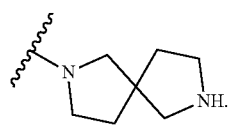 [SMILES: *N1CCC2(CCNC2)C1]
In some embodiments, R² is
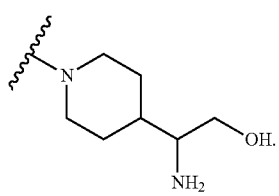 [SMILES: *N1CCC(C(N)CO)CC1]
In some embodiments, R² is
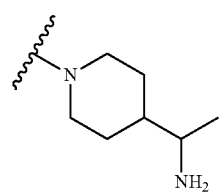
In some embodiments, R² is
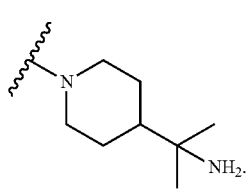 [SMILES: *N1CCC(C(C)(C)N)CC1]
In some embodiments, R² is
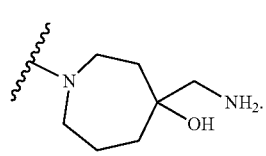 [SMILES: *N1CCCC(O)(CN)CC1]
In some embodiments, R² is
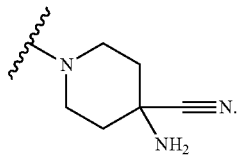 [SMILES: *N1CCC(N)(C#N)CC1]
In some embodiments, R² is
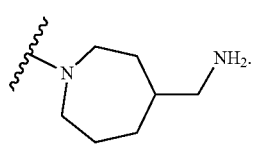 [SMILES: *N1CCCC(CN)CC1]
In some embodiments, R² is
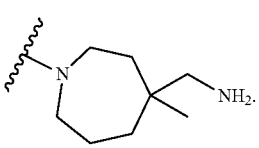 [SMILES: *N1CCCC(C)(CN)CC1]
In some embodiments, R² is
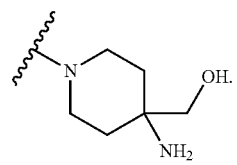
In some embodiments, R² is
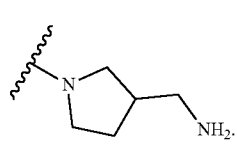
In some embodiments, R² is
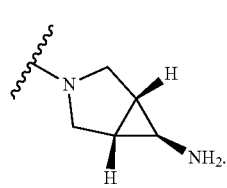 [SMILES: *N1C[C@@H]2[C@@H](N)[C@@H]2C1]

In some embodiments, R² is

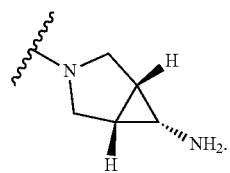 [SMILES: *N1C[C@@H]2[C@H](N)[C@@H]2C1]

In some embodiments, R² is

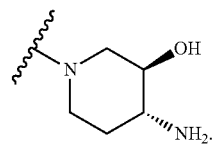 [SMILES: *N1CC[C@@H](N)[C@H](O)C1]

In some embodiments, R² is

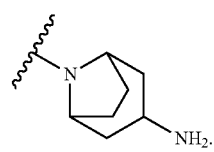

In some embodiments, R² is

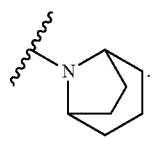 [SMILES: *N1C2CCCC1CC2 ; "."]

In some embodiments, R² is

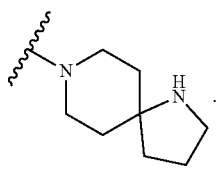 [SMILES: *N1CCC2(CCCN2)CC1 ; "."]

In some embodiments, R² is

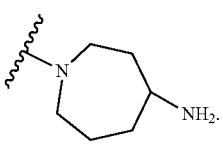 [SMILES: *N1CCCC(N)CC1]

In some embodiments, R² is

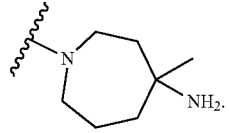 [SMILES: *N1CCCC(C)(N)CC1]

In some embodiments, R² is

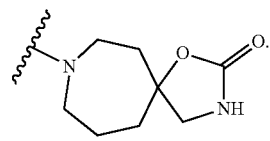 [SMILES: *N1CCCC2(CC1)CNC(=O)O2]

In some embodiments, R² is

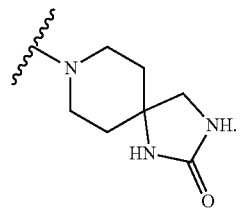 [SMILES: *N1CCC2(CC1)CNC(=O)N2]

In some embodiments, R² is

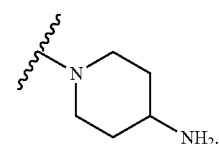

In some embodiments, R² is

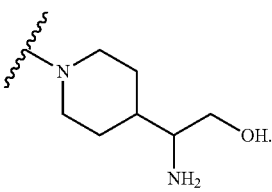 [SMILES: *N1CCC(C(N)CO)CC1]

In some embodiments, R² is

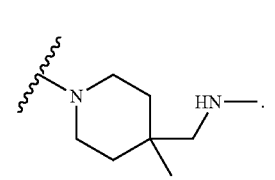 [SMILES: *N1CCC(C)(CNC)CC1 ; "."]

In some embodiments, m is an integer selected from 0, 1, 2, or 3 and n is an integer selected from 0, 1, 2, or 3. In some embodiments, m is an integer selected from 0, 1, or 2 and n is an integer selected from 0, 1, or 2. In some embodiments, m is an integer selected from 0 or 1 and n is an integer selected from 0 or 1. In some embodiments, m is 0 and n is 0. In some embodiments, m is 0 and n is 1. In some embodiments, m is 0 and n is 2. In some embodiments, m is 0 and n is 3. In some embodiments, m is 1 and n is 0. In some embodiments, m is 1 and n is 1. In some embodiments, m is 1 and n is 2. In some embodiments, m is 1 and n is 3. In some embodiments, m is 2 and n is 0. In some embodiments, m is 2 and n is 1. In some embodiments, m is 2 and n is 2. In some embodiments, m is 3 and n is 0. In some embodiments, m is 3 and n is 1.

In some embodiments, SHP2 phosphatase inhibitors described herein encompass compounds of Formula (II) or pharmaceutically acceptable salts thereof, wherein Formula (II) is represented by:

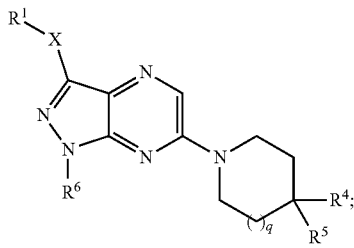

wherein

X is selected from the group consisting of: —N—$R^{66}$—, —O—, —$CR^{13}R^{14}$—, —C(O)—, —S(O)$_w$— (where w is 0, 1 or 2), and —C(=C($R^{15}R^{16}$))—;

q is 0 or 1;

$R^1$ is selected from the group consisting of phenyl, a 5-10 membered monocyclic or bicyclic heteroaryl, and a 4-7 membered heterocycle, wherein $R^1$ is optionally substituted with one, two or more substituents each independently selected from the group consisting of —$R^{10}$, —N($R^6$)$_2$, —C(O)N($R^6$)$_2$, oxo, halogen, and nitrile;

$R^{10}$ is independently selected for each occurrence from the group consisting of —(C$_1$-C$_6$)alkyl, —(C$_1$-C$_6$)haloalkyl, —(C$_3$-C$_6$)cycloalkyl, heterocycloalkyl, phenyl, and heteroaryl, wherein $R^{10}$ may be substituted one, two or three or more substituents each selected from the group consisting of halo, C(O)$R^{20}$, C$_{1-6}$alkyl and C$_{1-6}$haloalkyl;

$R^{20}$ is selected from the group consisting of —OH, halo, or —(C$_1$-C$_6$)alkyl;

$R^4$ and $R^5$ are each independently, selected from the group consisting of H, C$_1$-C$_6$)alkyl, —C(O)N($R^6$)$_2$, —N($R^6$)$_2$, halogen, and nitrile, wherein said —(C$_1$-C$_6$)alkyl is optionally substituted with one or more substituents selected from the group consisting of —OH, —N($R^6$)$_2$, oxo, and halogen, or $R^4$ and $R^5$, taken together with the carbon to which they are attached, form a 3-7 membered carbocyclic or heterocyclic ring, which ring is optionally substituted with one or two substituents each independently selected from the group consisting of (C$_1$-C$_6$)alkyl, —O(C$_1$-C$_6$)alkyl, —N($R^6$)$_2$, —C(O)N($R^6$)$_2$, halogen, oxo, or nitrile;

$R^6$ is independently for each occurrence selected from the group consisting of H, —(C$_1$-C$_6$)alkyl and phenyl;

$R^{66}$ is selected from the group consisting of H, —(C$_1$-C$_6$)alkyl and phenyl, or together with $R^1$ and the nitrogen to which they are attached form a nitrogen ring moiety selected from the group consisting of 5-7 membered monocyclic heteroaryl, a 8-12 membered bicyclic moiety with one saturated ring and one aromatic or heteroaromatic ring, a 8-12 membered bicyclic heteroaryl, and a 4-7 membered heterocycle, wherein the nitrogen ring moiety is optionally substituted with one, two or more substituents each independently selected from the group consisting of —$R^{10}$, —O$R^{10}$, —S(O)$_w R^{10}$ (wherein w is 0, 1 or 2), —N($R^{10}$)$_2$, —OS(O)$_w$—$R^{10}$ (wherein w is 0, 1, or 2), —S(O)$_w$—N($R^{10}$)$_2$ (wherein w is 0, 1 or 2), —S(O)(NH)$R^{10}$, —P(O)($R^{10}$)$_2$, —C(O)$R^{10}$, —C(O)N($R^{10}$)$_2$, oxo, halogen, nitrile, phenyl (optionally substituted with one, two or three halo, C$_{1-3}$alkyl or C$_{1-3}$haloalkyl), C$_{1-3}$alkyl, C$_{1-3}$haloalkyl, and heteroaryl (optionally substituted with one, two or three halo, C$_{1-3}$alkyl or C$_{1-3}$haloalkyl);

$R^{13}$ and $R^{14}$ for each occurrence, are independently selected from the group consisting of H, —OH, —(C$_1$-C$_6$)alkyl, —O(C$_1$-C$_6$)alkyl, —C(O)N($R^6$)$_2$, —N($R^6$)$_2$, halogen, —(C$_1$-C$_6$)alkyl-N($R^6$)$_2$, or $R^{13}$ and $R^{14}$ taken together with the carbon to which they are attached form a C$_{3-4}$cycloalkyl, or $R^1$ and $R^{13}$, together with the carbon to which they are attached, form a carbon ring moiety selected from the group consisting of phenyl, a 5-7 membered monocyclic heteroaryl, a 8-10 membered bicyclic heteroaryl, and a 5-7 membered heterocycle, wherein the carbon ring moiety is optionally substituted with one, two or more substituents each independently selected from the group consisting of —$R^{10}$, —N($R^6$)$_2$, —C(O)N($R^6$)$_2$, oxo, halogen, and nitrile, where $R^{14}$ is H or is absent; and $R^{15}$ and $R^{16}$ for each occurrence, are independently selected from the group consisting of H, —OH, —(C$_1$-C$_6$)alkyl, —O(C$_1$-C$_6$)alkyl, —C(O)N($R^6$)$_2$, —N($R^6$)$_2$, halogen, —(C$_1$-C$_6$)alkyl-N($R^6$)$_2$, or $R^{15}$ and $R^{16}$ taken together with the carbon to which they are attached may form a C$_{3-4}$cycloalkyl.

In some embodiments, $R^6$ is hydrogen. In some embodiments, $R^4$ and $R^5$ are independently selected from the group consisting of —(C$_1$-C$_3$)alkyl and —N($R^6$)$_2$, wherein said —(C$_1$-C$_3$)alkyl is optionally substituted with one or more substituents selected from the group consisting of —OH, —N($R^6$)$_2$, and halogen. In some embodiments, $R^4$ and $R^5$ are independently selected from the group consisting of —NH$_2$, —CH$_3$, and —CH$_2$NH$_2$. In some embodiments, q is 1.

Examples of compounds of the invention include:

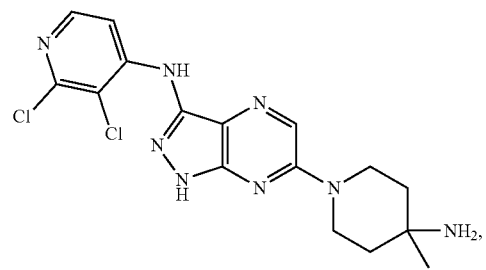

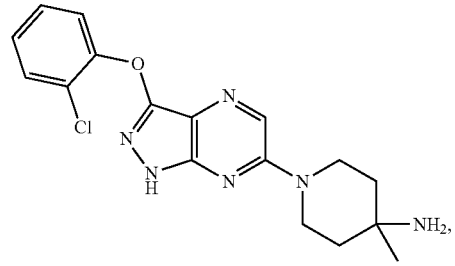

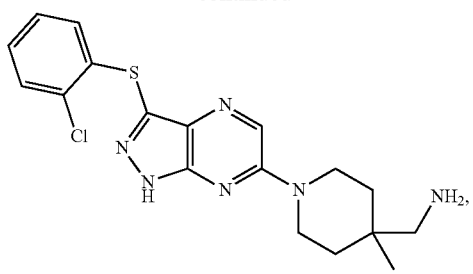
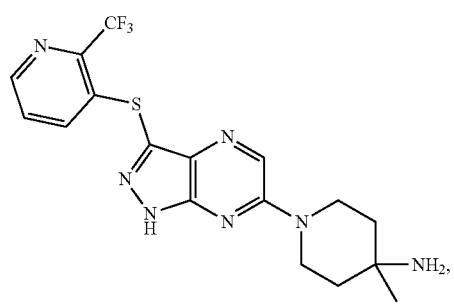
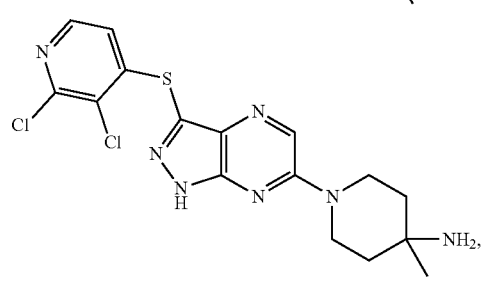
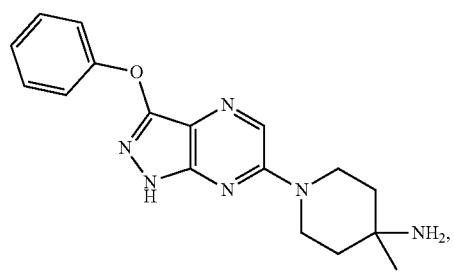
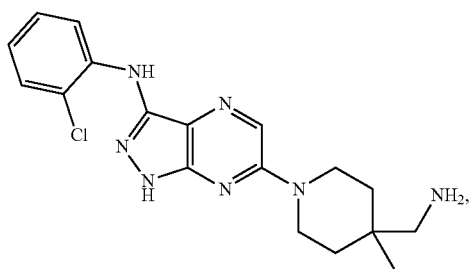
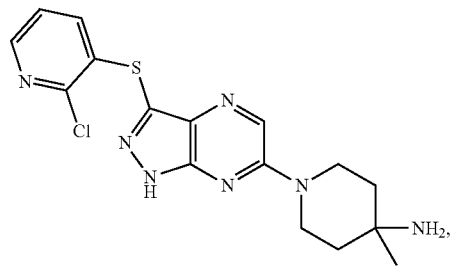
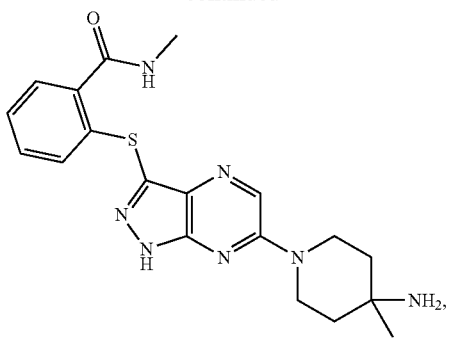
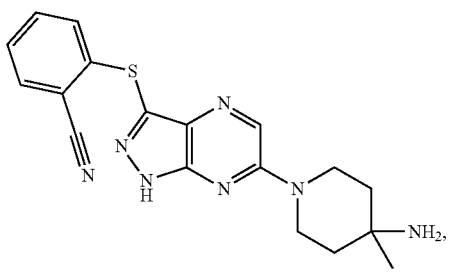
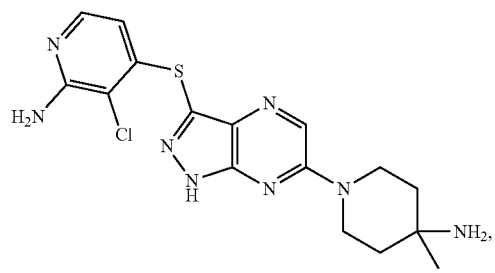
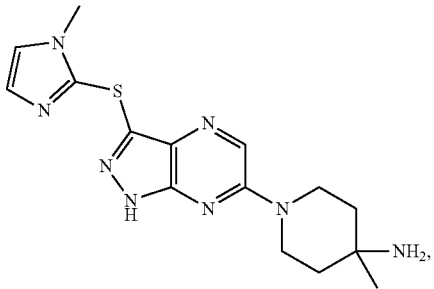
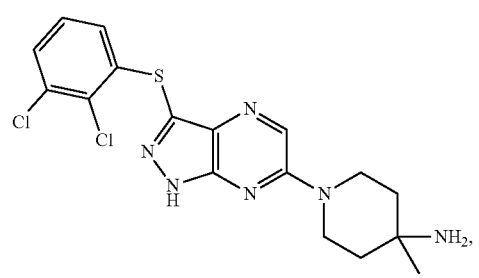
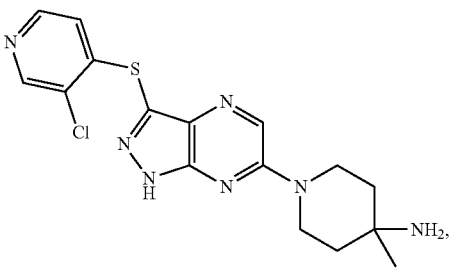

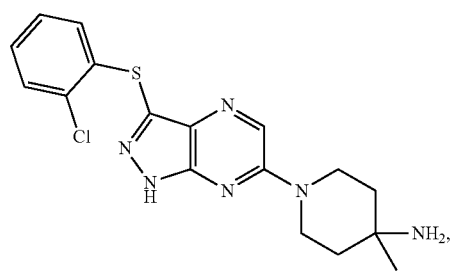
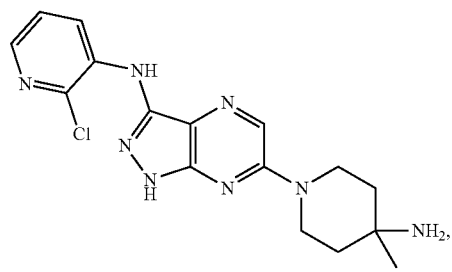
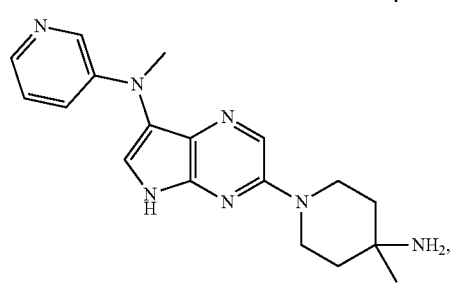
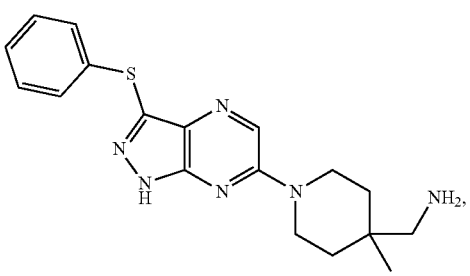
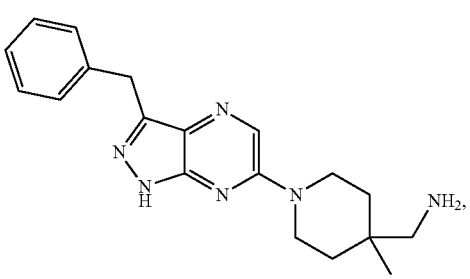
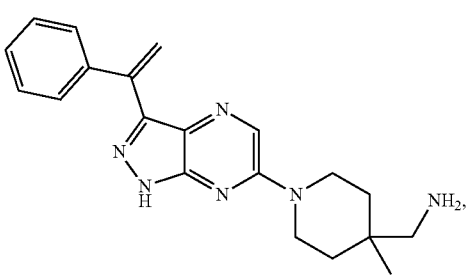
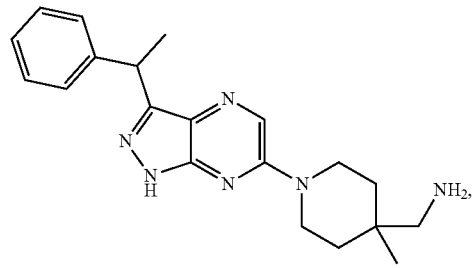
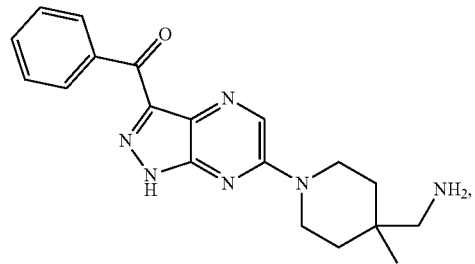
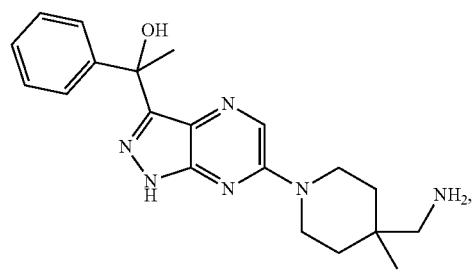
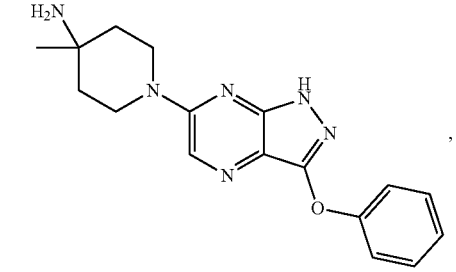
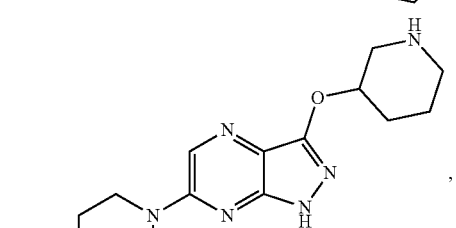
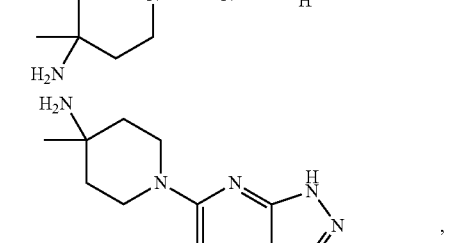
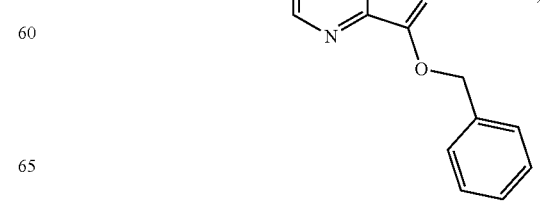

45
-continued
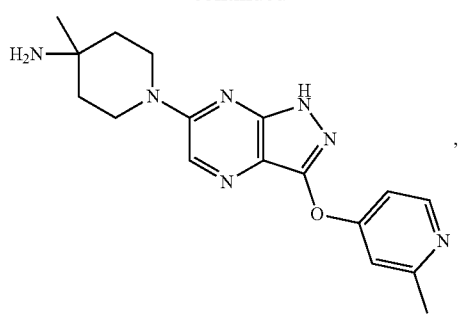
,
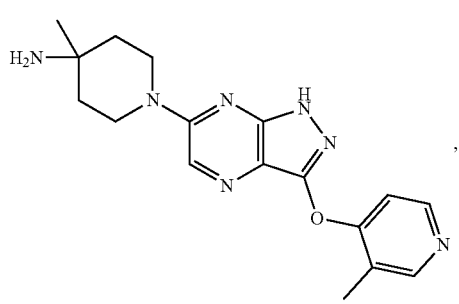
,
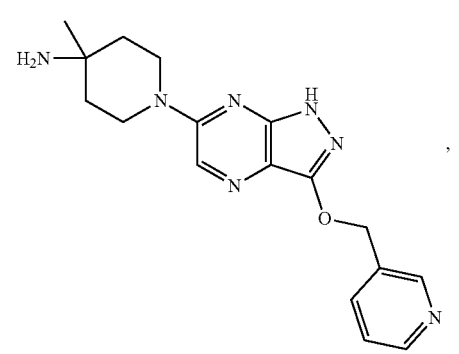
,
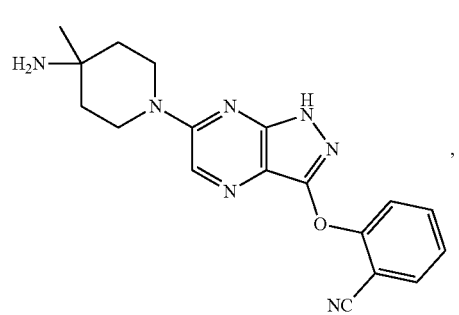
,
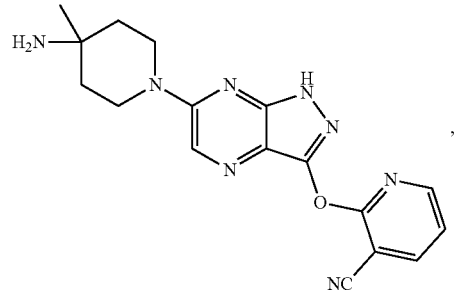
,
46
-continued
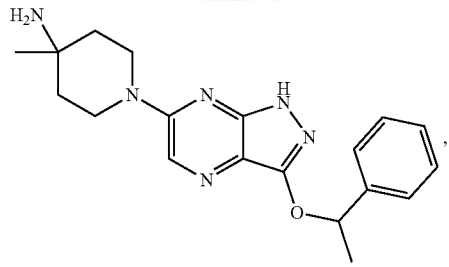
,
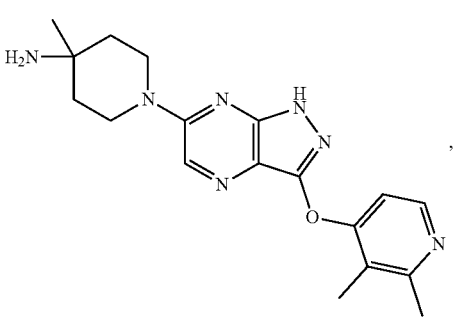
,
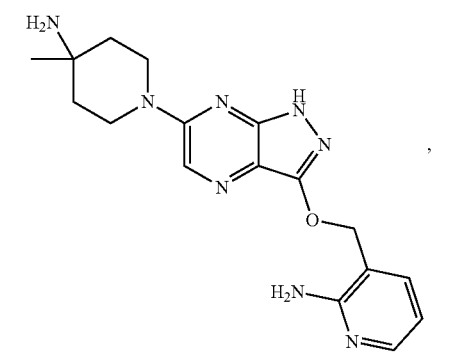
,
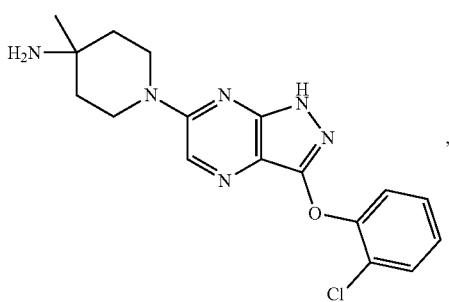
,
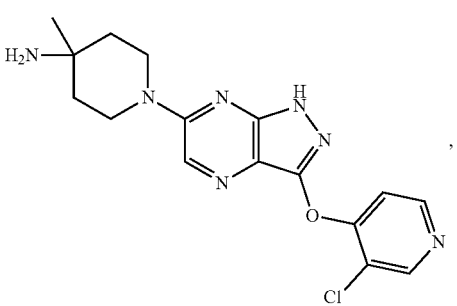
,

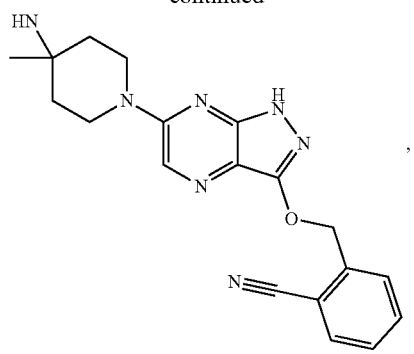
,
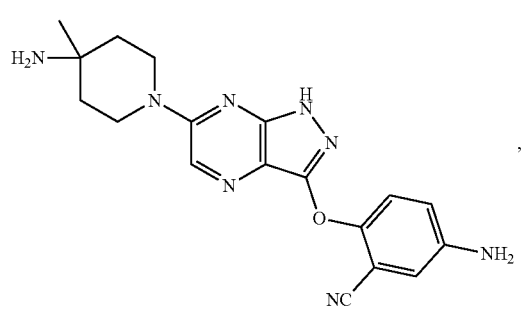
,
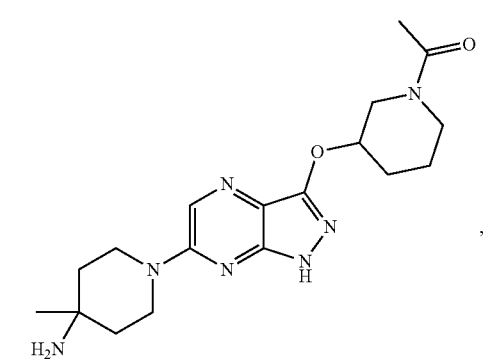
,
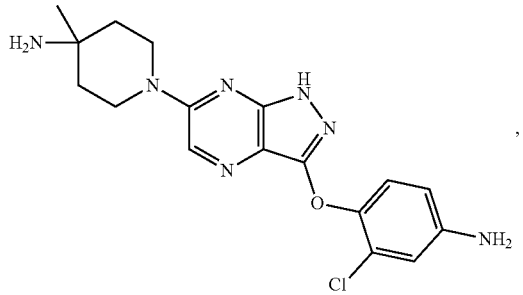
,
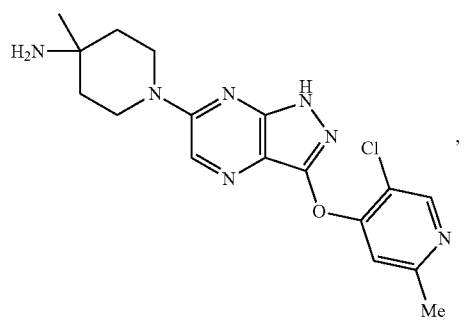
,
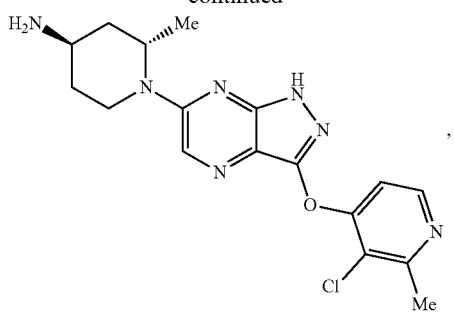
,
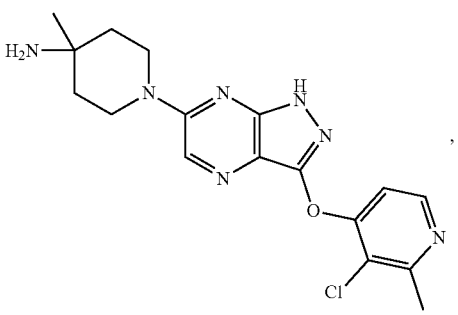
,
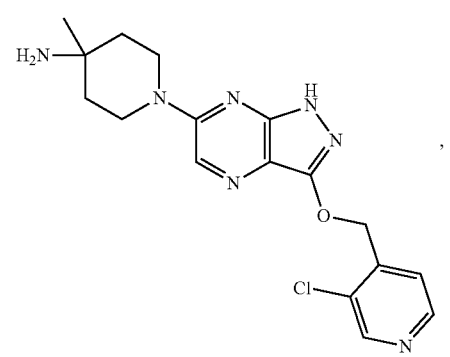
,
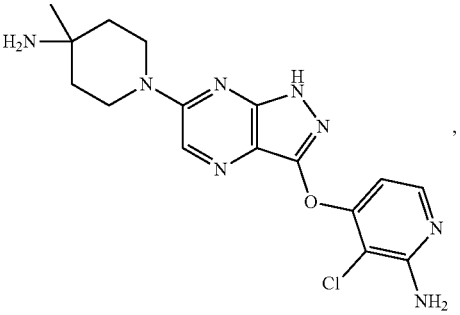
,
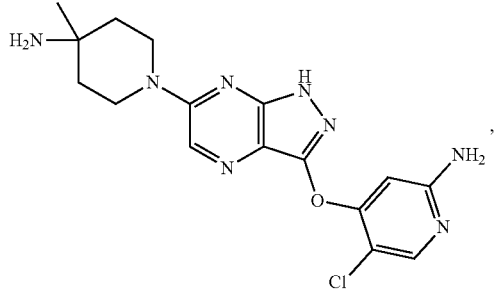
,

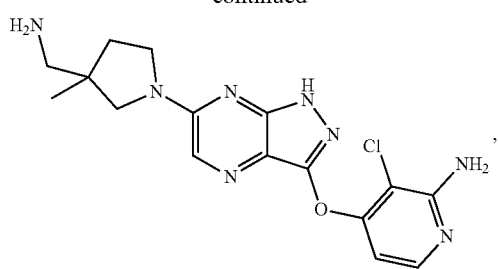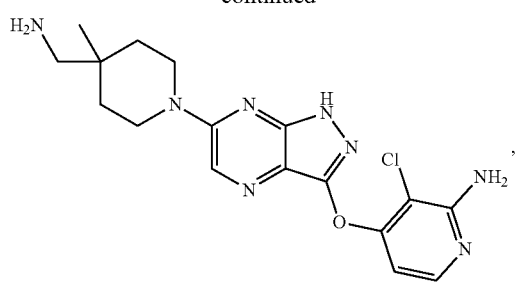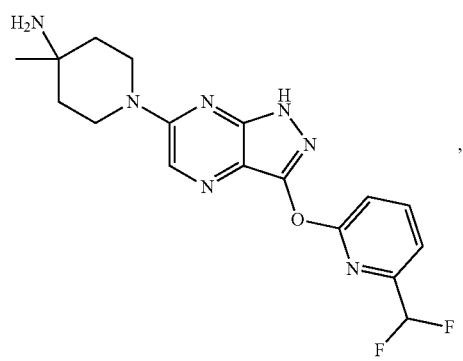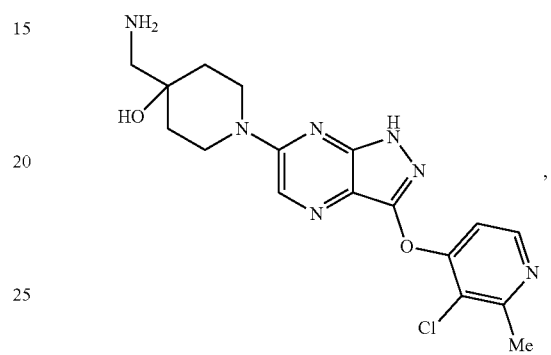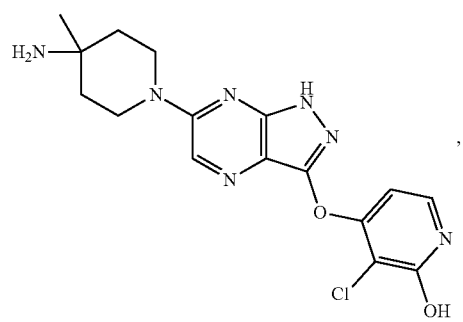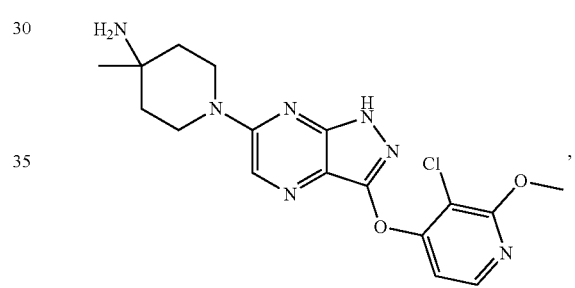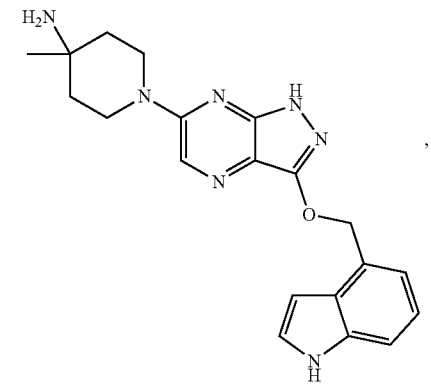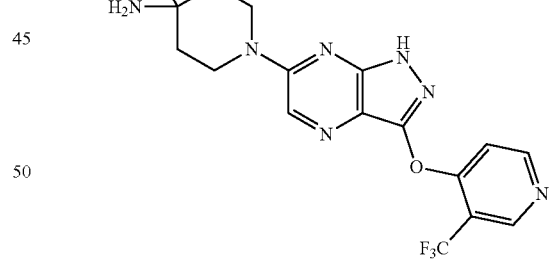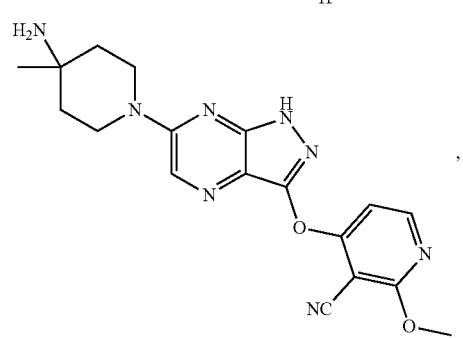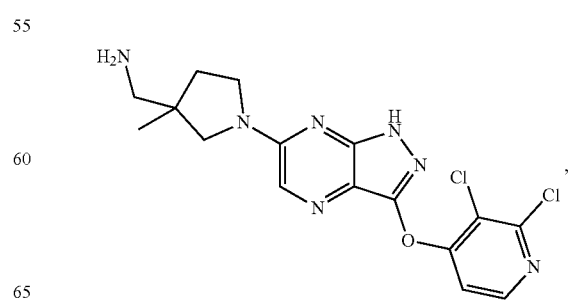

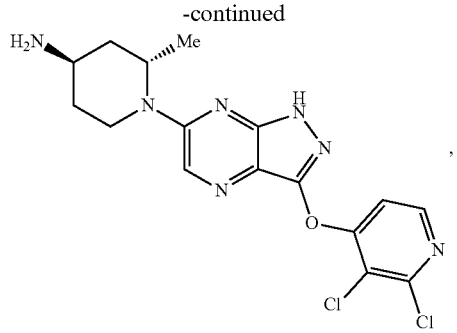
,
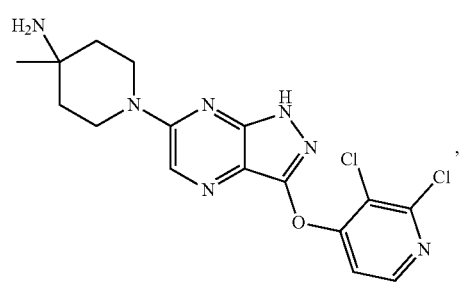
,
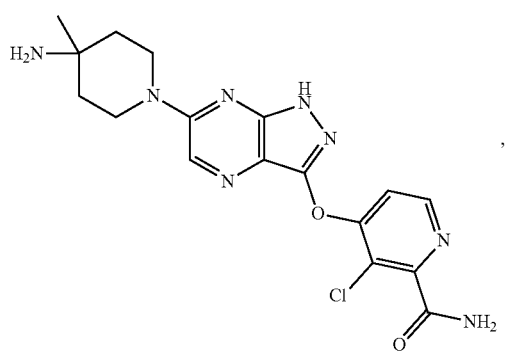
,
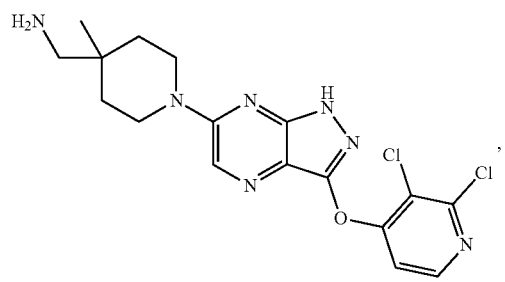
,
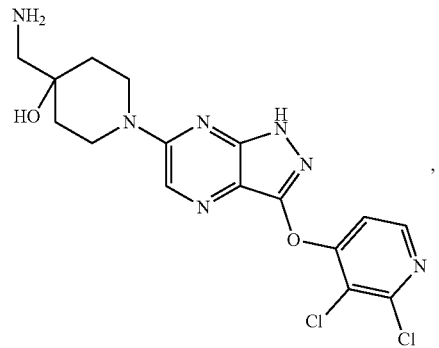
,
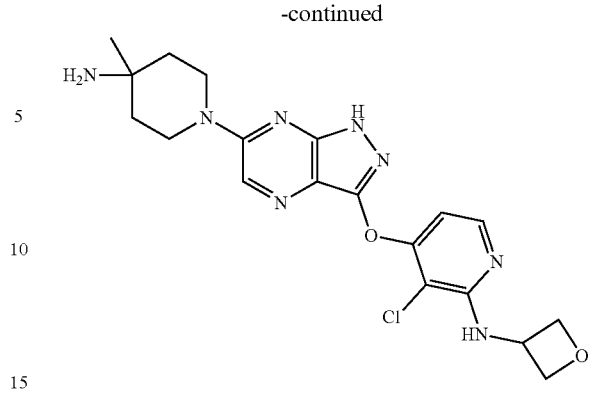
,
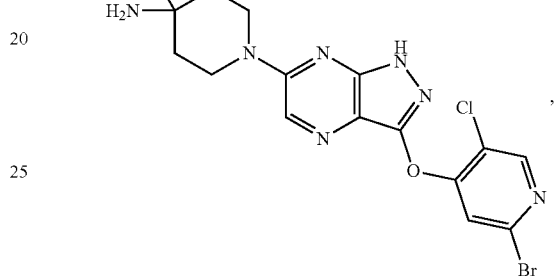
,
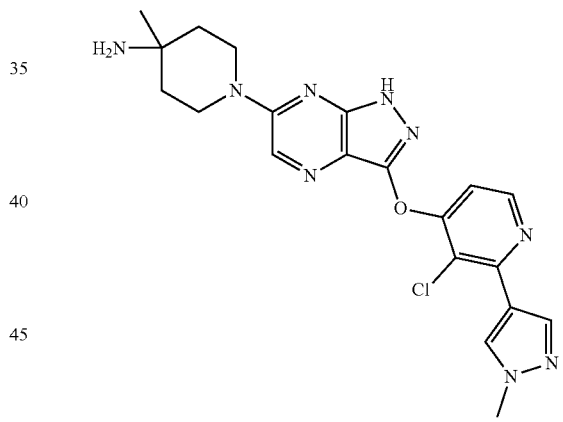
,
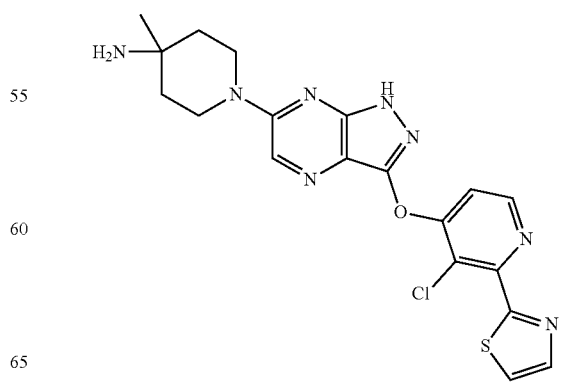
,

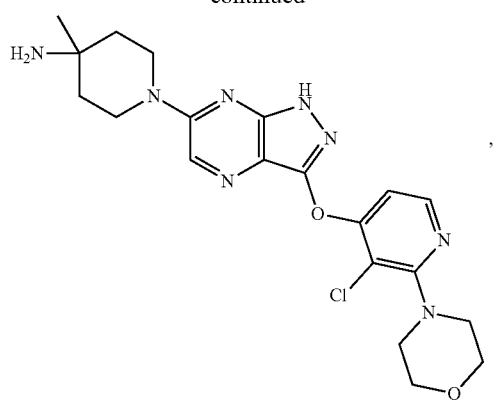
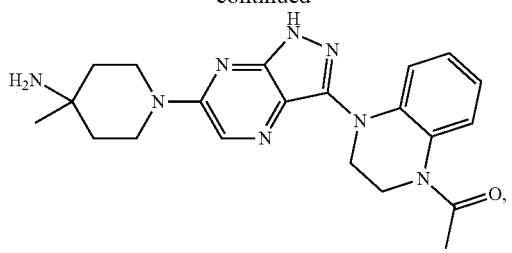
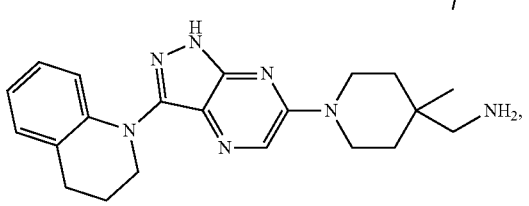
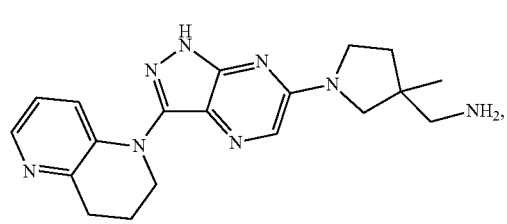
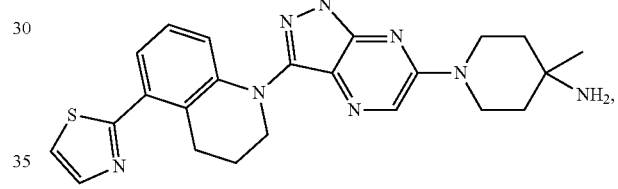
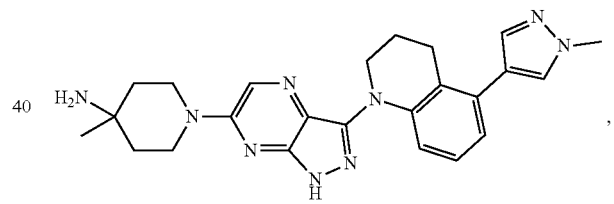
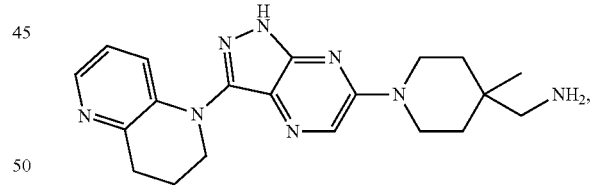
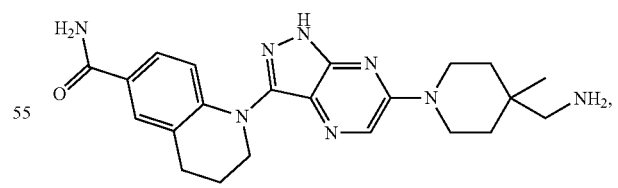
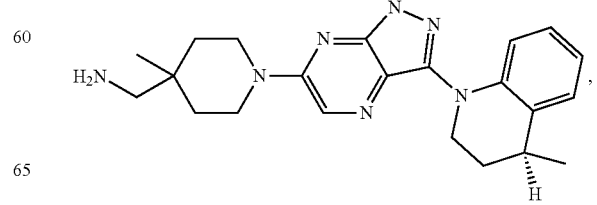

-continued
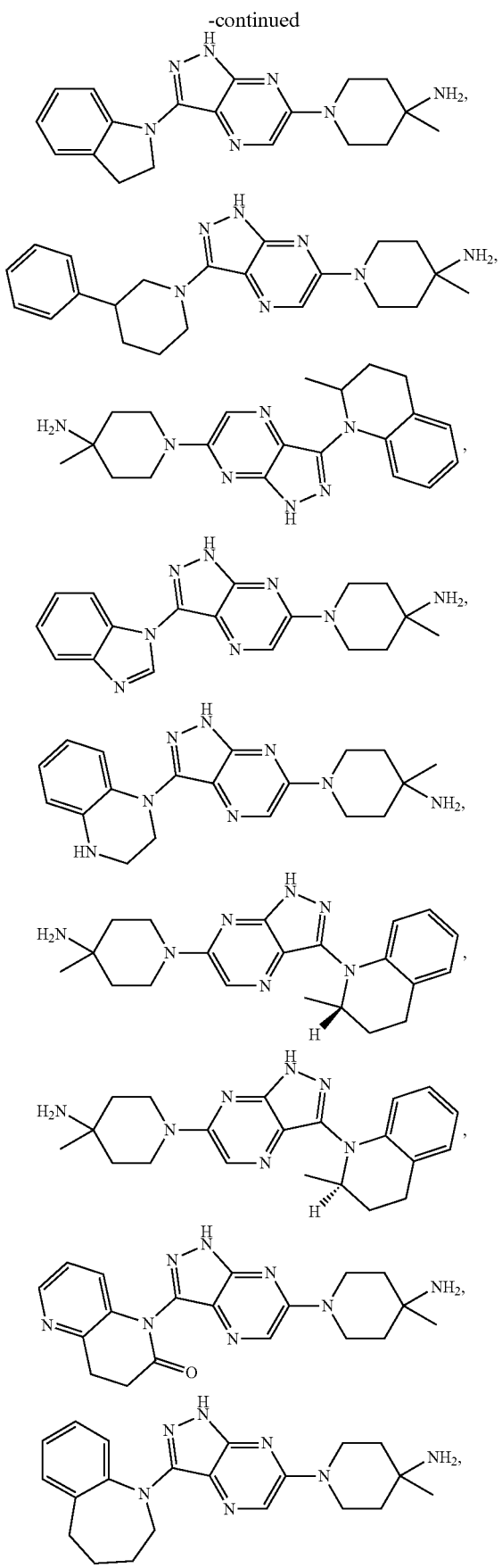
-continued
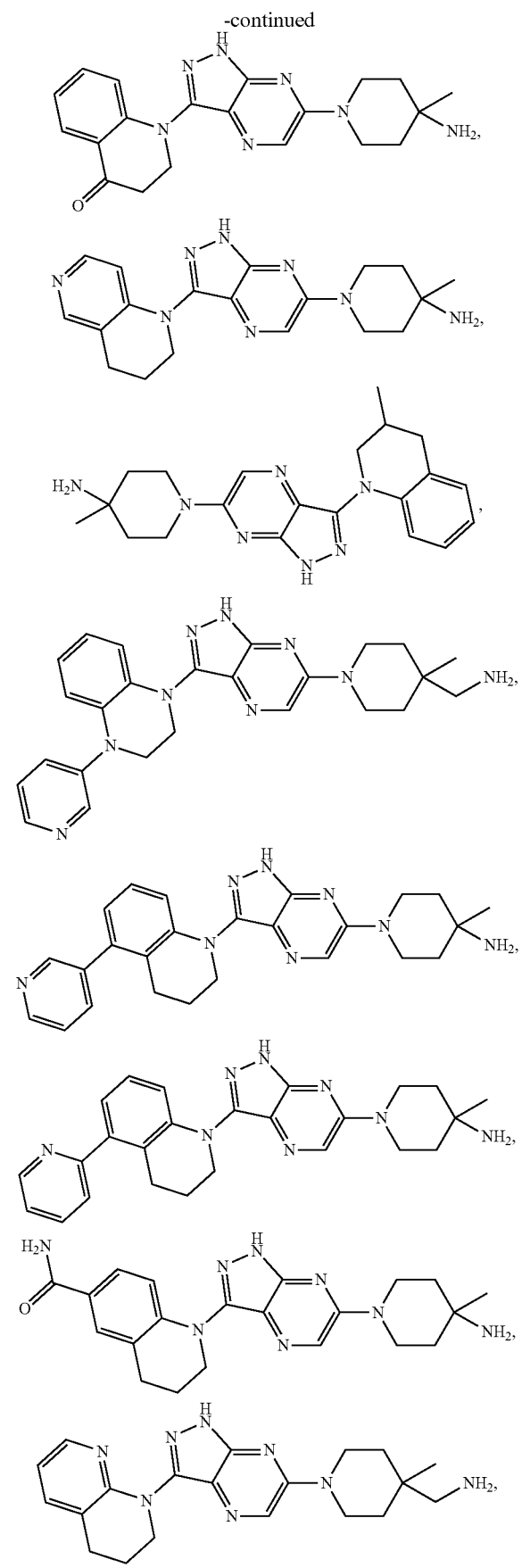

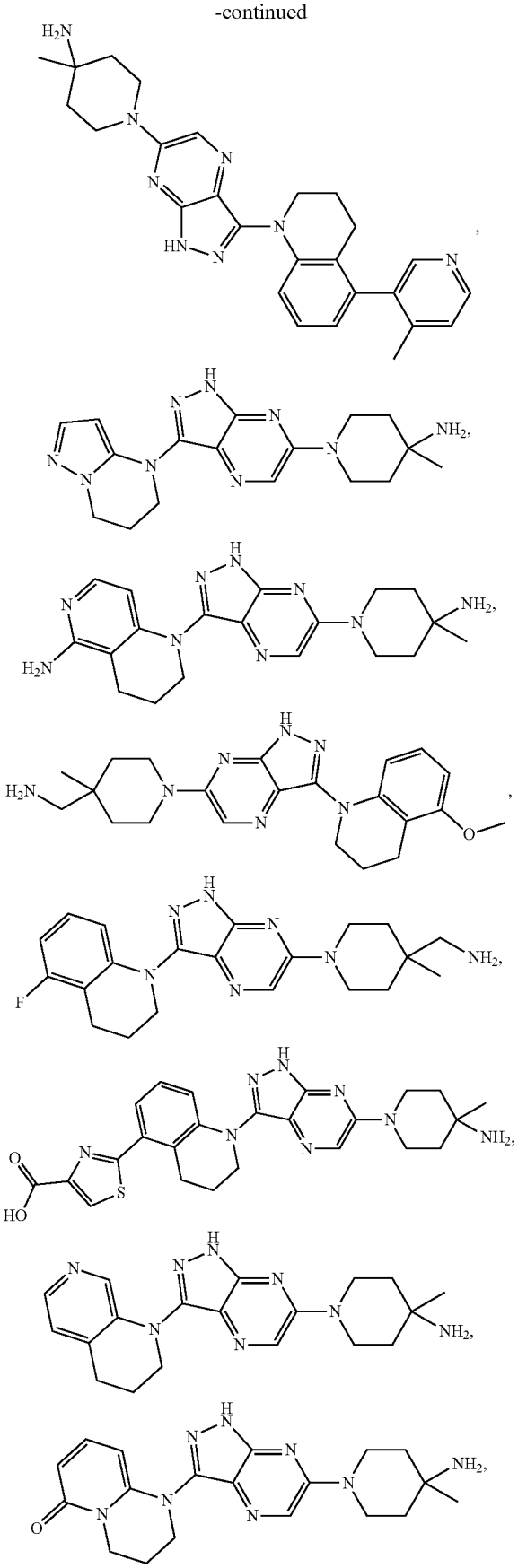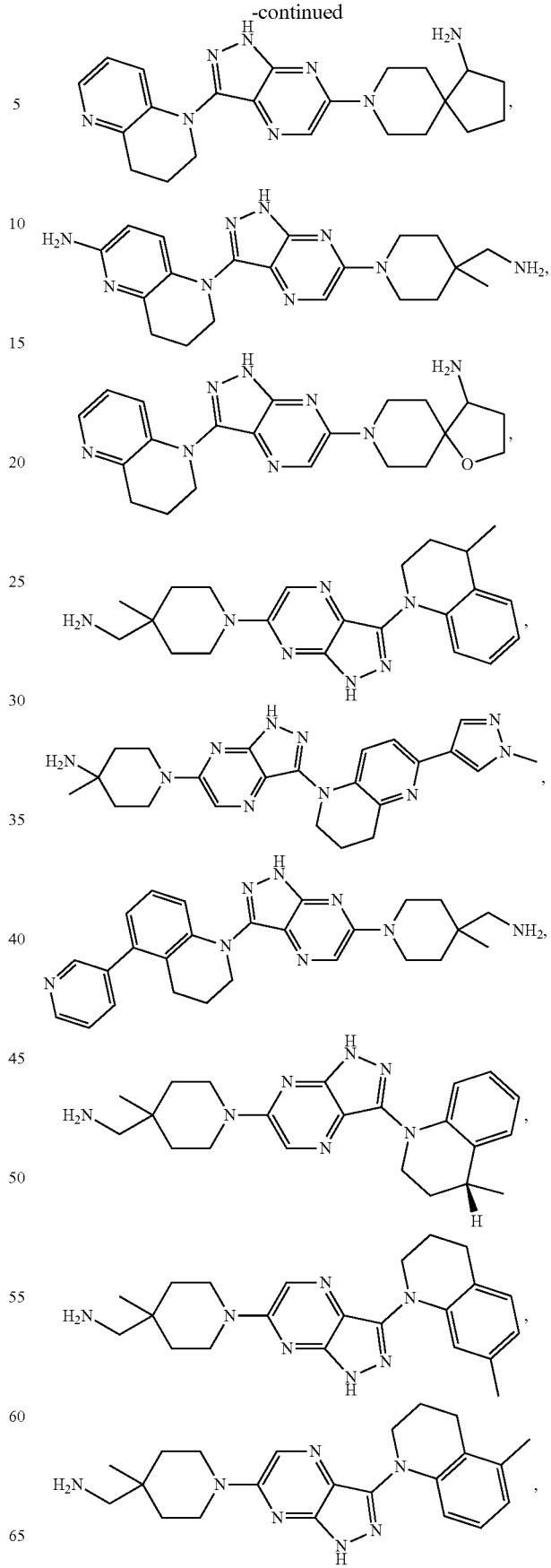

-continued
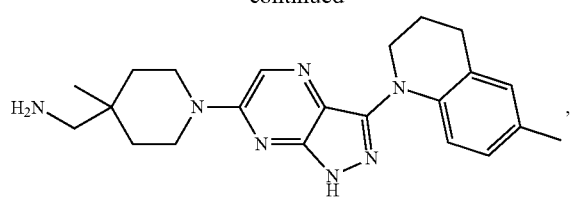
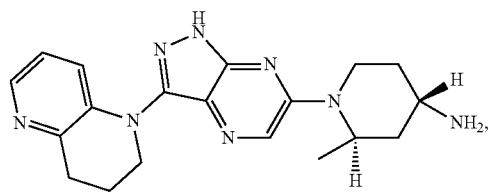
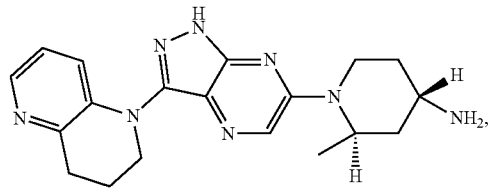
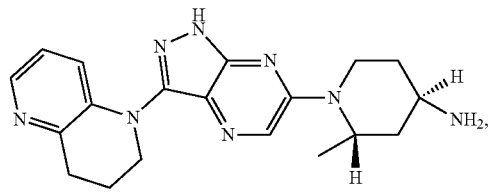
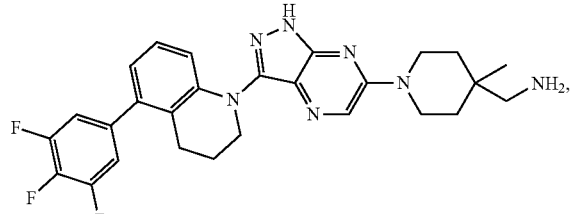
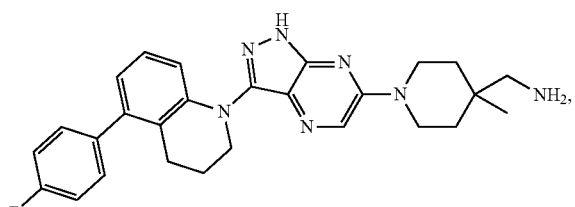
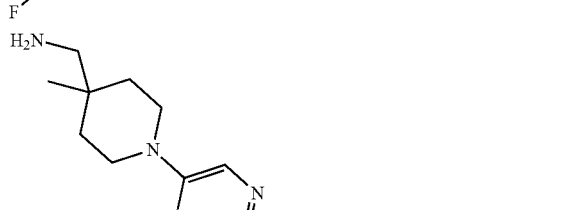
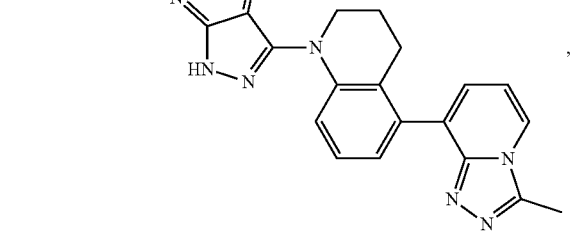
-continued
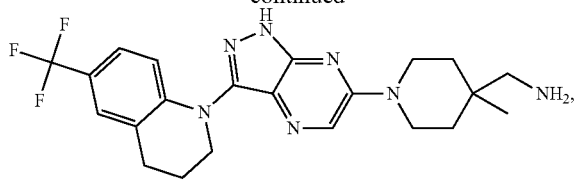
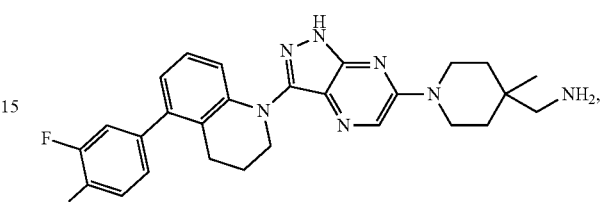
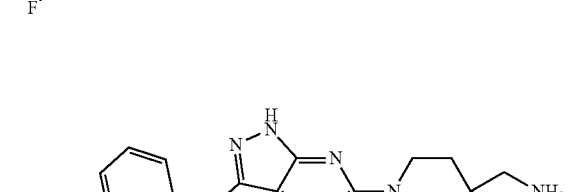
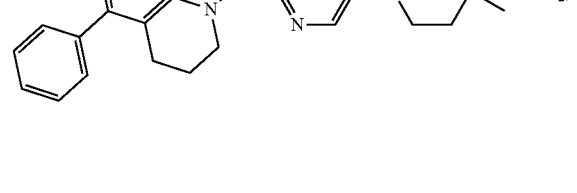
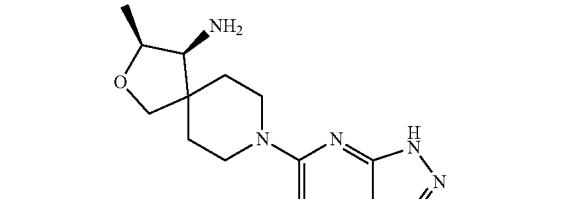
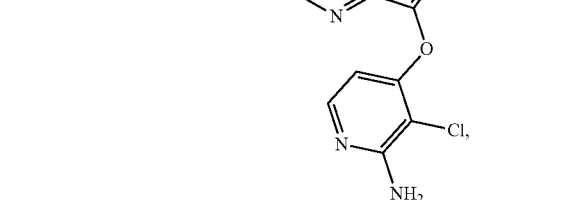
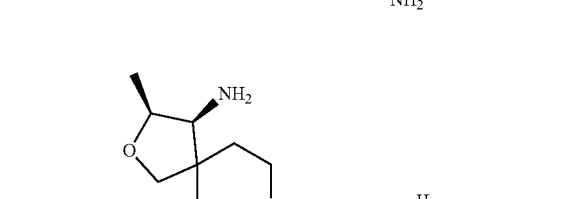
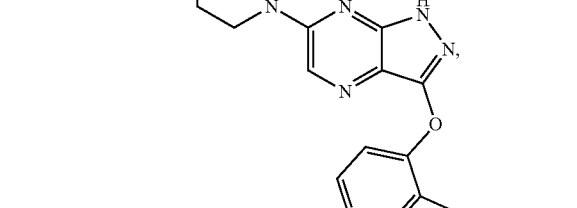

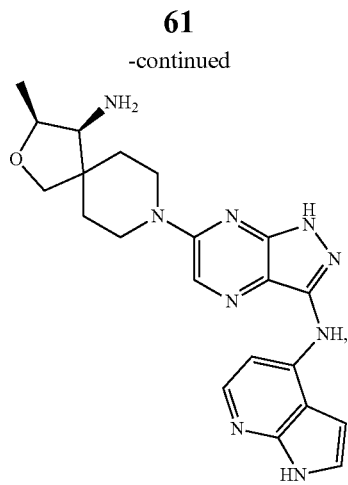

and a pharmaceutically acceptable salt or stereoisomer thereof.

Synthesis

The compounds described herein can be prepared according to known processes. Examples described herein represent synthetic schemes for preparing compounds of Formula (I) and Formula (II). These schemes are illustrative and are not meant to limit the possible techniques one skilled in the art may use to prepare compounds disclosed herein. Different methods will be evident to those skilled in the art. Additionally, the various steps in the synthesis may be performed in an alternate sequence or order to provide the compound(s). Various modifications to these methods may be envisioned by those skilled in the art to achieve similar results to that of the inventors provided below. For example, optional protecting groups can be used as described, e.g., in Greene et al., Protective Groups in Organic Synthesis (4$^{th}$ ed. 2006).

The compounds of Formula (I) and Formula (II) can generally be prepared according to exemplary Scheme 1:

Scheme 1

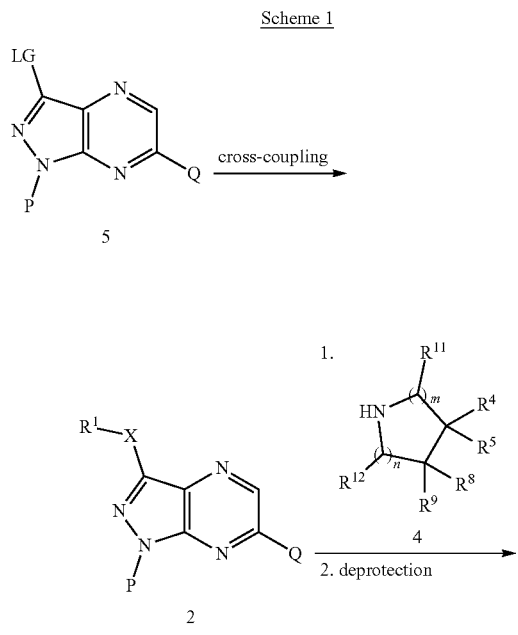

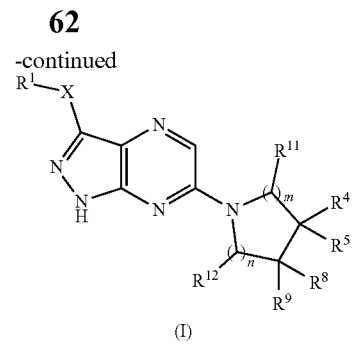

where X, $R^1$, $R^4$, $R^5$, $R^8$, $R^9$, $R^{11}$, and $R^{12}$ are as defined herein, Q is independently a halogen, such as Cl, Br, I, and the like, or any other leaving group, such as $OSO_2Me$, OMs, OTs, OTf, and the like, LG is a leaving group, such as Cl, Br, I, OTs, OTf, and the like, and P is a protecting group, such as tetrahydropyran and the like. Alternative protecting groups that can be used are described, e.g., in Greene et al., Protective Groups in Organic Synthesis (4$^{th}$ ed. 2006).

As shown in Scheme 1, an aryl compound such as 5 undergoes a cross-coupling reaction to provide a compound of Formula 2. The compound of Formula 2 then undergoes a substitution reaction with an amine such as 4, followed by removal of the protecting group to provide a compound of Formula (I) or Formula (II). In some embodiments, LG is I. In some embodiments, LG is Cl. In some embodiments, LG is OTf or OTs.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH. Conditions for removal of the protecting group will depend on the nature of the protecting group. Conditions for the removal of various protecting groups can be found, e.g., in Greene et al., Protective Groups in Organic Synthesis (4$^{th}$ ed. 2006).

Compounds or compositions of the invention can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in *Nature*, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g., J. Wang et al., in *J. Clin. Invest.* 2016, 126, 2077-2092; and references cited therein; each of which hereby incorporated by reference in its entirety.)

In some embodiments, compounds or compositions of the invention can be useful in suppressing tumor cell growth. In some embodiments, compounds or compositions of the invention can be useful in ameliorating the pathogenesis of systemic lupus erythematosus. In some embodiments, compounds or compositions of the invention can be useful in the treatment of various other disorders, including Noonan syndrome (NS), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the invention can be used in combination with other treatments and/or cancer therapies. For example, compounds or compositions of the invention can be used in combination with, but are not limited to, antibodies, antibody-drug conjugates, kinase inhibitors, immunomodulators, and histone deacetylase inhibitors. The compounds or compositions of the invention can also be used in combination with other treatments and/or cancer therapies as disclosed in WO 2015/107495; and references cited therein; each of which is hereby incorporated by reference in its entirety. For example, the compounds disclosed herein (or pharmaceutical compositions containing them) can be used in the treatment of one or more of the diseases mentioned herein, alone or in combination with another therapeutic agent. For example, a compound of formula (I) or formula (II) can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[(1S,4R)-6-[[4-(Cyclobutylamino)-5-(tjifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-1H-indazol-6-yl]sulfanyl]benzamide, brivanib alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate), motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo[4,5-c]quinolin-1-yl]phenyl]propionitrile, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CS1 antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.570, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: bacillus calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Anti-mitotic agents: Docetaxel. Adrenal steroid inhibitors aminoglutethimide Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK1 inhibitors: Alvocidib, palbociclib, ribociclib, trilaciclib, abemaciclib. Gonadotropin—releasing hormone (GnRH) receptor agonists: Leuprolide or leuprolide acetate. Taxane anti-neoplastic agents: Cabazitaxel (1-hydroxy^, 10-dimethoxy-9-oxo-5,20-epoxytax-11-ene-2a,4,13a-triyl-4-acetate-2-benzoate-13-[(2R,3 S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate). 5HT1a receptor agonists: Xaliproden (also known as SR57746, 1-[2-(2-naphthyl)ethyl]-4-[3-(trifluoromethyl)phenyl]-1,2,3,6-tetrahydropyridine. HPC vaccines: Cervarix® sold by GlaxoSmithKline, Gardasil® sold by Merck; Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine. Plant Alkaloids: Paclitaxel protein-bound; vinblastine, vincristine, vinorelbine, paclitaxel. Retinoids: Alitretinoin, tretinoin (all-trans retinoic acid, also known as ATRA), Isotretinoin (13-cis-retinoic acid, bexarotene. Glucocorticosteroids: Hydrocortisone (also known as cortisone, hydrocortisone sodium succinate, hydrocortisone sodium phosphate), dexamethazone ((8S,9R,10S,11S,13S,14S,16R, 17R)-9-fluoro-11,17-dihydroxy-17-(2-hydroxy acetyl)-10, 13,16-trimethyl-6,7,8,9,10,11,12,13,14,15,16,17-dodecahydro-3H-cyclopentatalphenanthren-3-one), prednisolone, prednisone, methylprednisolone (also known as 6-Methylprednisolone, Methylprednisolone Acetate, Methylprednisolone Sodium Succinate,). Cytokines: interleukin-2 (also known as aldesleukin and IL-2), interleukin-11 (also known as oprevelkin), alpha interferon alfa (also known as IFN-alpha). Estrogen receptor downregulators: Fulvestrant. Antiestrogens: tamoxifen. Toremifene. Selective estrogen receptor modulators (SERMs): Raloxifene. Leutinizing hormone releasing hormone (LHRH) agonists: Goserelin; Progesterones: megestrol (also known as megestrol acetate); Miscellaneous cytotoxic agents: Arsenic trioxide, asparaginase (also known as L-asparaginase, Erwinia L-asparaginase). Anti-nausea drugs: NK-1 receptor antagonists: Casopitant; and Cytoprotective agents: Amifostine, leucovorin (also known as calcium leucovorin, citrovorum factor and folinic acid). Immune checkpoint inhibitors: The term "immune checkpoints" refers to a group of molecules on the cell surface of CD4 and CD8 T cells Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present invention, include, but are not limited to, inhibitors of PD-L1, PD-L2, CTLA4, TIM3, LAG3, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the invention can be used in combination with an antibody. In some embodiments, compounds or compositions of the invention can be used in combination with an antibody-drug conjugate. In some embodiments, compounds or compositions of the invention can be used in combination with a kinase inhibitor. In some embodiments, compounds or compositions of the invention can be used in combination with an immunomodulator. In some embodiments, compounds or compositions of the invention can be used in combination with a histone deacetylase inhibitor.

In some embodiments, compounds of Formula (I) or Formula (II) can be administered to a subject in need of treatment at dosages ranging from about 0.0001 mg to about 100 mg/kg body weight of the subject to be treated per day, such as from about 1.0 to 10 mg/kg. However, additional variations are within the scope of the invention.

The compound of Formula (I) or Formula (II) can be administered alone or in combination with pharmaceutically acceptable carriers, such as diluents, fillers, aqueous solution, and even organic solvents. The compound and/or compositions of the invention can be administered as a tablet, powder, lozenge, syrup, injectable solution, and the like. Additional ingredients, such as flavoring, binder, excipients, and the like are within the scope of the invention.

In some embodiments, pharmaceutically acceptable compositions can contain a compound of Formula (I) or Formula (II) and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present invention provides for the use of pharmaceutical compositions and/or medicaments comprised of a compound of Formula (I) or Formula (II), or a pharmaceutically acceptable salt thereof, in a method of treating a disease state, and/or condition caused by or related to SHP2 phosphatase.

In some embodiments, the method of treatment comprises the steps of: i) identifying a subject in need of such treatment; (ii) providing a compound of Formula (I) or Formula (II), or a pharmaceutically acceptable salt thereof; and (iii) administering said compound of Formula (I) or Formula (II) in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a compound of Formula (I) or Formula (II), or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to, humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the compound or composition is administered orally. In some embodiments, the compound or composition is administered intravenously.

In some embodiments, the methods comprise administering to the subject an effective amount of a compound of Formula (I) or Formula (II), or a pharmaceutically acceptable salt thereof; or a composition comprising a compound of Formula (I) or Formula (II), or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, 5$^{th}$ Ed. (Alexander T. Florence, Juergen Siepmann, CRC Press (2009)); Handbook of Pharmaceutical Excipients, 7$^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a compound of Formula (I) or Formula (II), or a pharmaceutically acceptable salt thereof; or a composition comprising a compound of Formula (I) or Formula (II), or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the invention are formulated into pharmaceutical compositions for administration to subjects in a biologically compatible form suitable for administration in vivo. According to another aspect, the present invention provides a pharmaceutical composition comprising a compound of Formula (I) or Formula (II) in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula N$^+$R'R''R'''R''''Y$^-$, in which the R radicals are identical or different optionally hydroxylated hydrocarbon radicals and Y$^-$ is an anion of a strong acid, such as halide, sulfate and sulfonate anions; cetyltrimethylammonium bromide is one of the cationic surfactants which can be used, amine salts of formula N$^+$R'R''R''', in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the compound of Formula (I) or Formula (II) and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present invention are administered to a human or animal subject by known procedures including oral administration, sublingual or buccal administration. In some embodiments, the compound and/or composition is administered orally.

For oral administration, a formulation of the compounds of the invention may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present invention, the compounds of the invention are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the invention. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the invention, suitable dose ranges for oral administration of the compounds of the invention are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the invention may be provided in a kit comprising the compounds and/or compositions. Thus, in some embodiments, the compound and/or composition of the invention is provided in a kit.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples serve to illustrate the exemplary modes of making and practicing the invention. However, the scope of the invention is not to be construed as limited to specific embodiments disclosed in these Examples, which are illustrative only.

Instrumentation and Methods:

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: H$_2$O (10.0 mM NH$_4$HCO$_2$), mobile phase B: CH$_3$CN. HPLC conditions were: XBridge C18 column, 4.6×30 mm, 3.5 μm, 0.0-0.2 mM isocratic (5% B), 0.2-2.0 mM gradient (5-100% B), 3.0-3.0 mM isocratic (100% B); flow rate: 3.0 mL/min; UV channel 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2× Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

Nuclear Magnetic resonance: NMR spectra were recorded on Bruker Avance II Ultra shield spectrometer (500 MHz).

Example 1

Preparation of benzyl ((1-(3-iodo-1-(tetrahydro-2H-pyran-2-yl)-1H-pyrazolo[3,4-b]pyrazin-6-yl)-4-methylpiperidin-4-yl)methyl)carbamate Benzyl ((1-(3-iodo-1-(tetrahydro-2H-pyran-2-yl)-1H-pyrazolo[3,4-b]pyrazin-6-yl)-4-methylpiperidin-4-yl) methyl)carbamate was prepared as schematically illustrated below.

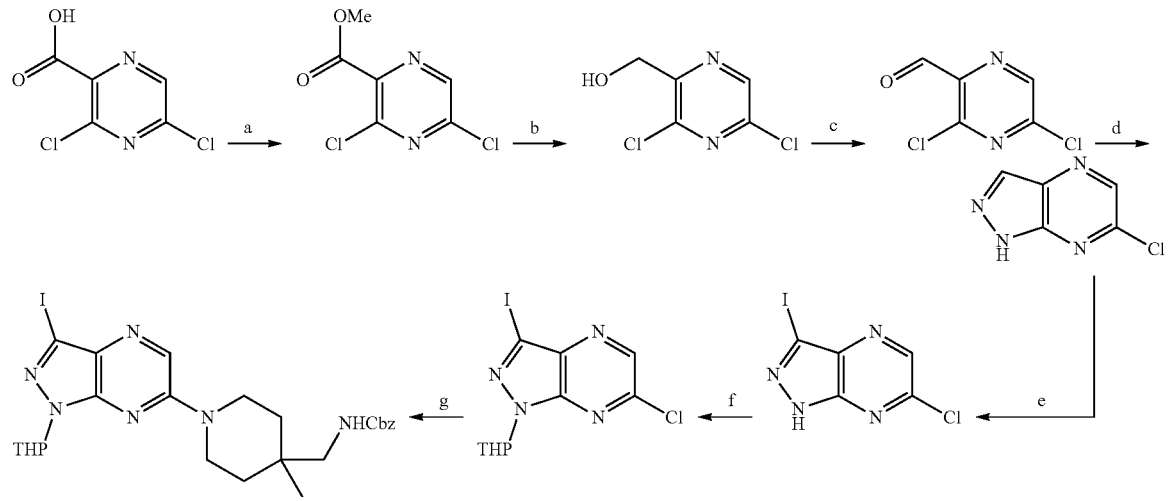

Step a: To a 100 mL round-bottomed flask, 3,5-dichloropyrazine-2-carboxylic acid (3.65 g, 18.9 mmol) and NaHCO$_3$ (4.70 g, 22.7 mmol) are dissolved in dimethylformamide (38 mL). Iodomethane (7.14 mL, 113 mmol) is added dropwise and the resulting mixture is stirred overnight at room temperature. The mixture is diluted in water (50 mL) and extracted with ethyl acetate (3×15 mL). The combined organic layers are washed with brine (4×10 mL), dried over anhydrous Na$_2$SO$_4$, filtered and concentrated under reduced pressure. Methyl 3,5-dichloropyrazine-2-carboxylate (3.77 g, 96%) is obtained as a yellowish solid after drying under high vacuum for 2-3 h. NMR $^1$H (500 MHz, CDCl$_3$) δ 8.57 (s, 1H), 4.03 (s, 3H).

Step b: To a 500 mL round-bottomed flask, methyl 3,5-dichloropyrazine-2-carboxylate (5.0 g, 24.2 mmol) is dissolved in a 9:1 mixture of dry tetrahydrofuran (242 mL) and methanol (27 mL). The reaction mixture is cooled to 1.5-2° C. with an ice/water bath and stirred at this temperature for 10 min A 2 M solution of lithium borohydride in THF (13.3 mL, 26.6 mmol) is then added carefully—Caution: reaction temperature must be below 4-5° C. After the end of addition, the reaction mixture is stirred for an additional 10-15 min at 0-4° C. Methanol (120 mL) is added to the flask and the mixture is stirred for 15 min at room temperature. The reaction is slowly poured into a mixture of 1 M HCl solution (100 mL) and ethyl acetate (200 mL). The resulting mixture is stirred at room temperature for 15 min. After this time, the layers are separated. The aqueous layer is extracted with ethyl acetate (3×150 mL). The combined organic layers are washed with brine (2×100 mL), dried over anhydrous MgSO$_4$, filtered and concentrated under reduced pressure. (3,5-dichloropyrazin-2-yl)methanol (4.3 g, 99%) is obtained as a crude yellow oil after drying under high vacuum for 2 h. NMR $^1$H (500 MHz, CDCl$_3$) δ 8.52 (s, 1H), 4.85 (s, 2H).

Step c: To a 250 mL round-bottomed flask, (3,5-dichloropyrazin-2-yl)methanol (4.3 g, 24 mmol) is dissolved in dichloromethane (100 mL). MnO$_2$ (20.2 g, 240 mmol) is then added in one portion and the resulting dark heterogeneous mixture is stirred for 16 h at room temperature. After this time, the reaction mixture is sonicated for 5 min, additional MnO$_2$ (4 g) is added to the flask and the resulting suspension is stirred for 2 h at room temperature. The mixture is then filtered over a pad of celite and the cake is rinsed with dichloromethane. The filtrate is concentrated under reduced pressure, affording 3,5-dichloropyrazine-2-carbaldehyde (2.36 g, 56%) as pale yellow crude oil after drying under high vacuum for 30 min NMR $^1$H (500 MHz, CDCl$_3$) δ 10.29 (s, 1H), 8.71 (s, 1H).

Step d: To a 50 mL round-bottomed flask, 3,5-dichloropyrazine-2-carbaldehyde (2.9 g, 16.4 mmol) is dissolved in N-methyl-2-pyrrolidone (16 mL) and hydrazine hydrate (0.78 mL, 49.2 mmol) is added dropwise. The resulting brown suspension is stirred at 65° C. for 40 min After this time, additional hydrazine hydrate (0.4 mL) is added and the mixture is stirred at 65° C. for 2 h more. The mixture is cooled to room temperature, poured into 1 M HCl solution (100 mL) and ethyl acetate (400 mL) is added. The layers are separated and the aqueous layer is extracted with ethyl acetate (2×100 mL). The organic layers are combined, washed with brine (300 mL), dried over anhydrous MgSO$_4$, filtered and concentrated under reduced pressure. The yellow crude residue is purified by reverse phase chromatography (0 to 50% gradient of acetonitrile/10 mM aqueous ammonium formate) affording 6-chloro-1H-pyrazolo[3,4-b]pyrazine (800 mg, 32%) as a light brown solid after lyophilization. NMR $^1$H (500 MHz, CD$_3$OD) δ 8.58 (s, 1H), 8.34 (s, 1H).

Step e: To a 50 mL round-bottomed flask, 6-chloro-1H-pyrazolo[3,4-b]pyrazine is dissolved in acetonitrile (24 mL). N-iodosuccinimide (3.43 g, 14.5 mmol) and 48% in water tetrafluoroboric acid solution (2.8 mL, 21.7 mmol) are successively added. The resulting brown/orange mixture is then stirred at reflux for 2 h. A beige/brown precipitate has formed overtime. The mixture is cooled to room temperature, then placed into an ice/water bath for 5 min. The solid in suspension is filtered through filter paper using a Buchner funnel. The flask and solid are washed with cold acetonitrile to give 6-chloro-3-iodo-1H-pyrazolo[3,4-b]pyrazine (1.81 g, 89%) as a yellow solid after drying under high vacuum. MS m/z 280.9 [M+H]$^+$ (weak). NMR $^1$H (500 MHz, CDCl$_3$) δ 8.59 (s, 1H).

Step f: To a 50 mL round-bottomed flask, 6-chloro-3-iodo-1H-pyrazolo[3,4-b]pyrazine (850 mg, 3 mmol) is dissolved in dichloromethane (15 mL). 3,4-dihydro-2H-pyran (0.85 mL, 9.1 mmol) and p-toluene sulfonic acid monohydrate (176 mg, 0.91 mmol) are successively added to the flask. The resulting mixture is stirred at room temperature for 10 min. The mixture becomes homogeneous and darkish overtime. After this time, a saturated aqueous solution of NaHCO$_3$ (20 mL) is added to the flask and biphasic mixture is stirred for 10 min. The layers are separated and organic layer is washed with brine (20 mL), dried over anhydrous Na$_2$SO$_4$, filtered and concentrated under reduced pressure. The crude residue is purified by flash chromatography (0 to 50% gradient of ethyl acetate/hexanes) to give 6-chloro-3-iodo-1-(tetrahydro-2H-pyran-2-yl)-1H-pyrazolo[3,4-b]pyrazine (1.02 g, 93%) as an off-white solid after drying under high vacuum overnight. MS m/z 364.9 [M+H]$^+$ (weak); 281.0 [M-THP+H]$^+$; $^1$H NMR (500 MHz, CDCl$_3$) δ 8.56 (s, 1H), 5.96 (dd, J=10.4, 2.6 Hz, 1H), 4.16-4.06 (m, 1H), 3.82-3.74 (m, 1H), 2.72-2.58 (m, 1H), 2.21-2.11 (m, 1H), 2.01-1.94 (m, 1H), 1.89-1.70 (m, 2H), 1.69-1.59 (m, 1H).

Step g: To a 25 mL round-bottomed flask, 6-chloro-3-iodo-1-(tetrahydro-2H-pyran-2-yl)-1H-pyrazolo[3,4-b]pyrazine (1.0 g, 2.61 mmol), benzyl ((4-methylpiperidin-4-yl)methyl)carbamate (752 mg, 2.87 mmol) and cesium fluoride (1.2 g, 7.82 mmol) are suspended in dimethylacetamide (10 mL). The resulting heterogeneous mixture is then heated at 80° C. for 5 h. The mixture is then cooled to room temperature and poured into water (20 mL). The yellowish precipitate is filtered through a filter paper using a Buchner funnel, washed with water (3×5 mL). The cake is dried for 1 h by suction. Benzyl ((1-(3-iodo-1-(tetrahydro-2H-pyran-2-yl)-1H-pyrazolo[3,4-b]pyrazin-6-yl)-4-methylpiperidin-4-yl) methyl)carbamate (1.51 g, 98%) is obtained as a pale yellow solid after drying under high vacuum overnight. MS m/z 591.3 [M+H]$^+$; $^1$H NMR (500 MHz, CDCl$_3$) δ 8.16 (s, 1H), 7.40-7.29 (m, 5H), 5.77 (dd, J=10.4, 2.6 Hz), 5.11 (s, 1H), 4.90-4.81 (m, 1H), 4.15-4.07 (in, 1H), 4.02-3.93 (in. 1H), 3.77-3.71 (m, 1H), 3.62-3.51 (m, 2H), 3.18 (d, J=6.7 Hz, 2H), 2.69-2.58 (m, 1H), 2.19-2.10 (m, 1H), 1.97-1.89 (m, 1H), 1.84-1.69 (m, 2H), 1.64-1.57 (m, 4H), 1.51-1.42 (m, 2H). 1.03 (s, 3H).

Example 2

Preparation of (4-methyl-1-(3-(phenylthio)-1H-pyrazolo[3,4-b]pyrazin-6-yl)piperidin-4-yl)methanamine (Compound 6)

(4-methyl-1-(3-(phenylthio)-1H-pyrazolo[3,4-b]pyrazin-6-yl)piperidin-4-yl)methanamine was prepared as schematically illustrated below.

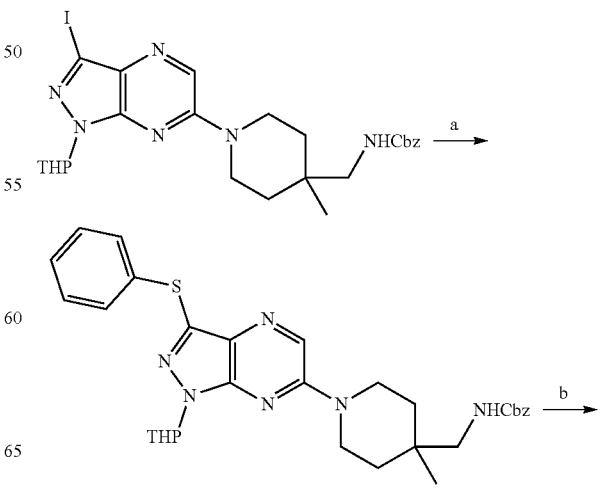

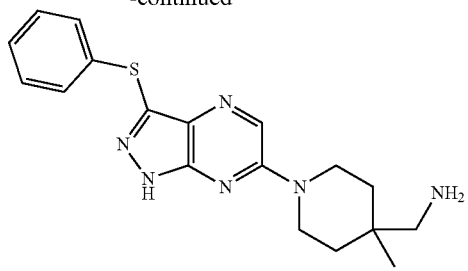

Step a: To a 5 mL vial, benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (50 mg, 0.085 mmol) is dissolved in i-PrOH (0.9 mL). Copper iodide (16 mg, 0.085 mmol), potassium carbonate (24 mg, 0.170 mmol), ethylene glycol (10 μL, 0.17 mmol) and thiophenol (19 μL, 0.102 mmol) are successively added. the vial is flushed with $N_2$, sealed and placed in a preheated oil bath at 100° C. The resulting yellow heterogeneous mixture is stirred at this temperature for 5 h. After this time, additional copper iodide (16 mg) and thiophenol (19 μL) are added. The resulting mixture is heated overnight at 100° C. After full conversion, the mixture is cooled to room temperature, filtered through a piece of cotton. The vial and cotton are rinsed with ethyl acetate. The filtrate is washed with aqueous ammonia (2×10 mL), brine (2×10 mL). The organic layer is then dried over anhydrous $Na_2SO_4$, filtered and concentrated under reduced pressure. The crude material is purified by flash chromatography using a gradient of ethyl acetate in hexanes (0 to 70%), affording benzyl ((4-methyl-1-(3-(phenylthio)-1-(tetrahydro-2H-pyran-2-yl)-1H-pyrazolo[3,4-b]pyrazin-6-yl)piperidin-4-yl)methyl)carbamate (45 mg, 93%) as a pale yellow oil. MS m/z 573.1 $[M+H]^+$.

Step b: In a 10-mL round bottomed flask, benzyl ((4-methyl-1-(3-(phenylthio)-1-(tetrahydro-2H-pyran-2-yl)-1H-pyrazolo[3,4-b]pyrazin-6-yl)piperidin-4-yl)methyl)carbamate (45 mg, 0.079 mmol) is slowly dissolved in 33% hydrobromic acid in acetic acid (1 mL), at 0-4° C. The resulting yellow-orange mixture is stirred at this temperature for 5 min and allowed to progressively reach room temperature. The reaction is stirred an additional 40 min at room temperature. The mixture is slowly dropped into diethyl ether (20 mL). The gummy yellow precipitate formed is redissolved in water (10 mL) and layers are separated. The aqueous layer is then basified with sat. aq. $Na_2CO_3$ solution (30 mL) and dichloromethane (20 mL) is added. The layers are separated and aqueous layer is back-extracted with dichloromethane (3×10 mL). The organic layers are combined, dried over anhydrous $Na_2SO_4$, filtered and concentrated under reduced pressure. (4-methyl-1-(3-(phenylthio)-1H-pyrazolo[3,4-b]pyrazin-6-yl)piperidin-4-yl) methanamine (17.7 mg, 64%) is obtained as an off-white solid after lyophilization. MS m/z 355.3 $[M+H]^+$; $^1H$ NMR (500 MHz, DMSO-$d_6$) δ 8.38 (s, 1H), 7.29-7.21 (m, 4H), 7.20-7.16 (m, 1H), 3.97-3.86 (m, 2H), 3.53-3.41 (in, 2H), 2.41 (br s, 2H), 1.55-1.43 (m, 2H), 1.37-1.27 (m, 211), 0.94 (s, 311).

Example 3

Preparation of (1-(3-((2-chlorophenyl)thio)-1H-pyrazolo[3,4-b]pyrazin-6-yl)-4-methylpiperidin-4-yl)methanamine (Compound 7)

(1-(3-((2-chlorophenyl)thio)-1H-pyrazolo[3,4-b]pyrazin-6-yl)-4-methylpiperidin-4-yl)methanamine was prepared as schematically illustrated below.

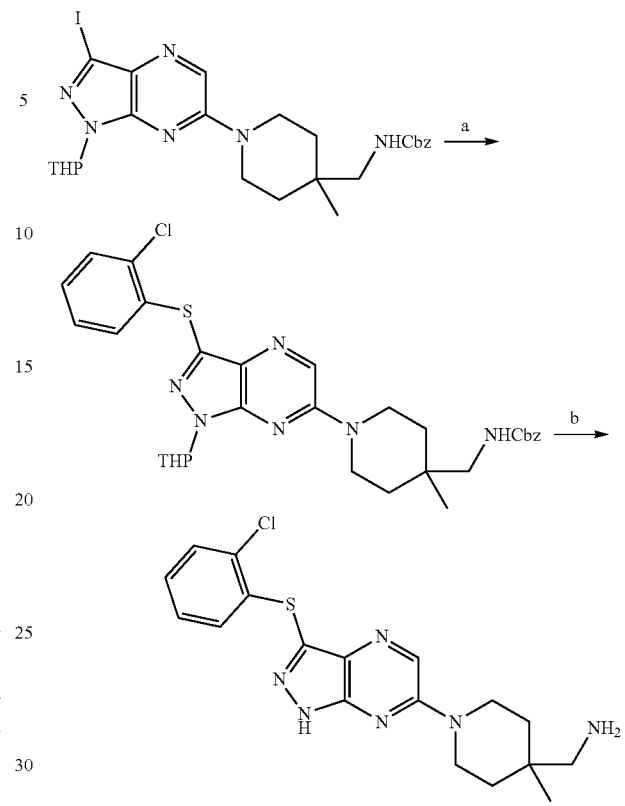

Step a: To a 5 mL vial, benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (50 mg, 0.085 mmol) is dissolved in i-PrOH (0.9 mL). Copper iodide (32 mg, 0.17 mmol), potassium carbonate (24 mg, 0.170 mmol), ethylene glycol (10 μL, 0.17 mmol) and 2-chloro-thiophenol (20 μL, 0.17 mmol) are successively added. The vial is flushed with $N_2$, sealed and placed in a preheated oil bath at 100° C. The resulting yellow heterogeneous mixture is stirred at this temperature for 5 h. After this time, additional copper iodide (16 mg) and 2-chloro-thiophenol (19 μL) are added. The resulting mixture is heated overnight at 100° C. The mixture is cooled to room temperature, filtered through a piece of cotton. The vial and cotton are rinsed with ethyl acetate. The filtrate is washed with aqueous ammonia (2×10 mL), brine (2×10 mL). The organic layer is then dried over anhydrous $Na_2SO_4$, filtered and concentrated under reduced pressure. The crude material is purified by flash chromatography using a gradient of ethyl acetate in hexanes (0 to 70%), affording benzyl ((1-(3-((2-chlorophenyl)thio)-1-(tetrahydro-2H-pyran-2-yl)-1H-pyrazolo[3,4-b]pyrazin-6-yl)-4-methylpiperidin-4-yl)methyl)carbamate (40 mg, 60% purity by LCMS). MS m/z 607.4 $[M+H]^+$.

Step b: In a 10-mL round bottomed flask, benzyl ((1-(3-((2-chlorophenyl)thio)-1-(tetrahydro-2H-pyran-2-yl)-1H-pyrazolo[3,4-b]pyrazin-6-yl)-4-methylpiperidin-4-yl) methyl)carbamate (20 mg, 0.033 mmol) is slowly dissolved in 33% hydrobromic acid in acetic acid (1 mL), at 0-4° C. The resulting yellow-orange mixture is stirred at this temperature for 5 min and allowed to progressively reach room temperature. The reaction is stirred an additional 40 min at room temperature. The mixture is slowly dropped into diethyl ether (20 mL). The gummy yellow precipitate formed is redissolved in water (10 mL) and layers are separated. The aqueous layer is then basified with sat. aq. Na$_2$CO$_3$ solution (30 mL) and dichloromethane (20 mL) is added. The layers are separated and aqueous layer is back-extracted with dichloromethane (3×10 mL). The organic layers are combined, dried over anhydrous Na$_2$SO$_4$, filtered and concentrated under reduced pressure. The crude residue is purified by reverse phase chromatography (15 to 70% gradient of acetonitrile/10 mM aqueous ammonium formate) to give (1-(3-((2-chlorophenyl)thio)-1H-pyrazolo[3,4-b]pyrazin-6-yl)-4-methylpiperidin-4-yl)methanamine (4.1 mg, 32%) as a pale yellow solid after lyophilization. MS m/z 389.3 [M+H]$^+$; $^1$H NMR (500 MHz, MeOD)) δ 8.52 (br s, 1H), 8.30 (s, 1H), 7.42-7.37 (m, 1H), 7.17-7.09 (m, 1H), 7.09-7.02 (m, 1H), 6.83-6.76 (m, 1H), 4.20-4.10 (m, 2H), 3.62-3.51 (m, 2H), 2.90 (br s, 2H), 1.70-1.55 (m, 4H), 1.21 (s, 3H).

Example 4

Preparation of 1-(3-bromo-1-(4-methoxybenzyl)-1H-pyrazolo[3,4-b]pyrazin-6-yl)-4-methylpiperidin-4-amine 1-(3-bromo-1-(4-methoxybenzyl)-1H-pyrazolo[3,4-b]pyrazin-6-yl)-4-methylpiperidin-4-amine was prepared as schematically illustrated below.

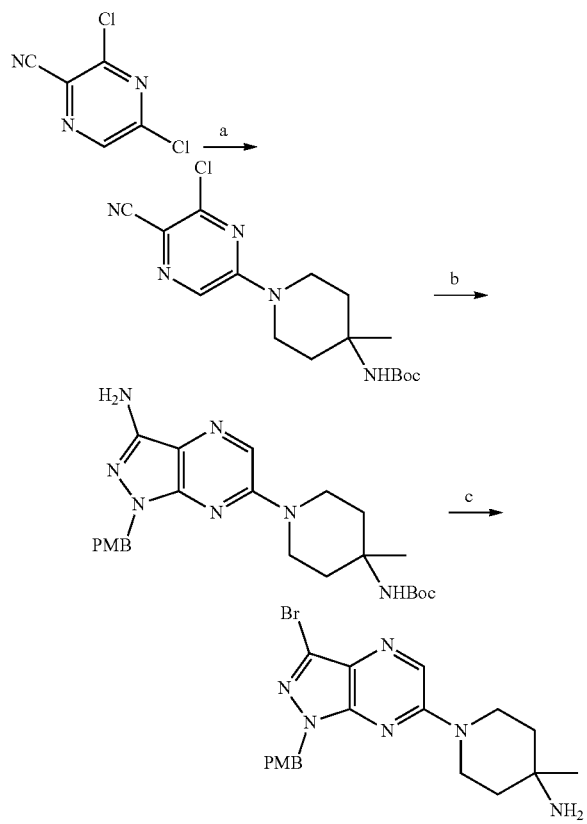

Step a: A round bottomed flask was charged with 3,5-dichloropyrazine-2-carbonitrile (0.3 g, 1.7 mmol, 1.0 equiv), tert-butyl N-(4-methyl-4-piperidyl)carbamate (0.37 g, 1.7 mmol, 1.0 eq), and CsF (0.78 g, 5.2 mmol, 3.0 eq). Dimethylsulfoxide (5.7 mL) was added, and the reaction mixture was stirred at 70° C. for 2.5 hours. The reaction mixture was diluted with EtOAc (100 mL), washed with saturated NaHCO$_3$ (30 mL), H$_2$O (30 mL×2) and brine (30 mL). The organic layer was dried over anhydrous Na$_2$SO$_4$, filtered and concentrated to give a yellow solid. The residue was purified by column chromatography (Petroleum ether/Ethyl acetate=5:1~3:1) to afford the product of tert-butyl N-[1-(6-chloro-5-cyano-pyrazin-2-yl)-4-methyl-4-piperidyl]carbamate (0.5 g, 83% yield) as a yellow solid. LCMS: M/Z 295 (M-tBu)$^+$.

Step b: The compound tert-butyl N-[1-(6-chloro-5-cyano-pyrazin-2-yl)-4-methyl-4-piperidyl] carbamate (4.0 g, 11.4 mmol, 1.0 eq), Et$_3$N (5.7 g, 56.8 mmol, 7.9 mL, 5.0 eq) and (4-methoxyphenyl)methylhydrazine (3.1 g, 13.6 mmol, 1.2 eq, 2HCl) were placed into the solvent of EtOH (50.0 mL). The mixture was stirred at 90° C. for 16 hours. A second reaction was run with the same ratio of materials, starting from 1 g of tert-butyl N-[1-(6-chloro-5-cyano-pyrazin-2-yl)-4-methyl-4-piperidyl] carbamate. Both reaction mixtures were combined and concentrated under reduced pressure to give a residue, which was triturated with H$_2$O (50 mL), extracted with ethyl acetate (100 mL×2). The combined organic layers were washed with brine (50 mL) and dried over anhydrous sodium sulfate, filtered, and concentrated to give a residue. The residue was purified by flash silica gel chromatography (eluting with ethyl acetate/petroleum ether) to afford tert-butyl-N-[1-[3-amino-1-[(4-methoxyphenyl)methyl]pyrazolo[3,4-b]pyrazin-6-yl]-4-methyl-4-piperidyl] carbamate (4.8 g) as a yellow solid. LCMS: M/Z 468 (M+H)$^+$.

Step c: A round bottomed flask was charged with tert-butyl N-[1-[3-amino-1-[(4-methoxyphenyl)methyl]pyrazolo[3,4-b]pyrazin-6-yl]-4-methyl-4-piperidyl]carbamate (8.2 g, 17.5 mmol, 1.0 eq) and NaNO$_2$ (1.4 g, 21.0 mmol, 1.2 eq). Acetonitrile (150 mL) was added, followed by HBr (30.0 mL, 47% purity), and the mixture was stirred at 0° C. for 1 h. CuBr (251 mg, 1.7 mmol, 0.10 eq) was added at 0° C., and the reaction mixture was allowed to warm to 25° C. for 1 h. The mixture was adjusted to pH=10 with ammonium hydroxide and extracted with ethyl acetate (150 mL×3). The combined organic layers were washed with H$_2$O (100 mL) and brine (100 mL), dried over anhydrous sodium sulfate, filtered, and concentrated to give a residue. The residue was purified by flash silica gel chromatography (eluting with methylene chloride and methanol) to afford 1-[3-bromo-1-[(4-methoxyphenyl)methyl]pyrazolo[3,4-b]pyrazin-6-yl]-4-methyl-piperidin-4-amine (6.6 g, 76.7% yield) as a red solid. LCMS: M/Z 431/433 (M+H)$^+$.

Example 5

Preparation of 1-(3-((2-chlorophenyl)thio)-1H-pyrazolo[3,4-b]pyrazin-6-yl)-4-methylpiperidin-4-amine (Compound 8)

1-(3-((2-chlorophenyl)thio)-1H-pyrazolo[3,4-b]pyrazin-6-yl)-4-methylpiperidin-4-amine was prepared as schematically illustrated below.

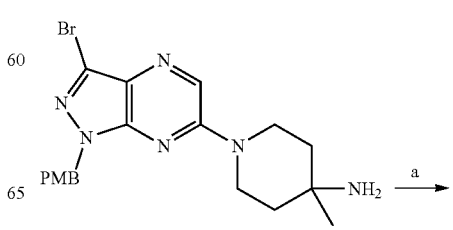

-continued

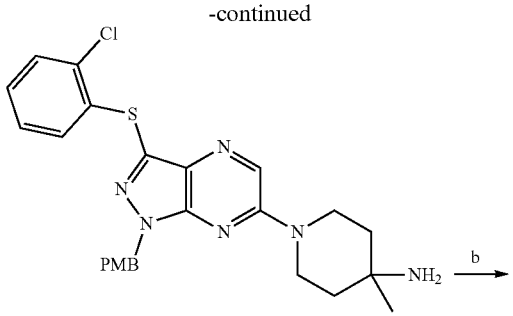

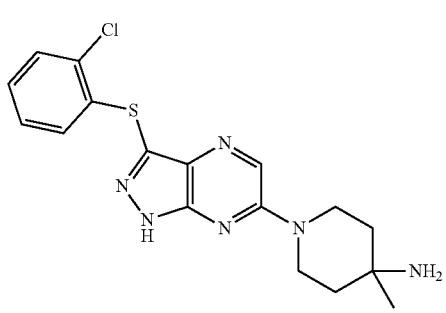

Step a: To a 5 mL vial were added 1-(3-bromo-1-(4-methoxybenzyl)-1H-pyrazolo[3,4-b]pyrazin-6-yl)-4-methylpiperidin-4-amine (50 mg, 0.12 mmol), Pd$_2$dba$_3$ (5 mg, 5 mol %), XantPhos (7 mg, 10 mol %), 2-chloro-thiophenol (16 μL, 0.14 mmol), and N,N-diisopropylethylamine (41 μL, 0.23 mmol), followed by dioxane (0.2 mL). The resulting mixture was sealed, degassed with nitrogen, and heated under microwave irradiation at 130° C. for 1.5 h. After full conversion, the volatiles were evaporated under reduced pressure. The resulting residue was purified by reverse phase chromatography (eluting with acetonitrile and water with 0.1% ammonium formate) to give 1-(3-((2-chlorophenyl)thio)-1-(4-methoxybenzyl)-1H-pyrazolo[3,4-b]pyrazin-6-yl)-4-methylpiperidin-4-amine (55 mg, 96%) as an off-white solid after lyophilization. MS m/z 496.2 [M+H]$^+$.

Step b: In a 25-mL round bottomed flask, 1-(3-((2-chlorophenyl)thio)-1-(4-methoxybenzyl)-1H-pyrazolo[3,4-b]pyrazin-6-yl)-4-methylpiperidin-4-amine (57 mg, 0.115 mmol) was slowly dissolved in 33% hydrobromic acid in acetic acid (1 mL), at room temperature. The resulting yellow-orange mixture was then placed in a preheated oil bath at 70° C. and stirred at this temperature for 45 min After this time, the mixture cooled to room temperature. The mixture was slowly dropped into diethyl ether (20 mL), and the yellow/orange precipitate was filtered through a piece of cotton. The gummy residue was redissolved in water (3-4 mL) and neutralized with a solution of saturated sodium bicarbonate until the pH was neutral. The resulting aqueous solution was loaded on a reverse phase chromatography column and purified using a gradient of acetonitrile in 0.1% formic acid in water (10 to 50%) to give 1-(3-((2-chlorophenyl)thio)-1H-pyrazolo[3,4-b]pyrazin-6-yl)-4-methylpiperidin-4-amine (24.2 mg, 56%) as an off-white solid. MS m/z 375.2 [M+H]$^+$. $^1$H NMR (500 MHz, DMSO) δ 8.43 (s, 1H), 8.34 (s, 1H), 7.49 (dd, J=7.8, 1.5 Hz, 1H), 7.16 (dtd, J=23.5, 7.4, 1.5 Hz, 2H), 6.78 (dd, J=7.9, 1.6 Hz, 1H), 3.94-3.83 (m, 2H), 3.74-3.63 (m, 2H), 1.67-1.57 (m 4H), 1.24 (s, 3H).

Example 6

Preparation of 6-(4-(aminomethyl)-4-methylpiperidin-1-yl)-N-(2-chlorophenyl)-1H-pyrazolo[3,4-b]pyrazin-3-amine (Compound 9)

6-(4-(aminomethyl)-4-methylpiperidin-1-yl)-N-(2-chlorophenyl)-1H-pyrazolo[3,4-b]pyrazin-3-amine was prepared as schematically illustrated below.

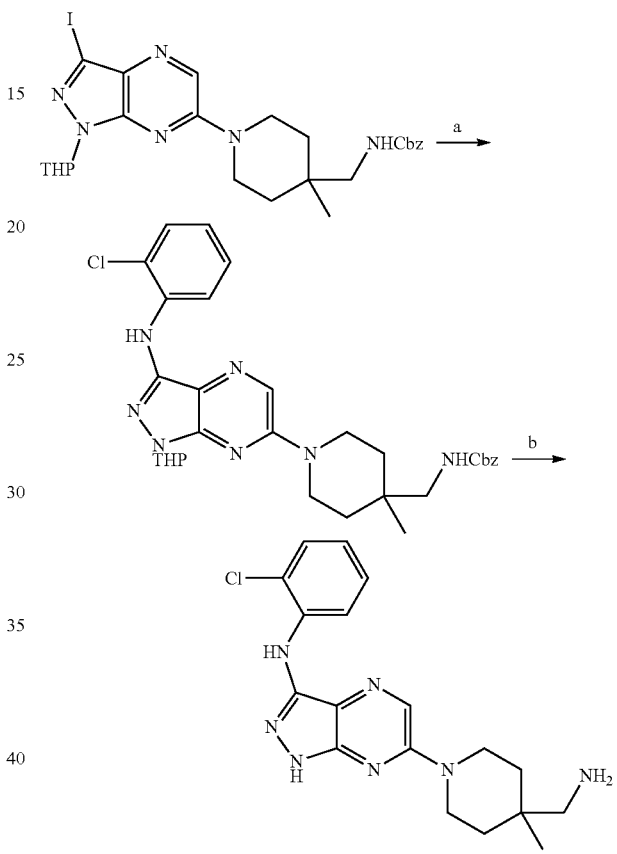

Step a: To a 5 mL vial, benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (70 mg, 0.119 mmol), SPhos Pd G1 (4.6 mg, 5 mol %), 2-chloroaniline (45 mg, 0.136 mmol) and potassium phosphate (50 mg, 0.237 mmol) are successively added, followed by degassed dioxane (0.6 mL) and degassed water (0.2 mL). The resulting mixture is sealed, degassed with N$_2$ and heated at 100° C. overnight. After full conversion, the volatiles are evaporated under reduced pressure. The crude residue is purified by flash chromatography (0 to 100% gradient of ethyl acetate/hexanes) to give benzyl ((1-(3-((2-chlorophenyl)amino)-1-(tetrahydro-2H-pyran-2-yl)-1H-pyrazolo[3,4-b]pyrazin-6-yl)-4-methylpiperidin-4-yl)methyl)carbamate (10 mg, 14%) as an yellow solid. MS m/z 590.2 [M+H]$^+$.

Step b: In a 10-mL round bottomed flask, benzyl ((1-(3-((2-chlorophenyl)amino)-1-(tetrahydro-2H-pyran-2-yl)-1H-pyrazolo[3,4-b]pyrazin-6-yl)-4-methylpiperidin-4-yl)methyl)carbamate (10 mg, 0.0169 mmol) is slowly dissolved in 33% hydrobromic acid in acetic acid (1 mL), at 0-4° C. The resulting yellow-orange mixture is stirred at this temperature for 5 min and allowed to progressively reach room temperature. The reaction is stirred an additional 70 min at room temperature. Diethyl ether (2.5 mL) was then added to the mixture. The liquid is removed and the precipitate formed is triturated with diethyl ether (2 mL). The crude residue is purified by reverse phase chromatography (0 to 50% gradient of acetonitrile/10 mM aqueous ammonium formate) to 6-(4-(aminomethyl)-4-methylpiperidin-1-yl)-N-(2-chlorophenyl)-1H-pyrazolo[3,4-b]pyrazin-3-amine (2.5 mg, 33%) as an off white solid after lyophilization. MS m/z 372.2 [M+H]⁺; ¹H NMR (500 MHz, DMSO) δ 8.27 (d, J=3.7 Hz, 1H), 8.06 (dd, J=8.3, 1.5 Hz, 1H), 7.42 (dd, J=8.0, 1.4 Hz, 1H), 7.29-7.20 (m, 1H), 6.91-6.81 (m, 1H), 3.94 (d, J=13.3 Hz, 2H), 3.43 (dd, J=21.4, 8.2 Hz, 2H), 2.55 (d, J=15.5 Hz, 2H), 1.49 (d, J=9.8 Hz, 2H), 1.37 (s, 2H), 0.99 (s, 3H).

Example 7

Preparation of 4-methyl-1-(3-((2-(trifluoromethyl)pyridin-3-yl)thio)-1H-pyrazolo[3,4-b]pyrazin-6-yl)piperidin-4-amine (Compound 10)

4-methyl-1-(3-((2-(trifluoromethyl)pyridin-3-yl)thio)-1H-pyrazolo[3,4-b]pyrazin-6-yl)piperidin-4-amine was prepared as schematically illustrated below.

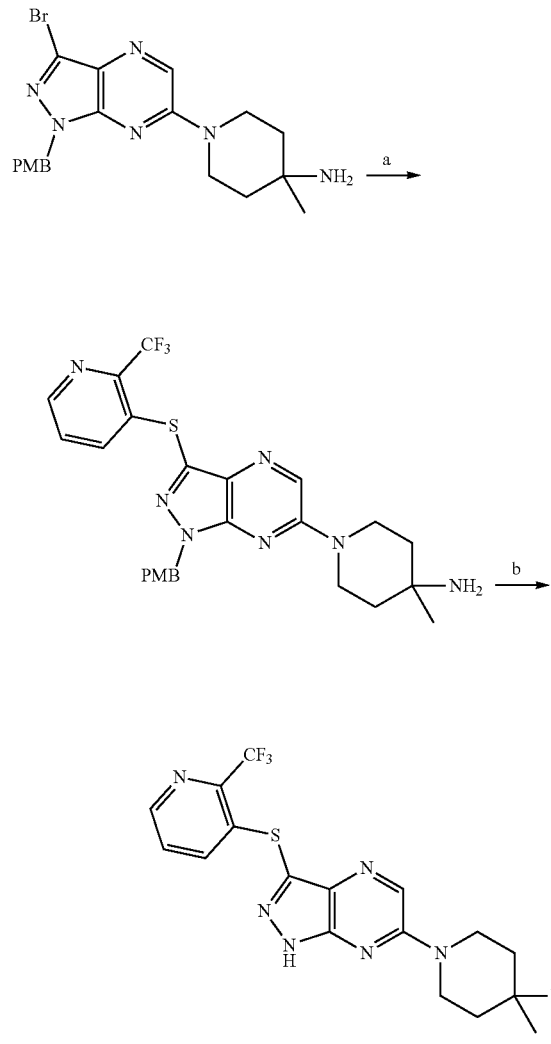

Step a: To a 5 mL vial, 1-(3-bromo-1-(4-methoxybenzyl)-1H-pyrazolo[3,4-b]pyrazin-6-yl)-4-methylpiperidin-4-amine (50 mg, 0.12 mmol), Pd₂dba₃ (53 mg, 0.06 mmol), XantPhos (69 mg, 0.12 mmol), 2-chloro-thiophenol (42 mg, 0.23 mmol) and N,N-diisopropylethylamine (41 μL, 0.23 mmol) are successively added, followed by dioxane (0.3 mL). The resulting mixture is sealed, degassed with N₂ and heated under microwave irradiation at 130° C. for 1 h 30. After full conversion, the volatiles are evaporated under reduced pressure. The resulting residue is purified by reverse phase chromatography (25 to 65% gradient of acetonitrile/10 mM aqueous ammonium formate) to give 1-(1-(4-methoxybenzyl)-3-((2-(trifluoromethyl)pyridin-3-yl)thio)-1H-pyrazolo[3,4-b]pyrazin-6-yl)-4-methylpiperidin-4-amine (32 mg, 52%) as an off-white solid after lyophilization. MS m/z 530.5 [M+H]⁺.

Step b: In a 25-mL round bottomed flask, 1-(1-(4-methoxybenzyl)-3-((2-(trifluoromethyl)pyridin-3-yl)thio)-1H-pyrazolo[3,4-b]pyrazin-6-yl)-4-methylpiperidin-4-amine (32 mg, 0.06 mmol) is slowly dissolved in 33% hydrobromic acid in acetic acid (1 mL), at room temperature. The resulting yellow-orange mixture is then placed in a preheated oil bath at 70° C. and stirred at this temperature for 1 h. After this time, the mixture is allowed to cool to room temperature. The mixture is slowly dropped into diethyl ether (20 mL). The yellow/orange precipitate formed is filtered through a piece of cotton. The gummy residue is redissolved in water (3-4 mL), loaded on a reverse phase chromatography column and purified using a gradient of acetonitrile/0.1% formic acid in water (0 to 50%) to give 4-methyl-1-(3-((2-(trifluoromethyl)pyridin-3-yl)thio)-1H-pyrazolo[3,4-b]pyrazin-6-yl)piperidin-4-amine (16 mg, 65%) as an off-white solid. MS m/z 410.2 [M+H]⁺. ¹H NMR (500 MHz, DMSO) δ 8.52-8.49 (m, 1H), 8.43 (s, 1H), 8.37 (s, 1H), 7.53-7.46 (m, 2H), 3.90-3.79 (m, 2H), 3.76-3.64 (m, 2H), 1.68-1.52 (m, 4H), 1.22 (s, 3H).

Example 8

Preparation of 1-(3-((2,3-dichlorophenyl)thio)-1H-pyrazolo[3,4-b]pyrazin-6-yl)-4-methylpiperidin-4-amine (Compound 11)

1-(3-((2,3-dichlorophenyl)thio)-1H-pyrazolo[3,4-b]pyrazin-6-yl)-4-methylpiperidin-4-amine was prepared as schematically illustrated below.

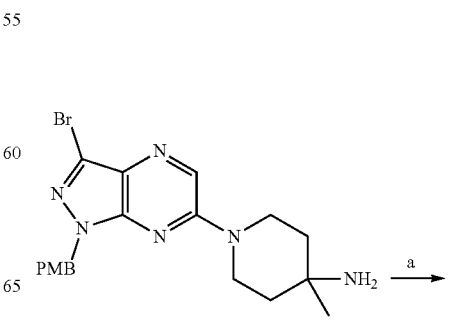

-continued

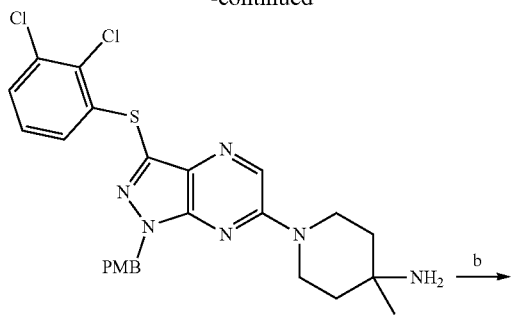

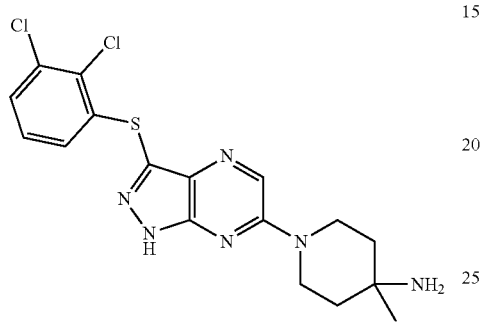

Step a: To a 5 mL vial, 1-(3-bromo-1-(4-methoxybenzyl)-1H-pyrazolo[3,4-b]pyrazin-6-yl)-4-methylpiperidin-4-amine (70 mg, 0.16 mmol), Pd$_2$dba$_3$ (15 mg, 0.02 mmol), XantPhos (19 mg, 0.03 mmol), 2,3-dichlorothiophenol (35 mg, 0.20 mmol) and N,N-diisopropylethylamine (57 µL, 0.33 mmol) are successively added, followed by dioxane (0.3 mL). The resulting mixture is sealed, degassed with N$_2$ and heated under microwave irradiation at 130° C. for 1 h 30. After full conversion, the mixture is filtered over a pad of celite. The cake is washed with EtOAc (20 mL) and filtrate is concentrated under reduced pressure. The resulting residue is purified by reverse phase chromatography (35 to 75% gradient of acetonitrile/10 mM aqueous ammonium formate) to give 1-(3-((2,3-dichlorophenyl)thio)-1-(4-methoxybenzyl)-1H-pyrazolo[3,4-b]pyrazin-6-yl)-4-methylpiperidin-4-amine (45 mg, 52%) as a pale orange solid after lyophilization. MS m/z 529.4 [M+H]$^+$.

Step b: In a 25-mL round bottomed flask 1-(3-((2,3-dichlorophenyl)thio)-1-(4-methoxybenzyl)-1H-pyrazolo[3,4-b]pyrazin-6-yl)-4-methylpiperidin-4-amine (45 mg, 0.08 mmol) is slowly dissolved in 33% hydrobromic acid in acetic acid (2 mL), at room temperature. The resulting yellow-orange mixture is then placed in a preheated oil bath at 70° C. and stirred at this temperature for 1 h. After this time, the mixture is allowed to cool to room temperature. The mixture is slowly dropped into diethyl ether (20 mL). The yellow/orange precipitate formed is filtered through a piece of cotton. The gummy residue is redissolved in water (3-4 mL), loaded on a reverse phase chromatography column and purified using a gradient of acetonitrile/0.1% formic acid in water (0 to 55%) to give 1-(3-((2,3-dichlorophenyl)thio)-1H-pyrazolo[3,4-b]pyrazin-6-yl)-4-methylpiperidin-4-amine (27 mg, 77%) as a pale yellow solid. MS m/z 409.2 [M+H]$^+$. $^1$H NMR (500 MHz, DMSO) δ 8.44 (s, 1H), 8.32 (s, 1H), 7.44 (dd, J=8.0, 1.4 Hz, 1H), 7.21-7.06 (m, 1H), 6.70 (dd, J=8.1, 1.4 Hz, 1H), 4.02-3.87 (m, 2H), 3.71-3.59 (m, 2H), 1.74-1.59 (m, 4H), 1.27 (s, 3H).

Example 9

Preparation of 6-(4-amino-4-methylpiperidin-1-yl)-N-(2-chloropyridin-3-yl)-1H-pyrazolo[3,4-b]pyrazin-3-amine (Compound 12)

6-(4-amino-4-methylpiperidin-1-yl)-N-(2-chloropyridin-3-yl)-1H-pyrazolo[3,4-b]pyrazin-3-amine was prepared as schematically illustrated below.

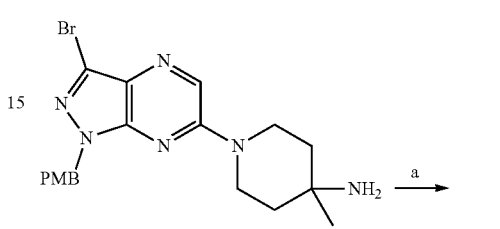

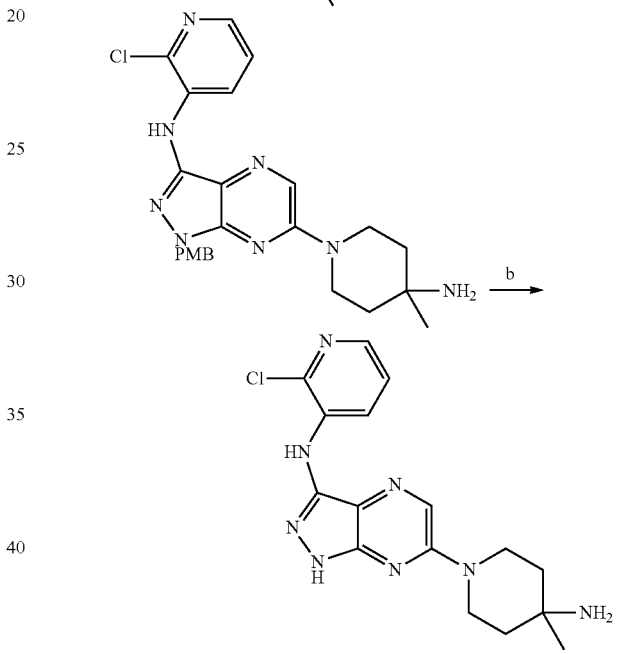

Step a: To a 5 mL vial, 1-(3-bromo-1-(4-methoxybenzyl)-1H-pyrazolo[3,4-b]pyrazin-6-yl)-4-methylpiperidin-4-amine (70 mg, 0.162 mmol), tBuXPhos Pd G1 (11.2 mg, 10 mol %), 2-chloropyridin-3-amine (63 mg, 0.487 mmol) and sodium tert-butoxide (31 mg, 0.3246 mmol) are successively added, followed by degassed toluene (0.8 mL). The resulting mixture is sealed, degassed with N$_2$ and heated at 100° C. overnight. After full conversion, the volatiles are evaporated under reduced pressure. The crude residue is purified by flash chromatography (0 to 100% gradient of methanol/dichloromethane) to give 6-(4-amino-4-methylpiperidin-1-yl)-N-(2-chloropyridin-3-yl)-1-(4-methoxybenzyl)-1H-pyrazolo[3,4-b]pyrazin-3-amine (5 mg, 06%) as an yellow solid. MS m/z 479.2 [M+H]$^+$.

Step b: To a 5 mL vial, 6-(4-amino-4-methylpiperidin-1-yl)-N-(2-chloropyridin-3-yl)-1-(4-methoxybenzyl)-1H-pyrazolo[3,4-b]pyrazin-3-amine (5 mg, 0.0130 mmol) is slowly dissolved in 33% hydrobromic acid in acetic acid (1 mL), at 0-4° C. The resulting yellow-orange mixture is stirred at this temperature for 5 min and heated to 80° C. for 4 hours. Diethyl ether (2.5 mL) was then added to the mixture. The liquid is removed and the precipitate formed is triturated with diethyl ether (2 mL). The crude residue is purified by reverse phase chromatography (0 to 50% gradient of acetonitrile/10 mM aqueous ammonium formate) to 6-(4-amino-4-methylpiperidin-1-yl)-N-(2-chloropyridin-3-yl)-1H-pyrazolo[3,4-b]pyrazin-3-amine (1.3 mg, 33%) as an brownish solid after lyophilization. MS m/z 359.2 [M+H]+; 1H NMR (400 MHz, CD3OD) δ 8.69 (dd, J=8.2, 1.6 Hz, 1H), 8.28 (s, 1H), 7.87 (dt, J=5.9, 2.9 Hz, 1H), 7.37-7.30 (m, 1H), 4.30 (dd, J=9.7, 4.4 Hz, 2H), 3.51 (ddd, J=14.1, 9.1, 4.8 Hz, 2H), 1.89 (h, J=9.3 Hz, 4H), 1.51 (s, 3H).

Example 10

Preparation of 4-methyl-1-(3-((1-methyl-1H-imidazol-2-yl)thio)-1H-pyrazolo[3,4-b]pyrazin-6-yl)piperidin-4-amine (Compound 13)

4-methyl-1-(3-((1-methyl-1H-imidazol-2-yl)thio)-1H-pyrazolo[3,4-b]pyrazin-6-yl)piperidin-4-amine was prepared as schematically illustrated below.

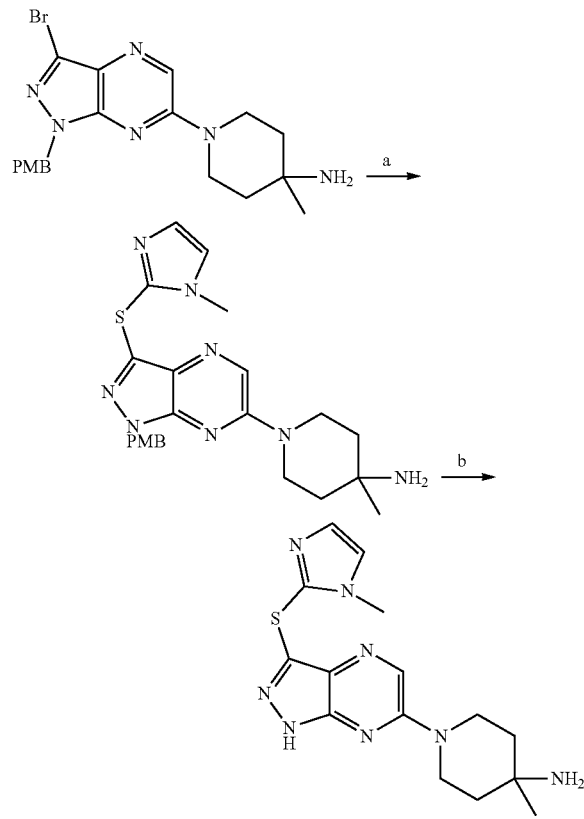

Step a: 1-(3-bromo-1-(4-methoxybenzyl)-1H-pyrazolo[3,4-b]pyrazin-6-yl)-4-methylpiperidin-4-amine (50 mg, 0.12 mmol), 1-methyl-1H-imidazole-2-thiol (40 mg, 0.35 mmol), Pd2(dba)3 (33 mg, 0.06 mmol) and XantPhos (67 mg, 0.12 mmol) were all added to a nitrogen flushed microwave vial. A previously degassed (by sparging) mixture of dioxane (1 mL) and DIPEA (0.04 mL, 0.23 mmol) was added to the flushed microwave vial. The entire mixture was then heated to 110° C. for 1 hour in the microwave. After, the LC-MS showed full conversion to the desired product. This reaction was then filtered over a pad of celite while washing with MeOH and the mixture was concentrated under vacuum. The desired product was purified using reverse phase flash chromatography with a 0-60% gradient of MeCN in 10 mM ammonium formate. This gave 1-(1-(4-methoxybenzyl)-3-((1-methyl-1H-imidazol-2-yl)thio)-1H-pyrazolo[3,4-b]pyrazin-6-yl)-4-methylpiperidin-4-amine as a white solid (31.6 mg, 57% yield) post lyophilization. MS m/z 465.4 [M+H]+.

Step b: To a 10 mL round bottom flask, 4-methyl-1-(3-((1-methyl-1H-imidazol-2-yl)thio)-1H-pyrazolo[3,4-b]pyrazin-6-yl)piperidin-4-amine (31.6 mg, 0.07 mmol) is slowly dissolved in 33% hydrobromic acid in acetic acid (3 mL). The resulting mixture is then heated to 80° C. for 4 hours. Diethyl ether (4 mL) was then added to the mixture to form a yellow precipitate. The liquid is removed and the precipitate formed is triturated with diethyl ether (4 mL). This mixture was concentrated under vacuum The desired product was purified using reverse phase flash chromatography with a 0-60% gradient of MeCN in 10 mM ammonium bicarbonate. This gave 4-methyl-1-(3-((1-methyl-1H-imidazol-2-yl)thio)-1H-pyrazolo[3,4-b]pyrazin-6-yl)piperidin-4-amine as a white solid (12 mg, 52% yield) post lyophilization. MS m/z 345.2 [M+H]+; 1H NMR (400 MHz, DMSO-d6) δ 8.34 (s, 1H), 7.34 (d, J=1.2 Hz, 1H), 6.92 (d, J=1.2 Hz, 1H), 3.81 (m, 2H), 3.73 (s, 3H), 3.65 (m, 2H), 1.45 (m, 4H), 1.09 (s, 3H).

Example 11

Preparation of (4-methyl-1-(3-(1-phenylvinyl)-1H-pyrazolo[3,4-b]pyrazin-6-yl)piperidin-4-yl)methanamine (Compound 14)

(4-methyl-1-(3-(1-phenylvinyl)-1H-pyrazolo[3,4-b]pyrazin-6-yl)piperidin-4-yl)methanamine was prepared as schematically illustrated below.

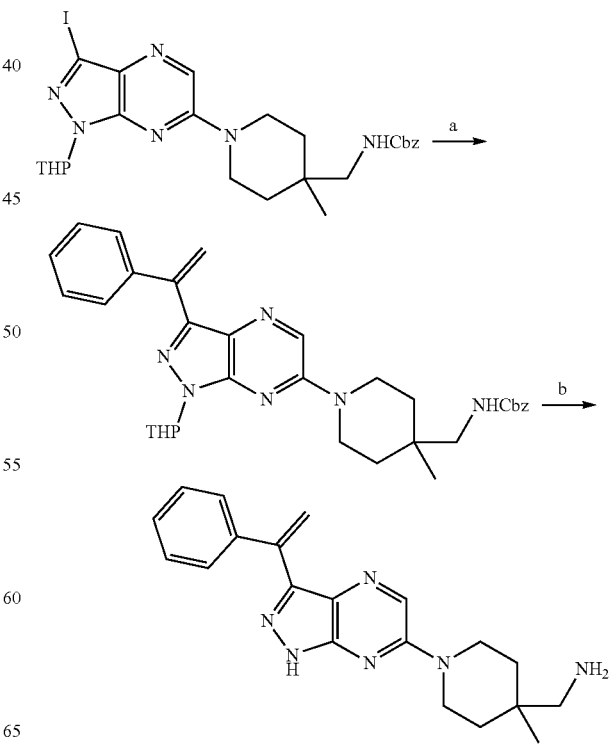

Step a: To a microwave vial, benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (100 mg, 0.17 mmol) is dissolved in acetonitrile (1.7 mL) and the mixture is degassed with N₂ for 10 min. After this time, (1-phenylvinyl)boronic acid (0.038 g, 0.25 mmol), Pd(dppf)Cl₂—CH₂Cl₂ (7.7 mg, 8.47 µmol) and potassium carbonate (70 mg, 0.508 mmol) are added. Vial is sealed and resulting mixture is heated at 120° C. under microwave irradiation for 45 min. The reaction mixture is then concentrated under reduced pressure with silica to give a crude material dry pack and purified by flash chromatography using a gradient of ethyl acetate in hexanes (0 to 100%), affording benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (89 mg, 93%) as a yellow oil. MS m/z 567.5 [M+H]⁺.

Step b: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (40 mg, 0.071 mmol) in acetic acid (2.7 ml) is added very slowly 33% w/w hydrogen bromide in acetic acid (0.8 mL). The resulting mixture is stirred at room temperature for 2 h. After full conversion, diethyl ether is added to the flask to form a precipitate that is isolated by filtration. The crude residue is purified by reverse phase chromatography using a gradient of acetonitrile in 0.1% formic acid in water (0 to 100%) to give (4-methyl-1-(3-(1-phenylvinyl)-1H-pyrazolo[3,4-b]pyrazin-6-yl)piperidin-4-yl)methanamine (16 mg, 57%) as yellow formate salt after lyophilization. MS m/z 349.3 [M+H]⁺; ¹H NMR (500 MHz, DMSO) δ 8.43 (s, 1H), 8.36 (s, 1H), 7.55-7.45 (m, 2H), 7.41-7.29 (m, 3H), 6.47 (d, J=1.7 Hz, 1H), 5.70 (d, J=1.7 Hz, 1H), 3.96 (dt, J=10.0, 4.5 Hz, 2H), 3.47-3.45 (m, 2H), 2.54 (s, J=13.7 Hz, 2H), 1.52 (ddd, J=13.4, 7.0, 3.9 Hz, 2H), 1.37 (dt, J=13.7, 4.0 Hz, 2H), 0.99 (s, 3H).

Example 12

Preparation of (4-methyl-1-(3-(1-phenylethyl)-1H-pyrazolo[3,4-b]pyrazin-6-yl)piperidin-4-yl)methanamine (Compound 15)

(4-methyl-1-(3-(1-phenylethyl)-1H-pyrazolo[3,4-b]pyrazin-6-yl)piperidin-4-yl)methanamine was prepared as schematically illustrated below.

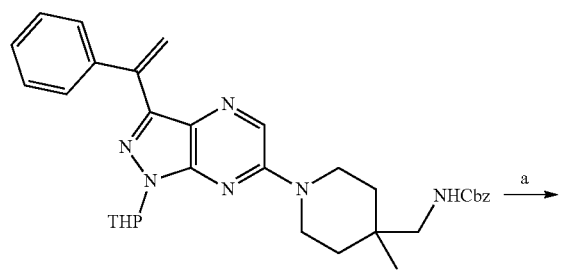

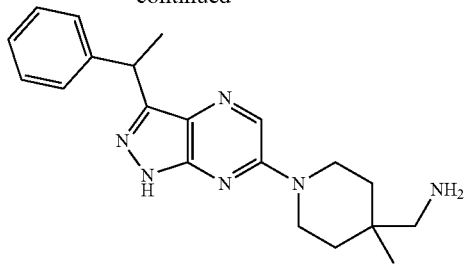

Step a: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (40 mg, 0.071 mmol) in methanol/ethyl acetate (0.7 mL, 1:1 ratio) was added Palladium on Carbon (7.5 mg, 7.06 µmol) and di-tert-butyl dicarbonate (31 mg, 0.141 mmol). Reaction mixture is then hydrogenated under 45 psi of H₂ for 18 h at room temperature. After full conversion, mixture was filtered over a pad of celite, eluted with ethyl acetate. The filtrate is concentrated under reduced pressure, affording tert-butyl ((4-methyl-1-(3-(1-phenylethyl)-1-(tetrahydro-2H-pyran-2-yl)-1H-pyrazolo[3,4-b]pyrazin-6-yl)piperidin-4-yl)methyl)carbamate (36 mg, 95%) as a crude intermediate. MS m/z 535.5 [M+H]⁺.

Step b: To a mixture of tert-butyl ((4-methyl-1-(3-(1-phenylethyl)-1-(tetrahydro-2H-pyran-2-yl)-1H-pyrazolo[3,4-b]pyrazin-6-yl)piperidin-4-yl)methyl)carbamate (0.040 g, 0.075 mmol) in dioxane (0.37 mL) was added hydrogen chloride (4 M in dioxane) (0.94 mL). After stirring for 3 h at room temperature, volatiles are evaporated off under reduced pressure. The crude residue was then purified by reverse phase chromatography using a gradient of acetonitrile in 0.1% formic acid in water (0 to 100%) to give (4-methyl-1-(3-(1-phenylethyl)-1H-pyrazolo[3,4-b]pyrazin-6-yl)piperidin-4-yl)methanamine (11 mg, 37%) as a yellow formate salt after lyophilization. MS m/z 351.4 [M+H]⁺; ¹H NMR (500 MHz, DMSO) δ 8.36 (s, 1H), 8.31 (s, 1H), 7.37 (dd, J=8.2, 1.0 Hz, 2H), 7.25 (t, J=7.6 Hz, 2H), 7.17-7.11 (m, 1H), 4.47 (q, J=7.2 Hz, 1H), 3.96-3.87 (m, 2H), 3.43 (dd, J=13.6, 9.7 Hz, 2H), 2.54 (s, J=12.5 Hz, 2H), 1.72 (d, J=7.3 Hz, 3H), 1.49 (t, J=9.9 Hz, 2H), 1.37-1.30 (m, 2H), 0.98 (s, 3H).

Example 13

Preparation of (6-(4-(aminomethyl)-4-methylpiperidin-1-yl)-1H-pyrazolo[3,4-b]pyrazin-3-yl)(phenyl)methanone (Compound 16)

(6-(4-(aminomethyl)-4-methylpiperidin-1-yl)-1H-pyrazolo[3,4-b]pyrazin-3-yl)(phenyl)methanone was prepared as schematically illustrated below.

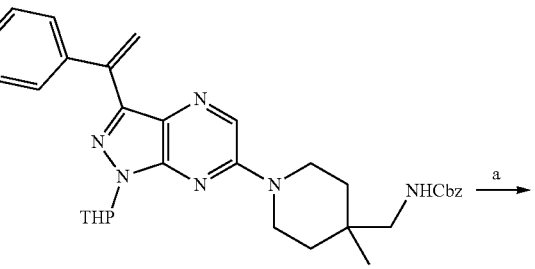

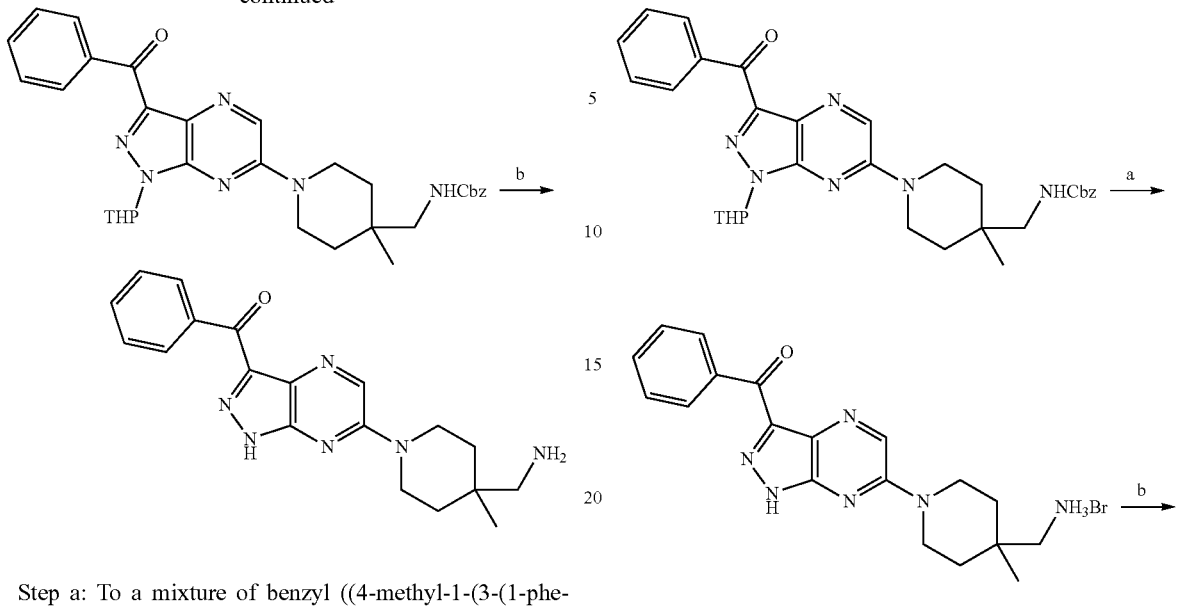

Step a: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (160 mg, 0.282 mmol) in acetonitrile (2.8 mL) was added sodium periodate (302 mg, 1.412 mmol) and osmium(VIII) oxide (90 μL, 0.014 mmol). The resulting mixture is stirred for 15 h at 60° C. The reaction was cooled to room temperature and concentrated under reduced pressure with silica to give a crude material dry pack. This crude material was purified by flash chromatography using a gradient of ethyl acetate in hexanes (0 to 100%) to give benzyl ((1-(3-benzoyl-1-(tetrahydro-2H-pyran-2-yl)-1H-pyrazolo[3,4-b]pyrazin-6-yl)-4-methylpiperidin-4-yl)methyl)carbamate (118 mg, 73%) as a yellow oil. MS m/z 569.5 [M+H]$^+$.

Step b: To a mixture of benzyl ((1-(3-benzoyl-1-(tetrahydro-2H-pyran-2-yl)-1H-pyrazolo[3,4-b]pyrazin-6-yl)-4-methylpiperidin-4-yl)methyl)carbamate (30 mg, 0.053 mmol) in acetic acid (0.53 mL) was added 33% w/w hydrogen bromide in acetic acid (0.60 mL). The resulting mixture is stirred at room temperature for 3 h. After full conversion, reaction mixture was concentrated under reduced pressure and the crude residue was purified by reverse phase chromatography using a gradient of acetonitrile in 0.1% formic acid in water (0 to 100%) to give (6-(4-(aminomethyl)-4-methylpiperidin-1-yl)-1H-pyrazolo[3,4-b]pyrazin-3-yl)(phenyl)methanone (18 mg, 86%) as a yellow formate salt after lyophilization. MS m/z 351.2 [M+H]$^+$; $^1$H NMR (500 MHz, DMSO) δ 8.58 (s, 1H), 8.29 (s, 1H), 8.09 (dd, J=8.4, 1.3 Hz, 2H), 7.70-7.63 (m, 1H), 7.55 (dd, J=7.7 Hz, 2H), 4.01 (dt, J=9.7, 4.6 Hz, 2H), 3.56-3.47 (m, 2H), 2.61 (s, 2H), 1.54 (ddd, J=13.5, 9.6, 3.9 Hz, 2H), 1.48-1.34 (m, 2H), 1.03 (s, 3H).

Example 14

Preparation of 1-(6-(4-(aminomethyl)-4-methylpiperidin-1-yl)-1H-pyrazolo[3,4-b]pyrazin-3-yl)-1-phenylethanol (Compound 17)

1-(6-(4-(aminomethyl)-4-methylpiperidin-1-yl)-1H-pyrazolo[3,4-b]pyrazin-3-yl)-1-phenylethanol was prepared as schematically illustrated below.

Step a: To a mixture of benzyl ((1-(3-benzoyl-1-(tetrahydro-2H-pyran-2-yl)-1H-pyrazolo[3,4-b]pyrazin-6-yl)-4-methylpiperidin-4-yl)methyl)carbamate (30 mg, 0.053 mmol) in acetic acid (0.53 mL) was added 33% w/w hydrogen bromide in acetic acid (0.60 mL). The resulting mixture is stirred at room temperature for 3 h. After full conversion, diethyl ether is added to the flask to form a precipitate that is isolated by filtration as a yellow powder. MS m/z 351.2 [M+H]$^+$.

Step b: To a mixture of (6-(4-(aminomethyl)-4-methylpiperidin-1-yl)-1H-pyrazolo[3,4-b]pyrazin-3-yl)(phenyl)methanone hydrobromide (18 mg, 0.042 mmol) in anhydrous tetrahydrofuran (2 mL) was added methylmagnesium bromide (3 M in diethyl ether) (70 μL, 0.209 mmol). The resulting mixture is stirred for 5 h at room temperature. The reaction was quenched with a sat. aq. NaHCO$_3$ solution (1 mL) and diluted in DMF (1 mL). The mixture is concentrated under reduced pressure to dryness. The resulting crude material was purified by reverse phase chromatography using a gradient of acetonitrile in 0.1% formic acid in water (0 to 100%) to give 1-(6-(4-(aminomethyl)-4-methylpiperidin-1-yl)-1H-pyrazolo[3,4-b]pyrazin-3-yl)-1-phenylethanol (10 mg, 58%) as a yellow powder after lyophilization. MS m/z 367.5 [M+H]$^+$. $^1$H NMR (500 MHz, DMSO) δ 8.34 (s, 1H), 8.31 (s, 1H), 7.50 (dd, J=8.3, 1.1 Hz, 2H), 7.24 (t, J=7.7 Hz, 2H), 7.14 (t, J=7.3 Hz, 1H), 5.61 (s, 1H), 3.91 (dd, J=13.5, 4.9 Hz, 2H), 2.55 (s, 2H), 1.96 (s, 14.4 Hz, 3H), 1.54-1.42 (m, 2H), 1.34 (d, J=13.9 Hz, 2H), 0.98 (s, J=20.3 Hz, 3H).

Example 15

Preparation of (1-(3-benzyl-1H-pyrazolo[3,4-b]pyrazin-6-yl)-4-methylpiperidin-4-yl)methanamine (Compound 18)

(1-(3-benzyl-1H-pyrazolo[3,4-b]pyrazin-6-yl)-4-methylpiperidin-4-yl)methanamine was prepared as schematically illustrated below.

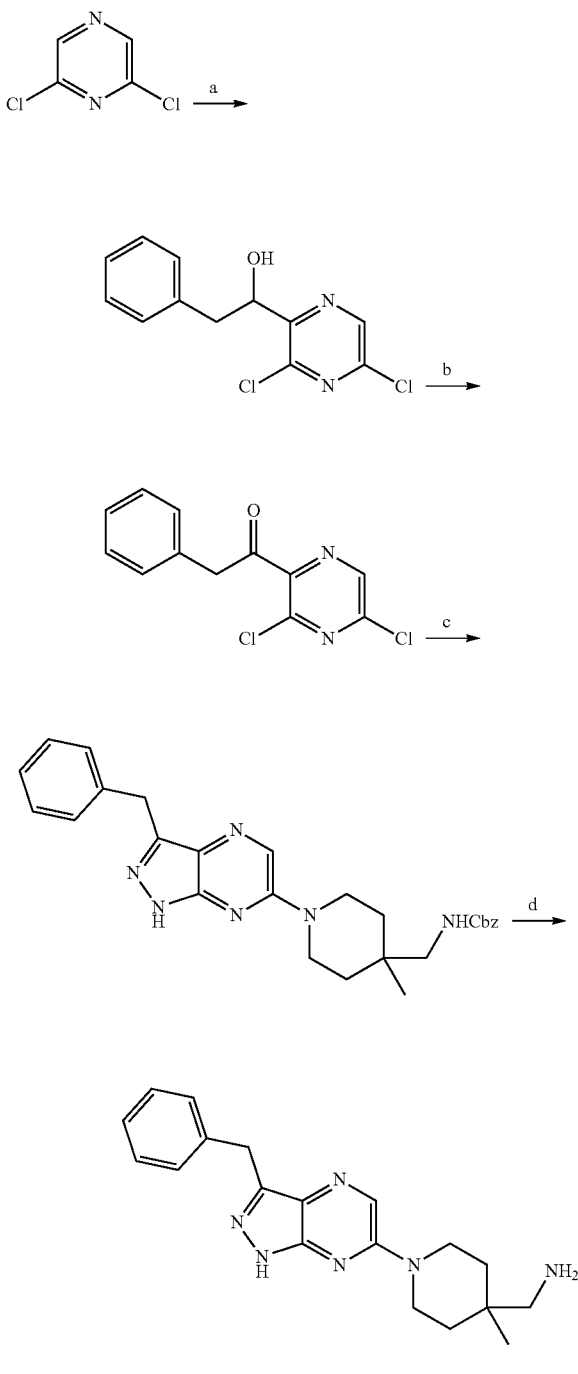

Step a: To a cold (−78° C.) solution of 2,2,6,6-tetramethylpiperidine (1.46 mL, 8.7 mmol) in THF (67 mL) was added n-BuLi (2.5 M, 3.2 mL, 8.1 mmol), then the mixture was warmed up to 0° C. and stirred for 30 min. The mixture was cooled down to −78° C. and 2,6-dichloropyrimidine (1.0 g, 6.7 mmo) in THF (3 mL) was added dropwise to the mixture. After stirring at −78° C. for 30 min, a solution of 2-phenylacetaldehyde (1.2 mL, 10.1 mmol) was added to the mixture and stirred at −78° C. for 3 h and allowed to warmed-up. The reaction mixture was diluted with saturated aqueous ammonium chloride solution then extracted with dichloromethane. The organic layer was dried over magnesium sulfate, filtered and evaporated off. The resulting residue was purified by column chromatography on silica gel (AcOEt hexane) to give alcohol 1-(3,5-dichloropyrazin-2-yl)-2-phenylethanol (595 mg, 33%) as an orange oil. MS (ES+) m/z 251.1 $[M-H_2O]^+$.

Step b: In a round bottom flask, (1-(3,5-dichloropyrazin-2-yl)-2-phenylethanol (160 mg, 0.60 mmol) was dissolved with dichloromethane (3 mL). DessMartin periodinane (322 mg, 0.82 mmol) was added and the mixture was stirred until completion. An aqueous solution of $NaHCO_3$ and $Na_2S_2O_3$ was then added. The mixture was stirred until the white solid went into the aqueous phase. The aqueous layer was extracted with DCM two more times. The combined organic extract was dried over magnesium sulfate, filtered and evaporated off, affording 1-(3,5-dichloropyrazin-2-yl)-2-phenylethanone (89 mg, 56%) as an yellow solid. MS (ES+) m/z 267.0 $[M+H]^+$.

Step c: To a solution (1-(3,5-dichloropyrazin-2-yl)-2-phenylethanone (89 mg, 0.33 mmol) in DMAc (1.5 mL) was slowly added benzyl ((4-methylpiperidin-4-yl)methyl)carbamate (87 mg, 0.33 mmol) at 0-5° C., and finally cesium fluoride (152 mg, 1.0 mmol) was added. The mixture was stirred at 75° C. for 3 hr. Then, hydrazine monohydrate (470 μL, 1.0 mmol) was slowly added at 0-5° C. (exothermic). After complete addition, the reaction mixture was heated at 90° C. for 1-5 h. The reaction mixture was cooled to 0° C., and water (10 mL) and EtOAc (10 mL) were added. After phase separation, the aqueous layer was extracted with EtOAc (10 mL). The combined organic layers were washed with water (10 mL), brine (10 mL), dried over magnesium sulfate and concentrated. The residue was purified by chromatography on silica gel (hexane/EtOAc=1:1, 1:3) to afford desired product benzyl ((1-(3-benzyl-1H-pyrazolo[3,4-b]pyrazin-6-yl)-4-methylpiperidin-4-yl)methyl)carbamate (53 mg, 32%) as a yellow foam. $^1$H NMR (500 MHz, DMSO-$d_6$) δ 12.75 (s, 1H), 8.32 (s, 1H), 7.37-7.27 (m, 7H), 7.27-7.22 (m, 2H), 7.18-7.13 (m, 1H), 5.02 (s, 2H), 4.15 (s, 2H), 3.95-3.84 (m, 2H), 3.52-3.41 (m, 2H), 2.96 (d, J=6.4 Hz, 2H), 1.50-1.41 (m, 2H), 1.34-1.25 (m, 2H), 0.93 (s, 3H). MS (ES+) m/z 471.2 $[M+H]^+$.

Step d: HBr in acid acetic (33% wt %, 1.0 mL) was added dropwise to benzyl ((1-(3-benzyl-1H-pyrazolo[3,4-b]pyrazin-6-yl)-4-methylpiperidin-4-yl)methyl)carbamate (50 mg, 0.11 mmol). The mixture was stirred for 1 hr at room temperature. The reaction mixture was diluted in DMF and water and evaporated off affording a yellow oil, which was diluted in DMF and purified by reverse phase chromatography (C18, 0 to 80% gradient of MeCN/(10 mM $NH_4HCO_3$ in water, pH 10) to give (1-(3-benzyl-1H-pyrazolo[3,4-b]pyrazin-6-yl)-4-methylpiperidin-4-yl)methanamine (28 mg, 78%) as a white solid. $^1$H NMR (500 MHz, DMSO-d6+ $D_2O$) δ 8.26 (s, 1H), 7.31-7.27 (m, 2H), 7.27-7.21 (m, 2H), 7.17-7.11 (m, 1H), 4.13 (s, 2H), 3.45-3.35 (m, 2H), 2.43 (s, 2H), 1.48-1.37 (m, 2H), 1.36-1.29 (m, 2H), 0.94 (s, 3H). MS (ES+) m/z 337.2 $[M+H]^+$.

Example 16

Following synthetic procedures similar to those described herein, the following compounds were prepared.

| Compound | Structure | ¹H NMR | LCMS |
|---|---|---|---|
| 19 | 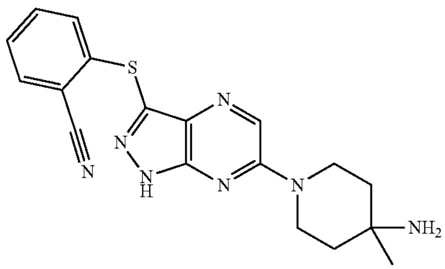 [SMILES: CC1(N)CCN(c2cnc3c(Sc4ccccc4C#N)n[nH]c3n2)CC1] | | |
| 20 | 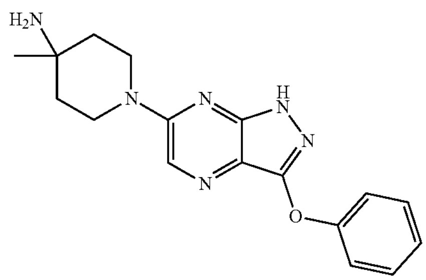 [SMILES: CC1(N)CCN(c2cnc3c(Oc4ccccc4)n[nH]c3n2)CC1] | (400 MHz, CD₃OD): δ 8.28 (s, 1H), 7.30-7.37 (m, 2H), 7.10-7.20 (m, 3H), 4.20-4.40 (m, 2H), 3.40-3.60 (m, 2H), 1.75-2.00 (m, 4H), 1.52 (s, 3H). | 324.9 |
| 21 | 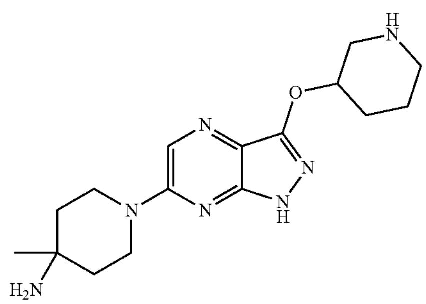 [SMILES: CC1(N)CCN(c2cnc3c(OC4CCCNC4)n[nH]c3n2)CC1] | (400 MHz, CD₃OD): δ 8.39 (s, 1H), 5.38 (s, 1H), 4.34 (d, J = 14.0 Hz, 2H), 3.70-3.48 (m, 5H), 3.28-3.20 (m, 1H), 2.24-1.88 (m, 8H), 1.55 (s, 3H). | 332.1 |
| 22 | 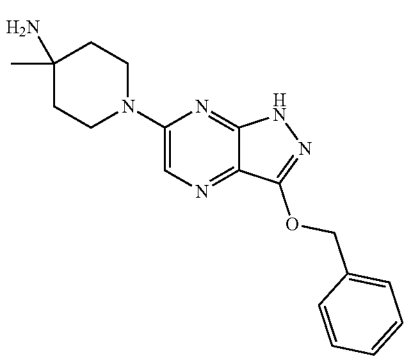 [SMILES: CC1(N)CCN(c2cnc3c(OCc4ccccc4)n[nH]c3n2)CC1] | (400 MHz, DMSO_d₆): δ 12.05 (s, 1H), 8.26 (s, 1H), 7.31-7.52 (m, 5H), 5.38 (s, 2H), 3.82-3.87 (m, 2H), 3.57-3.64 (m, 2H), 1.42-1.49 (m, 4H), 1.09 (s, 3H). | 339.0 |
| 23 | 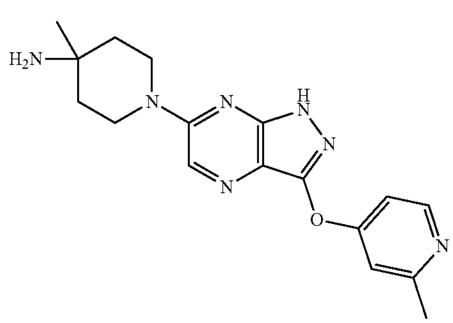 [SMILES: Cc1cc(Oc2n[nH]c3nc(N4CCC(C)(N)CC4)cnc23)ccn1] | (400 MHz, DMSO-d6): δ ppm 8.30-8.35 (m, 2H), 6.95 (d, J = 2.20 Hz, 1H), 6.89 (dd, J = 5.74, 2.32 Hz, 1H), 6.65 (br s, 1H), 3.88 (dt, J = 13.31, 4.58 Hz, 2H), 3.61 (ddd, J = 13.18, 8.91, 4.27 Hz, 2H), 2.40 (s, 3H), 1.40-1.50 (m, 4H), 1.08 (s, 3H). | 340.2 |

| Compound | Structure | ¹H NMR | LCMS |
|---|---|---|---|
| 24 | 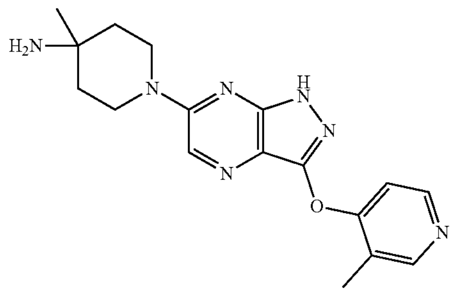 [SMILES: Cc1cnccc1Oc1n[nH]c2nc(N3CCC(C)(N)CC3)cnc12] | | 340.2 |
| 25 | 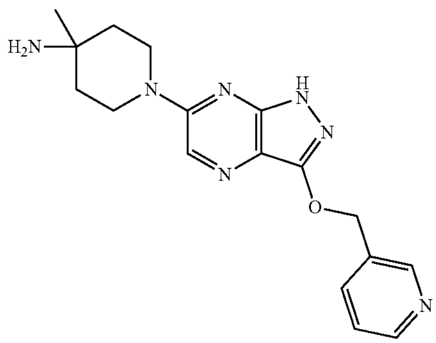 [SMILES: CC1(N)CCN(c2cnc3c(OCc4cccnc4)n[nH]c3n2)CC1] | (400 MHz, DMSO-d6): δ 12.12 (br s, 1H), 8.70 (d, J = 1.46 Hz, 1H), 8.51-8.57 (m, 1H), 8.33 (s, 1H), 8.26 (s, 1H), 7.91 (br d, J = 7.81 Hz, 1H), 7.42 (dd, J = 4.88, 7.81 Hz, 1H), 5.42 (s, 2H), 3.77-3.90 (m, 2H). 3.58-3.71 (m, 2H), 1.58 (br t, J = 5.25 Hz, 4H), 1.21 (s, 3H). | 340.2 |
| 26 | 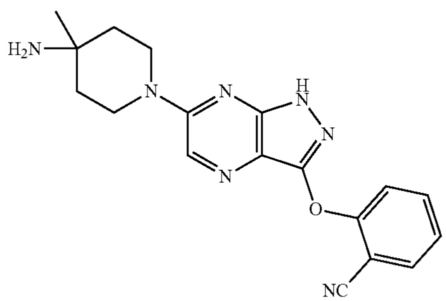 [SMILES: CC1(N)CCN(c2cnc3c(Oc4ccccc4C#N)n[nH]c3n2)CC1] | (400 MHz, DMSO-d6): δ 12.64-12.87 (m, 1H), 8.36 (d, J = 5.13 Hz, 2H), 7.90 (d, J = 7.57 Hz, 1H), 7.65 (t, J = 8.06 Hz, 1H), 7.32 (t, J = 7.57 Hz, 1H), 7.20 (d, J = 8.54 Hz, 1H), 6.62-6.90 (m, 1H), 3.76 (br s, 4H), 1.54 (br s, 4H), 1.16 (s, 3H). | 350.2 |
| 27 | 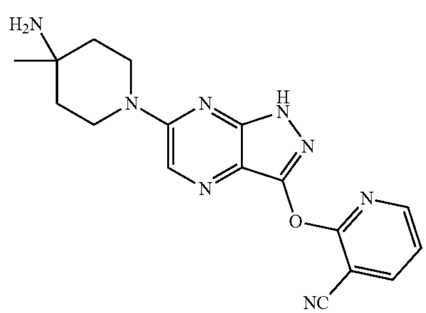 [SMILES: CC1(N)CCN(c2cnc3c(Oc4ncccc4C#N)n[nH]c3n2)CC1] | (400 MHz, DMSO-$d_6$): δ 12.92 (s, 1H), 8.49 (dd, J = 1.95, 7.57 Hz, 1H), 8.32-8.40 (m, 2H), 7.89 (br s, 2H), 7.40 (dd, J = 5.00, 7.69 Hz, 1H), 6.51 (s, 1H), 4.11-4.21 (m, 2H), 3.43 (td, J = 6.74, 14.10 Hz, 2H), 1.70-1.79 (m, 3H), 1.38 (s, 2H). | 351.2 |
| 28 | 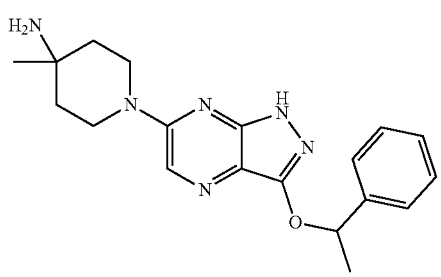 [SMILES: CC(Oc1n[nH]c2nc(N3CCC(C)(N)CC3)cnc12)c1ccccc1] | (400 MHz, DMSO_$d_6$): δ 11.94 (s, 1H), 8.24 (s, 1H), 7.46-7.43 (m, 2H), 7.36-7.31 (m, 2H), 7.28-7.25 (m, 1H), 6.03-5.97 (m, 1H), 3.83-3.79 (m, 2H), 3.64-3.61 (m, 2H), 1.64-1.61 (m, 3H), 1.49-1.40 (m, 4H), 1.08 (s, 3H). | 353.1 |

| Compound | Structure | ¹H NMR | LCMS |
|---|---|---|---|
| 29 | 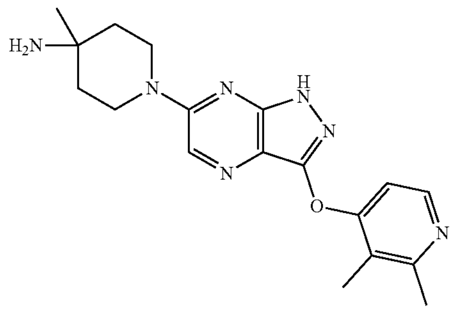 [SMILES: Cc1nccc(Oc2n[nH]c3nc(N4CCC(C)(N)CC4)cnc23)c1C] | (400 MHz, DMSO-d6): δ ppm 8.32 (s, 1H), 8.08 (d, J = 5.61 Hz, 1H), 6.67 (d, J = 5.62 Hz, 1H), 3.87 (dt, J = 13.18, 4.52 Hz, 2H), 3.60 (ddd, J = 13.18, 8.79, 4.15 Hz, 2H), 2.47 (s, 3H), 2.26 (s, 3 H), 1.39-1.50 (m, 4H), 1.07 (s, 3 H). | 354.2 |
| 30 | 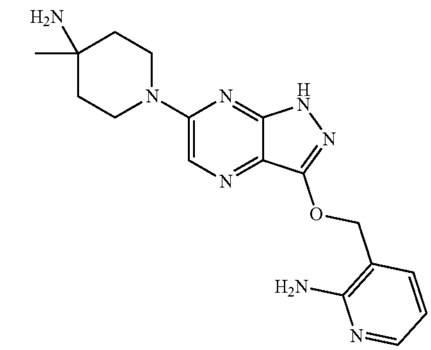 [SMILES: CC1(N)CCN(c2cnc3c(OCc4cccnc4N)n[nH]c3n2)CC1] | (400 MHz, CD₃OD): δ 8.20 (s, 1H), 7.93-7.95 (m, 1H), 7.68-7.71 (m, 1H), 6.67-6.71 (m, 1H), 5.39 (s, 2H), 3.92-3.98 (m, 2H), 3.68-3.74 (m, 2H), 1.65-1.75 (m, 4H), 1.29 (s, 3H). | 354.9 |
| 31 | 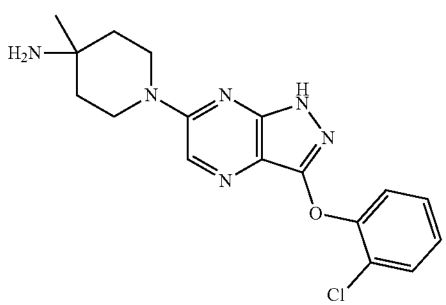 [SMILES: CC1(N)CCN(c2cnc3c(Oc4ccccc4Cl)n[nH]c3n2)CC1] | (400 MHz, DMSO-d6): δ 12.58 (br s, 1H), 8.38 (s, 1H), 7.54-7.60 (m, 1H), 7.27-7.35 (m, 1H), 7.16-7.24 (m, 2H), 6.53 (s, 1H), 4.07-4.19 (m, 2H), 3.41-3.50 (m, 2H), 1.74 (br t, J = 5.25 Hz, 4H), 1.37 (s, 3H). | 359.2 |
| 32 | 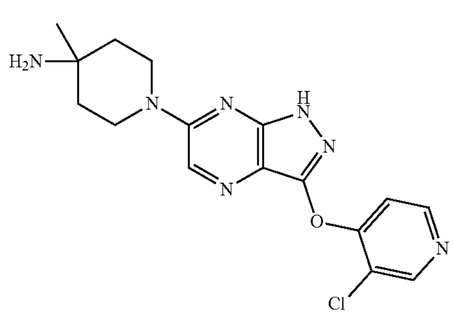 [SMILES: CC1(N)CCN(c2cnc3c(Oc4ccncc4Cl)n[nH]c3n2)CC1] | (400 MHz, DMSO-d6): δ 12.96 (s, 1H), 8.71 (s, 1H), 8.42 (s, 1H), 8.38 (d, J = 5.62 Hz, 1H), 7.98 (br s, 2H), 7.09 (d, J = 5.62 Hz, 1H), 4.11-4.21 (m, 2H), 3.45 (td, J = 6.77, 13.79 Hz, 2H), 1.76 (br t, J = 5.25 Hz, 4H), 1.38 (s, 3H). | 359.9 |

-continued

| Compound | Structure | ¹H NMR | LCMS |
|---|---|---|---|
| 33 | 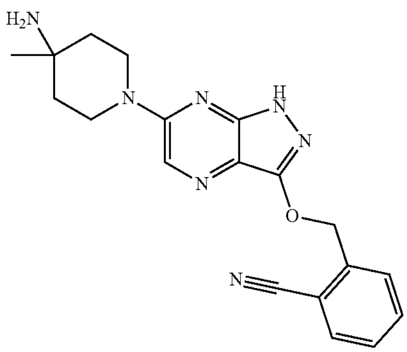 [SMILES: CC1(N)CCN(c2cnc3c(OCc4ccccc4C#N)n[nH]c3n2)CC1] | (400 MHz, DMSO-d$_6$): δ 12.11 (br, 1H), 8.27 (s, 1H), 7.92 (d, J = 7.6 Hz, 1H), 7.77-7.76 (m, 2H), 7.60-7.58 (m, 1H), 5.55 (s, 2H), 3.87-3.83 (m, 2H), 3.64-3.60 (m, 2H), 1.50-1.41 (m, 4H), 1.08 (s, 3H). | 364.0 |
| 34 | 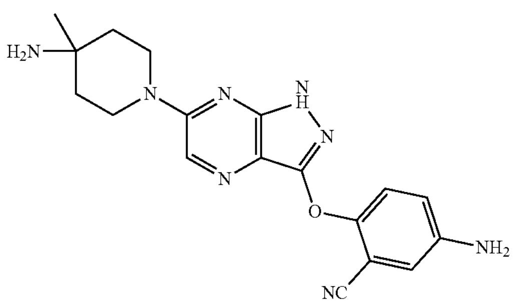 [SMILES: CC1(N)CCN(c2cnc3c(Oc4ccc(N)cc4C#N)n[nH]c3n2)CC1] | (400 MHz, DMSO-d6): δ 12.28-12.67 (m, 1H), 8.39 (s, 1H), 8.34 (s, 1H), 7.01 (d, J = 8.79 Hz, 1H), 6.86 (d, J = 2.69 Hz, 1H), 6.82 (dd, J = 2.81, 8.91 Hz, 1H), 5.43 (br s, 2H), 3.65-3.82 (m, 4H), 1.56 (br t, J = 5.37 Hz, 4H), 1.18 (s, 3H). | 365.2 |
| 35 | 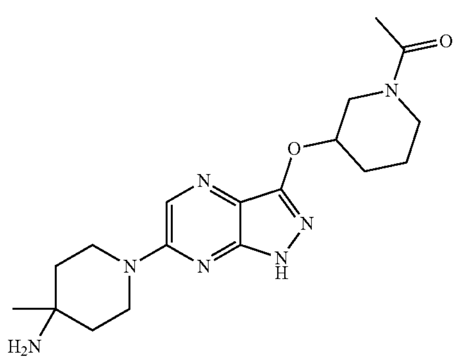 [SMILES: CC(=O)N1CCCC(Oc2n[nH]c3nc(N4CCC(C)(N)CC4)cnc23)C1] | (400 MHz, CD$_3$OD): δ 8.48 (d, J = 16.0 Hz, 1H), 5.42 (d, J = 46.4 Hz, 1H), 4.40-4.36 (m, 2H), 4.05-3.91 (m, 2H), 3.63-3.37 (m, 4H), 2.20-1.97 (m, 10H), 1.75-1.68 (m, 1H), 1.56 (s, 3H). | 374.1 |
| 36 | 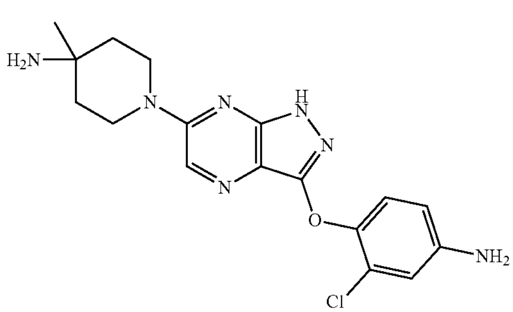 [SMILES: CC1(N)CCN(c2cnc3c(Oc4ccc(N)cc4Cl)n[nH]c3n2)CC1] | (400 MHz, DMSO-d6): δ 12.24 (br d, J = 4.64 Hz, 1H), 8.40 (s, 1H), 8.31 (s, 1H), 6.96 (d, J = 8.79 Hz, 1H), 6.66 (d, J = 2.69 Hz, 1H), 6.47 (dd, J = 2.69, 8.79 Hz, 1H), 5.24 (br s, 2H), 3.75-3.86 (m, 2H), 3.64-3.74 (m, 2H), 1.56 (br t, J = 5.37 Hz, 4H), 1.19 (s, 3H). | 374.3 |

-continued

| Compound | Structure | ¹H NMR | LCMS |
|---|---|---|---|
| 37 | 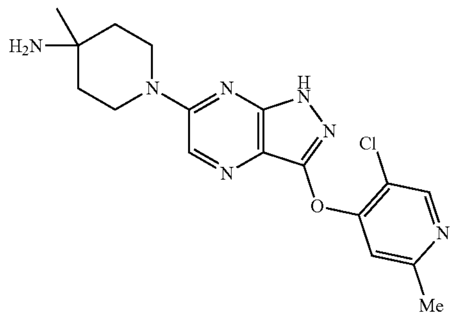 [SMILES: Cc1cc(Oc2n[nH]c3nc(N4CCC(C)(N)CC4)cnc23)c(Cl)cn1] | (400 MHz, DMSO-d₆) δ 8.48-8.60 (m, 1 H), 8.40 (s, 1 H), 8.25 (br s, 2 H), 6.95 (s, 1 H), 3.97 (br d, J = 13.67 Hz, 2 H), 3.51-3.70 (m, 2 H), 3.16 (s, 3 H), 1.67 (br s, 4 H), 1.28 (s, 3 H). | 374.2 |
| 38 | 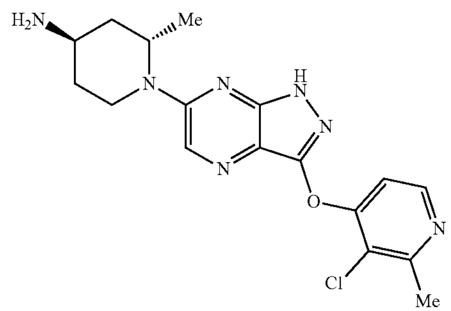 | (400 MHz, CD₃OD) δ 8.33 (d, J = 13.76 Hz, 2 H), 8.19 (d, J = 5.67 Hz, 1 H), 6.83-7.00 (m, 1 H), 5.01-5.18 (m, 1 H), 4.60 (br d, J = 13.76 Hz, 1 H), 3.67 (tt, J = 12.25, 4.08 Hz, 1 H), 3.21-3.28 (m, 1 H), 2.59-2.77 (m, 3 H), 2.13-2.28 (m, 1 H), 2.07 (dt, J = 12.55, 2.09 Hz, 1 H), 1.83 (td, J = 12.68, 5.40 Hz, 1 H), 1.56-1.71 (m, 1 H), 1.34 (d, J = 7.02 Hz, 3 H). | 374.3 |
| 39 | 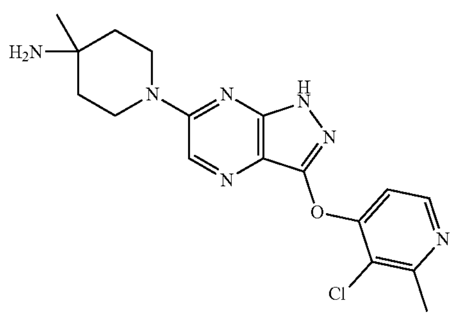 [SMILES: Cc1nccc(Oc2n[nH]c3nc(N4CCC(C)(N)CC4)cnc23)c1Cl] | (400 MHz, DMSO-d6): δ ppm 8.39 (s, 1H), 8.26 (br s, 1H), 8.23 (d, J = 5.62 Hz, 1H), 6.90 (d, J = 5.62 Hz, 1H), 3.94-4.03 (m, 2H), 3.54-3.64 (m, 2H), 2.60 (s, 3H), 1.66 (br t, J = 5.25 Hz, 4H), 1.29 (s, 3H). | 374.2 |
| 40 | 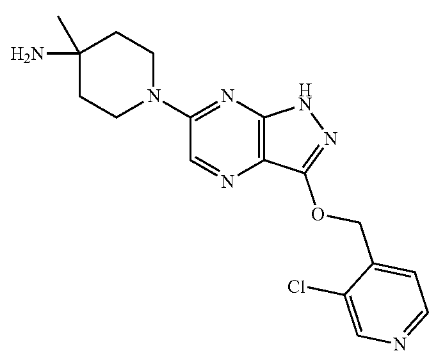 [SMILES: CC1(N)CCN(c2cnc3c(OCc4ccncc4Cl)n[nH]c3n2)CC1] | (400 MHz, DMSO-d6): δ 12.22 (s, 1H), 8.66 (s, 1H), 8.54 (d, J = 4.88 Hz, 1H), 8.34 (s, 1H), 7.91 (br s, 3H), 7.56 (d, J = 4.88 Hz, 1H), 6.52 (br s, 1H), 5.54 (s, 2H), 4.05-4.22 (m, 2H), 3.38-3.48 (m, 2H), 1.74 (br t, J = 5.25 Hz, 4H), 1.37 (s, 3H). | 374.2 |
| 41 | 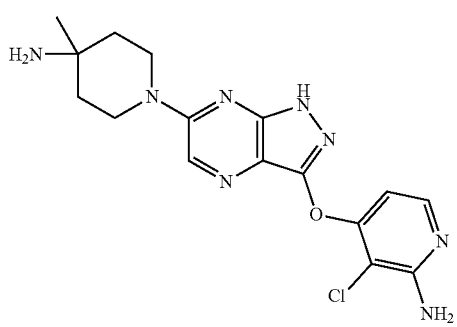 [SMILES: CC1(N)CCN(c2cnc3c(Oc4ccnc(N)c4Cl)n[nH]c3n2)CC1] | (400 MHz, DMSO-d6): δ 12.90 (s, 1H), 8.42 (s, 1H), 7.94 (br s, 2H), 7.76 (d, J = 6.10 Hz, 1H), 6.81 (br s, 2H), 6.22 (d, J = 6.10 Hz, 1H), 4.10-4.22 (m, 2H), 3.44 (td, J = 6.71, 13.92 Hz, 2H), 1.75 (br t, J = 5.13 Hz, 4H), 1.38 (s, 3H). | 375.2 |

| Compound | Structure | ¹H NMR | LCMS |
|---|---|---|---|
| 42 | 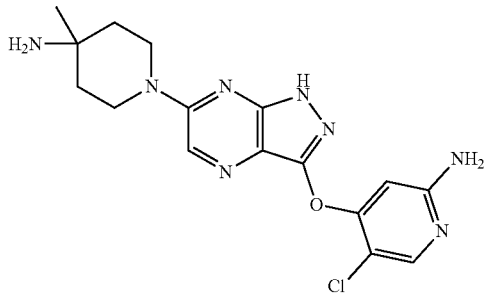 [SMILES: CC1(N)CCN(c2cnc3c(Oc4cc(N)ncc4Cl)n[nH]c3n2)CC1] | (400 MHz, DMSO-d6): δ 13.01 (s, 1H), 8.45 (s, 1H), 8.06 (s, 1H), 7.96 (br s, 2H), 6.58 (br dd, J = 6.35, 13.92 Hz, 2H), 6.10 (s, 1H), 4.12-4.20 (m, 2H), 3.45 (td, J = 6.62, 13.85 Hz, 2H), 1.76 (br t, J = 5.13 Hz, 4H), 1.38 (s, 3H). | 375.1 |
| 43 | 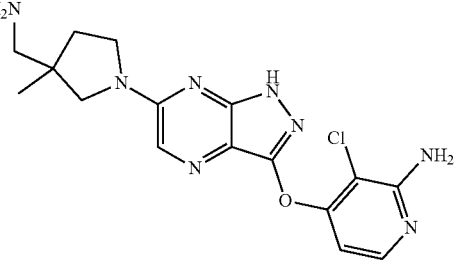 | (400 MHz, DMSO-d₆): δ 13.08 (br, 1H), 8.19 (br, 3H), 8.01 (s, 1H), 7.96-7.94 (d, J = 6.8 Hz, 1H), 6.60-6.57 (d, J = 7.6 Hz, 1H), 3.68-3.65 (m, 3H), 3.41-3.37 (m, 1H), 2.92 (s, 2H), 2.06-2.04 (m, 1H), 1.88-1.86 (m, 1H), 1.19 (s, 3H). | 375.1 |
| 44 | 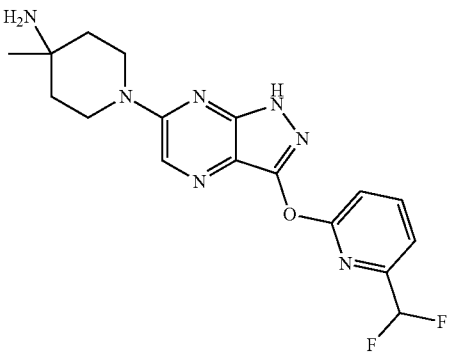 [SMILES: CC1(N)CCN(c2cnc3c(Oc4cccc(C(F)F)n4)n[nH]c3n2)CC1] | (400 MHz, DMSO-d6): δ ppm 12.78 (br s, 1 H), 8.35 (s, 1 H), 8.07 (t, J = 7.81 Hz, 1 H), 7.48 (d, J = 7.32 Hz, 1 H), 7.33 (br d, J = 8.30 Hz, 1 H), 6.87 (s, 1 H), 6.73 (s, 1 H), 6.59 (s, 1 H), 6.53 (s, 1 H), 4.09 (br d, J = 13.92 Hz, 2 H), 3.41-3.52 (m, 2 H), 1.73 (br d, J = 4.88 Hz, 3 H), 1.35 (s, 2 H). | 376.2 |
| 45 | 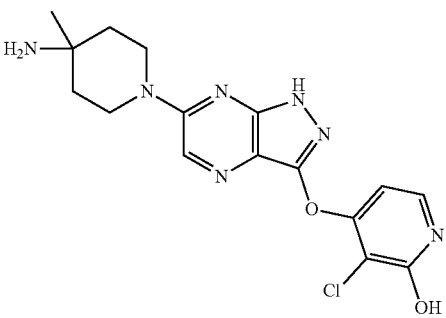 [SMILES: CC1(N)CCN(c2cnc3c(Oc4ccnc(O)c4Cl)n[nH]c3n2)CC1] | (400 MHz, DMSO-d6): δ 8.41 (s, 1H), 8.25 (s, 1H), 7.34 (d, J = 7.57 Hz, 1H), 5.93 (d, J = 7.32 Hz, 1H), 3.88-4.07 (m, 2H), 3.52-3.67 (m, 2H), 1.65 (br s, 4H), 1.27 (s, 3H). | 376.2 |

-continued

| Compound | Structure | ¹H NMR | LCMS |
|---|---|---|---|
| 46 | 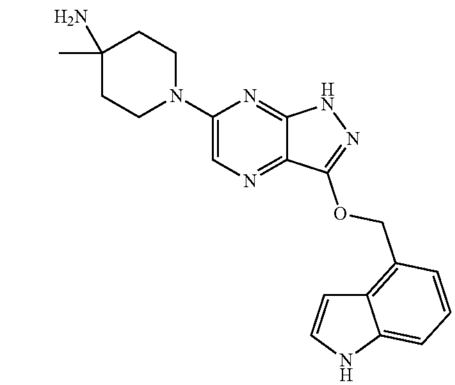 [SMILES: CC1(N)CCN(c2cnc3c(OCc4cccc5[nH]ccc45)n[nH]c3n2)CC1] | (400 MHz, DMSO-d₆): δ 12.03 (br, 1H), 11.20 (br, 1H), 8.23 (s, 1H), 7.37 (s 2H), 7.10 (s, 2H), 6.55 (s, 1H), 5.62 (s, 2H), 3.82 (s, 2H), 3.61 (s, 2H), 1.44 (s, 4H), 1.08 (s, 3H). | 378.0 |
| 47 | 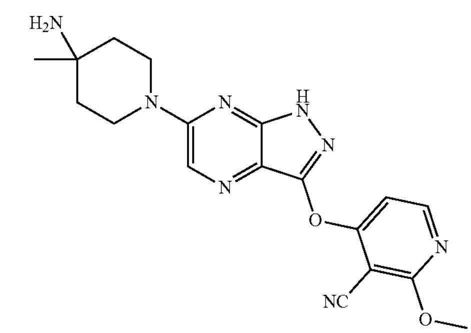 | (400 MHz, DMSO-d6): 8.41 (s, 1 H), 8.25-8.32 (m, 2 H), 6.77 (d, J = 6.10 Hz, 1 H), 6.27 (br s, 1H), 4.02 (s, 2 H), 3.82-3.91 (m, 2 H), 3.66-3.75 (m, 2 H), 1.60 (br t, J = 5.25 Hz, 3 H), 1.22 (s, 2 H). | 381.3 |
| 48 | 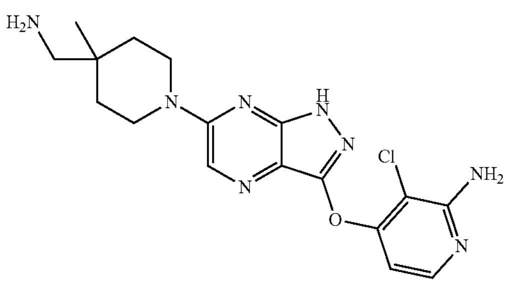 [SMILES: CC1(CN)CCN(c2cnc3c(Oc4ccnc(N)c4Cl)n[nH]c3n2)CC1] | (400 MHz, CD₃OD): δ 8.28 (s, 1H), 7.75-7.73 (d, J = 6 Hz, 1H), 6.29-6.27 (d, J = 5.6 Hz, 1H), 4.13-4.08 (m, 2H), 3.59-3.53 (m, 2H), 2.61 (s, 2H), 1.64-1.50 (m, 4H), 1.11 (s, 1H). | 389.0 |
| 49 | 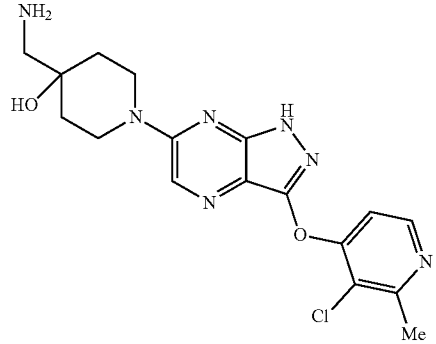 [SMILES: Cc1nccc(Oc2n[nH]c3nc(N4CCC(O)(CN)CC4)cnc23)c1Cl] | (400 MHz, DMSO-d₆) δ 8.40 (s, 1 H), 8.23 (d, J = 5.61 Hz, 1 H), 6.91 (d, J = 5.62 Hz, 1 H), 4.17 (br d, J = 13.43 Hz, 2 H), 3.39-3.51 (m, 2 H), 2.75 (br s, 2 H), 2.60 (s, 3 H), 1.37-1.77 (m, 4 H). | 390.2 |

| Compound | Structure | ¹H NMR | LCMS |
|---|---|---|---|
| 50 | 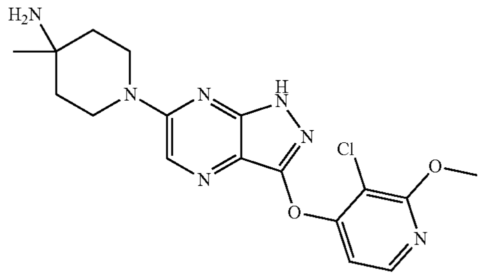 | (400 MHz, DMSO-d6): δ 8.32-8.42 (m, 2H), 7.97 (d, J = 5.86 Hz, 1H), 6.69 (d, J = 5.86 Hz, 1H), 3.97 (s, 3H), 3.79-3.89 (m, 2H), 3.67-3.76 (m, 2H), 1.58 (br t, J = 5.37 Hz, 4H), 1.20 (s, 3H). | 390.2 |
| 51 | 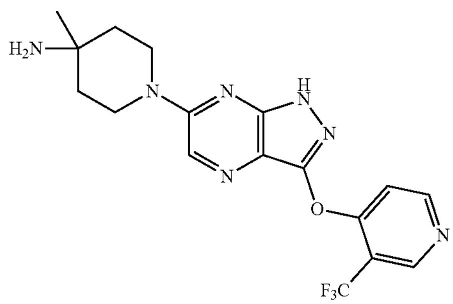 [SMILES: CC1(N)CCN(c2cnc3c(Oc4ccncc4C(F)(F)F)n[nH]c3n2)CC1] | (400 MHz, DMSO-d6): δ ppm 8.91 (s, 1H), 8.68 (d, J = 5.61 Hz, 1H), 8.39 (s, 1H), 8.34 (s, 1H), 7.18 (d, J = 5.86 Hz, 1H), 3.84-3.91 (m, 2H), 3.65-3.73 (m, 2H), 1.62 (br t, J = 5.25 Hz, 4H), 1.23 (s, 3H). | 394.2 |
| 52 | 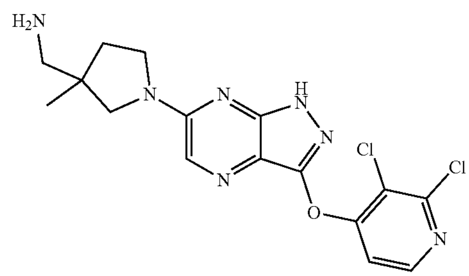 [SMILES: CC1(CN)CCN(c2cnc3c(Oc4ccnc(Cl)c4Cl)n[nH]c3n2)C1] | (400 MHz, DMSO-d$_6$): δ 8.24-8.22 (d, J = 5.6 Hz, 1H), 8.0 (s, 1H), 7.15-7.13 (d, J = 5.6 Hz, 1H), 3.63-3.59 (m, 4H), 3.24-3.19 (m, 2H), 1.95-1.1.93 (m, 1H), 1.72-1.66 (m, 1H), 1.07 (s, 3H). | 393.9 |
| 53 | 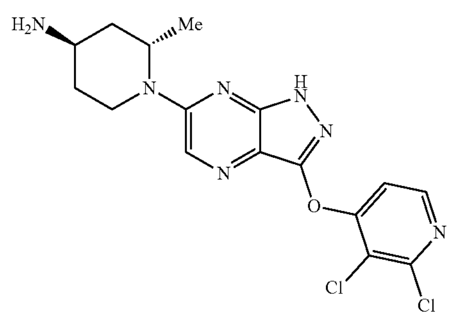 [SMILES: C[C@H]1C[C@H](N)CCN1c1cnc2c(Oc3ccnc(Cl)c3Cl)n[nH]c2n1] | (400 MHz, CD$_3$OD) δ 8.33 (s, 1 H), 8.27 (s, 1 H), 8.16 (d, J = 5.67 Hz, 1 H), 7.09 (d, J = 5.67 Hz, 1 H), 5.06-5.15 (m, 1 H), 4.60 (br d, J = 14.57 Hz, 1 H), 3.67 (tt, J = 12.28, 4.05 Hz, 1 H), 3.21-3.28 (m, 1 H), 2.13-2.23 (m, 1 H), 2.08 (dt, J = 12.68, 1.89 Hz, 1 H), 1.83 (td, J = 12.62, 5.53 Hz, 1 H), 1.64 (qd, J = 12.50, 4.59 Hz, 1 H), 1.34 (d, J = 7.02 Hz, 3 H). | 394.2 |
| 54 | 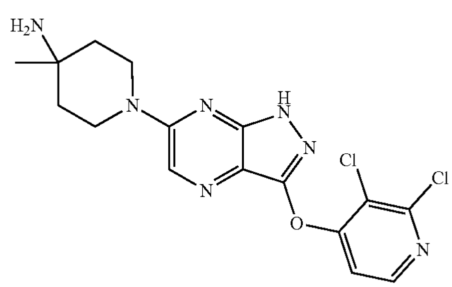 [SMILES: CC1(N)CCN(c2cnc3c(Oc4ccnc(Cl)c4Cl)n[nH]c3n2)CC1] | (400 MHz, DMSO-d6): δ 8.41 (s, 1H), 8.30 (s, 1H), 8.23 (d, J = 5.62 Hz, 1H), 7.16 (d, J = 5.62 Hz, 1H), 3.89-3.98 (m, 2H), 3.59-3.68 (m, 3H), 1.64 (br t, J = 5.25 Hz, 4H), 1.26 (s, 3 H). | 394.2 |

| Compound | Structure | ¹H NMR | LCMS |
|---|---|---|---|
| 55 | 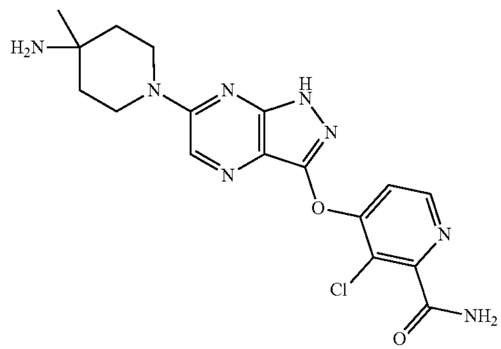 [SMILES: CC1(N)CCN(c2cnc3c(Oc4ccnc(C(N)=O)c4Cl)n[nH]c3n2)CC1] | (400 MHz, DMSO-d6): δ 8.37 (s, 1H), 8.33 (br d, J = 5.37 Hz, 1H), 8.07 (br s, 1H), 7.76 (br s, 1H), 7.13 (d, J = 5.37 Hz, 1H), 6.54 (br s, 1H), 3.82-3.97 (m, 2H), 3.63 (ddd, J = 4.27, 8.67, 13.18 Hz, 2H), 1.35-1.58 (m, 4H), 1.08 (s, 3H). | 403.3 |
| 56 | 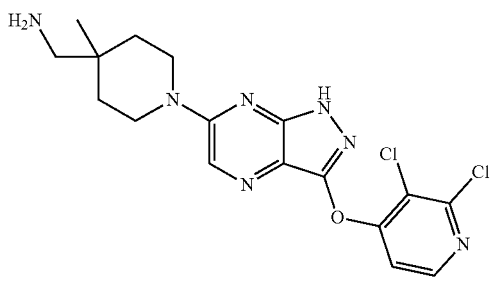 [SMILES: CC1(CN)CCN(c2cnc3c(Oc4ccnc(Cl)c4Cl)n[nH]c3n2)CC1] | (400 MHz, CD$_3$OD): δ 8.3 (s, 1H), 8.18-8.16 (d, J = 7.2 Hz, 1H), 7.10-7.07 (d, J = 7.2 Hz, 1H), 4.13-4.08 (m, 2H), 3.60-3.53 (m, 2H), 2.60 (s, 2H), 1.64-1.49 (m, 4H), 1.11 (s, 3H). | 408.0 |
| 57 | 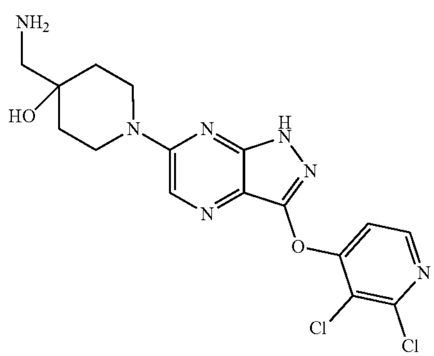 [SMILES: NCC1(O)CCN(c2cnc3c(Oc4ccnc(Cl)c4Cl)n[nH]c3n2)CC1] | (400 MHz, DMSO-d$_6$) δ 8.28-8.46 (m, 1 H), 8.23 (br d, J = 5.62 Hz, 1 H), 7.07-7.26 (m, 1 H), 4.18 (br d, J = 13.18 Hz, 2 H), 2.60-2.70 (m, 2 H), 1.55 (br s, 4 H). | 410.2 |
| 58 | 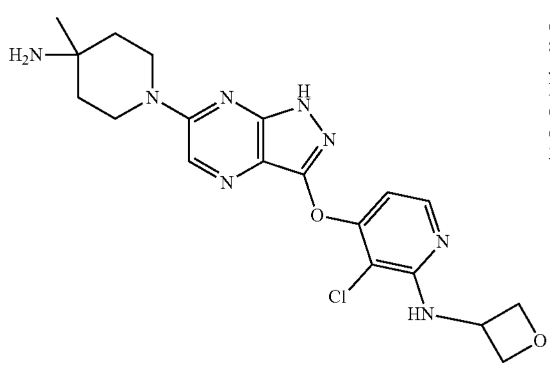 [SMILES: CC1(N)CCN(c2cnc3c(Oc4ccnc(NC5COC5)c4Cl)n[nH]c3n2)CC1] | (400 MHz, DMSO-d6): δ ppm 8.36 (s, 1H), 8.36 (s, 1H), 7.31 (d, J = 7.32 Hz, 1H), 5.40 (d, J = 7.32 Hz, 1H), 4.72 (br s, 1H), 4.05-4.17 (m, 2H), 3.82-3.96 (m, 3H), 3.62 (ddd, J = 13.18, 8.54, 4.39 Hz, 2H), 3.51 (br d, J = 10.50 Hz, 1H), 1.40-1.54 (m, 4H), 1.08 (s, 3H). | 431.4 |

-continued

| Compound | Structure | ¹H NMR | LCMS |
|---|---|---|---|
| 59 | 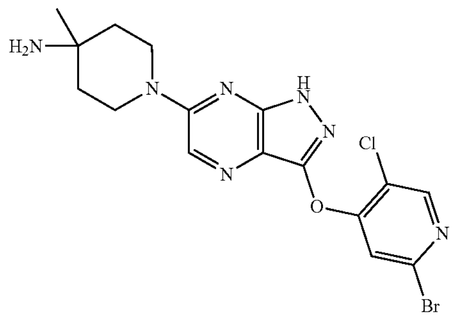 [SMILES: CC1(N)CCN(c2cnc3c(Oc4cc(Br)ncc4Cl)n[nH]c3n2)CC1] | (400 MHz, DMSO-d6): δ ppm 8.57 (s, 1H), 8.41 (s, 1H), 8.34 (s, 1H), 7.43 (s, 1H), 3.73-3.85 (m, 5H), 1.57 (br t, J = 5.37 Hz, 4H), 1.19 (s, 3H). | 440.2 |
| 60 | 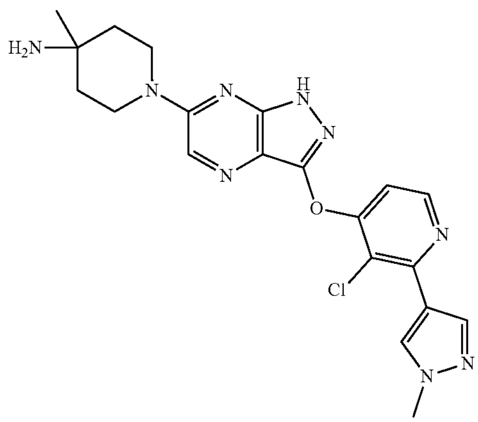 [SMILES: Cn1cc(-c2nccc(Oc3n[nH]c4nc(N5CCC(C)(N)CC5)cnc34)c2Cl)cn1] | (400 MHz, DMSO-d6): δ 8.51 (s, 1H), 8.38 (s, 1H), 8.33 (d, J = 5.37 Hz, 2H), 8.13 (s, 1H), 6.88 (d, J = 5.62 Hz, 1H), 3.93 (s, 3H), 3.80-3.89 (m, 2H), 3.67-3.75 (m, 2H), 1.59 (br t, J = 5.25 Hz, 4H), 1.21 (s, 3H). | 440.3 |
| 61 | 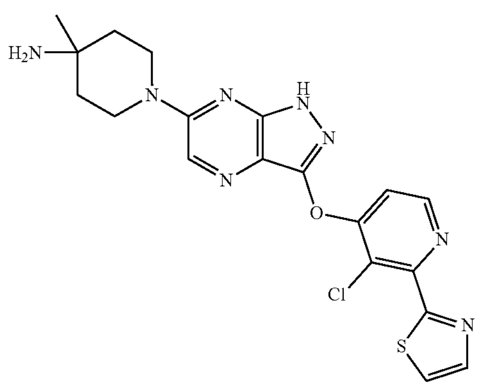 [SMILES: CC1(N)CCN(c2cnc3c(Oc4ccnc(-c5nccs5)c4Cl)n[nH]c3n2)CC1] | (400 MHz, DMSO-d6): δ 8.29 (br d, J = 5.29 Hz, 1H), 8.11 (br s, 1H), 7.92-8.05 (m, 1H), 7.52 (br d, J = 3.33 Hz, 1H), 7.00 (br d, J = 5.48 Hz, 1H), 4.05 (br d, J = 4.70 Hz, 2H), 3.44-3.61 (m, 2H), 1.93 (br s, 2H), 1.80 (br s, 2H), 1.30-1.54 (m, 3H). | 443.3 |
| 62 | 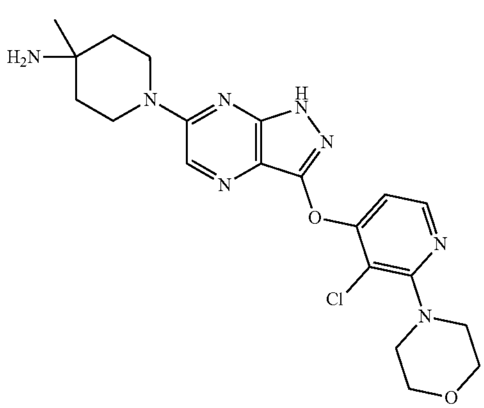 [SMILES: CC1(N)CCN(c2cnc3c(Oc4ccnc(N5CCOCC5)c4Cl)n[nH]c3n2)CC1] | (400 MHz, DMSO-d6): δ ppm 8.37 (s, 1H), 8.32 (s, 1H), 8.05 (d, J = 5.62 Hz, 1H), 6.66 (d, J = 5.62 Hz, 1H), 3.79-3.88 (m, 2H), 3.67-3.78 (m, 6H), 3.26-3.31 (m, 4H), 1.58 (br t, J = 5.25 Hz, 4H), 1.20 (s, 3H). | 445.3 |

| Compound | Structure | ¹H NMR | LCMS |
|---|---|---|---|
| 63 | 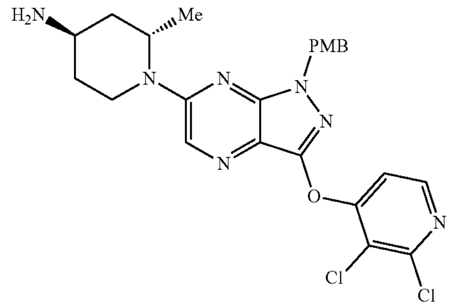 | (400 MHz, CDCl₃) δ 7.97-8.23 (m, 2 H), 7.17-7.41 (m, 2 H), 6.95-7.09 (m, 1 H), 6.84 (br d, J = 8.54 Hz, 2 H), 5.34 (s, 2 H), 4.98 (br s, 1 H), 4.51 (br d, J = 13.42 Hz, 1 H), 3.65-3.88 (m, 3 H), 3.53 (br d, J = 12.45 Hz, 1 H), 3.18 (br t, J = 12.57 Hz, 1 H), 1.77-1.97 (m, 2 H), 1.68 (br d, J = 7.81 Hz, 2 H), 1.31 (br d, J = 6.83 Hz, 3 H). | 514.2 |
| 64 | 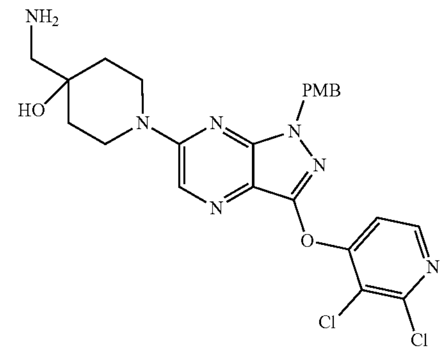 | (400 MHz, DMSO-d₆) δ 8.31-8.50 (m, 1 H), 8.14-8.29 (m, 1 H), 7.24 (d, J = 8.54 Hz, 2 H), 7.17 (d, J = 5.62 Hz, 1 H), 6.88 (d, J = 8.54 Hz, 2 H), 5.31 (s, 2 H), 4.28 (br d, J = 13.43 Hz, 2 H), 3.70 (s, 3 H), 3.41 (br t, J = 10.86 Hz, 2 H), 2.63 (s, 2 H), 1.47-1.69 (m, 4 H). | 530.2 |

Example 17

Synthesis of 1-(3-(1H-benzo[d]imidazol-1-yl)-1H-pyrazolo[3,4-b]pyrazin-6-yl)-4-methylpiperidin-4-amine, Compound 65

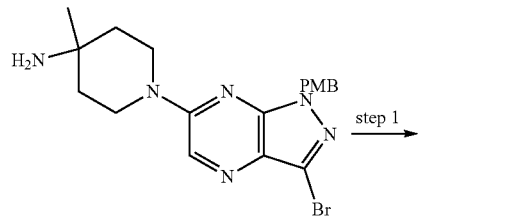

step 1

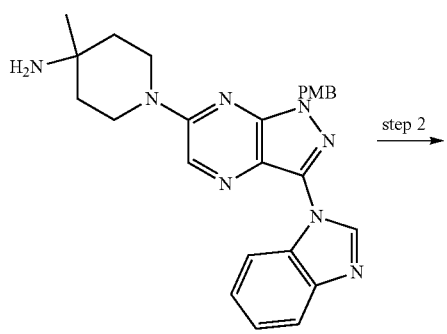

step 2

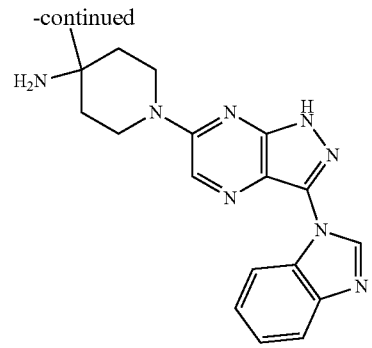

Step 1: To a flame-dried, nitrogen-flushed Biotage 0.5-2.0 mL vial equipped with a conic magnetic stirbar and a 14/20 white septa was added 1-(3-bromo-1-(4-methoxybenzyl)-1H-pyrazolo[3,4-b]pyrazin-6-yl)-4-methylpiperidin-4-amine (43 mg, 0.10 mmol, 1.0 equiv) and anhydrous dimethylsulfoxide (0.50 mL, 0.20 M). The solution was degassed by flowing nitrogen from a balloon through the solution for 5 min. The following reactants/catalysts were successively added to the vial: copper(II)oxide (2.86 mg, 0.010 mmol, 0.20 equiv), 4,7-di-methoxy-1,10-phenanthroline (9.6 mg, 0.04 mmol, 0.4 equiv), benzimidazole (17.8 mg, 0.150 mmol, 1.5 equiv), PEG-4000 (20 mg), and cesium carbonate (65 mg, 0.20 mmol, 2.0 equiv). The septum was removed from the vial, and a blue microwave cap was rapidly crimped on the vial. The solution was heated to 130° C. using an oil bath and heated for 16 hours. The solution was cooled, and LCMS of an aliquot showed full conversion to the desired product. The vial was opened to air and transferred to a 60 mL extraction funnel using dichloromethane, where the reaction was quenched with a saturated aqueous solution of sodium bicarbonate (approx. 10 mL).

The biphasic mixture was extracted, and the layers were separated. The aqueous layer was further extracted with dichloromethane (3×10 mL), and the organic layers were combined, washed with brine (3×10 mL), dried over sodium sulfate, filtered, and concentrated in vacuo. The resulting yellow film was pure enough by NMR to be taken directly to next step. LCMS: 469 [M+H]+.

Step 2: To a 20 mL scintillation vial was added 1-(3-(1H-benzo[d]imidazol-1-yl)-1-(4-methoxybenzyl)-1H-pyrazolo [3,4-b]pyrazin-6-yl)-4-methylpiperidin-4-amine (46 mg, 0.100 mmol, 1.0 equiv), which was dissolved in anhydrous dichloroethane (1.0 mL, 0.100 M). Then, hydrobromic acid (33% in acetic acid) (1.0 mL, excess) was added to the reaction. The vial was capped firmly with a Teflon cap, and the solution was heated to 80° C. using an oil bath and secured behind a blast shield. The solution was stirred until it was judged to be finished by LCMS. Full conversion to that product was observed after heating for 16 hours. The reaction was cooled and quenched by addition of diethyl ether (10 mL), which crashed out the product as an orange/red suspension. The suspension was stirred for 10 min before stirring was stopped. The solid was decanted, and the ether supernatant was disposed of. This trituration step was repeated three times before evaporation of residual ether was done with a stream of nitrogen. Then, the solid was dissolved in a minimum of dimethylformamide and aqueous sodium carbonate and purified by reverse C18 chromatography using a SNAP Biotage 12 g column (eluting with acetonitrile/water/0.1% ammonium carbonate). Fractions with the highest purity were combined, and excess of MeCN was evaporated before being the remainder was lyophilized to yield 1-(3-(1H-benzoldlimidazol-1-yl)-1H-pyrazolo[3,4-b]pyrazin-6-yl)-4-methylpiperidin-4-amine as an off-white solid (12 mg, 34%).

Example 18

Synthesis of 1-(3-(3,4-dihydroquinolin-1(2H)-yl)-1H-pyrazolo[3,4-b]pyrazin-6-yl)-4-methylpiperidin-4-amine hydrochloride, Compound 68

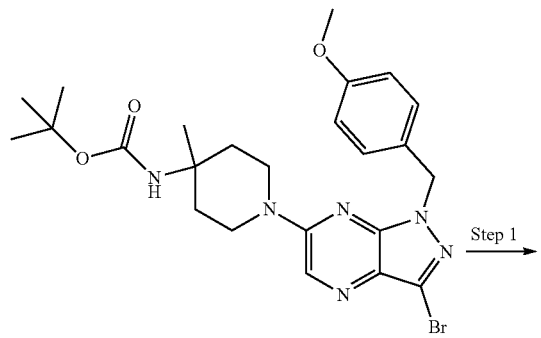

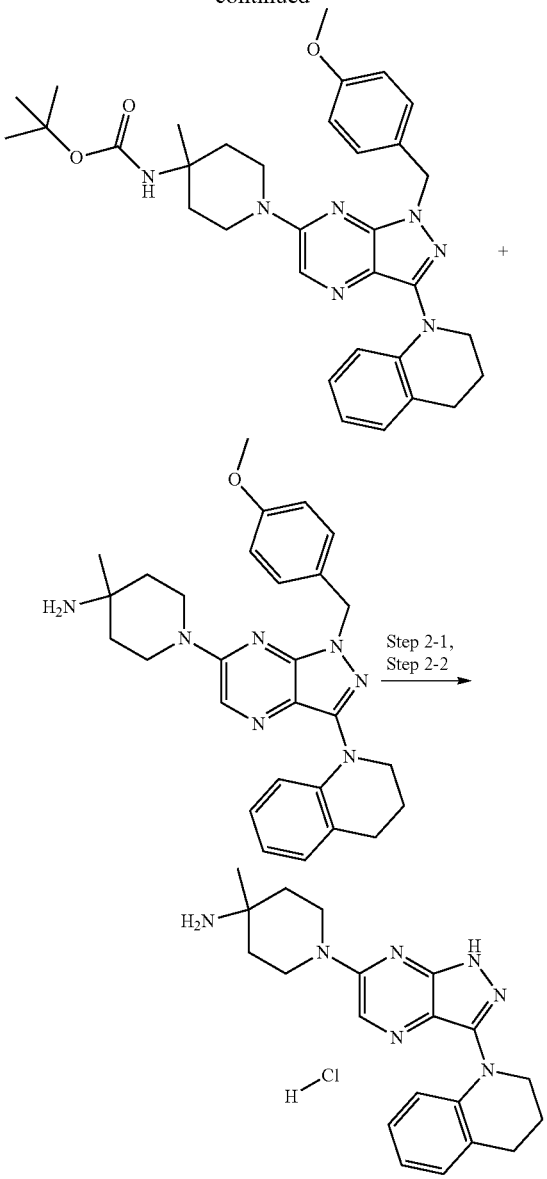

Step 1: tert-butyl (1-(3-bromo-1-(4-methoxybenzyl)-1H-pyrazolo[3,4-b]pyrazin-6-yl)-4-methylpiperidin-4-yl)carbamate (300 mg, 0.56 mmol, 1.0 eq) (prepared using tert-butyl (4-methylpiperidin-4-yl)carbamate), 1,2,3,4-tetrahydroquinoline (83 mg, 0.62 mmol, 1.1 eq), RuPhos (26 mg, 56 umol, 0.1 eq), Ruphos Pd G4 (48 mg, 56 umol, 0.1 eq), and t-BuONa (163 mg, 1.7 mmol, 3.0 eq) were added into dioxane (10 mL). The mixture was evacuated and backfilled with nitrogen three times before being stirred at 120° C. for 10 h. The mixture was concentrated in vacuo, diluted with ethyl acetate (70 mL), washed with saturated sodium bicarbonate (30 mL×2), water (30 mL), and brine (30 mL×2). The organic layer was dried over anhydrous sodium sulfate, filtered, and concentrated to give a yellow oil, which was purified by silica gel chromatography to afford tert-butyl N-[1-[3-(3,4-dihydro-2H-quinolin-1-yl)-1-[(4-methoxyphenyl)methyl]pyrazolo[3,4-b]pyrazin-6-yl]-4-methyl-4-piperidyl]carbamate (0.2 g) as a yellow oil and 1-[3-(3,4-dihydro-2H-quinolin-1-yl)-1-[(4-methoxyphenyl)methyl]pyrazolo[3,4-b]pyrazin-6-yl]-4-methyl-piperidin-4-amine (0.1 g) as a yellow oil.

Step 2-1: tert-butyl N-[1-[3-(3,4-dihydro-2H-quinolin-1-yl)-1-[4-methoxyphenyl)methyl]pyrazolo[3,4-b]pyrazin-6-yl]-4-methyl-4-piperidyl]carbamate (200 mg, 0.34 mmol, 1.0 eq) was dissolved in trifluoroacetic acid (5 mL) and trifluoromethyl sulfonic acid (0.5 mL). The reaction mixture was stirred at 100° C. for 1 h before being combined with Step 2-2 for purification.

Step 2-2: 1-[3-(3,4-dihydro-2H-quinolin-1-yl)-1-[(4-methoxyphenyl)methyl]pyrazolo[3,4-b]pyrazin-6-yl]-4-methyl-piperidin-4-amine (100 mg, 0.2 mmol, 1.0 eq) was dissolved in trifluoroacetic acid (5 mL) and trifluoromethyl sulfonic acid (0.5 mL). The mixture was stirred at 100° C. for 1 h. Following combination with the crude reaction mixture of Step 2-1, the solvent was removed in vacuo, the residue was diluted with ethyl acetate (70 mL), washed with saturated sodium bicarbonate (30 mL×2), water (30 mL), and brine (30 mL×2). The organic layer was dried over anhydrous sodium sulfate, filtered, and concentrated to give a yellow oil, which was purified by prep-HPLC (eluting with acetonitrile/water/0.1% HCl) to afford 1-(3-(3,4-dihydroquinolin-1(2H)-yl)-1H-pyrazolo[3,4-b]pyrazin-6-yl)-4-methylpiperidin-4-amine hydrochloride (16 mg) as a brown solid.

The following compounds were synthesized via the same route as Compound 68, using the corresponding building blocks: Compound 66, Compound 67, Compound 72, Compound 73, Compound 74, Compound 75, Compound 76, Compound 77, Compound 79, Compound 80, Compound 81, Compound 82, Compound 83, Compound 88, Compound 92, Compound 101, Compound 104, Compound 105, Compound 106, Compound 107, Compound 109, Compound 112, Compound 116.

Example 19

Syntheses of Compounds 69 and 70

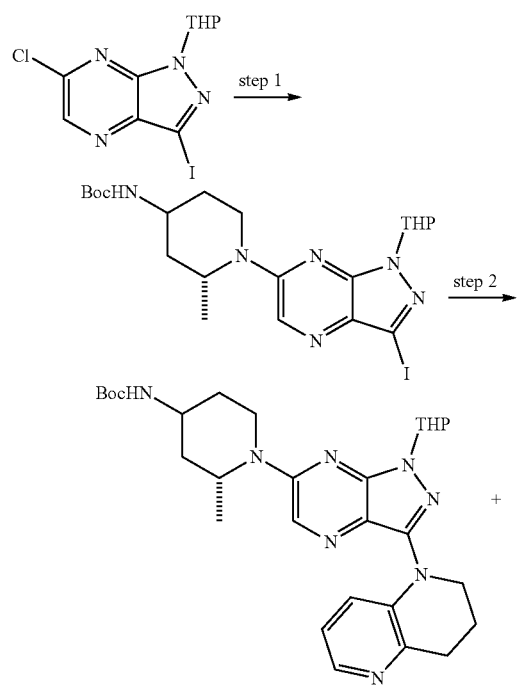

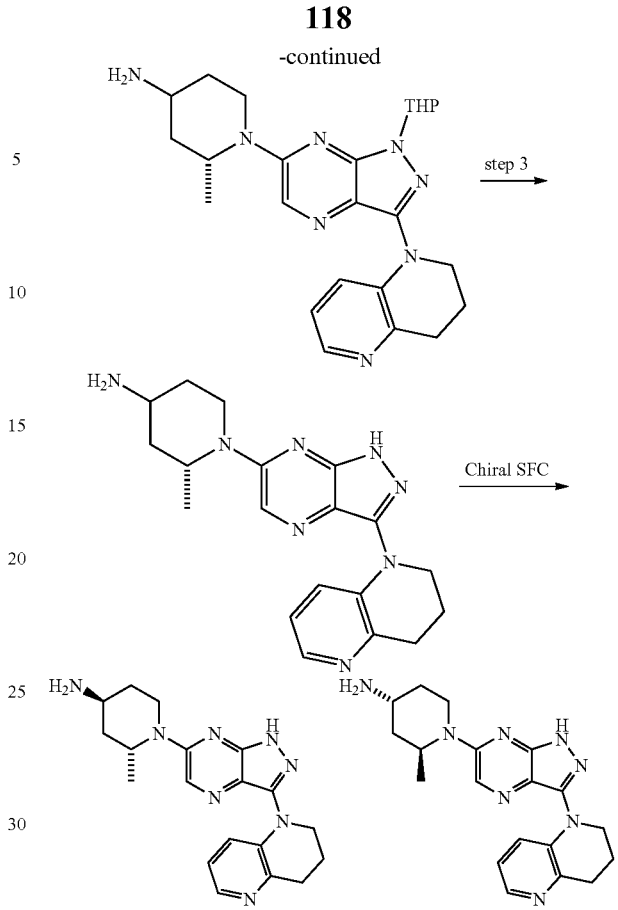

Step 1: A mixture of 6-chloro-3-iodo-1-(tetrahydro-2H-pyran-2-yl)-1H-pyrazolo[3,4-b]pyrazine (300.0 mg, 822 µmol), tert-butyl (2-methylpiperidin-4-yl)carbamate (176.0 mg, 822 µmol), and diisopropylethyl amine (428.0 µL, 2.46 mmol) in dimethylsulfoxide (15.0 mL) was stirred at 80° C. for 3 h. TLC (Petroleum ether:EtOAc=2:1) indicated the starting material was consumed completely and one main spot formed. The combined reaction mixture was diluted with ethyl acetate (100.0 mL), washed with water (50.0 mL×3), brine (30.0 mL), dried over anhydrous sodium sulfate, filtered, and concentrated in vacuo to give a residue that was purified by flash silica gel chromatography (eluting with petroleum ether/ethyl acetate) to afford tert-butyl (1-(3-iodo-1-(tetrahydro-2H-pyran-2-yl)-1H-pyrazolo[3,4-b]pyrazin-6-yl)-2-methylpiperidin-4-yl)carbamate (700.0 mg, combined product) as a yellow solid.

Step 2: A mixture of tert-butyl (1-(3-iodo-1-(tetrahydro-2H-pyran-2-yl)-1H-pyrazolo[3,4-b]pyrazin-6-yl)-2-methylpiperidin-4-yl)carbamate (360.0 mg, 663 µmol), 1,2,3,4-tetrahydro-1,5-naphthyridine (88.9 mg, 663 µmol), RuPhos-Pd-G4 (57.0 mg, 66.3 µmol), RuPhos (30.8 mg, 66.3 mol), and t-BuONa (190.0 mg, 2.0 mmol) in dioxane (20.0 mL) was evacuated and backfilled with nitrogen three times before being stirred at 80° C. for 12 h. The combined reaction mixture was concentrated in vacuo and purified by flash silica gel chromatography (eluting with petroleum ether/ethyl acetate, then dichloromethane/methanol) to afford tert-butyl (1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-yl)carbamate (5, 400.0 mg, combined product) as a yellow solid and 1-(3-(3,4-dihydro-1,5-naphthyridin-1(2H)-yl)-1-(tetrahydro-2H- pyran-2-yl)-1H-pyrazolo[3,4-b]pyrazin-6-yl)-2-methylpiperidin-4-amine (5a, 300.0 mg, combined product) as a yellow solid.

Step 3: Tert-butyl ((2R,4S)-1-(3-(3,4-dihydro-1,5-naphthyridin-1(2H)-yl)-1H-pyrazolo[3,4-b]pyrazin-6-yl)-2-methylpiperidin-4-yl)carbamate (400.0 mg, 861 μmol) was added to 4N HCl/methanol (10.0 mL), the reaction mixture was stirred at 25° C. for 12 hours. The combined reaction mixture was concentrated in vacuo and purified by prep-HPLC (eluting with acetonitrile/water/0.1% ammonium hydroxide) to afford rac-(2R,4S)-1-(3-(3,4-dihydro-1,5-naphthyridin-1(2H)-yl)-1H-pyrazolo[3,4-b]pyrazin-6-yl)-2-methylpiperidin-4-amine (150.0 mg, combined product) as a yellow solid. LCMS M/Z: 365.3 [M+H]+. 1HNMR (400 MHz, DMSO-d6): δ 8.26 (s, 1H), 7.91-7.89 (m, 1H), 7.49-7.46 (m, 1H), 6.98-6.94 (m, 1H), 4.86-4.83 (m, 1H), 4.35-4.30 (m, 1H), 3.96-3.93 (m, 2H), 3.04-2.93 (m, 4H), 2.10-2.04 (m, 2H), 1.88-1.73 (m, 2H), 1.40-1.35 (m, 1H), 1.19-1.16 (m, 4H).

Separation of Compounds 69 and 70

(2R,4S)-1-(3-(3,4-dihydro-1,5-naphthyridin-1(2H)-yl)-1H-pyrazolo[3,4-b]pyrazin-6-yl)-2-methylpiperidin-4-amine (120.0 mg, 329 mol) was purified by chiral SFC. (Column: Chiralpak AD-3 100×4.6 mm I.D, 3 μm Mobile phase: A: CO2 B: ethanol (0.1% ethanolamine) Gradient: from 5% to 40% of B in 4.5 min and hold 40% for 2.5 min, then 5% of B for 1 min. Flow rate: 2.8 mL/min Column temperature: 40° C.). Rel-(2R,4S)-1-(3-(3,4-dihydro-1,5-naphthyridin-1(2H)-yl)-1H-pyrazolo[3,4-b]pyrazin-6-yl)-2-methylpiperidin-4-amine (40.9 mg, 112 mol, e.e.=100%) was obtained as a yellow solid. LCMS M/Z 365.3 [M+H]+. 1HNMR (400 MHz, DMSO-d6): δ 8.26 (s, 1H), 7.91-7.88 (m, 1H), 7.49-7.47 (m, 1H), 6.98-6.94 (m, 1H), 4.86-4.82 (m, 1H), 4.34-4.30 (m, 1H), 3.96-3.92 (m, 2H), 3.07-2.92 (m, 4H), 2.10-2.05 (m, 2H), 1.88-1.73 (m, 2H), 1.39-1.37 (m, 1H), 1.22-1.13 (m, 4H).

Rel-(2R,4S)-1-(3-(3,4-dihydro-1,5-naphthyridin-1(2H)-yl)-1H-pyrazolo[3,4-b]pyrazin-6-yl)-2-methylpiperidin-4-amine (38.4 mg, 105 μmol, e.e.=91.7%) was obtained as a yellow solid. LCMS M/Z: 365.3 [M+H]+. 1HNMR (400 MHz, DMSO-d6): δ 8.31 (s, 1H), 7.96-7.94 (m, 1H), 7.55-7.52 (m, 1H), 7.03-6.99 (m, 1H), 4.96-4.88 (m, 1H), 4.40-4.36 (m, 1H), 4.02-3.98 (m, 2H), 3.12-2.97 (m, 4H), 2.15-2.08 (m, 2H), 1.94-1.79 (m, 2H), 1.46-1.43 (m, 1H), 1.28-1.21 (m, 4H).

Example 20

Synthesis of (1-(3-(3,4-dihydro-1,5-naphthyridin-1(2H)-yl)-1H-pyrazolo[3,4-b]pyrazin-6-yl)-3-methylpyrrolidin-3-yl)methanamine dihydrochloride, Compound 71

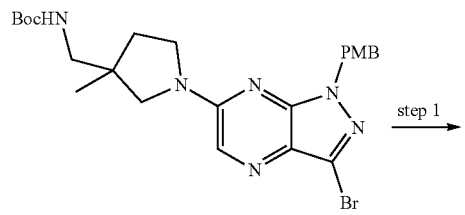

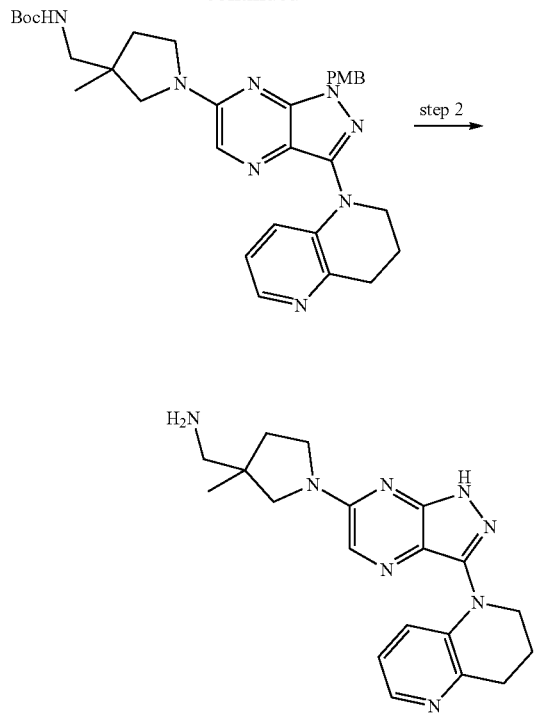

Step 1: Tert-butyl-((1-(3-bromo-1-(4-methoxybenzyl)-1H-pyrazolo[3,4-b]pyrazin-6-yl)-3-methylpyrrolidin-3-yl)methyl)carbamate (200 mg, 376 μmol) (prepared from 3,6-dichloropyrazine-2-carbonitrile and tert-butyl ((3-methylpyrrolidin-3-yl)methyl)carbamate), 1,2,3,4-tetrahydro-1,5-naphthyridine (55.4 mg, 413 μmol), RuPhos (17.5 mg, 37.6 μmol), RuPhos-Pd-G4 (31.9 mg, 37.6 μmol), and t-BuONa (107 mg, 1.12 mmol) were combined in dioxane (10.0 mL), and the mixture was stirred at 120° C. for 10 h. LCMS showed the starting material was consumed completely and a new peak with desired MS was detected. The reaction mixture was concentrated in vacuo to give a yellow solid, which was purified by silica gel chromatography (eluting with petroleum ether:ethyl acetate=100:0 to 100:50). Tert-butyl-((1-(3-(3,4-dihydro-1,5-naphthyridin-1(2H)-yl)-1-(4-methoxybenzyl)-1H-pyrazolo[3,4-b]pyrazin-6-yl)-3-methylpyrrolidin-3-yl)methyl)carbamate (150 mg, 256 μmol) was obtained as a yellow solid.

Step 2: Tert-butyl ((1-(3-(3,4-dihydro-1,5-naphthyridin-1(2H)-yl)-1-(4-methoxybenzyl)-1H-pyrazolo[3,4-b]pyrazin-6-yl)-3-methylpyrrolidin-3-yl)methyl)carbamate (150 mg, 308 μmol) was taken up in trifluoroacetic acid (5 mL) and trfluoromethylsulfonic acid (0.4 mL), and the mixture was stirred at 85° C. for 30 min. LCMS showed complete consumption of the starting material, and a new peak with desired M/Z was detected. The reaction mixture was concentrated in vacuo to give a yellow solid. The residue was purified by prep-HPLC (eluting with acetonitrile/water/0.1% hydrochloric acid). Lyophilization yielded (1-(3-(3,4-dihydro-1,5-naphthyridin-1(2H)-yl)-1H-pyrazolo[3,4-b]pyrazin-6-yl)-3-methylpyrrolidin-3-yl)methanamine dihydrochloride (33.5 mg, 25.0% yield, HCl salt) as a yellow solid.

Example 21

Synthesis of (1-(3-(3,4-dihydroquinolin-1(2H)-yl)-1H-pyrazolo[3,4-b]pyrazin-6-yl)-4-methylpiperidin-4-yl)methanamine, Compound 78

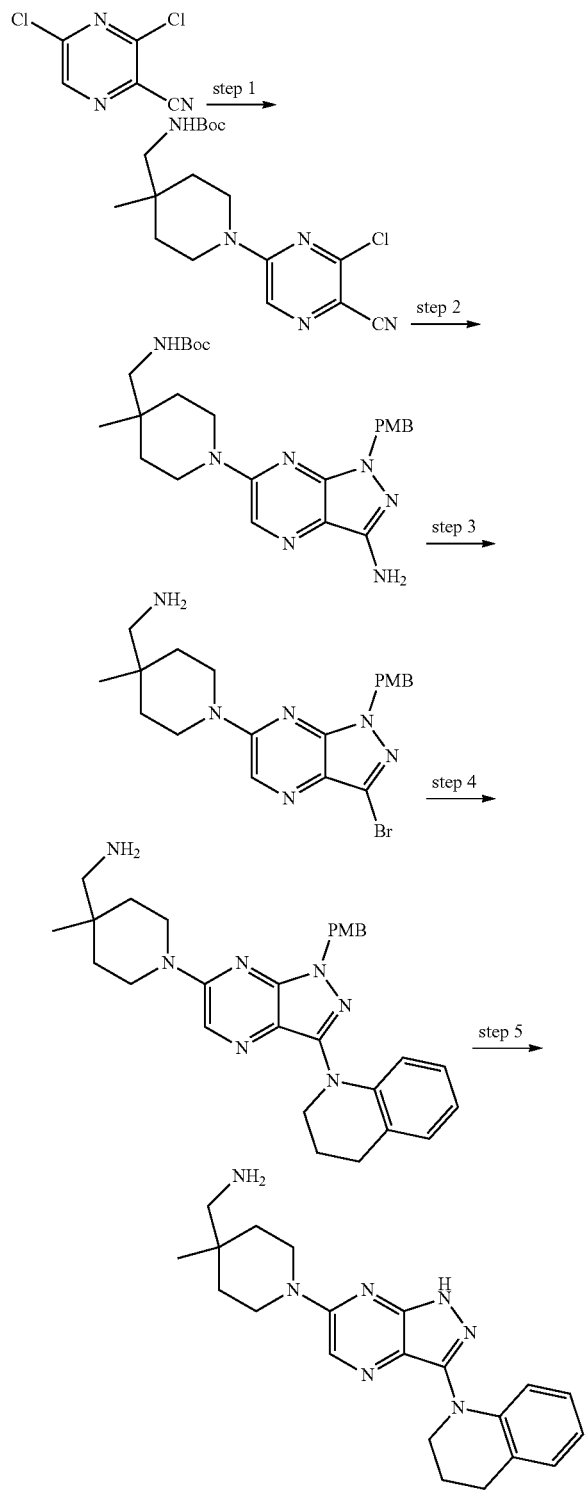

Step 1: 3,5-Dichloropyrazine-2-carbonitrile (500 mg, 2.9 mmol), tert-butyl ((4-methylpiperidin-4-yl)methyl)carbamate hydrochloride (655 mg, 2.9 mmol) and diisopropyl ethylamine (1.5 mL, 287 μmol) were combined in dimethyl sulfoxide (10 mL) and stirred at 70° C. for 1 h. LCMS indicated 44% of desired product formed. The reaction mixture was diluted with ethyl acetate (100 mL), washed with water (50 mL×4), brine (30 mL), dried over anhydrous sodium sulfate, filtered, concentrated in vacuo before being purified by flash silica gel chromatography (eluting with ethyl acetate:petroleum ether=0:100 to 50:100) to afford tert-butyl ((1-(6-chloro-5-cyanopyrazin-2-yl)-4-methylpiperidin-4-yl)methyl)carbamate (900.0 mg, 86% yield) as a yellow solid.

Step 2: Tert-butyl ((1-(6-chloro-5-cyanopyrazin-2-yl)-4-methylpiperidin-4-yl)methyl)carbamate (900.0 mg, 2.5 mmol), (4-methoxybenzyl)hydrazine (447.0 mg, 2.9 mmol) and triethylamine (1.7 mL, 12.2 mmol) were combined in ethanol (10.0 mL) and stirred at 90° C. for 12 h. LCMS indicated 58% of desired product formed. The reaction mixture was concentrated in vacuo and purified by silica gel chromatography (petroleum ether:ethyl acetate=100:0 to 100:80) to afford tert-butyl ((1-(3-amino-1-(4-methoxybenzyl)-1H-pyrazolo[3,4-b]pyrazin-6-yl)-4-methylpiperidin-4-yl)methyl)carbamate (900 mg, 77% yield) as a yellow solid.

Step 3: Tert-butyl ((1-(3-amino-1-(4-methoxybenzyl)-1H-pyrazolo[3,4-b]pyrazin-6-yl)-4-methylpiperidin-4-yl)methyl)carbamate (900 mg, 1.2 mmol), sodium nitrite (153 mg, 2.2 mmol) and hydrogen bromide (5.4 mL, 48% aq, 46.5 mmol) were combined in acetonitrile (10.0 mL), and the reaction was stirred at 0° C. for 1 h. Copper(I)bromide (53.3 mg, 0.37 mmol) was added at 0° C. and then warmed to 25° C. before being stirred for another 1 h. LCMS indicated ~67% of desired product formed. The reaction mixture was concentrated in vacuo and purified by flash column chromatography (petroleum ether:ethyl acetate=100:0 to 100:20) to afford tert-butyl ((1-(3-bromo-1-(4-methoxybenzyl)-1H-pyrazolo[3,4-b]pyrazin-6-yl)-4-methylpiperidin-4-yl)methyl)carbamate (500 mg, 50% yield) as a yellow solid.

Step 4: (1-(3-Bromo-1-(4-methoxybenzyl)-1H-pyrazolo[3,4-b]pyrazin-6-yl)-4-methylpiperidin-4-yl)methanamine (300 mg, 0.67 mmol), 1,2,3,4-tetrahydroquinoline (99 mg, 0.74 mmol), RuPhos (31 mg, 67 μmol), RuPhos-Pd-G4 (58 mg, 67 μmol) and t-BuONa (193 mg, 2.0 mmol) were combined in dioxane (5.0 mL), and the reaction was evacuated and refilled three times with nitrogen before being stirred at 120° C. for 12 h. LCMS indicated 43% of desired product formed. The reaction mixture was concentrated in vacuo and purified by silica gel chromatography (petroleum ether:etOAc=100:0 to 100:30) to afford the product of (1-(3-(3,4-dihydroquinolin-1(2H)-yl)-1-(4-methoxybenzyl)-1H-pyrazolo[3,4-b]pyrazin-6-yl)-4-methylpiperidin-4-yl)methanamine (60 mg, 13% yield) as a yellow solid.

Step 5: (1-(3-(3,4-dihydroquinolin-1(2H)-yl)-1-(4-methoxybenzyl)-1H-pyrazolo[3,4-b]pyrazin-6-yl)-4-methylpiperidin-4-yl)methanamine (60 mg, 0.12 mmol) was added to the mixture of trifluoromethylsulfonic acid (0.2 mL) and trifluoroacetic acid (2.0 mL), and the reaction was stirred at 90° C. for 0.5 h. LCMS indicated ~52% of desired product formed. The reaction mixture was concentrated under reduced pressure, diluted with methanol (5 mL), adjusted to pH=9 by adding ammonium hydroxide (aq.), and purified by prep-HPLC (eluting with acetonitrile and water, both with 0.1% ammonium hydroxide). Lyophilization afforded (1-(3-(3,4-dihydroquinolin-1(2H)-yl)-1H-pyrazolo[3,4-b]pyrazin-6-yl)-4-methylpiperidin-4-yl)methanamine (4.0 mg, 8.8% yield) as a yellow solid. LCMS: calc. for $C_{21}H_{27}N_7$: 377.2, found: [M+H]+ 378.1. HPLC: 98.5% purity at 254 nm.

The following compounds were synthesized via the same route as Compound 78 using the appropriate building blocks (synthesis outlined below where not commercially available): Compound 85, Compound 86, Compound 89, Compound 90, Compound 91, Compound 92, Compound 93, Compound 94, Compound 102, Compound 108, Compound 110, Compound 111, Compound 1138, Compound 114, Compound 115, Compound 117, Compound 118.

Syntheses of Intermediates

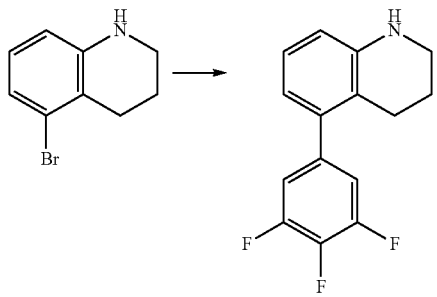 [SMILES: Brc1cccc2c1CCCN2 ; Fc1cc(-c2cccc3c2CCCN3)cc(F)c1F]

5-Bromo-1,2,3,4-tetrahydroquinoline (300.0 mg, 1.4 mmol), (3,4,5-trifluorophenyl)boronic acid (248.0 mg, 1.4 mmol), Pd(dppf)Cl2 (103.0 mg, 141 µmol), and cesium carbonate (919.0 mg, 2.8 mmol) were added to a mixture of dioxane (20.0 mL) and water (2.0 mL). The reaction mixture was evacuated and refilled with nitrogen three times before being stirred at 100° C. for 12 h. LCMS indicated 53% of the desired product was formed. The reaction mixture was concentrated in vacuo to give a residue that was purified by silica gel chromatography (eluting with petroleum ether/ethyl acetate). Concentration in vacuo led to 5-(3,4,5-trifluorophenyl)-1,2,3,4-tetrahydroquinoline (200.0 mg, 53.9% yield) as a yellow solid.

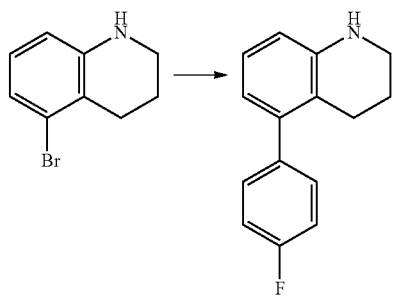 [SMILES: Brc1cccc2c1CCCN2 ; Fc1ccc(-c2cccc3c2CCCN3)cc1]

5-Bromo-1,2,3,4-tetrahydroquinoline (300.0 mg, 1.4 mmol), (4-fluorophenyl)boronic acid (216.0 mg, 1.6 mmol), Pd(dppf)Cl2 (103.0 mg, 141 µmol), and cesium carbonate (919.0 mg, 2.8 mmol) were added to a mixture of dioxane (20.0 mL) and water (2.0 mL). The reaction mixture was evacuated and refilled with nitrogen three times before being stirred at 100° C. for 12 h. LCMS indicated 71% of desired product formed. The reaction mixture was concentrated in vacuo to give a residue that was purified by flash silica gel chromatography (eluting with petroleum ether/ethyl acetate). 5-(4-fluorophenyl)-1,2,3,4-tetrahydroquinoline (300.0 mg, 93.7% yield) was isolated as a yellow solid.

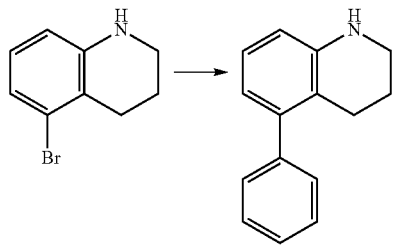 [SMILES: Brc1cccc2c1CCCN2 ; c1ccc(-c2cccc3c2CCCN3)cc1]

A mixture of 5-bromo-1,2,3,4-tetrahydroquinoline (300 mg, 1.4 mmol, 1.0 eq), phenylboronic acid (188 mg, 1.5 mmol, 1.1 eq), cesium carbonate (1.37 g, 4.2 mmol, 3.0 eq), and Pd(dppeCl2 (103 mg, 141 µmol, 0.1 eq) in dioxane (10 mL) and water (1 mL) was evacuated and refilled with nitrogen three times. The the mixture was stirred at 100° C. for 15 h before being concentrated in vacuo. The residue was purified by silica gel chromatography (eluting with petroleum ether/ethyl acetate) to afford 5-phenyl-1,2,3,4-tetrahydroquinoline (270 mg, 91.5% yield) as a yellow oil.

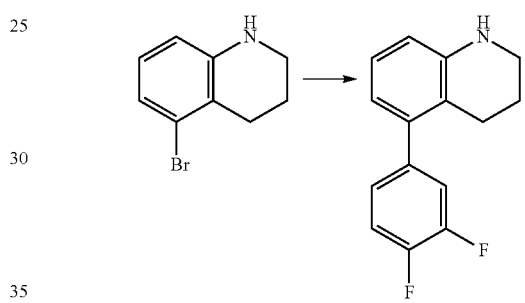

A mixture of 5-bromo-1,2,3,4-tetrahydroquinoline (300 mg, 1.4 mmol, 1.0 eq), (3,4-difluorophenyl)boronic acid (244 mg, 1.5 mmol, 1.1 eq), cesium carbonate (1.37 g, 4.2 mmol, 3.0 eq), and Pd(dppeCl2 (103 mg, 141 µmol, 0.1 eq) in dioxane (10 mL) and water (1 mL) was evacuated and refilled with nitrogen three times. The mixture was stirred at 100° C. for 15 h under nitrogen before being concentrated in vacuo and purified by column chromatography (eluting with petroleum ether/ethyl acetate) to afford 5-(3,4-difluorophenyl)-1,2,3,4-tetrahydroquinoline (340 mg, 98.5% yield) as a colorless oil.

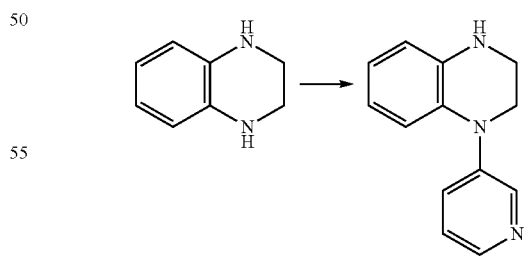

A round bottomed flask was charged with 1,2,3,4-tetrahydroquinoxaline (500.0 mg, 3.7 mmol, 1.0 eq), 3-iodopyridine (840.3 mg, 4.1 mmol, 1.1 eq), RuPhos (173.9 mg, 372.6 umol, 0.1 eq), RuPhos-Pd-G4 (313.8 mg, 372.6 umol, 0.1 eq), and tBuONa (1.1 g, 11.2 mmol, 3.0 eq). Dioxane (8 mL) was added, and the reaction mixture was evacuated and refilled 3 times with nitrogen before being stirred at 80° C.

for 12 h. LCMS indicated one main desired spot formed. The reaction mixture was concentrated in vacuo and purified by flash silica gel chromatography (eluting with dichloromethane and methanol) to afford 4-(3-pyridyl)-2,3-dihydro-1H-quinoxaline (0.5 g, 63.5% yield) as a black brown solid.

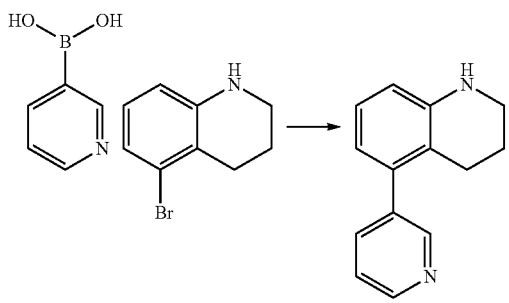

A solution of pyridin-3-ylboronic acid (115 mg, 0.943 mmol), 5-bromo-1,2,3,4-tetrahydroquinoline (100 mg, 0.4715 mmol), tetrakis(triphenylphosphine)palladium (54.4 mg, 0.04715 mmol), and potassium carbonate (259 mg, 1.88 mmol) in dioxane (4 mL) and water (1 mL) was stirred at 95° C. for 2 h. The reaction mixture was concentrated in vacuo. The residue was purified by normal phase using 0-65% ethyl acetate in heptanes. The product 5-(pyridin-3-yl)-1,2,3,4-tetrahydroquinoline (82.0 mg, 0.3899 mmol, 83% yield) was obtained as an off-white solid.

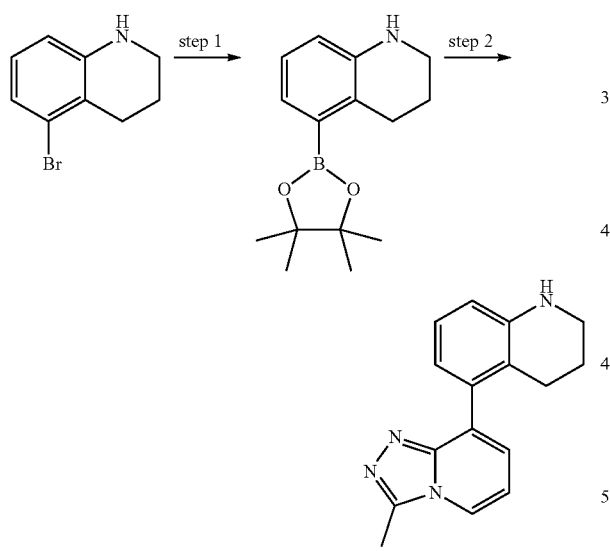

Step 1: 5-bromo-1,2,3,4-tetrahydroquinoline (500 mg, 2.35 mmol), 5-bromo-1,2,3,4-tetrahydroquinoline (500 mg, 2.35 mmol), Pddppf-dichloromethane adduct (97.1 mg, 0.1175 mmol) and potassium acetate (922 mg, 9.40 mmol) were dissolved in dioxane (10 mL) and stirred at 100° C. 18 h. The mixture was cooled to room temperature, diluted with ethyl acetate, and filtered through a pad of celite. Purified by silica gel chromatography (eluting with 0-100% ethyl acetate in heptanes). Product-containing fractions were combined and concentrated in vacuo to give 5-(4,4,5,5-tetramethyl-1,3,2-dioxaborolan-2-yl)-1,2,3,4-tetrahydroquinoline (413 mg, 1.59 mmol, 67.8% yield).

Step 2: 5-(4,4,5,5-tetramethyl-1,3,2-dioxaborolan-2-yl)-1,2,3,4-tetrahydroquinoline (100 mg, 0.3858 mmol), 8-bromo-3-methyl-[1,2,4]triazolo[4,3-a]pyridine (63 mg, 0.2967 mmol), tetrakis(triphenylphosphine)Palladium (34 mg, 0.02967 mmol), and potassium carbonate (82 mg, 0.5935 mmol) were dissolved in dioxane (4 mL) and water (1 mL) and stirred at 95° C. for 3 h. The mixture was cooled to room temperature and partitioned between water and ethyl acetate. Following separation of the layers, the organic phase was dried over sodium sulfate, filtered, and concentrated in vacuo. The crude residue was purified by silica gel chromatography (eluting with 0-100% ethyl acetate in heptanes). Product-containing fractions were combined and concentrated in vacuo to give 5-(3-methyl-[1,2,4]triazolo[4,3-a]pyridin-8-yl)-1,2,3,4-tetrahydroquinoline (31.8 mg, 0.1203 mmol, 41% yield).

Example 22

Synthesis of 1-[6-(4-amino-4-methyl-1-piperidyl)-1H-pyrazolo[3,4-b]pyrazin-3-yl]-3,4-dihydro-1,5-naphthyridin-2-one, Compound 84

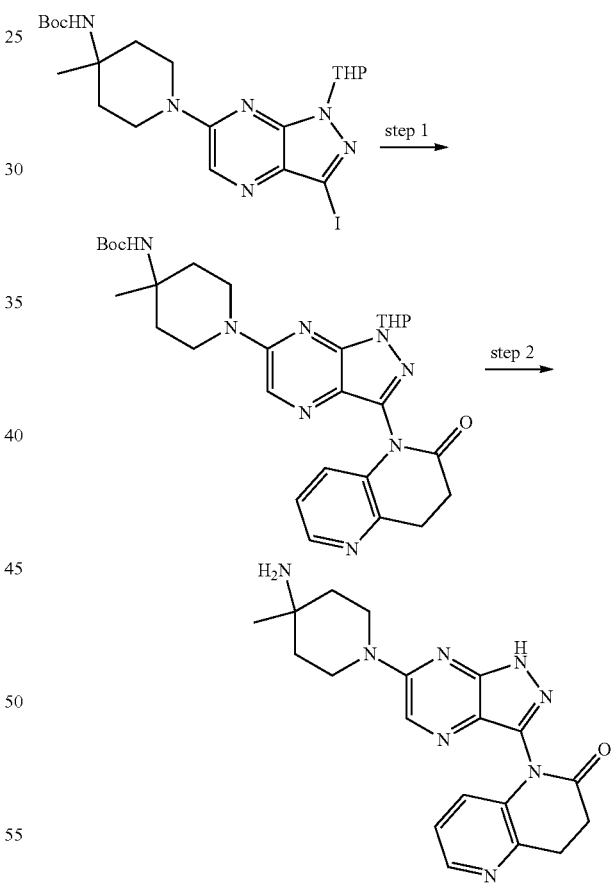

Step 1: Tert-butyl (1-(3-iodo-1-(tetrahydro-2H-pyran-2-yl)-1H-pyrazolo[3,4-b]pyrazin-6-yl)-4-methylpiperidin-4-yl)carbamate (200.0 mg, 368.0 µmol) (Intermediate A), 3,4-dihydro-1,5-naphthyridin-2(1H)-one (162.0 mg, 1.1 mmol), CuI (7.0 mg, 36.8 µmol), potassium carbonate (152.0 mg, 1.1 mmol), and (1S,2S)—N1,N2-dimethylcyclohexane-1,2-diamine (5.2 mg, 36.8 µmol) were combined in toluene (5.0 mL), the reaction flask was evacuated and refilled 3 times with nitrogen, and the mixture was stirred at 110° C. for 12 h. LCMS indicated 65% of desired product formed. The reaction mixture was concentrated in vacuo to give a residue that was purified by silica gel chromatography (eluting with petroleum ether:ethyl acetate=10:0 to 10:3) to afford tert-butyl (4-methyl-1-(3-(2-oxo-3,4-dihydro-1,5-naphthyridin-1(2H)-yl)-1-(tetrahydro-2H-pyran-2-yl)-1H-pyrazolo[3,4-b]pyrazin-6-yl)piperidin-4-yl)carbamate (100.0 mg, 48.3% yield) as a yellow solid.

Step 2: A flask was charged with tert-butyl N-[4-methyl-1-[3-(2-oxo-3,4-dihydro-1,5-naphthyridin-1-yl)-1-tetrahydropyran-2-yl-pyrazolo[3,4-b]pyrazin-6-yl]-4-piperidyl]carbamate (180.0 mg, 319.9 umol) followed by trifluoroacetic acid (2.0 mL), and the reaction mixture was stirred at 50° C. for 12 h. LCMS indicated one main desired peak formed. The reaction mixture was concentrated in vacuo, and the residue was purified by prep-HPLC (eluting with acetonitrile/water/0.1% hydrochloric acid) to afford 1-[6-(4-amino-4-methyl-1-piperidyl)-1H-pyrazolo[3,4-b]pyrazin-3-yl]-3,4-dihydro-1,5-naphthyridin-2-one (22.0 mg, 15.9% yield, HCl salt) as a yellow solid.

Example 23

Synthesis of 1-(6-(4-amino-4-methylpiperidin-1-yl)-1H-pyrazolo[3,4-b]pyrazin-3-yl)-1,2,3,4-tetrahydro-1,6-naphthyridin-5-amine Compound 87

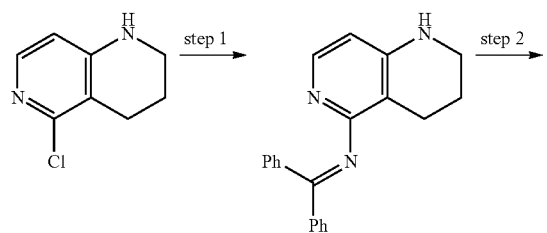

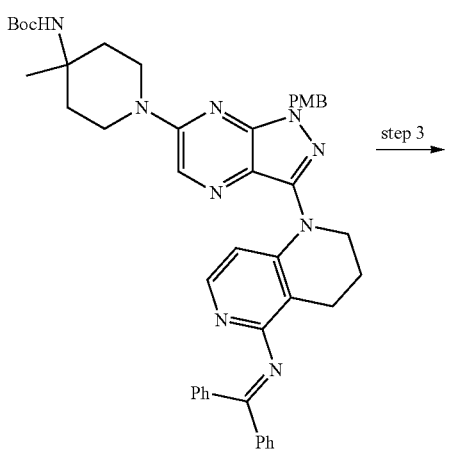

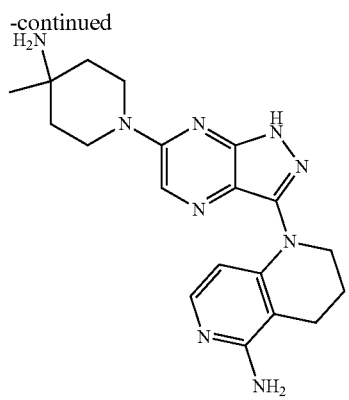

Step 1: To a solution of 5-chloro-1,2,3,4-tetrahydro-1,6-naphthyridine (150 mg, 889 μmol) and diphenylmethanimine (177 mg, 977 μmol) in toluene (5 mL) was added t-BuONa (170 mg, 1.77 mmol), Pd$_2$(dba)$_3$ (81.3 mg, 177 μmol) and 2,2'-bis(diphenylphosphino)-1,1'-binaphthyl (110 mg, 177 μmol). The mixture was degassed and purged with nitrogen three times. The mixture was stirred at 110° C. for 12 h under a nitrogen atmosphere. LCMS showed the starting material was consumed completely and 25% desired product was formed. The reaction mixture was concentrated in vacuo, and the residue was purified by silica gel chromatography (eluting with petroleum ether/ethyl acetate=100:0 to 100:100). The product N-(diphenylmethylene)-1,2,3,4-tetrahydro-1,6-naphthyridin-5-amine (180 mg, 574 μmol, 64.7% yield) was obtained as a light yellow solid.

Step 2: To a solution of tert-butyl (1-(3-bromo-1-(4-methoxybenzyl)-1H-pyrazolo[3,4-b]pyrazin-6-yl)-4-methylpiperidin-4-yl)carbamate (200 mg, 376 μmol) and N-(diphenylmethylene)-1,2,3,4-tetrahydro-1,6-naphthyridin-5-amine (117 mg, 376 μmol) in dioxane (5 mL) was added RuPhos-Pd-G4 (91.3 mg, 112 μmol), t-BuONa (72.2 mg, 752 μmol), and RuPhos (52.2 mg, 112 μmol). The reaction mixture was purged with nitrogen for 3 min, and the reaction was stirred at 120° C. for 12 h under a nitrogen atmosphere. LCMS showed most starting material was consumed and 40% desired product was formed. The reaction mixture was concentrated in vacuo. The residue was purified by silica gel chromatography (eluting with petroleum ether/ethyl acetate=100:0 to 100:80). The product, tert-butyl (1-(3-(5-((diphenylmethylene)amino)-3,4-dihydro-1,6-naphthyridin-1(2H)-yl)-1-(4-methoxybenzyl)-1H-pyrazolo[3,4-b]pyrazin-6-yl)-4-methylpiperidin-4-yl)carbamate (200 mg, 261 μmol, 69.6% yield) was obtained as a yellow gum.

Step 3: A solution of tert-butyl (1-(3-(5-((diphenylmethylene)amino)-3,4-dihydro-1,6-naphthyridin-1(2H)-yl)-1-(4-methoxybenzyl)-1H-pyrazolo[3,4-b]pyrazin-6-yl)-4-methylpiperidin-4-yl)carbamate (180 mg, 235 μmol) in trifluoroacetic acid (5 mL) was stirred at 80° C. for 50 h and then 100° C. for 22 h. LCMS showed most of the starting material was consumed and 22% desired product was formed. The reaction mixture was concentrated in vacuo. The residue was diluted with methanol and adjusted to pH=10 with ammonium hydroxide (aq.). The residue was purified by prep-HPLC (eluting with acetonitrile/water/0.1% ammonium hydroxide). The product, 1-(6-(4-amino-4-methylpiperidin-1-yl)-1H-pyrazolo[3,4-b]pyrazin-3-yl)-1,2,3,4-tetrahydro-1,6-naphthyridin-5-amine (35.0 mg, 92.2 μmol, 39.2% yield) was obtained as an off-white solid.

Example 24

Synthesis of 5-(6-(4-(aminomethyl)-4-methylpiperidin-1-yl)-1H-pyrazolo[3,4-b]pyrazin-3-yl)-5,6,7,8-tetrahydro-1,5-naphthyridin-2-amine, Compound 96

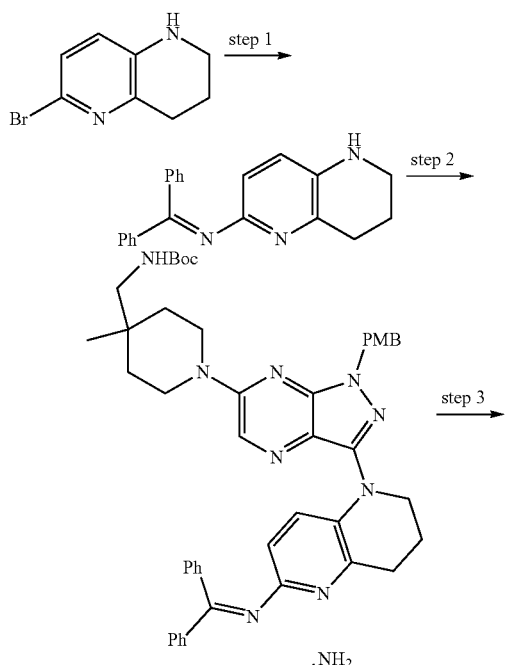

Step 1: To a solution of 6-bromo-1,2,3,4-tetrahydro-1,5-naphthyridine (30 mg, 140 μmol) and diphenylmethanimine (27.9 mg, 154 μmol) in toluene (5 mL) were added Pd$_2$(dba)$_3$ (12.8 mg, 14.0 μmol), BINAP (8.71 mg, 14.0 μmol) and sodium tert-butoxide (26.8 mg, 280 μmol). The mixture was degassed and purged with nitrogen three times before being stirred at 110° C. for 12 h under nitrogen atmosphere. LCMS showed the starting material was consumed completely and 30% desired product was formed. The reaction mixture was concentrated in vacuo. The residue was purified by silica gel chromatography (eluting with petroleum ether/ethyl acetate). N-(diphenylmethylene)-5,6,7,8-tetrahydro-1,5-naphthyridin-2-amine (230 mg, 733 μmol, 71.4% yield) was obtained as a brown solid.

Step 2: To a solution of tert-butyl ((1-(3-bromo-1-(4-methoxybenzyl)-1H-pyrazolo[3,4-b]pyrazin-6-yl)-4-methylpiperidin-4-yl)methyl)carbamate (360 mg, 659 μmol) and N-(diphenylmethylene)-5,6,7,8-tetrahydro-1,5-naphthyridin-2-amine (226 mg, 724 μmol) in dioxane (10 mL) were added RuPhos (65.9 μmol, 30.7 mg), RuPhos-Pd-G4 (65.9 μmol, 56.0 mg), and sodium tert-butoxide (1.31 mmol, 125 mg). The reaction mixture was evacuated and backfilled with nitrogen three times. The reaction mixture was stirred at 100° C. for 12 h. LCMS showed the starting material was consumed completely and 33% desired product was formed. The reaction mixture was concentrated in vacuo. The residue was purified by column chromatography (eluting with dichloromethane and methanol). The product of tert-butyl ((1-(3-(6-((diphenylmethylene)amino)-3,4-dihydro-1,5-naphthyridin-1(2H)-yl)-1-(4-methoxybenzyl)-1H-pyrazolo[3,4-b]pyrazin-6-yl)-4-methylpiperidin-4-yl)methyl)carbamate (500 mg, 449 μmol, 97.6% yield) was obtained as a yellow solid.

Step 3: A solution of tert-butyl ((1-(3-(6-((diphenylmethylene)amino)-3,4-dihydro-1,5-naphthyridin-1(2H)-yl)-1-(4-methoxybenzyl)-1H-pyrazolo[3,4-b]pyrazin-6-yl)-4-methylpiperidin-4-yl)methyl)carbamate (480 mg, 617 μmol) in trifluoroacetic acid (10 mL) and trifluoromethylsulfonic acid (2.0 mL) was stirred at 20° C. for 6 h. LCMS showed the starting material was consumed completely and that 41% desired product was formed. The reaction mixture was concentrated under reduced pressure. The residue was diluted with methanol (5.0 mL) and dimethylformamide (5.0 mL) and adjusted to pH=7-10 with ammonium hydroxide. The residue was purified by prep-HPLC (eluting with acetonitrile/water/0.1% formic acid). 5-(6-(4-(aminomethyl)-4-methylpiperidin-1-yl)-1H-pyrazolo[3,4-b]pyrazin-3-yl)-5,6,7,8-tetrahydro-1,5-naphthyridin-2-amine (100 mg, 254 μmol, 41.3% yield) was obtained as a yellow solid.

Example 25

Synthesis of 8-(3-(3,4-dihydro-1,5-naphthyridin-1(2H)-yl)-1H-pyrazolo[3,4-b]pyrazin-6-yl)-8-azaspiro[4.5]decan-1-amine, Compound 98

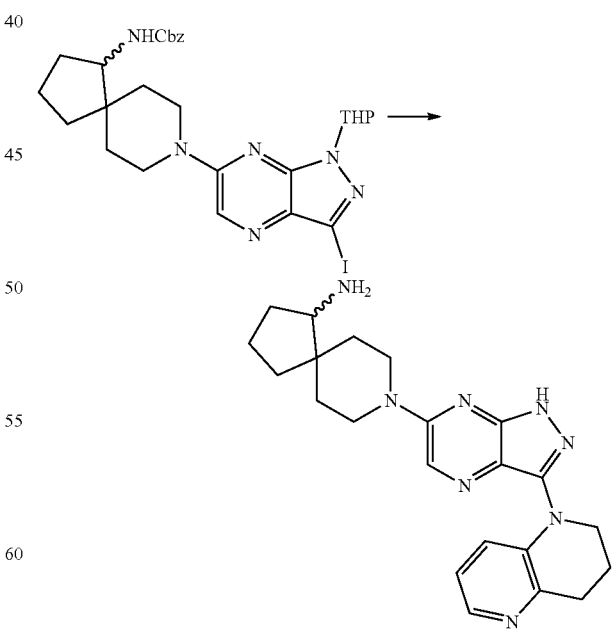

A resealable reaction vial was charged with benzyl (8-(3-iodo-1-(tetrahydro-2H-pyran-2-yl)-1H-pyrazolo[3,4-b]pyrazin-6-yl)-8-azaspiro[4.5]decan-1-yl)carbamate (131 mg, 0.2124 mmol) (prepared via a similar route to that described in example 1), 1,2,3,4-tetrahydro-1,5-naphthyridine (31.3 mg, 0.2336 mmol), sodium 2-methylpropan-2-olate (40.8 mg, 0.4248 mmol), RuPhos/Pd G4 (18.0 mg, 0.02124 mmol), and dioxane (5 mL). Nitrogen was bubbled through the mixture for 10 min, the vial was sealed, and the mixture was stirred at 90° C. At 2 h, LCMS showed complete consumption of starting material and partial deprotection of the Cbz group. Stirring was continued for 3 h before the reaction mixture was diluted with ethyl acetate and brine. The layers were separated, and the organic phase was dried with sodium sulfate. Filtration and concentration in vacuo resulted in a residue that was purified by reverse phase HPLC (eluting with acetonitrile/water/0.1% ammonium formate). Lyophilization yielded 8-(3-(3,4-dihydro-1,5-naphthyridin-1(2H)-yl)-1H-pyrazolo[3,4-b]pyrazin-6-yl)-8-azaspiro[4.5]decan-1-amine (2 mg) as an amorphous off-white solid.

Example 26

Synthesis of 1-(6-(4-amino-4-methylpiperidin-1-yl)-1H-pyrazolo[3,4-b]pyrazin-3-yl)-1,2,3,4-tetrahydroquinoline-6-carboxamide, Compound 99

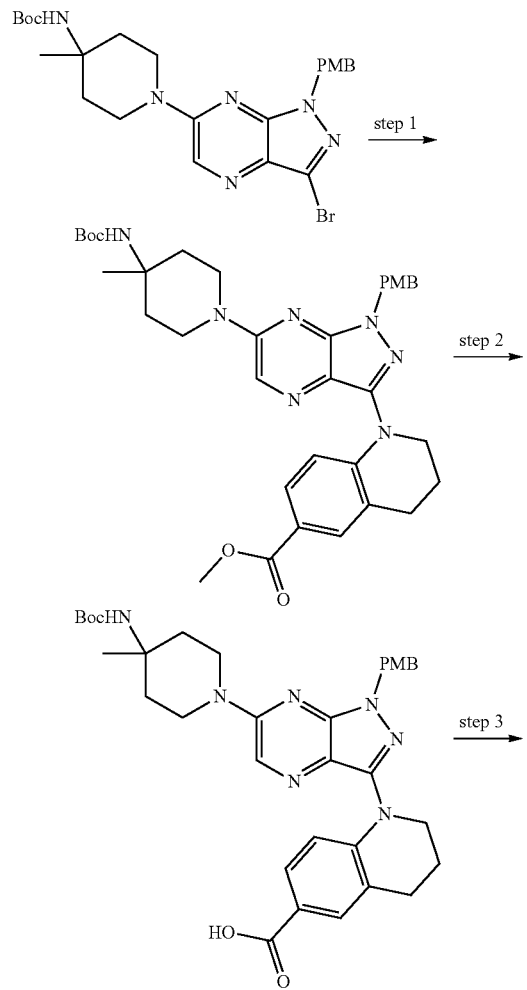

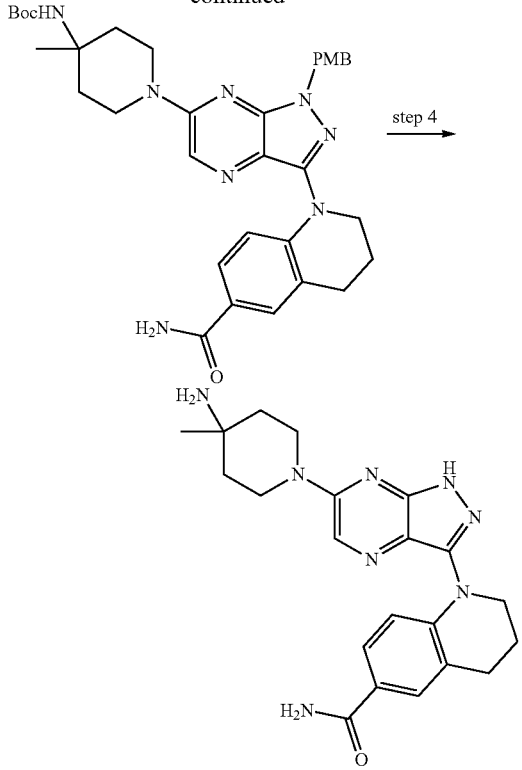

Step 1: Tert-butyl (1-(3-bromo-1-(4-methoxybenzyl)-1H-pyrazolo[3,4-b]pyrazin-6-yl)-4-methylpiperidin-4-yl)carbamate (0.2 g, 376.0 μmol), methyl 1,2,3,4-tetrahydroquinoline-6-carboxylate (71.9 mg, 375.0 μmol), RuPhos (17.5 mg, 37.6 μmol), RuPhos-Pd-G4 (31.9 mg, 37.6 μmol), and t-BuONa (107.0 mg, 1.1 mmol) were combined in dioxane (10 mL). The reaction mixture was evacuated and backfilled three times with nitrogen before being stirred at 120° C. for 12 h. LCMS indicated 63% of desired product formed. The reaction mixture was concentrated in vacuo, and the crude residue was purified by silica gel chromatography (eluting with ethyl acetate/petroleum ether=0:100 to 30:100) to afford methyl 1-(6-(4-(((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylate (180.0 mg, 74.6% yield) as a yellow solid.

Step 2: To methyl 1-(6-(4-(((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylate (160.0 mg, 249 μmol) dissolved in methanol (3.0 mL) was added sodium hydroxide (19.9 mg, 498.0 μmol) in water (1.0 mL), and the reaction mixture was stirred at 70° C. for 12 h. LCMS indicated 94% of desired product formed. The reaction mixture was concentrated in vacuo and diluted with water (20.0 mL), adjusted to pH=5 by adding 2N hydrochloric acid, and extracted with dichloromethane (30.0 mL×2). The organic phase was washed with brine, dried over anhydrous sodium sulfate, filtered, and concentrated in vacuo to give 1-(6-(4-(((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylic acid (160.0 mg, 96.1% yield) which as a yellow solid.

Step 3: To a solution of 1-(6-(4-(((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6- carboxylic acid (150.0 mg, 238.0 µmol), and HATU (180.0 mg, 476.0 µmol) in a mixture of tetrahydrofuran (12.0 mL) and dichloromethane (6.0 mL) and triethylamine (96.3 mg, 952.0 µmol) were added in one portion and stirred for 15 min. Ammonium carbonate (91.3 mg, 952.0 µmol) was added, and the mixture was stirred for another 2 h. LCMS indicated 71% of desired product formed. The reaction mixture was diluted with ethyl acetate (30 mL), washed with brine (20 mL×2), and concentrated in vacuo to afford tert-butyl (1-(3-(6-carbamoyl-3,4-dihydroquinolin-1(2H)-yl)-1-(4-methoxybenzyl)-1H-pyrazolo[3,4-b]pyrazin-6-yl)-4-methylpiperidin-4-yl)carbamate (150.0 mg, crude) as a yellow solid.

Step 4: Tert-butyl (1-(3-(6-carbamoyl-3,4-dihydroquinolin-1(2H)-yl)-1-(4-methoxybenzyl)-1H-pyrazolo[3,4-b]pyrazin-6-yl)-4-methylpiperidin-4-yl)carbamate (150.0 mg, 239 µmol) and trifluoromethylsulfonic acid (0.2 mL) were combined in trifluoroacetic acid (2.0 mL), and the reaction was stirred at 90° C. for 30 min. LCMS indicated 93% of desired product formed. The reaction mixture was concentrated under reduced pressure, diluted with methanol (5.0 mL), and adjusted to pH=9 by adding ammonium hydroxide before being purified by prep-HPLC (eluting with acetonitrile/water/0.1% hydrochloric acid) to afford 1-(6-(4-amino-4-methylpiperidin-1-yl)-1H-pyrazolo[3,4-b]pyrazin-3-yl)-1,2,3,4-tetrahydroquinoline-6-carboxamide (43.2 mg, 44.4% yield) as a yellow solid.

Example 27

Synthesis of 8-(3-(3,4-dihydro-1,5-naphthyridin-1(2H)-yl)-1H-pyrazolo[3,4-b]pyrazin-6-yl)-1-oxa-8-azaspiro[4.5]decan-4-amine, Compound 100

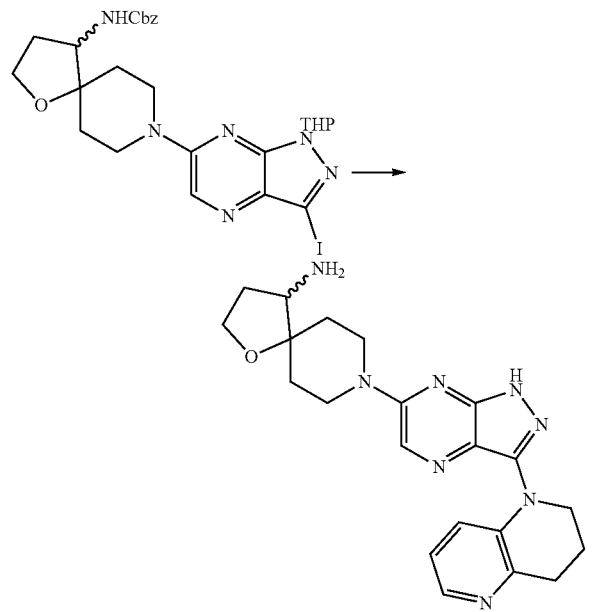

A resealable reaction vial was charged with 8-(3-iodo-1-(tetrahydro-2H-pyran-2-yl)-1H-pyrazolo[3,4-b]pyrazin-6-yl)-N-(4-methoxybenzyl)-1-oxa-8-azaspiro[4.5]decan-4-amine (125 mg, 0.2067 mmol) (prepared via a route similar to that described in example 1), 1,2,3,4-tetrahydro-1,5-naphthyridine (30.4 mg, 0.2273 mmol), sodium 2-methylpropan-2-olate (39.7 mg, 0.4134 mmol), RuPhos/Pd G4 (17.5 mg, 0.02067 mmol), and dioxane (5 mL). Nitrogen was bubbled through the mixture for 10 min, the vial was sealed, and the mixture was stirred at 90° C. 3 h. The mixture was cooled to room temperature and concentrated in vacuo. The residue was dissolved in trifluoroacetic acid (3 mL) (turned dark green) and heated to 100° C. in the microwave for 1 h then at 130° C. 1 h. The reaction was diluted with methanol, concentrated in vacuo, stripped with methanol, and dissolved in dimethysulfoxide (with 0.2 mL aqueous ammonium hydroxide) for purification by reverse phase HPLC (eluting with acetonitrile/water/0.1% ammonium formate). The fraction containing the product was concentrated, combined with the remaining crude DMSO solution and partitioned between ethyl acetate and saturated aqueous sodium bicarbonate. The concentrated organic layer was dissolved in dimethylsulfoxide and purified by reverse phase HPLC (eluting with acetonitrile/water/0.1% ammonium formate). Lyophilization yielded 8-(3-(3,4-dihydro-1,5-naphthyridin-1(2H)-yl)-1H-pyrazolo[3,4-b]pyrazin-6-yl)-1-oxa-8-azaspiro[4.5]decan-4-amine (22 mg) as a yellow solid.

Example 28

Synthesis of 1-(6-(4-(aminomethyl)-4-methylpiperidin-1-yl)-1H-pyrazolo[3,4-b]pyrazin-3-yl)-1,2,3,4-tetrahydroquinoline-6-carboxamide, Compound 103

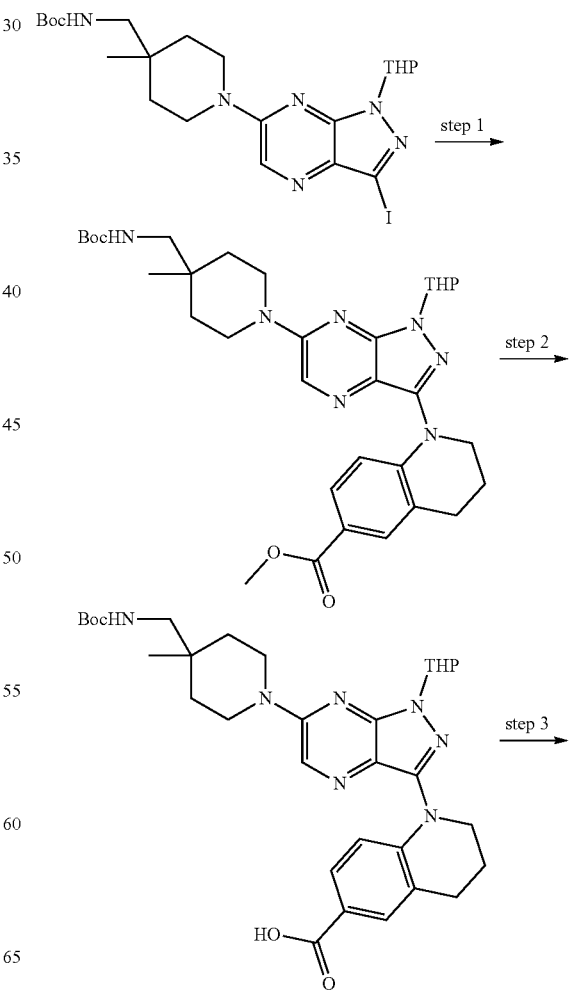

-continued

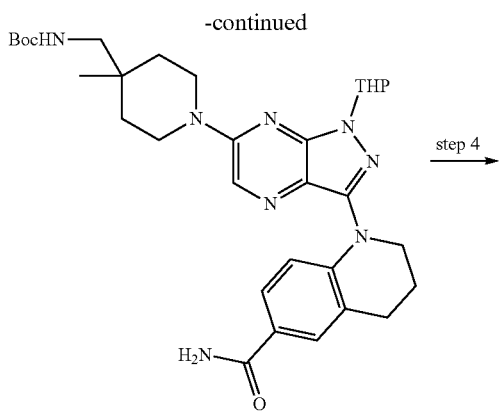

step 4 →

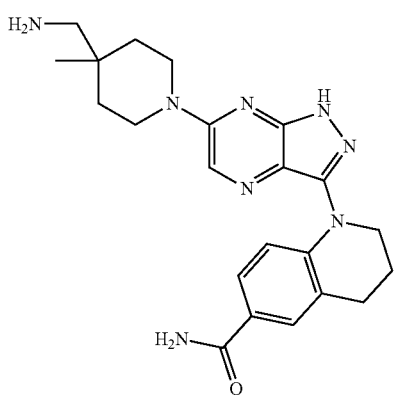

Step 1: Tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate (200.0 mg, 359 μmol), methyl 1,2,3,4-tetrahydroquinoline-6-carboxylate (68.6 mg, 359 μmol), RuPhos (33.4 mg, 71.8 μmol), RuPhos-Pd-G4 (61.7 mg, 71.8 μmol) and t-BuONa (68.9 mg, 718 μmol) were combined in dioxane (15.0 mL), and the reaction mixture was evacuated and backfilled with nitrogen three times before being stirred at 70° C. for 12 h. LCMS indicated 32% of desired product formed. The reaction mixture was concentrated in vacuo and purified by flash silica gel chromatography (eluting with petroleum ether/ethyl acetate) to afford methyl 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylate (160.0 mg, 72.0% yield) as a yellow solid.

Step 2: Methyl 1-(6-(4-(((tert-butoxycarbonyl)amino) methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylate (160.0 mg, 258 μmol) was dissolved in methanol (10.0 mL) for the addition of sodium hydroxide (30.9 mg, 774 μmol) and water (2.0 mL), and the reaction mixture was stirred at 70° C. for 12 h. LCMS indicated 98% of desired product formed. The reaction mixture was concentrated in vacuo and diluted with water (20.0 mL), adjusted to pH=5 by adding 2N hydrochloric acid, and extracted with dichloromethane (30.0 mL×2). The organic phase was washed with saturated brine (30.0 mL), dried with anhydrous sodium sulfate, filtered and concentrated in vacuo to give 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylic acid (130.0 mg, crude) as a yellow solid.

Step 3: 1-(6-(4-(((Tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylic acid (130.0 mg, 214 μmol) was dissolved in tetrahydrofuran (10.0 mL) for the addition of ethyl chloroformate1 (81.1 μL, 642 μmol) at 0° C., and the reaction mixture was stirred for 15 min Triethylamine (88.9 μL, 642 μmol) was added in one portion, and the reaction mixture was warmed to 25° C. and stirred for 12 h. LCMS indicated 44% of desired product formed. The reaction mixture was concentrated in vacuo and purified by flash silica gel chromatography (eluting with dichloromethane and methanol) to afford tert-butyl ((1-(3-(6-carbamoyl-3,4-dihydroquinolin-1 (2H)-yl)-1-(tetrahydro-2H-pyran-2-yl)-1H-pyrazolo[3,4-b] pyrazin-6-yl)-4-methylpiperidin-4-yl)methyl)carbamate (50.0 mg, 36.4% yield) as a yellow solid.

Step 4: Tert-butyl ((1-(3-(6-carbamoyl-3,4-dihydroquinolin-1(2H)-yl)-1-(tetrahydro-2H-pyran-2-yl)-1H-pyrazolo[3,4-b]pyrazin-6-yl)-4-methylpiperidin-4-yl)methyl)carbamate (50.0 mg, 99.2 μmol) was added to 4N HCl/methanol (5.0 mL), and the reaction was stirred at 25° C. for 2 h. LCMS indicated 88% of desired product formed. The reaction mixture was concentrated in vacuo and purified by prep-HPLC (eluting with acetonitrile/water/0.1% hydrochloric acid) to afford 1-(6-(4-(aminomethyl)-4-methylpiperidin-1-yl)-1H-pyrazolo[3,4-b]pyrazin-3-yl)-1,2,3,4-tetrahydroquinoline-6-carboxamide (18.0 mg, 51.8% yield, HCl salt) as a yellow solid.

Following synthetic procedures similar to those described herein, the following compounds were prepared. The characterization of compounds disclosed herein is shown below.

| Compound | Structure | Proton NMR | MS [M + 1] |
|---|---|---|---|
| 65 | ![structure] | $^1$H NMR (400 MHz, DMSO-d$_6$): δ 9.03 (s, 1H), 8.53 (s, 1H), 8.18 (d, J = 7.5 Hz, 1H) 7.79 (d, J = 7.5 Hz, 1H), 7.37 (dtd, J = 16.4, 73, 1.2 Hz, 2H), 3.91 (dt, J = 9.9, 4.7 Hz, 2H), 3.70 (ddd, J = 13.4, 8.6, 4.7 Hz, 2H), 1.55-1.45 (m, 4H), 1.11 (s, 3H). | 349.2 |

-continued

| Compound | Structure | Proton NMR | MS [M + 1] |
|---|---|---|---|
| 66 | 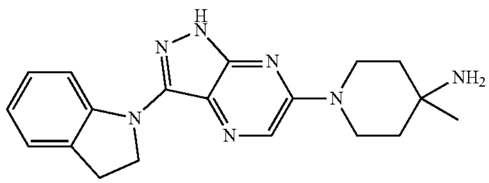 [SMILES: CC1(N)CCN(c2cnc3c(N4CCc5ccccc54)n[nH]c3n2)CC1] | (400 MHz, DMSO-d6): δ12.25 (s, 1H), 8.27 (s, 1H), 7.93-7.90 (d, 1H, J = 8.0 Hz), 7.20-7.17 (d, 1H, J = 7.2 Hz), 7.13-7.08 (t, 1H), 6.79-6.75 (t, 1H), 4.44-4.40 (t, 2H), 3.87-3.83 (t, 2H), 3.66-3.62 (q, 2H), 3.22-3.18(t, 2H), 1.49-1.46 (q, 4H), 1.09 (s, 3H). | 350.1 |
| 67 | 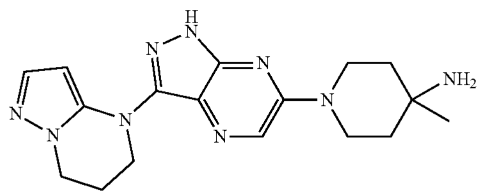 [SMILES: CC1(N)CCN(c2cnc3c(N4CCCn5nccc54)n[nH]c3n2)CC1] | (400 MHz, DMSO-d$_6$): δ = 12.33 (br s, 1H), 8.28 (s, 1H), 7.23 (d, J = 2.0 Hz, 1H), 6.34 (d, J = 2.0 Hz, 1H), 4.25-4.36 (m, 2H), 4.15 (t, J = 6.0 Hz, 2H), 3.86 (dt, J = 13.4, 4.5 Hz, 2H), 3.61 (ddd, J = 13.2, 8.9, 4.0 Hz, 2H), 2.24 (dt, J = 11.5, 5.8 Hz, 2H), 1.29-1.61 (m, 6H), 1.08 (s, 3H). | 354.2 |
| 68 | 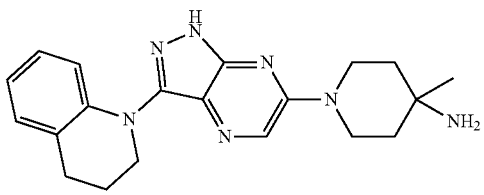 [SMILES: CC1(N)CCN(c2cnc3c(N4CCCc5ccccc54)n[nH]c3n2)CC1] | $^1$HNMR (400 MHz, DMSO-d$_6$): δ 8.38 (s, 3 H), 8.31 (s, 1H), 7.04-7.00 (m, 2H), 6.93-6.90 (m, 1H), 6.72-6.68 (m, 1H), 4.14 (m, 2H), 3.91-3.87 (m, 2H), 3.53-3.47 (m, 2H), 2.83-2.79 (m, 2H), 2.00-1.96 (m, 2H), 1.87-1.74 (m, 4H), 1.4 (s, 3H). | 364.0 |
| 69 and 70 | 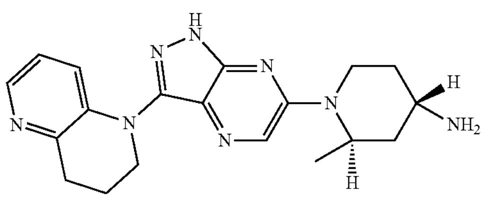 [SMILES: C[C@@H]1C[C@@H](N)CCN1c1cnc2c(N3CCCc4ncccc43)n[nH]c2n1] | $^1$HNMR (400 MHz, DMSO-d$_6$): δ 8.26 (s, 1H), 7.91-7.88 (m, 1H), 7.49-7.47 (m, 1H), 6.98-6.94 (m, 1H), 4.86-4.82 (m, 1H), 4.34-4.30 (m, 1H), 3.96-3.92 (m, 2H), 3.07-2.92 (m, 4H), 2.10-2.05 (m, 2H), 1.88-1.73 (m, 2H), 1.39-1.37 (m, 1H), 1.22-1.13 (m, 4H).<br>$^1$HNMR (400 MHz, DMSO-d$_6$): δ 8.31 (s, 1H), 7.96-7.94 (m, 1H), 7.55-7.52 (m, 1H), 7.03-6.99 (m, 1H), 4.96-4.88 (m, 1H), 4.40-4.36 (m, 1H), 4.02-3.98 (m, 2H), 3.12-2.97 (m, 4H), 2.15-2.08 (m, 2H), 1.94-1.79 (m, 2H), 1.46-1.43 (m, 1H), 1.28-1.21 (m, 4H). | 365.3 |
| 71 | 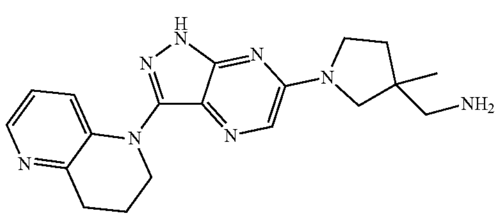 [SMILES: CC1(CN)CCN(c2cnc3c(N4CCCc5ncccc54)n[nH]c3n2)C1] | (400 MHz, DMSO-d$_6$): δ 12.99 (s, 1H), 8.16-8.21 (m, 3H), 8.12-8.14 (m, 1H), 8.09 (m, 1H), 7.97 (s, 1H), 7.57-7.60 (m, 1H), 4.02-4.05 (m, 2H), 3.23-3.40 (m, 2H), 2.92-2.93 (m, 2H), 2.14-2.17 (m, 1H), 2.04-2.08 (m, 1H), 1.86-1.88 (m, 1H), 1.23 (m, 1H), 1.19 (s, 3H). | 365.0 |
| 72 | 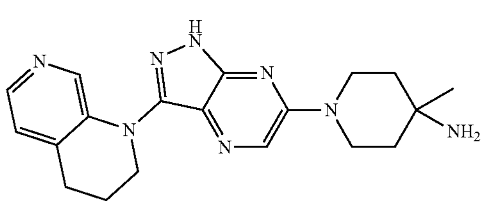 [SMILES: CC1(N)CCN(c2cnc3c(N4CCCc5ccncc54)n[nH]c3n2)CC1] | (400 MHz, DMSO_d6): δ 13.04 (br, 1H), 8.76 (s, 1H), 8.42 (s, 1H), 8.34 (br, 3H), 8.22 (d, J = 5.2 Hz, 1H), 7.78-7.76 (d, J = 5.2 Hz, 1H), 4.14 (s, 4H), 3.56-3.52 (m, 2H), 3.05-3.00 (m, 2H), 2.08-2.02 (m, 2H), 1.90-1.72 (m, 4H), 1.40 (s, 3H). | 365.1 |

-continued

| Compound | Structure | Proton NMR | MS [M + 1] |
|---|---|---|---|
| 73 | 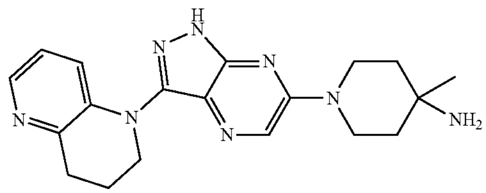 | (400 MHz, DMSO_d6): δ 12.57 (s, 1H), 8.29 (s, 1H), 7.89-7.91 (d, 1H), 7.47-7.50 (d, 1H), 6.94-6.98 (m, 1H), 3.93-3.97 (m, 2H), 3.84-3.89 (m, 2H), 3.58-3.65 (m, 2H), 2.92-2.96 (m, 2H), 2.05-2.09 (m, 2H), 1.44-1.52 (m, 4H), 1.09 (s, 3H). | 365.1 |
| 74 | 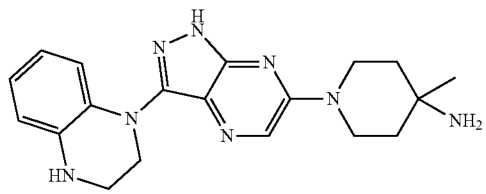 [SMILES: CC1(N)CCN(c2cnc3c(N4CCNc5ccccc54)n[nH]c3n2)CC1] | (400 MHz, DMSO_d6): δ 12.88 (br, 1H), 8.40-8.33 (m, 4H), 7.41 (s, 1H), 7.38-7.31 (m, 1H), 7.29-7.26 (m, 2H), 7.16-7.12 (m, 2H), 6.93-6.85 (m, 1H), 4.18-4.10 (m, 4H), 3.65-3.45 (m, 4H), 1.88-1.72 (m, 4H), 1.40 (s, 3H). | 365.1 |
| 75 | 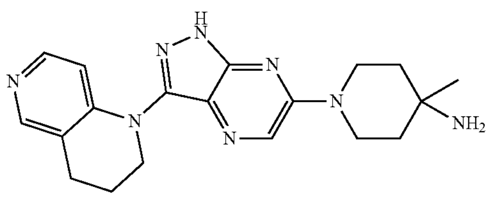 [SMILES: CC1(N)CCN(c2cnc3c(N4CCCc5cnccc54)n[nH]c3n2)CC1] | (400 MHz, DMSO-$d_6$ + TFA): δ 13.92 (br, 1H), 13.38 (br, 1H), 8.48 (s, 1H), 8.33-8.27 (m, 4H), 8.11-8.08 (m, 1H), 7.01-6.98 (m, 1H), 4.19-4.03 (m, 2H), 4.03-4.01 (m, 2H), 3.56-3.52 (m, 2H), 2.96-2.92 (m, 2H), 2.11-2.07 (m, 2H), 1.85-1.78 (m, 4H), 1.40 (s, 3H). | 365.1 |
| 76 | 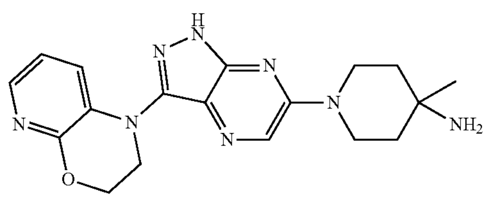 [SMILES: CC1(N)CCN(c2cnc3c(N4CCOc5ncccc54)n[nH]c3n2)CC1] | (400 MHz, Methanol-d4): δ 8.56 (d, J = 8.0 Hz, 1H), 8.40 (s, 1H), 7.83 (d, J = 5.6 Hz, 1H), 7.40-7.33 (m, 1H), 4.95-4.85 (m, 2H), 4.50-4.40 (m, 2H), 4.38-4.30 (m, 2H), 3.70-3.50 (m, 2H), 1.98-1.92 (m, 4H), 1.56 (s, 3H). | 367.1 |
| 77 | 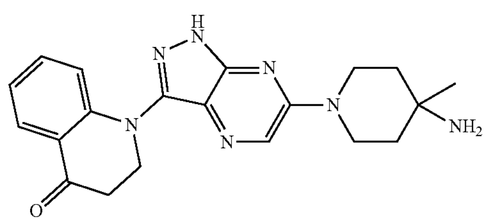 [SMILES: CC1(N)CCN(c2cnc3c(N4CCC(=O)c5ccccc54)n[nH]c3n2)CC1] | (400 MHz, DMSO-$d_6$): δ 12.95 (br, 1H), 8.40 (s, 1H), 8.10 (br, 3H), 7.82-7.80 (m, 1H), 7.36-7.33 (m, 1H), 7.05-7.02 (m, 1H), 6.91-6.86 (m, 1H), 4.19-4.14 (m, 4H), 3.52-3.45 (m, 2H), 2.85-2.80 (m, 2H), 1.81-1.74 (m, 4H), 1.40 (s, 3H). | 378.1 |
| 78 | 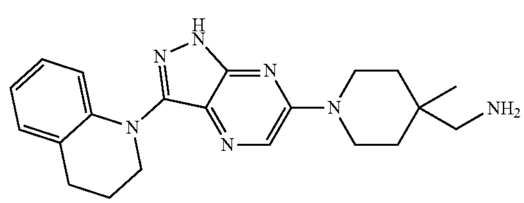 [SMILES: CC1(CN)CCN(c2cnc3c(N4CCCc5ccccc54)n[nH]c3n2)CC1] | (400 MHz, DMSO-d6): δ 12.51 (br, 1H), 8.26 (s, 1H), 7.04-7.00 (m, 2H), 6.95-6.85 (m, 1H), 6.72-6.63 (m, 1H), 3.98-3.84 (m, 4H), 3.55-3.40 (m, 4H), 2.85-2.77 (m, 2H), 2.00-1.93 (m, 2H), 1.50-1.44 (m, 2H), 1.35-1.27 (m, 2H), 0.95 (s, 3H). | 378.1 |
| 79 | 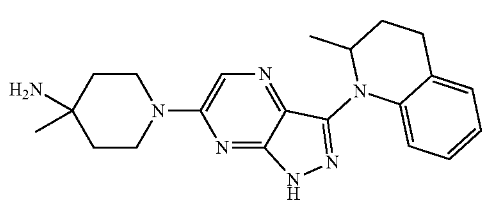 [SMILES: CC1CCc2ccccc2N1c1n[nH]c2nc(N3CCC(C)(N)CC3)cnc12] | (400 MHz, DMSO-d6): δ 12.54 (br, 1H), 8.23 (s, 1H), 7.00-6.97 (m, 1H), 6.80-6.79 (m, 1H), 6.66-6.58 (m, 2H), 4.32-4.28 (m, 1H), 3.83-3.77 (m, 2H), 3.63-3.57 (m, 2H), 2.83-2.76 (m, 2H), 1.98-1.95 (m, 1H), 1.83-1.81 (m, 1H), 1.46-1.41 (m, 4H), 1.11 (d, J = 6.4 Hz, 3H), 1.06 (s, 3H). | 378.1 |

-continued

| Compound | Structure | Proton NMR | MS [M + 1] |
|---|---|---|---|
| 80 | 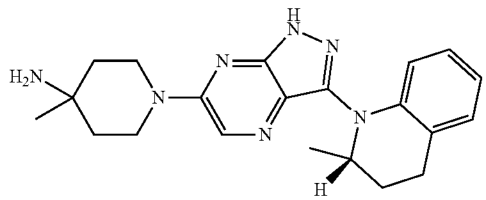 [SMILES: C[C@H]1CCc2ccccc2N1c1n[nH]c2nc(N3CCC(C)(N)CC3)cnc12] | (400 MHz, DMSO-d6): δ 12.54 (br, 1H), 8.23 (s, 1H), 7.00-6.97 (m, 1H), 6.80-6.79 (m, 1H), 6.66-6.58 (m, 2H), 4.32-4.28 (m, 1H), 3.83-3.77 (m, 2H), 3.63-3.57 (m, 2H), 2.83-2.76 (m, 2H), 1.98-1.95 (m, 1H), 1.83-1.81 (m, 1H), 1.46-1.41 (m, 4H), 1.11 (d, J = 6.4 Hz, 3H), 1.06 (s, 3H). | 378.1 |
| 81 | 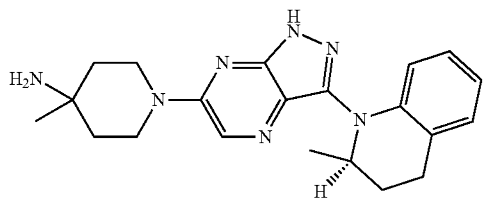 [SMILES: C[C@@H]1CCc2ccccc2N1c1n[nH]c2nc(N3CCC(C)(N)CC3)cnc12] | (400 MHz, DMSO-d6) δ 11.90 (s, 1H), 8.10 (s, 1H), 7.17-7.29 (m, 1H), 6.97-7.14 (m, 3H), 3.96-4.11 (m, 2H), 3.91 (br s, 2H), 3.34-3.50 (m, 2H), 2.68-2.81 (m, 2H), 1.54-1.82 (m, 6H), 1.33 (s, 3H). | 378 |
| 82 | 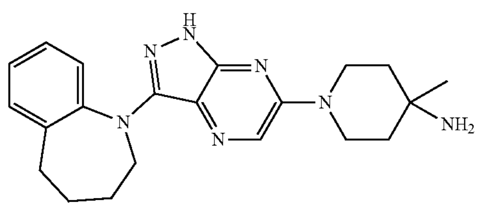 [SMILES: CC1(N)CCN(c2cnc3c(N4CCCCc5ccccc54)n[nH]c3n2)CC1] | (400 MHz, DMSO-d6) δ 11.90 (s, 1H), 8.10 (s, 1H), 7.17-7.29 (m, 1H), 6.97-7.14 (m, 3H), 3.96-4.11 (m, 2H), 3.91 (br s, 2H), 3.34-3.50 (m, 2H), 2.68-2.81 (m, 2H), 1.54-1.82 (m, 6H), 1.33 (s, 3H). | 378 |
| 83 | 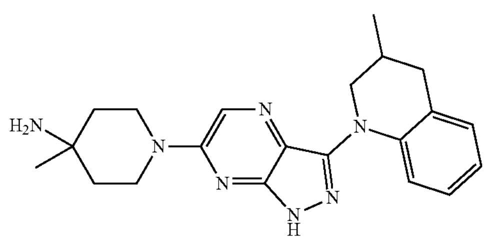 [SMILES: CC1Cc2ccccc2N(c2n[nH]c3nc(N4CCC(C)(N)CC4)cnc23)C1] | (400 MHz, DMSO_d6): δ 8.28 (s, 1H), 7.06-7.00 (m, 2H), 6.92-6.87 (m, 1H), 6.71-6.66 (m, 1H), 3.99-3.90 (m, 1H), 3.88-3.83 (m, 2H), 3.64-3.60 (m, 2H), 3.44-3.36 (m, 2H), 2.88-2.83 (m, 1H), 2.30-2.10 (m, 1H), 1.53-1.40 (m, 4H), 1.09 (s, 3H), 1.04 (d, J =6.8 Hz, 3H). | 378.1 |
| 84 | 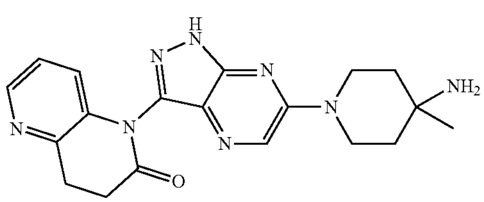 [SMILES: CC1(N)CCN(c2cnc3c(N4C(=O)CCc5ncccc54)n[nH]c3n2)CC1] | (400 MHz, DMSO-$d_6$): δ 13.62 (br, 1H), 8.48-8.43 (m, 4H), 7.62-7.56 (m, 1H), 7.38-7.34 (m, 1H), 4.18-4.13 (m, 4H), 3.59-3.52 (m, 4H), 3.10-3.02 (m, 2H), 1.93-1.75 (m, 4H), 1.41 (s, 3H). | 379.0 |
| 85 | 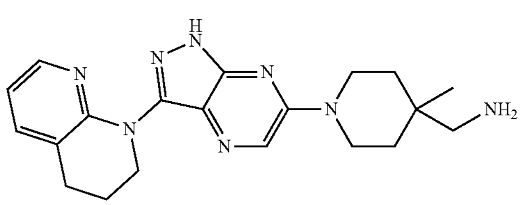 [SMILES: CC1(CN)CCN(c2cnc3c(N4CCCc5cccnc54)n[nH]c3n2)CC1] | (400 MHz, Methanol-$d_4$): δ 8.18 (s, 1H), 7.72-7.70 (d, J = 3.6 Hz, 1H), 7.44-7.41 (d, J = 6.4 Hz, 1H), 6.73-6.69 (m, 1H), 4.1 (m, 2H), 3.92 (m, 2H), 3.54 (m, 2H), 2.95 (m, 2H), 2.60 (s, 2H), 2.16(m, 2H), 1.58 (m, 2H), 1.50 (m, 2H), 1.10 (s, 3H). | 379.1 |
| 86 | 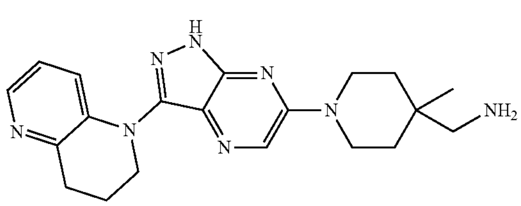 | (400 MHz, DMSO-$d_6$): δ 8.29 (s, 1H), 7.91-7.88 (m, 1H), 7.50-7.46 (m, 1H), 6.99-6.94 (m, 1H), 4.10-3.80 (m, 4H), 3.50-3.40 (m, 2H), 3.00-2.80 (m, 2H), 2.41 (s, 2H), 2.10-2.02 (m, 2H), 1.53-1.44 (m, 2H), 1.35-1.25 (m, 2H), 0.94 (s, 3H). | 379.1 |

| Compound | Structure | Proton NMR | MS [M + 1] |
|---|---|---|---|
| 87 | 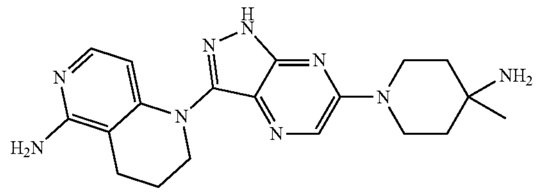 [SMILES: CC1(N)CCN(c2cnc3c(N4CCCc5c4ccnc5N)n[nH]c3n2)CC1] | (400 MHz, DMSO-d$_6$): δ 13.17 (s, 1H), 8.41 (s, 1H), 8.06 (br, 2H), 7.41-7.44 (d, J = 7.2, 1H), 7.29 (s, 2H), 6.19-6.22 (d, J = 7.2, 1H), 4.10-4.14 (m, 2H), 3.80-3.83 (m, 2H), 3.42-3.48 (m, 2H), 2.49-2.53 (m, 2H), 2.01-2.07 (m, 1H), 1.74 (br, 4H), 1.36 (s, 3H). | 380.1 |
| 88 | 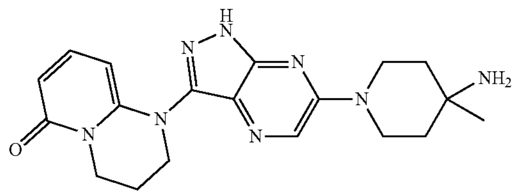 [SMILES: CC1(N)CCN(c2cnc3c(N4CCCn5c4cccc5=O)n[nH]c3n2)CC1] | (400 MHz, DMSO-d$_6$): δ = 12.93 (br s, 1H), 9.48 (br s, 1H), 8.84 (d, J = 9.3 Hz, 1H), 8.41 (s, 1H), 8.25 (s, 1H), 3.84-4.14 (m, 4H), 3.60 (dd, J = 13.4, 6.3 Hz, 2H), 3.48-3.56 (m, 2H), 1.90-2.11 (m, 2H), 1.54-1.76 (m, 4H), 1.28 (s, 3H). | 381.3 |
| 89 | 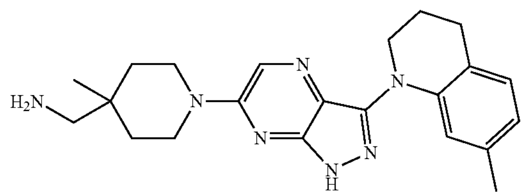 [SMILES: Cc1ccc2c(c1)N(c1n[nH]c3nc(N4CCC(C)(CN)CC4)cnc13)CCC2] | (400 MHz, DMSO-d$_6$) 12.46 (br d, J = 4.88 Hz, 1H), 8.25 (s, 1H), 6.89 (d, J = 7.57 Hz, 1H), 6.85 (s, 1H), 6.50 (br d, J = 7.32 Hz, 1H), 3.92 (td, J = 4.58, 13.55 Hz, 2H), 3.81-3.88 (m, 2H), 3.44 (ddd, J = 3.17, 9.83, 13.37 Hz, 2H), 2.75 (br t, J = 6.35 Hz, 2H), 2.06 (s, 3H), 1.94 (td, J = 6.04, 11.84 Hz, 2H), 1.42-1.56 (m, 2H), 1.29-1.38 (m, 2H), 0.97 (s, 3H). | 392.4 |
| 90 | 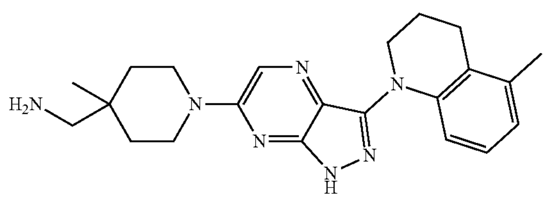 [SMILES: Cc1cccc2c1CCCN2c1n[nH]c2nc(N3CCC(C)(CN)CC3)cnc12] | (400 MHz, DMSO-d$_6$) 12.42 (br s, 1H), 8.25 (s, 1H), 6.75-6.84 (m, 2H), 6.60 (br d, J = 6.84 Hz, 1H), 3.89-3.97 (m, 2H), 3.79-3.84 (m, 2H), 3.44 (ddd, J = 2.93, 9.89, 13.31 Hz, 2H), 2.64-2.71 (m, 2H), 2.60 (s, 1H), 2.17 (s, 3H), 1.94-2.02 (m, 2H), 1.46-1.56 (m, 2H), 1.32-1.42 (m, 2H), 1.00 (s, 3H). | 392.4 |
| 91 | 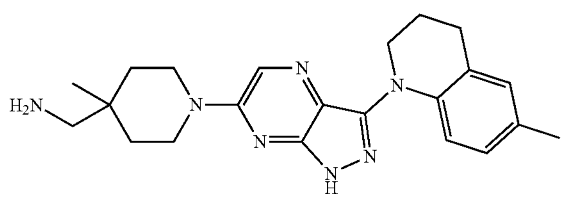 [SMILES: Cc1ccc2c(c1)CCCN2c1n[nH]c2nc(N3CCC(C)(CN)CC3)cnc12] | (400 MHz, DMSO-d$_6$) 12:31-12.46 (m, 1H), 8.35 (s, 1H), 8.23 (s, 1H), 6.98 (d, J = 8.30 Hz, 1H), 6.83 (s, 1H), 6.71 (dd, J = 1.46, 8.30 Hz, 1H), 3.84-3.96 (m, 5H), 3.43 (ddd, J = 3.17, 9.83, 13.37 Hz, 3H), 2.75 (t, J = 6.35 Hz, 2H), 2.53 (s, 2H), 2.16 (s, 3H), 1.94 (td, J = 6.20, 11.78 Hz, 2H), 1.46-1.54 (m, 2H), 1.30-1.38 (m, 2H), 0.98 (s, 3H). | 392.3 |
| 92 | 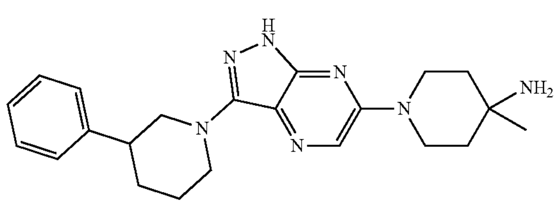 [SMILES: CC1(N)CCN(c2cnc3c(N4CCCC(c5ccccc5)C4)n[nH]c3n2)CC1] | (400 MHz, CD3OD): δ8.12 (s, 1H), 7.30-7.35 (m, 4H), 7.20-7.25 (m, 1H), 4.55-4.60 (m, 1H), 4.40-4.50 (m, 1H), 3.90-4.10 (m, 2H), 3.60-3.70 (m, 2H), 2.90-2.98 (m, 3H), 2.00-2.10 (m, 1H), 1.80-1.93 (m, 2H), 1.65-1.80 (m, 5H), 1.33 (s, 3H). | 392.1 |

-continued

| Compound | Structure | Proton NMR | MS [M + 1] |
|---|---|---|---|
| 93 | 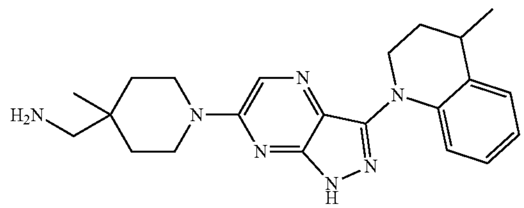 [SMILES: CC1CCN(c2n[nH]c3nc(N4CCC(C)(CN)CC4)cnc23)c2ccccc21] | (400 MHz, Methanol-$d_4$): δ 8.17 (s, 1H), 7.15-7.18 (m, 1H), 6.89-6.94 (m, 1H), 6.74-6.81 (m, 2H), 4.07-4.11 (m, 2H), 3.91-3.94 (m, 1H), 3.85-3.87 (m, 1H), 3.50-3.57 (m, 2H), 3.03-3.05 (m, 1H), 2.62 (s, 2H), 2.02-2.25 (m, 1H), 1.83-1.86 (m, 1H), 1.57-1.61 (m, 2H), 1.49-1.54 (m, 2H), 1.38-1.41 (d, J = 7.2 Hz, 3H), 1.11 (s, 3H). | 392.1 |
| 94 | 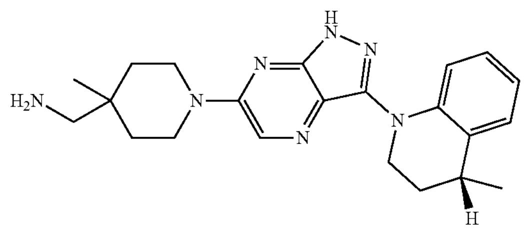 [SMILES: C[C@@H]1CCN(c2n[nH]c3nc(N4CCC(C)(CN)CC4)cnc23)c2ccccc21] | (400 MHz, Methanol-$d_4$): δ 8.16 (s, 1H), 7.15-7.18 (m, 1H), 6.89-6.93 (m, 1H), 6.74-6.81 (m, 2H), 4.06-4.10 (m, 2H), 3.84-3.94 (m, 1H), 3.85-3.87 (m, 1H), 3.50-3.57 (m, 2H), 3.03-3.07 (m, 1H), 2.60 (s, 2H), 2.16-2.24 (m, 1H), 1.80-1.87 (m, 1H), 1.57-1.64 (m, 2H), 1.48-1.54 (m, 2H), 1.38-1.41 (d, J = 7.2 Hz, 3H), 1.11 (s, 3H). | 392.1 |
| 95 | 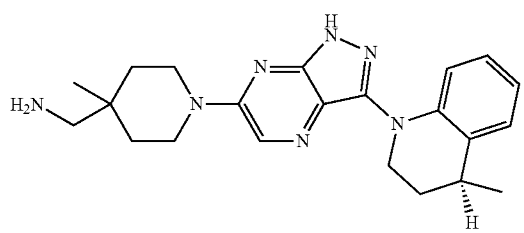 [SMILES: C[C@H]1CCN(c2n[nH]c3nc(N4CCC(C)(CN)CC4)cnc23)c2ccccc21] | (400 MHz, Methanol-$d_4$): δ 8.16 (s, 1H), 7.15-7.18 (m, 1H), 6.89-6.93 (m, 1H), 6.74-6.81 (m, 2H), 4.06-4.10 (m, 2H), 3.84-3.94 (m, 1H), 3.85-3.87 (m, 1H), 3.50-3.57 (m, 2H), 3.03-3.07 (m, 1H), 2.60 (s, 2H), 2.16-2.24 (m, 1H), 1.80-1.87 (m, 1H), 1.57-1.64 (m, 2H), 1.48-1.54 (m, 2H), 1.38-1.41 (d, J = 7.2 Hz, 3H), 1.11 (s, 3H). | 392.1 |
| 96 | 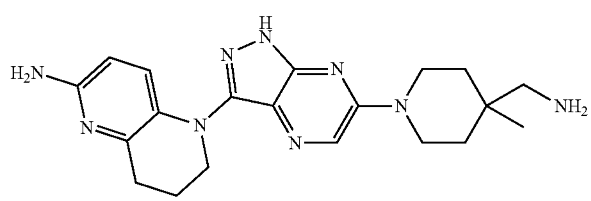 [SMILES: CC1(CN)CCN(c2cnc3c(N4CCCc5nc(N)ccc54)n[nH]c3n2)CC1] | (400 MHz, DMSO-$d_6$): δ 12.11 (s, 1H), 8.22 (d, J = 2.4 Hz, 1H), 7.44 (d, J = 8.8 Hz, 1H), 6.81 (s, 1H), 6-19-6.22 (d, J = 8.8 Hz, 1H), 5.42 (s, 2H), 3.89-3.99 (m, 4H), 2.90-2.92 (m, 2H), 2.67-2.70 (m, 2H), 1.87-1.90 (m, 2H), 1.44-1.48 (m, 2H), 1.28-1.31 (m, 2H), 0.94 (s, 3H). | 394.0 |
| 97 | 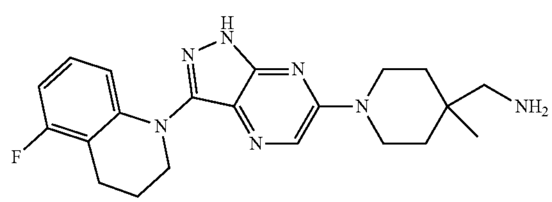 [SMILES: CC1(CN)CCN(c2cnc3c(N4CCCc5c(F)cccc54)n[nH]c3n2)CC1] | (400 MHz, DMSO-$d_6$): δ 8.29 (s, 1H), 6.94-6.87 (m, 1H), 6.81-6.78 (m, 1H), 6.55-6.50 (m, 1H), 3.93-3.84 (m, 4H), 3.46-3.41 (m, 2H), 2.79-2.75 (m, 2H), 2.42 (s, 2H), 2.01-1.98 (m, 2H), 1.49-1.29 (m, 2H), 0.94 (s, 3H). | 396.1 |
| 98 | 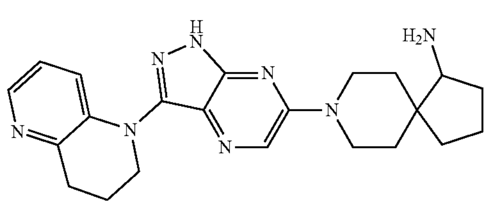 [SMILES: NC1CCCC12CCN(c1cnc3c(N4CCCc5ncccc54)n[nH]c3n1)CC2] | (400 MHz, DMSO-$d_6$): δ 12.54 (br d, J = 2.20 Hz, 1H), 8.28 (s, 1H), 7.88 (dd, J = 4.52, 1.34 Hz, 1H), 7.47 (dd, J = 8.42, 1.34 Hz, 1H), 6.95 (dd, J = 8.30, 4.64 Hz, 1H), 4.17-4.29 (m, 2H), 3.88-3.98 (m, 2H), 3.08-3.22 (m, 2H), 2.92 (t, J = 6.59 Hz, 2H), 2.68 (t, J = 7.32 Hz, 1H), 2.01-2.10 (m, 2H), 1.75-1.89 (m, 2H), 1.46-1.66 (m, 5H), 1.16-1.42 (m, 5H). | 405 |

-continued

| Compound | Structure | Proton NMR | MS [M + 1] |
|---|---|---|---|
| 99 | 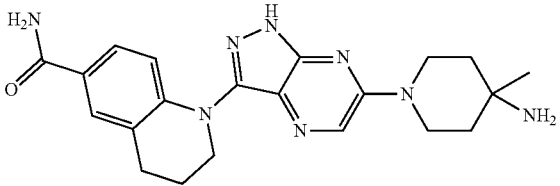 [SMILES: CC1(N)CCN(c2cnc3c(N4CCCc5cc(C(N)=O)ccc54)n[nH]c3n2)CC1] | (400 MHz, DMSO-d$_6$): δ 8.35 (s, 1H), 8.18 (br, 3H), 7.62-7.61 (m, 1H), 7.46-7.42 (m, 1H), 6.92-6.89 (d, J = 8.8 Hz, 1H), 4.17-4.12 (m, 2H), 3.51-3.44 (m, 2H), 2.88-2.83 (m, 2H), 2.55-2.52 (m, 1H), 2.05-2.00 (m, 2H), 1.82-1.74 (m, 4H), 1.40 (s, 3H). | 407.2 |
| 100 | 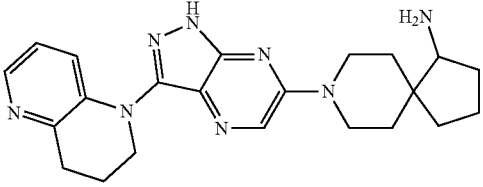 [SMILES: NC1CCCC12CCN(c1cnc3c(N4CCCc5ncccc54)n[nH]c3n1)CC2] | (400 MHz, DMSO-d$_6$): δ 12.56 (br s, 1H), 8.30 (s, 1H), 7.88 (dd, J = 4.64, 1.22 Hz, 1H), 7.47 (dd, J = 8.54, 1.22 Hz, 1H), 6.95 (dd, J = 8.30, 4.64 Hz, 1H), 4.19-4.32 (m, 2H), 3.90-3.97 (m, 2H), 3.80 (td, J = 8.42, 5.13 Hz, 1H), 3.68 (q, J = 7.98 Hz, 1H), 3.18-3.28 (m, 2H), 2.89-2.97 (m, 3H), 2.01-2.19 (m, 3H), 1.57-1.73 (m, 3H), 1.47-1.55 (m, 1H), 1.40 (br d, J = 13.43 Hz, 1H). | 407 |
| 101 | 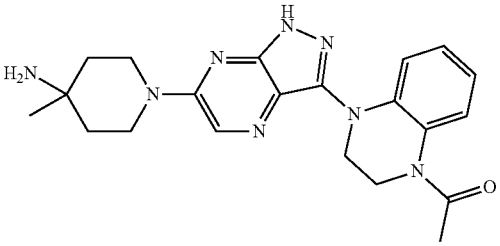 [SMILES: CC(=O)N1CCN(c2n[nH]c3nc(N4CCC(C)(N)CC4)cnc23)c2ccccc21] | (400 MHz, DMSO_d6): δ 8.39 (br, 2H), 8.31 (s, 1H), 7.35-7.25 (m, 1H), 7.18-7.13 (m, 1H), 6.95-6.90 (m, 1H), 6.80-6.70 (m, 1H), 4.12-4.05 (m, 2H), 4.00-3.88 (m, 4H), 3.50-3.42 (m, 2H), 2.18 (s, 3H), 1.85-1.68 (m, 4H), 1.36 (s, 3H). | 407.1 |
| 102 | 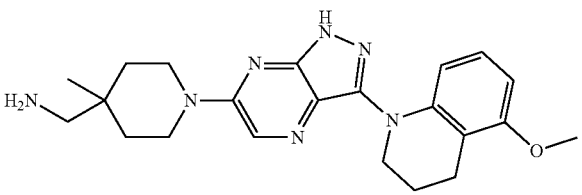 [SMILES: COc1cccc2c1CCCN2c1n[nH]c2nc(N3CCC(C)(CN)CC3)cnc12] | (400 MHz, DMSO-d$_6$): δ 8.30 (s, 1H), 7.87 (br, 3H), 6.89-6.84 (m, 1H), 6.66 (d, J = 8.4 Hz, 1H), 6.41 (d, J = 8.0 Hz, 1H), 4.05-3.96 (m, 2H), 3.76 (s, 3H), 3.51-3.44 (m, 2H), 2.79-2.77 (m, 2H), 2.69-2.65 (m, 2H), 2.53 (s, 2H), 1.96-1.92 (m, 2H), 1.60-1.42 (m, 4H), 1.09 (s, 3H). | 408.1 |
| 103 | 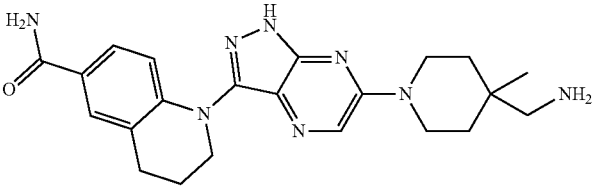 [SMILES: CC1(CN)CCN(c2cnc3c(N4CCCc5cc(C(N)=O)ccc54)n[nH]c3n2)CC1] | (400 MHz, DMSO-d$_6$): δ 8.32 (br, 1H), 8.10 (br, 3H), 7.61 (s, 1H), 7.44-7.42 (m, 1H), 6.92-6.90 (m, 1H), 3.96-3.88 (m, 4H), 3.51-3.46 (m, 2H), 2.90-2.72 (m, 4H), 2.12-1.90 (m, 2H), 1.65-1.40 (m, 4H), 1.09 (s, 3H). | 412.3 |
| 104 | 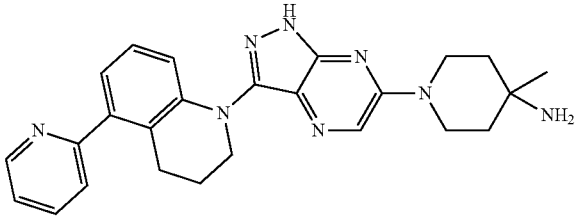 [SMILES: CC1(N)CCN(c2cnc3c(N4CCCc5c(-c6ccccn6)cccc54)n[nH]c3n2)CC1] | (400 MHz, DMSO-d$_6$): δ = 12.50 (br s, 1H), 8.65 (br d, J = 4.2 Hz, 1H), 8.25 (s, 1H), 7.86 (td, J = 7.7, 1.7 Hz, 1H), 7.48 (d, J = 7.8 Hz, 1H), 7.32-7.39 (m, 1H), 6.93-7.04 (m, 2H), 6.71-6.79 (m, 1H), 3.74-3.92 (m, 4H), 3.61 (ddd, J = 13.2, 9.0, 3.9 Hz, 2H), 2.73 (t, J = 6.3 Hz, 2H), 1.89 (dt, J = 11.9, 6.1 Hz, 2H), 1.33-1.55 (m, 4H), 1.08 (s, 3H). | 441.5 |

-continued

| Compound | Structure | Proton NMR | MS [M + 1] |
|---|---|---|---|
| 105 | 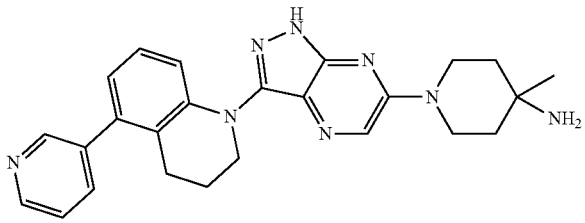 [SMILES: CC1(N)CCN(c2cnc3c(N4CCCc5c(-c6cccnc6)cccc54)n[nH]c3n2)CC1] | (400 MHz, DMSO-$d_6$): δ = 12.54 (br s, 1H), 8.58 (d, J = 2.9 Hz, 2H), 8.28 (s, 1H), 7.81 (dt, J = 7.8, 1.8 Hz, 1H), 7.48 (dd, J = 7.6, 4.9 Hz, 1H), 6.94-7.08 (m, 2H), 6.60-6.69 (m, 1H), 3.75-3.93 (m, 4H), 3.62 (ddd, J = 13.2, 8.9, 4.0 Hz, 2H), 2.64 (t, J = 6.3 Hz, 2H), 1.84-2.00 (m, 2H), 1.38-1.71 (m, 6H), 1.09 (s, 3H). | 441.4 |
| 106 | 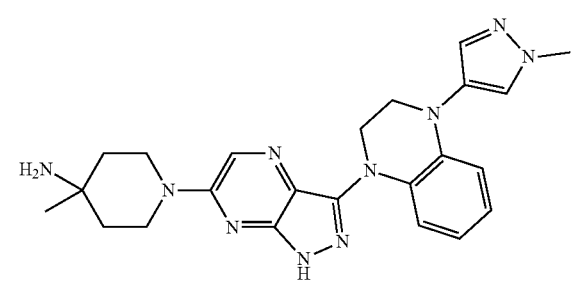 [SMILES: Cn1cc(N2CCN(c3n[nH]c4nc(N5CCC(C)(N)CC5)cnc34)c3ccccc32)cn1] | (400 MHz, DMSO-$d_6$): δ = 12.48 (br s, 1H), 8.25 (s, 1H), 7.87 (s, 1H), 7.58 (s, 1H), 6.81-6.95 (m, 2H), 6.74 (dd, J = 7.1, 1.2 Hz, 1H), 3.78-3.92 (m, 6H), 3.61 (ddd, J = 13.2, 9.0, 3.9 Hz, 2H), 2.82 (t, J = 6.3 Hz, 2H), 1.93 (dt, J = 11.8, 6.2 Hz, 2H), 1.38-1.63 (m, 6H), 1.08 (s, 3H). | 444.4 |
| 107 | 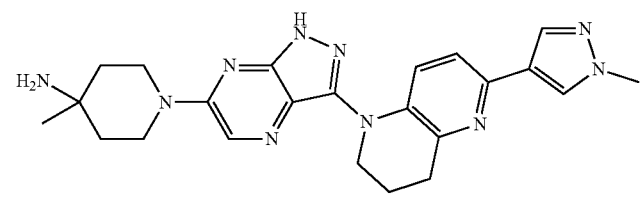 | (400 MHz, DMSO-$d_6$): δ = 12.51 (br s, 1H), 8.28 (s, 1H), 8.09 (s, 1H), 7.83 (s, 1H), 7.55 (d, J = 8.5 Hz, 1H), 7.24 (d, J = 8.5 Hz, 1H), 3.94-4.02 (m, 2H), 3.86 (s, 3H), 3.78-3.85 (m, 2H), 3.66 (ddd, J = 13.1, 8.4, 4.2 Hz, 2H), 2.94 (t, J = 6.5 Hz, 2H), 2.07 (quin, J = 6.0 Hz, 2H), 1.36-1.59 (m, 4H), 1.12 (s, 3H). | 445.5 |
| 108 | 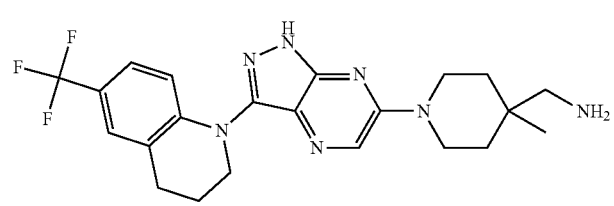 [SMILES: CC1(CN)CCN(c2cnc3c(N4CCCc5cc(C(F)(F)F)ccc54)n[nH]c3n2)CC1] | (400 MHz, DMSO-$d_6$): δ 8.33 (s, 1H), 7.98 (s, 3H), 7.36 (s, 1H), 7.19-7.22 (m, 1H), 6.98-7.01 (m, 1H), 3.87-4.00 (m, 4H), 3.45-3.51 (m, 2H), 2.87-2.91 (m, 2H), 2.76-2.79 (m, 2H), 2.00-2.05 (m, 2H), 1.54-1.59 (m, 2H), 1.44-1.48 (m, 2H), 1.09 (s, 3H). | 446.2 |
| 109 | 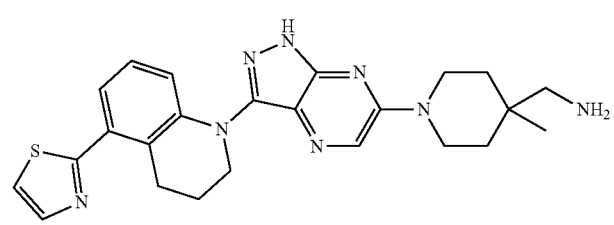 [SMILES: CC1(CN)CCN(c2cnc3c(N4CCCc5c(-c6nccs6)cccc54)n[nH]c3n2)CC1] | (400 MHz, DMSO-$d_6$): δ = 12.56 (br s, 1H), 8.27 (s, 1H), 7.97 (d, J = 3.2 Hz, 1H), 7.84 (d, J = 3.4 Hz, 1H), 6.98-7.12 (m, 3H), 3.78-3.98 (m, 4H), 3.63 (ddd, J = 13.2, 8.9, 4.0 Hz, 2H), 3.02 (t, J = 6.3 Hz, 2H), 1.96 (dt, J = 11.8, 6.2 Hz, 2H), 1.37-1.56 (m, 4H), 1.09 (s, 3H). | 447.4 |
| 110 | 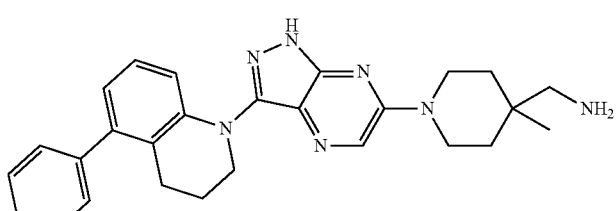 | (400 MHz, CDCl$_3$): δ 8.12 (s, 1H), 7.43-7.33 (m, 5H), 7.20-7.18 (d, J = 8.8 Hz, 1H), 7.09-7.05 (m, 1H), 6.80-6.78 (d, J = 7.2 Hz, 1H), 4.01-3.97 (m, 4H), 3.49-3.43 (m, 2H), 2.74-2.70 (m, 2H), 2.61 (s, 2H), 2.0-1.96 (m, 2H), 1.73-1.47 (m, 4H), 1.06 (s, 3H). | 454.2 |

| Compound | Structure | Proton NMR | MS [M + 1] |
|---|---|---|---|
| 111 | 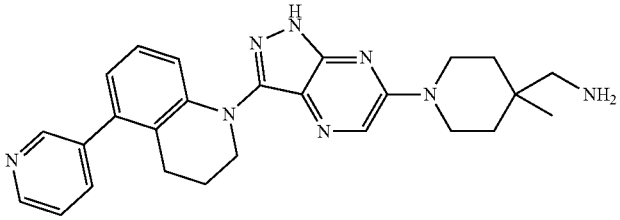 [SMILES: CC1(CN)CCN(c2cnc3c(N4CCCc5c(-c6cccnc6)cccc54)n[nH]c3n2)CC1] | (400 MHz, DMSO-d$_6$): δ 8.53-8.60 (m, 2H), 8.29 (s, 1H), 7.80 (td, J = 1.95, 7.81 Hz, 1H), 7.46 (dd, J = 5.00, 7.69 Hz, 1H), 6.97-7.01 (m, 2H), 6.62-6.67 (m, 1H), 3.92-4.01 (m, 2H), 3.83-3.88 (m, 2H), 3.46 (t, J = 10.01 Hz, 2H), 2.72 (s, 2H), 2.63 (t, J = 6.35 Hz, 2H), 1.90 (td, J = 6.20, 11.78 Hz, 2H), 1.49-1.58 (m, 2H), 1.37-1.45 (m, 2H), 1.05 (s, 3H) | 455.4 |
| 112 | 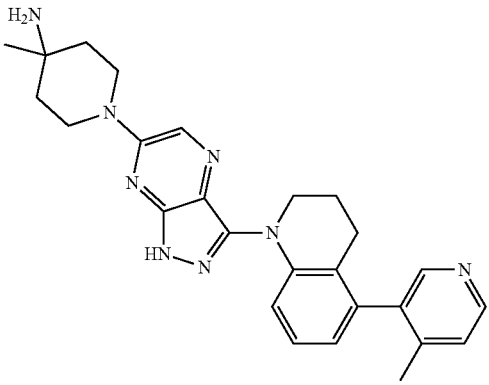 [SMILES: Cc1ccncc1-c1cccc2c1CCCN2c1n[nH]c2nc(N3CCC(C)(N)CC3)cnc12] | (400 MHz, DMSO-d$_6$): δ = 12.54 (br s, 1H), 8.44 (d, J = 4.9 Hz, 1H), 8.29 (d, J = 5.6 Hz, 2H), 7.34 (d, J = 4.9 Hz, 1H), 6.93-7.07 (m, 2H), 6.52 (dd, J = 6.7, 1.6 Hz, 1H), 3.85 (t, J = 5.0 Hz, 4H), 3.63 (ddd, J = 13.1, 9.0, 4.0 Hz, 2H), 2.17-2.46 (m, 2H), 2.10 (s, 3H), 1.83-1.97 (m, 2H), 1.66 (br s, 2H), 1.38-1.54 (m, 4H), 1.09 (s, 3H). | 455.5 |
| 113 | 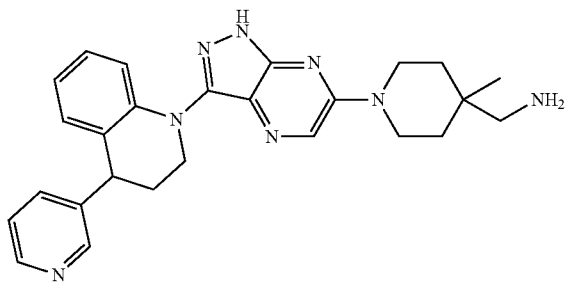 [SMILES: CC1(CN)CCN(c2cnc3c(N4CCC(c5cccnc5)c5ccccc54)n[nH]c3n2)CC1] | (400 MHz, DMSO-d$_6$): δ 8.53-8.52 (d, J = 2.0 Hz, 1H), 8.29 (s, 1H), 8.26-8.24 (m, 1H), 7.68-7.65 (d, J = 7.2 Hz, 1H), 7.41-7.35 (m, 1H), 7.31-7.25 (m, 1H), 6.73-6.65 (m, 2H), 6.82-6.77 (m, 1H), 4.10-4.05 (m, 2H), 3.95-3.75 (m, 4H), 2.40 (s, 1H), 1.50-1.40 (m, 2H), 1.35-1.20 (m, 4H), 0.95-0.92 (m, 3H). | 456.2 |
| 114 | 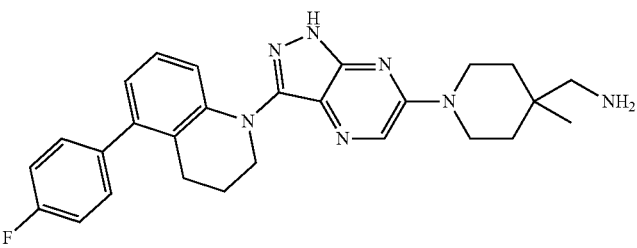 [SMILES: CC1(CN)CCN(c2cnc3c(N4CCCc5c(-c6ccc(F)cc6)cccc54)n[nH]c3n2)CC1] | (400 MHz, DMSO-d$_6$): δ 8.30 (s, 1H), 7.90 (br, 3H), 7.42-7.37 (m, 2H), 7.29-7.24 (m, 2H), 6.98-6.95 (m, 2H), 6.64-6.62 (m, 1H), 4.01-3.96 (m, 2H), 3.88-3.84 (m, 2H), 2.80-2.77 (m, 2H), 2.65-2.61 (m, 2H), 2.53 (s, 2H), 1.93-1.88 (m, 2H), 1.60-1.44 (m, 4H), 1.09 (s, 3H). | 472.1 |
| 115 | 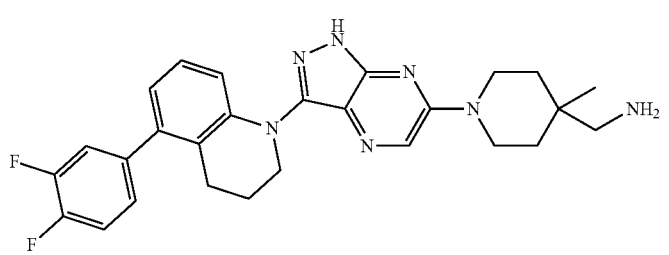 [SMILES: CC1(CN)CCN(c2cnc3c(N4CCCc5c(-c6ccc(F)c(F)c6)cccc54)n[nH]c3n2)CC1] | (400 MHz, CDCl$_3$): δ 8.12 (s, 1H), 7.20-7.13 (m, 3H), 7.08-7.03 (m, 2H), 6.73-6.71 (d, J = 7.2 Hz, 1H), 4.01-3.99 (m, 4H), 3.50-3.44 (m, 2H), 2.70-2.66 (m, 2H), 2.61 (s, 2H), 2.02-1.98 (m, 2H), 1.63-1.47 (m, 4H), 1.05 (s, 3H). | 490.1 |

-continued

| Compound | Structure | Proton NMR | MS [M + 1] |
|---|---|---|---|
| 116 | 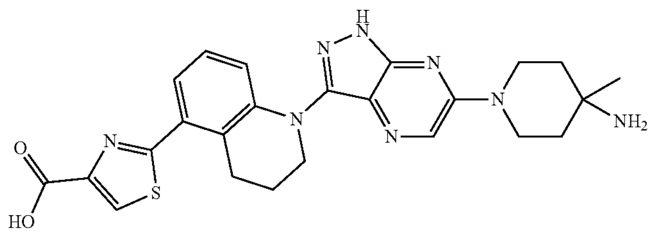 [SMILES: CC1(N)CCN(c2cnc3c(N4CCCc5c(-c6nc(C(=O)O)cs6)cccc54)n[nH]c3n2)CC1] | ND | 491.4 |
| 117 | 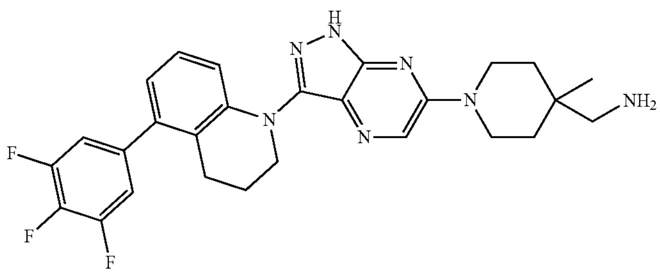 [SMILES: CC1(CN)CCN(c2cnc3c(N4CCCc5c(-c6cc(F)c(F)c(F)c6)cccc54)n[nH]c3n2)CC1] | (400 MHz, DMSO-$d_6$): δ 8.30 (s, 1H), 8.04 (br, 3H), 7.39-7.34 (m, 2H), 7.00-6.95 (m, 2H), 6.66-6.63 (m, 1H), 3.88-3.84 (m, 2H), 3.51-3.45 (m, 2H), 2.78-2.76 (m, 2H), 2.68-2.64 (m, 2H), 2.52 (s, 2H), 1.93-1.89 (m, 2H), 1.60-1.44 (m, 4H), 1.10 (s, 3H). | 508.2 |
| 118 | 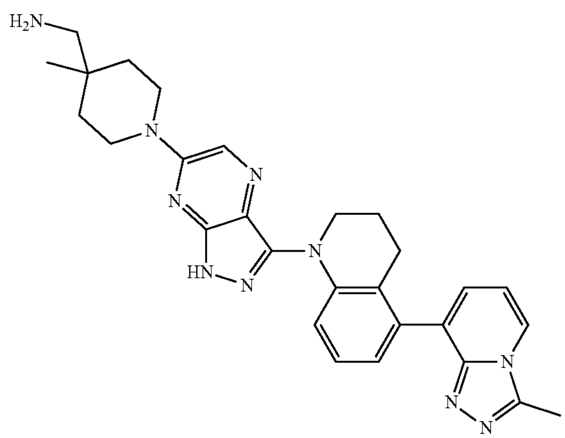 [SMILES: Cc1nnc2c(-c3cccc4c3CCCN4c3n[nH]c4nc(N5CCC(C)(CN)CC5)cnc34)cccn12] | (400 MHz, DMSO-$d_6$): Shift 12.48-12.62 (m, 1H), 8.36 (d, J = 6.84 Hz, 1H), 8.26-8.30 (m, 1H), 7.21 (d, J = 6.10 Hz, 1H), 6.97-7.08 (m, 3H), 6.72 (br dd, J = 1.10, 7.20 Hz, 1H), 3.91-3.99 (m, 2H), 3.83-3.89 (m, 2H), 3.42-3.50 (m, 2H), 2.71 (s, 3H), 2.55 (m, 2H), 1.86 (td, J = 6.20, 11.78 Hz, 2H), 1.47-1.56 (m, 2H), 1.36 (br d, J = 13.92 Hz, 2H), 0.99 (s, 3H) | 509.5 |
| 119 | 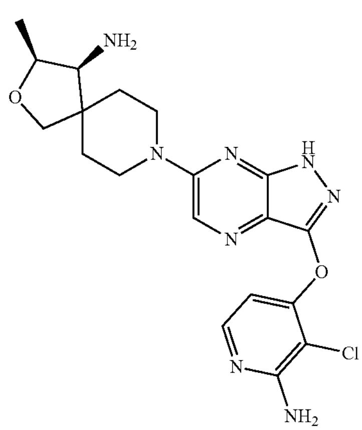 [SMILES: C[C@@H]1OCC2(CCN(c3cnc4c(Oc5ccnc(N)c5Cl)n[nH]c4n3)CC2)[C@@H]1N] | | |

| Compound | Structure | Proton NMR | MS [M + 1] |
|---|---|---|---|
| 120 | 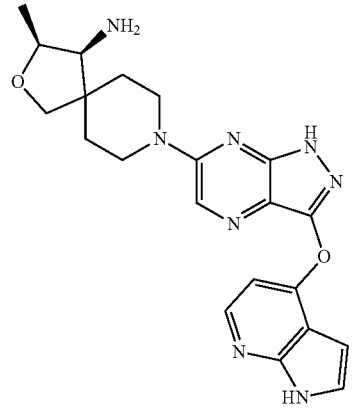 [SMILES: C[C@@H]1OCC2(CCN(c3cnc4c(Oc5ccnc6[nH]ccc56)n[nH]c4n3)CC2)[C@@H]1N] | | |
| 121 | 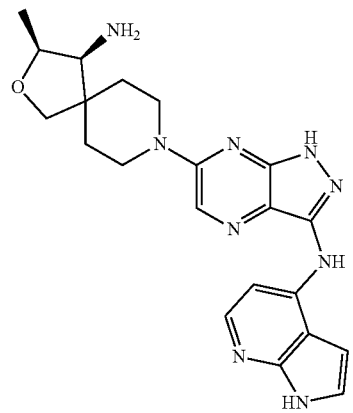 [SMILES: C[C@@H]1OCC2(CCN(c3cnc4c(Nc5ccnc6[nH]ccc56)n[nH]c4n3)CC2)[C@@H]1N] | | |

Example 30

SHP2 Allosteric Inhibition Assay

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PIT) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 96-well black polystyrene plate, flat bottom, low flange, non-binding surface (Corning, Cat #3575) using a final reaction volume of 50 μl and the following assay buffer conditions: 60 mM HEPES, pH 7.2, 75 mM NaCl, 75 mM KCl, 1 mM EDTA 0.005% Brij-35, 5 mM DTT.

The inhibition of SHP2 by compounds of the invention (concentrations varying from 0.003-100 μM) was monitored using an assay in which 0.25 nM of SHP2 was incubated with of 0.5 μM of peptide IRS1_psf 1172(dPEG8)pY1222 (sequence: H2N-LN(pY)IDLDLV(dPEG8)LST(pY)AS-INFQK-amide). After 30-60 minutes incubation at 25° C., the surrogate substrate DiFMUP (Invitrogen, cat #D6567, 100 μM final) was added to the reaction and the conversion of DiFMUP to 6,8-difluoro-7-hydroxyl-4-methylcoumarin (DiFMU) was monitored continuously for 10 minutes with excitation at 355 nm and emission at 460 nm using a microplate reader (PolarStar, BMG). The inhibitor dose response curves were analyzed using normalized $IC_{50}$ regression curve fitting with control based normalization. $IC_{50}$ results for compounds of the invention are shown in examples and Table 1. In Table 1, in Table 1, A means an $IC_{50}$ of less than 1 μM; B means an $IC_{50}$ equal to 1 μM but less than 10 μM; and C means an $IC_{50}$ of 10 μM or more

TABLE 1

SHP2 $IC_{50}$ Assay Results

| Compound Number | SHP2 $IC_{50}$ |
|---|---|
| 6 | A |
| 7 | A |
| 8 | A |
| 9 | A |
| 10 | A |
| 11 | A |
| 12 | B |
| 13 | C |
| 14 | A |
| 15 | B |
| 16 | B |
| 17 | B |
| 18 | B |
| 19 | A |

TABLE 1-continued

SHP2 IC$_{50}$ Assay Results

| Compound Number | SHP2 IC$_{50}$ |
|---|---|
| 20 | A |
| 21 | C |
| 22 | A |
| 23 | A |
| 24 | A |
| 25 | B |
| 26 | A |
| 27 | A |
| 28 | A |
| 29 | A |
| 30 | A |
| 31 | A |
| 32 | A |
| 33 | A |
| 34 | A |
| 35 | B |
| 36 | A |
| 37 | A |
| 38 | A |
| 39 | A |
| 40 | A |
| 41 | A |
| 42 | A |
| 43 | A |
| 44 | B |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | B |
| 59 | A |
| 60 | A |
| 61 | A |
| 62 | A |
| 63 | C |
| 64 | C |
| 65 | B |
| 66 | A |
| 67 | A |
| 68 | A |
| 69 | A |
| 70 | A |
| 71 | A |
| 72 | C |
| 73 | A |
| 74 | B |
| 75 | B |
| 76 | A |
| 77 | A |
| 78 | A |
| 79 | A |
| 80 | A |
| 81 | B |
| 82 | A |
| 83 | B |
| 84 | B |
| 85 | B |
| 86 | A |
| 87 | B |
| 88 | C |
| 89 | B |
| 90 | A |
| 91 | A |
| 92 | B |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A compound of formula (I), or a pharmaceutically acceptable salt thereof,

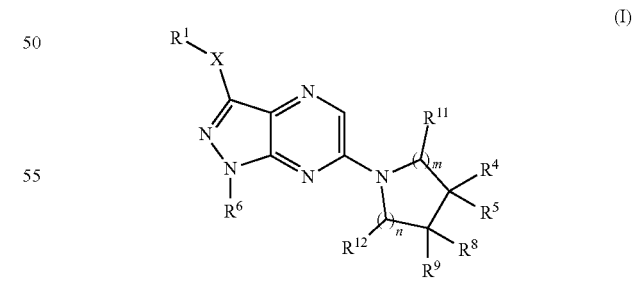

wherein:

X is N—R$^{66}$, O, S, S(O), SO$_2$, CR$^{13}$R$^{14}$, —O—C(R$^{13}$R$^{14}$)—, —C(R$^{13}$R$^{14}$)O—, C(O), or —C(=C(R$^{15}$R$^{16}$))—;

R$^1$ is selected from the group consisting of a 5-10 membered monocyclic or bicyclic aryl or heteroaryl, and a 4-7 membered heterocycle, wherein R$^1$ is optionally substituted with one or more substituents each independently selected from the group consisting of —R$^{10}$, —OR$^{10}$, —S(O)$_w$R$^{10}$ wherein w is 0, 1 or 2, —N(R$^{10}$)$_2$, —OS(O)$_w$—R$^{10}$ wherein w is 0, 1, or 2, —S(O)$_w$—N(R$^{10}$)$_2$ wherein w is 0, 1 or 2, —S(O)(NH)R$^{10}$, —P(O)(R$^{10}$)$_2$, —C(O)R$^{10}$, —C(O)N(R$^{10}$)$_2$, oxo, halogen and nitrile; wherein each R$^{10}$ is independently selected from the group consisting of H, —(C$_1$-C$_6$)alkyl, —(C$_1$-C$_6$)haloalkyl, (C$_3$-C$_6$)cycloalkyl, heterocycloalkyl, aryl, and heteroaryl, wherein R$^{10}$ in turn may be substituted with one or more substituents each selected from the group consisting of halo, —C(O)R$^{20}$, —(C$_1$-C$_6$)alkyl, and —(C$_1$-C$_6$)haloalkyl; wherein R$^{20}$ is —OH, halo, or —(C$_1$-C$_6$)alkyl;

R$^4$ and R$^5$ are each independently selected from the group consisting of H, —OH, —(C$_1$-C$_6$)alkyl, —O(C$_1$-C$_6$)alkyl, —(C$_1$-C$_6$)alkyl-O—R$^6$, —C(O)N(R$^6$)$_2$, —N(R$^6$)$_2$, halogen, —(C$_1$-C$_6$)alkyl-N(R$^6$)$_2$, and nitrile, wherein said —(C$_1$-C$_6$)alkyl, —O(C$_1$-C$_6$)alkyl, —(C$_1$-C$_6$)alkyl-O—R$^6$, or —(C$_1$-C$_6$)alkyl-N(R$^6$)$_2$ is optionally substituted with one or more substituents selected from the group consisting of —OH, —NH$_2$, oxo, and halogen, or R$^4$ and R$^5$, taken together with the atoms to which they are attached, form a 3-7 membered carbocyclic or heterocyclic saturated or partially unsaturated ring, which ring is optionally substituted with —OH, —(C$_1$-C$_6$)alkyl, —O(C$_1$-C$_6$)alkyl, —N(R$^6$)$_2$, halogen, oxo, or nitrile;

or R$^4$ and R$^8$, taken together with the atoms to which they are attached, form a 4-7 membered carbocyclic or heterocyclic ring, which ring is optionally substituted with —OH, —(C$_1$-C$_6$)alkyl, —O(C$_1$-C$_6$)alkyl, —N(R$^6$)$_2$, halogen, oxo, or nitrile;

or R$^4$ and R$^8$, taken together with the atoms to which they are attached, form a 3-membered carbocyclic or heterocyclic ring, which ring is optionally substituted with —OH, —(C$_1$-C$_6$)alkyl, —O(C$_1$-C$_6$)alkyl, —N(R$^6$)$_2$, halogen, oxo, or nitrile;

R$^6$ is independently for each occurrence selected from the group consisting of H, —(C$_1$-C$_6$)alkyl, and phenyl;

R$^{66}$ is selected from the group consisting of H, —(C$_1$-C$_6$)alkyl, and phenyl;

R$^{11}$ and R$^{12}$ are each independently selected from the group consisting of H, —OH, —(C$_1$-C$_6$)alkyl, —O(C$_1$-C$_6$)alkyl, —(C$_1$-C$_6$)alkyl-O—R$^6$, aryl, arylalkylene, heteroaryl, heteroarylalkylene, —C(O)N(R$^6$)$_2$, —N(R$^6$)$_2$, halogen, —(C$_1$-C$_6$)alkyl-N(R$^6$)$_2$, —CO$_2$H, and nitrile, wherein said —(C$_1$-C$_6$)alkyl, —O(C$_1$-C$_6$)alkyl, —(C$_1$-C$_6$)alkyl-O—R$^6$, aryl, arylalkylene, heteroaryl, heteroarylalkylene, or —(C$_1$-C$_6$)alkyl-N(R$^6$)$_2$ is optionally substituted with one or more substituents selected from the group consisting of —OH, —N(H)$_2$, and halogen;

or R$^{11}$ and R$^{12}$, taken together with the atoms to which they are attached, form a 5-7 membered heterocyclic ring;

or R$^4$ and R$^{12}$, taken together with the atoms to which they are attached, form a 5-7 membered carbocyclic or heterocyclic ring;

or R$^4$ and R$^{11}$, taken together with the atoms to which they are attached, form a 5-membered carbocyclic or heterocyclic ring;

R$^8$ and R$^9$ are each independently selected from the group consisting of H, —(C$_1$-C$_6$)alkyl, —(C$_1$-C$_6$)alkyl-N(R$^6$)$_2$, —OR$^6$, —(C$_1$-C$_6$)alkyl-O—R$^6$, —C(O)NH$_2$, —N(R$^6$)$_2$, halogen, and nitrile;

R$^{13}$ and R$^{14}$ for each occurrence, are independently selected from the group consisting of H, —OH, —(C$_1$-C$_6$)alkyl, —O(C$_1$-C$_6$)alkyl, —C(O)N(R$^6$)$_2$, —N(R$^6$)$_2$, halogen, and —(C$_1$-C$_6$)alkyl-N(R$^6$);

R$^{15}$ and R$^{16}$ for each occurrence, are independently selected from the group consisting of H, —OH, —(C$_1$-C$_6$)alkyl, —O(C$_1$-C$_6$)alkyl, —C(O)N(R$^6$)$_2$, —N(R$^6$)$_2$, halogen, and —(C$_1$-C$_6$)alkyl-N(R$^6$)$_2$, or R$^{15}$ and R$^{16}$ taken together with the carbon to which they are attached may form a (C$_3$-C$_4$)cycloalkyl;

and each of m and n is, independently, 0, 1, 2, or 3, with m+n being at least 2 and no more than 4.

2. The compound of claim 1, or a pharmaceutically acceptable salt thereof, wherein R$^1$ is selected from the group consisting of phenyl, pyridyl, indolyl, and indolinyl, wherein said phenyl, pyridyl, indolyl or indolinyl is optionally substituted with —R$^{10}$, —OR$^{10}$, —SR$^{10}$, —N(R$^{10}$)$_2$, —OSO$_2$R$^{10}$, —SO$_2$R$^{10}$, —C(O)N(R$^{10}$)$_2$, halogen, or nitrile.

3. The compound of claim 1, or a pharmaceutically acceptable salt thereof, wherein R$^1$ is pyridyl, wherein said pyridyl is optionally substituted with one, two, or three substituents each independently selected from the group consisting of —OR$^{10}$, halogen, and nitrile.

4. The compound of claim 1, or a pharmaceutically acceptable salt thereof, wherein R$^1$ is indolyl or indolinyl, wherein said indolyl or indolinyl is optionally substituted with one, two, or three substituents each independently selected from the group consisting of —OR$^{10}$, halogen, and nitrile.

5. The compound of claim 1, or a pharmaceutically acceptable salt thereof, wherein m is an integer selected from 1 or 2; and n is 1.

6. The compound of claim 1, or a pharmaceutically acceptable salt thereof, wherein R$^4$ and R$^5$ are independently selected from the group consisting of H, —OH, —(C$_1$-C$_3$)alkyl, —O(C$_1$-C$_3$)alkyl, —(C$_1$-C$_3$)alkyl-O—R$^6$, —C(O)NH$_2$, —N(R$^6$)$_2$, halogen, —(C$_1$-C$_3$)alkyl-N(R$^6$)$_2$, and nitrile, wherein said —(C$_1$-C$_3$)alkyl, —O(C$_1$-C$_3$)alkyl, —(C$_1$-C$_3$)alkyl-O—R$^6$, or —(C$_1$-C$_3$)alkyl-N(R$^6$)$_2$, is optionally substituted with one or more substituents selected from the group consisting of —OH, —NH$_2$, and halogen;

or R$^4$ and R$^5$, taken together with the atoms to which they are attached, form a 3-7 membered carbocyclic or heterocyclic ring;

or R$^4$ and R$^8$, taken together with the atoms to which they are attached, form a 4-7 membered carbocyclic or heterocyclic ring;

or R$^4$ and R$^8$, taken together with the atoms to which they are attached, form a 3-membered carbocyclic or heterocyclic ring; and each R$^6$ is independently H or —(C$_1$-C$_3$)alkyl.

7. A compound of formula II, or a pharmaceutically acceptable salt thereof, wherein formula II is represented by:

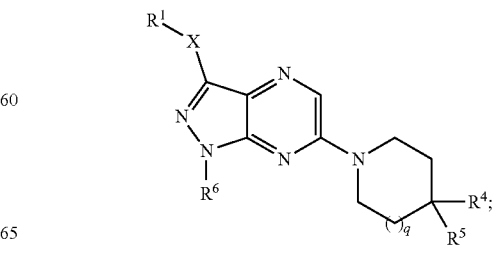

wherein:
- X is selected from the group consisting of: —N—R$^{66}$—, —O—, —CR$^{13}$R$^{14}$—, —C(O)—, —S(O)$_w$— wherein w is 0, 1 or 2, and —C(=C(R$^{15}$R$^{16}$))—;
- q is 0 or 1;
- R$^1$ is selected from the group consisting of phenyl, a 5-10 membered monocyclic or bicyclic heteroaryl, and a 4-7 membered heterocycle, wherein R$^1$ is optionally substituted with one, two or more substituents each independently selected from the group consisting of —R$^{10}$, —N(R$^6$)$_2$, —C(O)N(R$^6$)$_2$, oxo, halogen, and nitrile;
- R$^{10}$ is independently selected for each occurrence from the group consisting of —(C$_1$-C$_6$)alkyl, —(C$_1$-C$_6$)haloalkyl, (C$_3$-C$_6$)cycloalkyl, heterocycloalkyl, phenyl, and heteroaryl, wherein R$^{10}$ may be substituted with one, two or three or more substituents each selected from the group consisting of halo, C(O)R$^{20}$, —(C$_1$-C$_6$)alkyl, and —(C$_1$-C$_6$)haloalkyl;
- R$^{20}$ is selected from the group consisting of —OH, halo, and —(C$_1$-C$_6$)alkyl;
- R$^4$ and R$^5$ are each independently selected from the group consisting of H, —(C$_1$-C$_6$)alkyl, —C(O)N(R$^6$)$_2$, —N(R$^6$)$_2$, halogen, and nitrile, wherein said —(C$_1$-C$_6$)alkyl is optionally substituted with one or more substituents selected from the group consisting of —OH, —N(R$^6$)$_2$, oxo, and halogen,
- or R$^4$ and R$^5$, taken together with the carbon to which they are attached, form a 3-7 membered carbocyclic or heterocyclic ring, which ring is optionally substituted with one or two substituents each independently selected from the group consisting of —(C$_1$-C$_6$)alkyl, —O(C$_1$-C$_6$)alkyl, —N(R$^6$)$_2$, —C(O)N(R$^6$)$_2$, halogen, oxo, and nitrile;
- R$^6$ is independently for each occurrence selected from the group consisting of H, —(C$_1$-C$_6$)alkyl, and phenyl;
- R$^{66}$ is selected from the group consisting of H, —(C$_1$-C$_6$)alkyl, and phenyl;
- R$^{13}$ and R$^{14}$ for each occurrence, are independently selected from the group consisting of H, —OH, —(C$_1$-C$_6$)alkyl, —O(C$_1$-C$_6$)alkyl, —C(O)N(R$^6$)$_2$, —N(R$^6$)$_2$, halogen, and —(C$_1$-C$_6$)alkyl-N(R$^6$); and
- R$^{15}$ and R$^{16}$ for each occurrence, are independently selected from the group consisting of H, —OH, —(C$_1$-C$_6$)alkyl, —O(C$_1$-C$_6$)alkyl, —C(O)N(R$^6$)$_2$, —N(R$^6$)$_2$, halogen, and —(C$_1$-C$_6$)alkyl-N(R$^6$)$_2$, or R$^{15}$ and R$^{16}$ taken together with the carbon to which they are attached may form a (C$_3$-C$_4$)cycloalkyl.

8. The compound of claim 7, or a pharmaceutically acceptable salt thereof, wherein R$^6$ is H.

9. The compound of claim 7, a pharmaceutically acceptable salt thereof, wherein R$^4$ and R$^5$ are independently selected from the group consisting of —(C$_1$-C$_3$)alkyl and —N(R$^6$)$_2$, wherein said —(C$_1$-C$_3$)alkyl is optionally substituted with one or more substituents selected from the group consisting of —OH, —NH$_2$, and halogen.

10. The compound of claim 7, or a pharmaceutically acceptable salt thereof, wherein R$^4$ and R$^5$ are independently selected from the group consisting of —NH$_2$, —CH$_3$, and —CH$_2$NH$_2$.

11. The compound of claim 7, a pharmaceutically acceptable salt thereof, wherein q is 1.

12. A compound selected from the group consisting of:

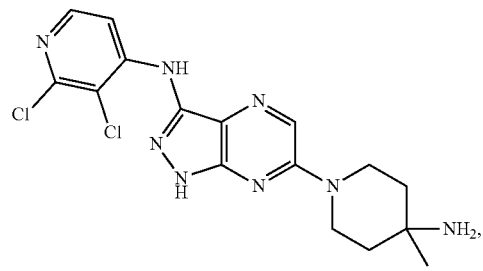

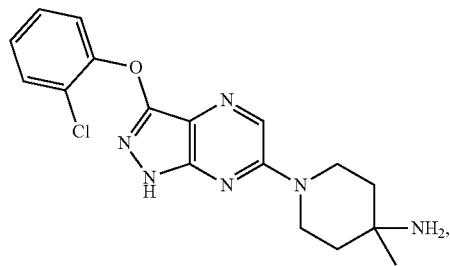

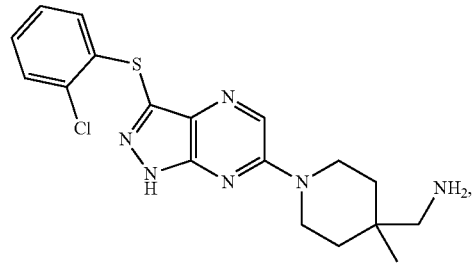

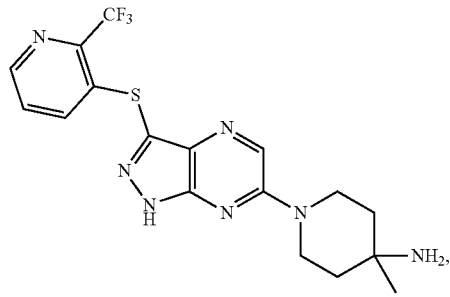

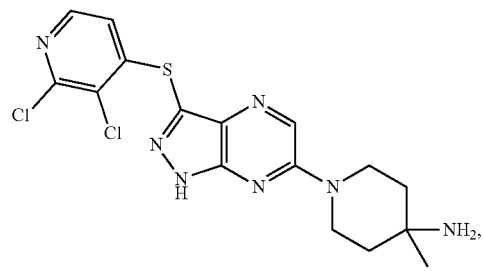

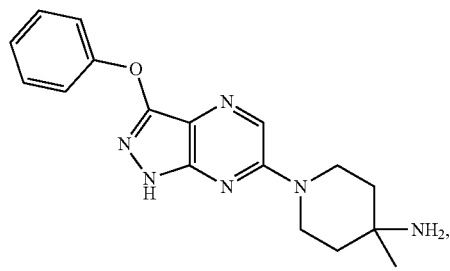

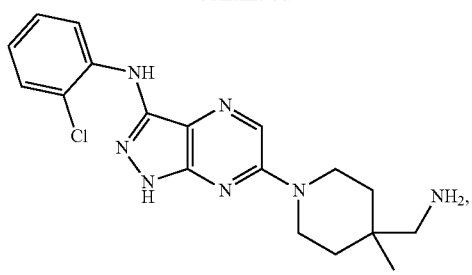
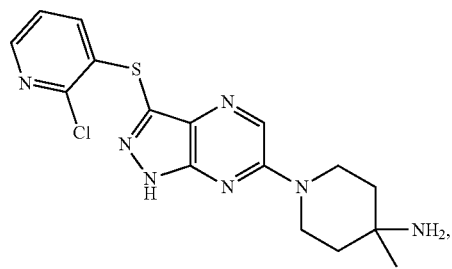
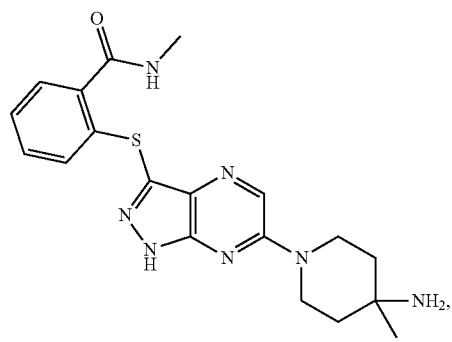
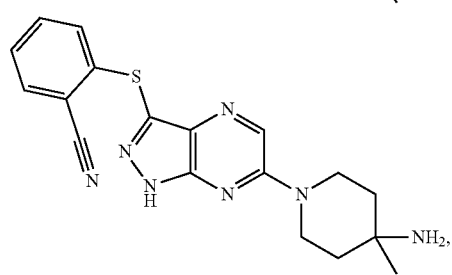
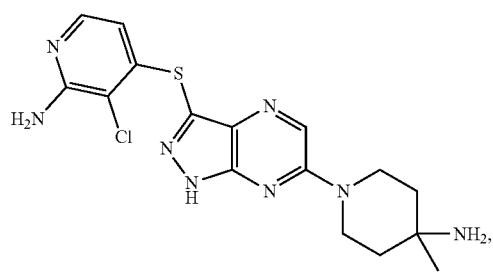
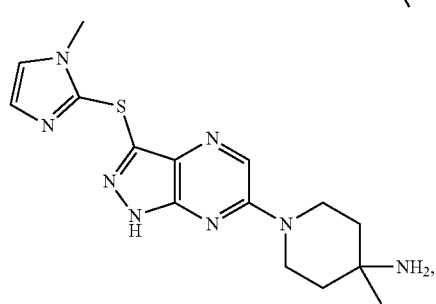
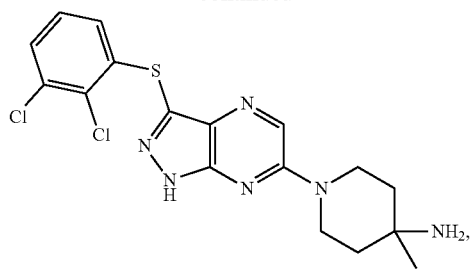
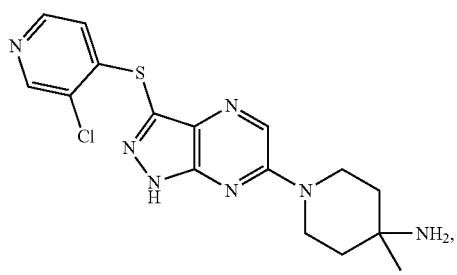
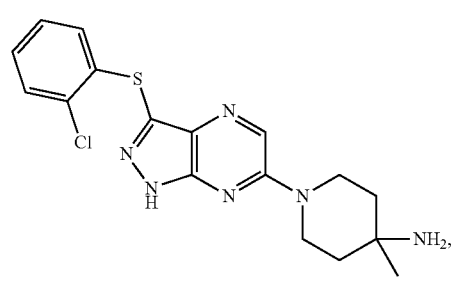
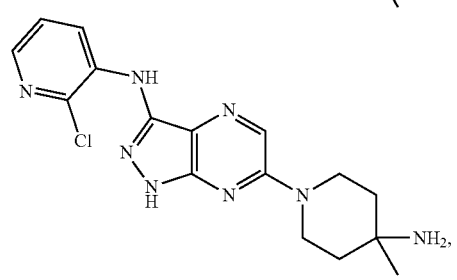
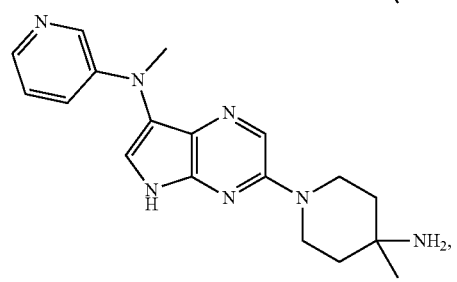
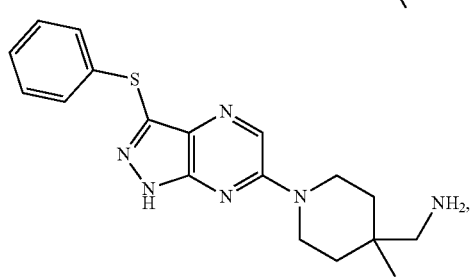

165
-continued
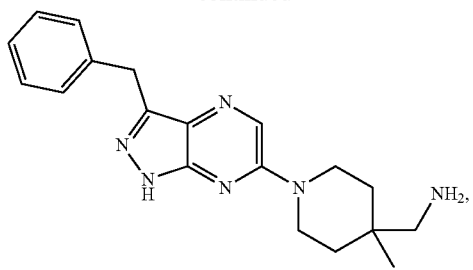
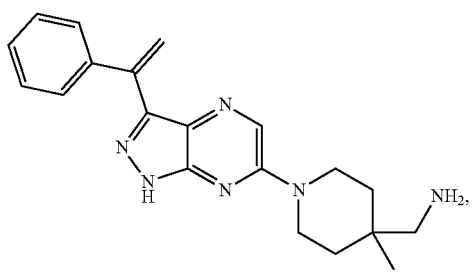
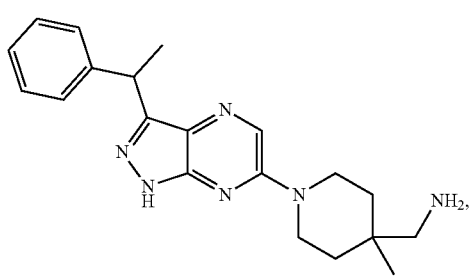
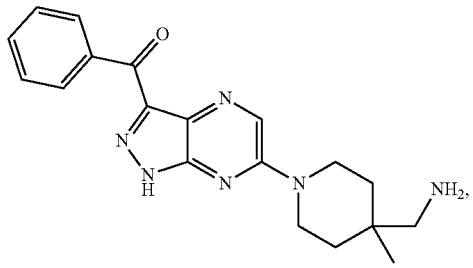
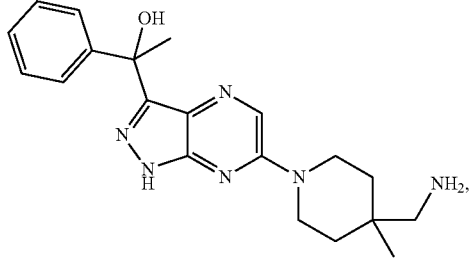
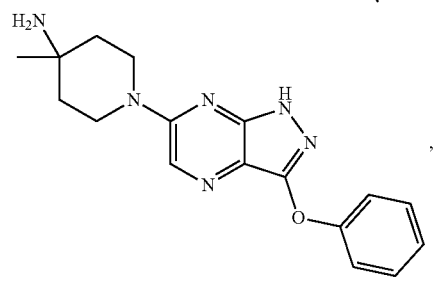
166
-continued
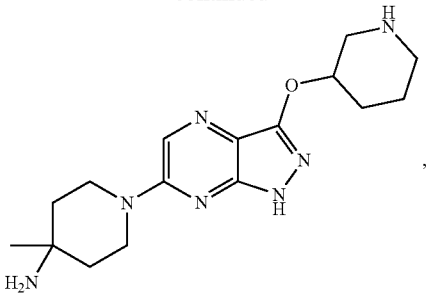
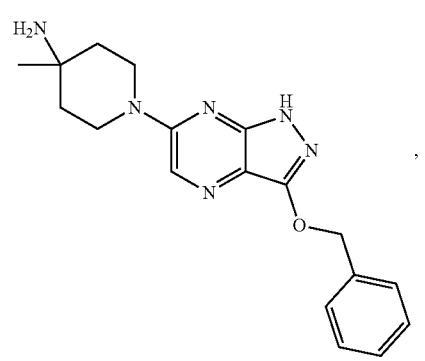
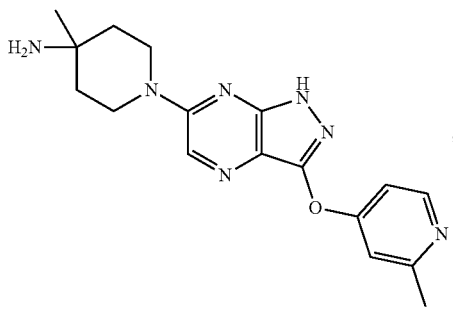
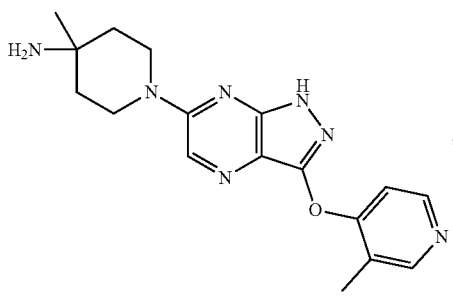
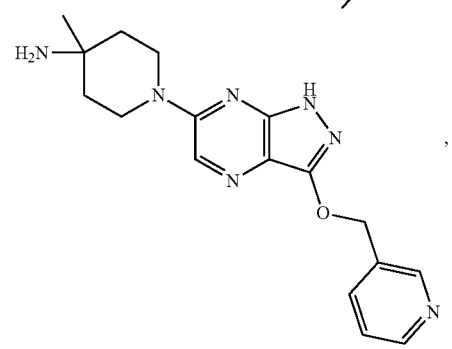

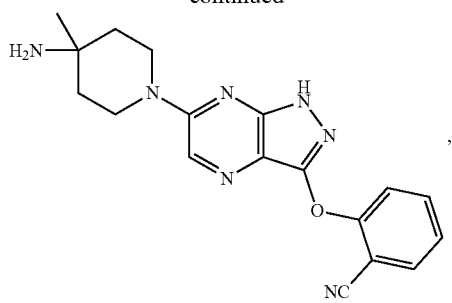
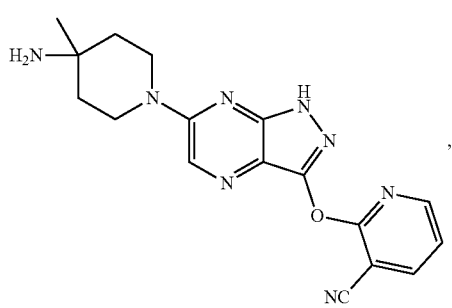
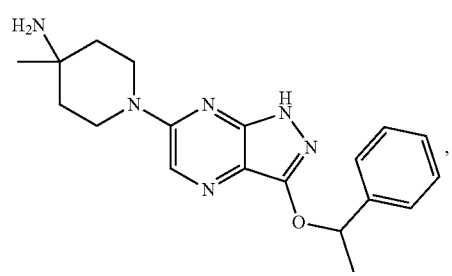
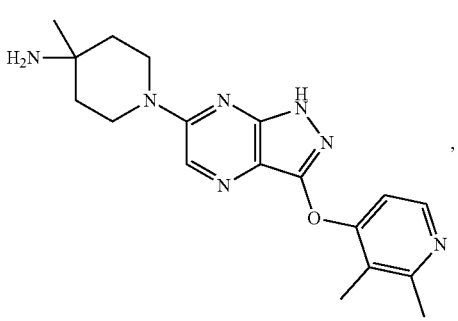
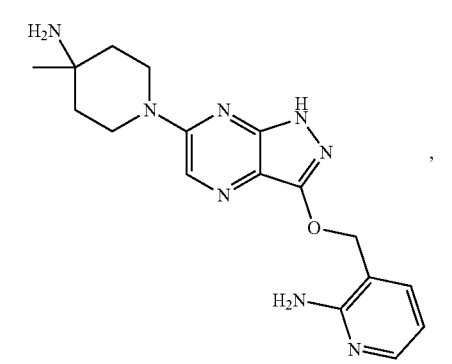
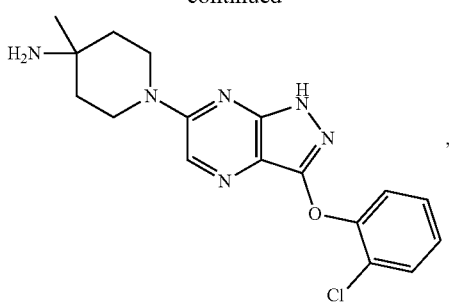
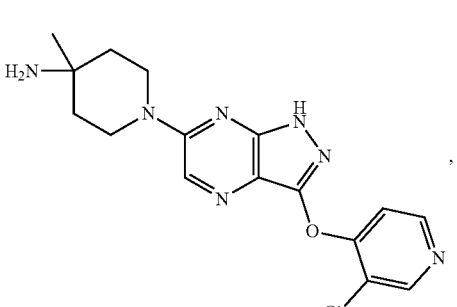
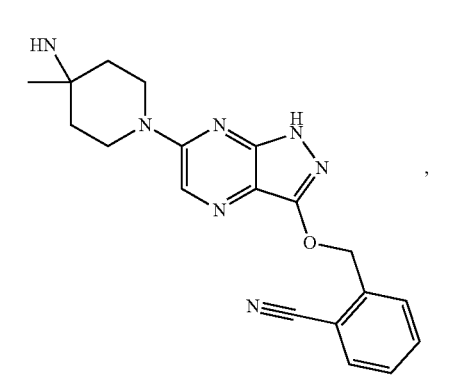
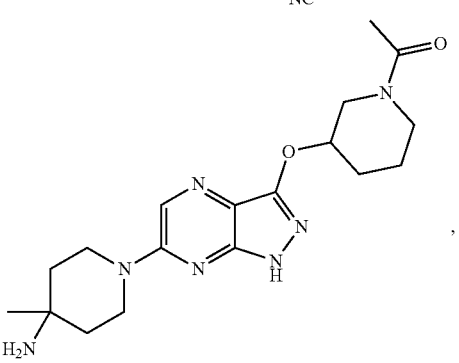

169
-continued
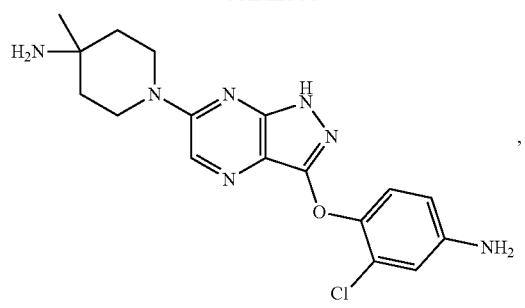
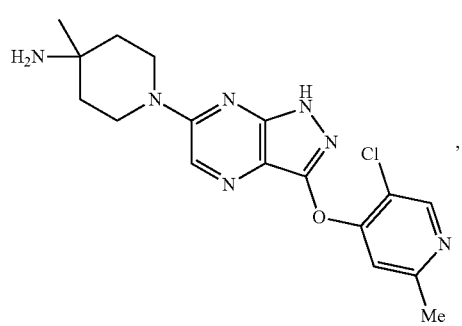
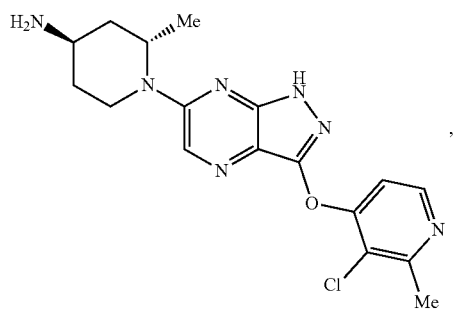
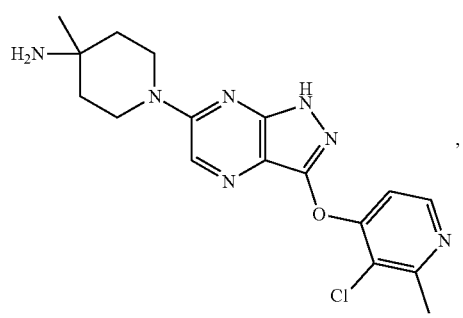
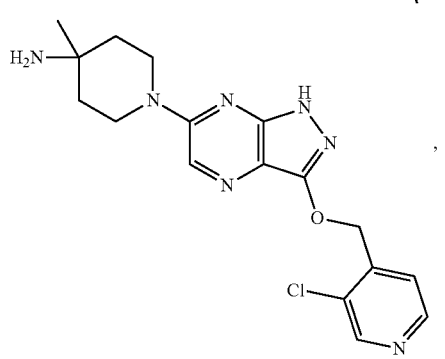
170
-continued
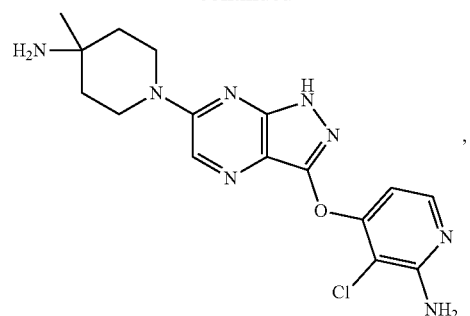
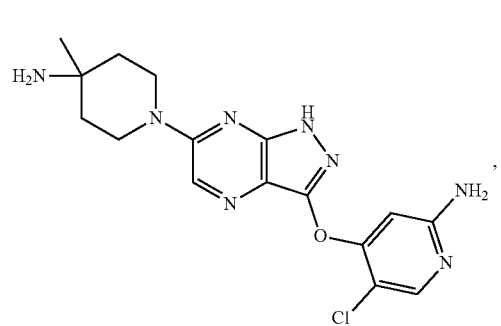
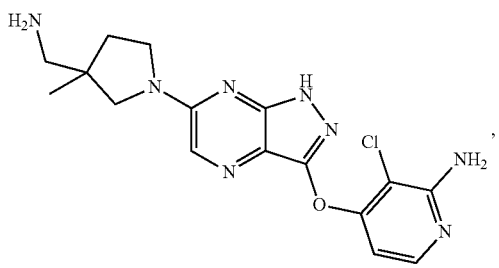
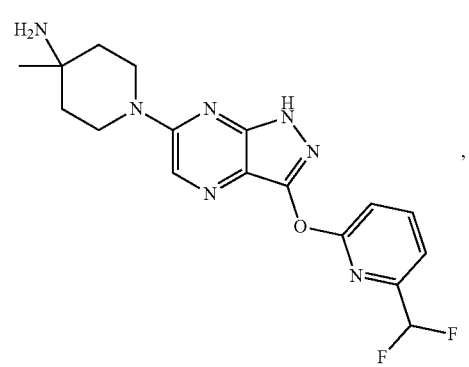
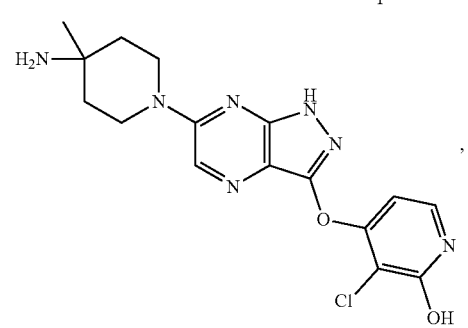

171
-continued
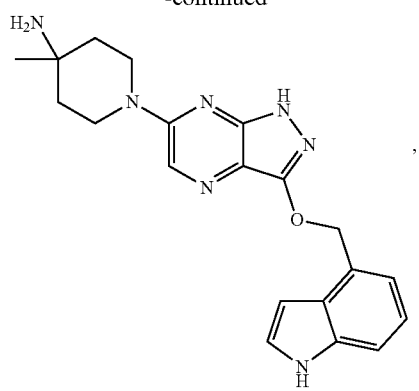
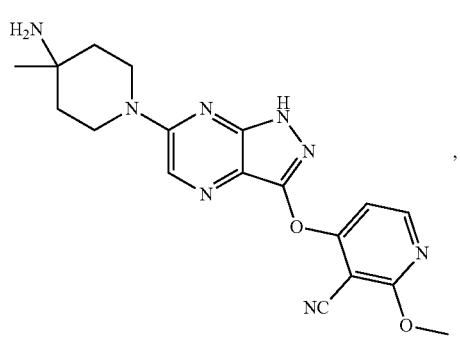
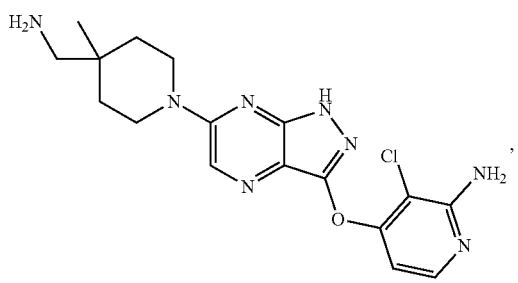
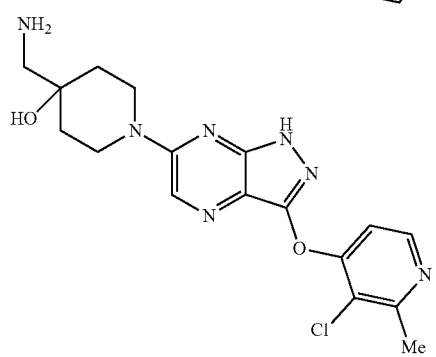
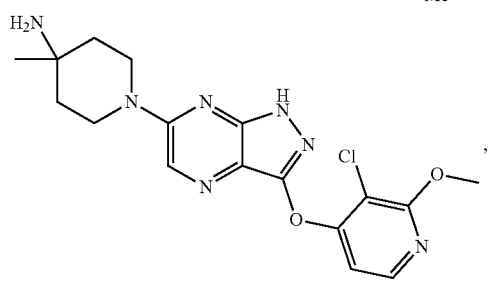
172
-continued
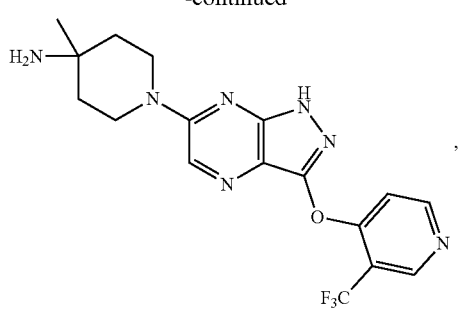
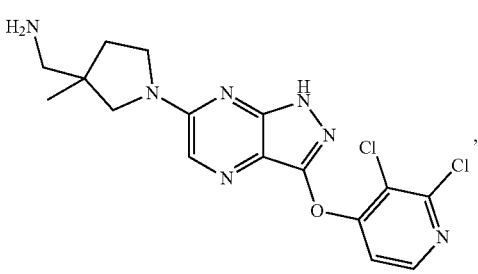
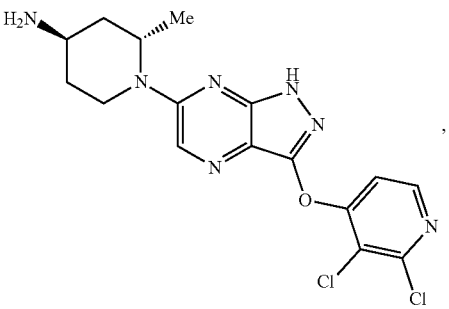
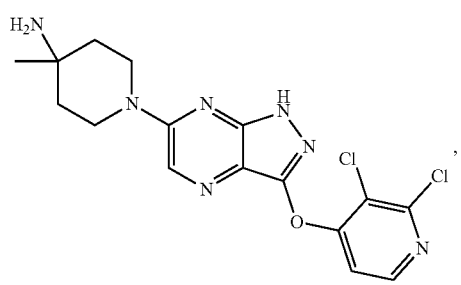
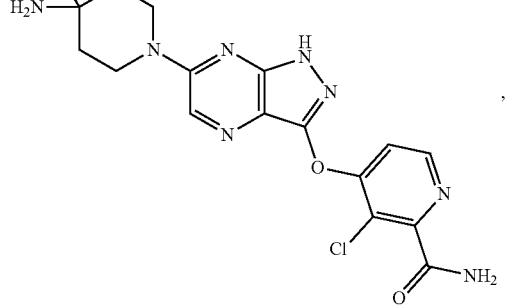

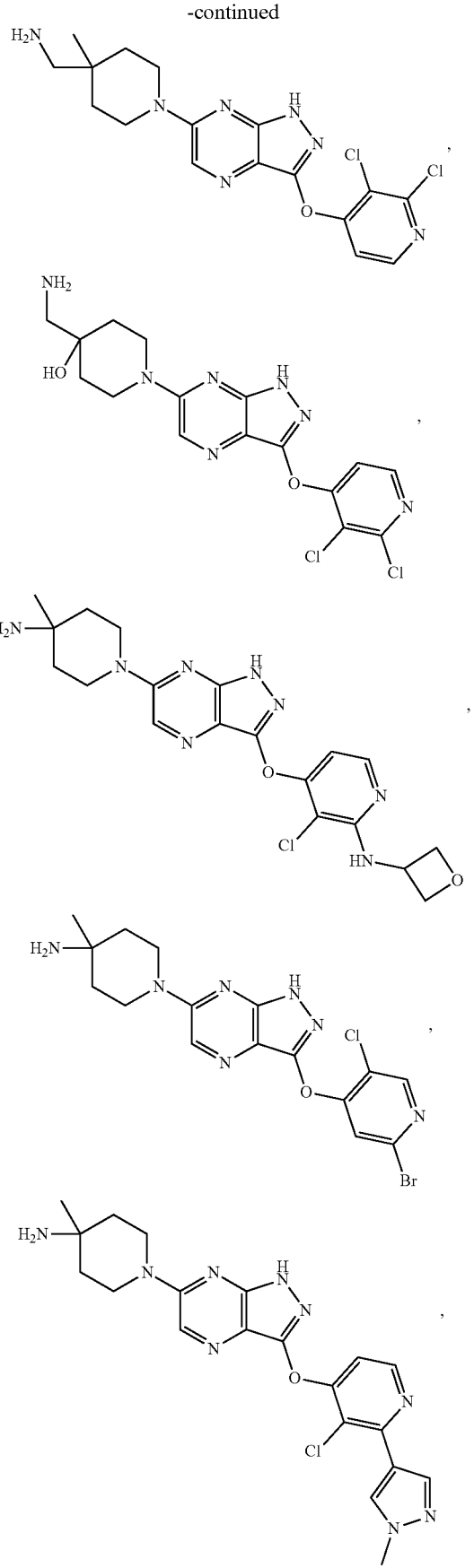
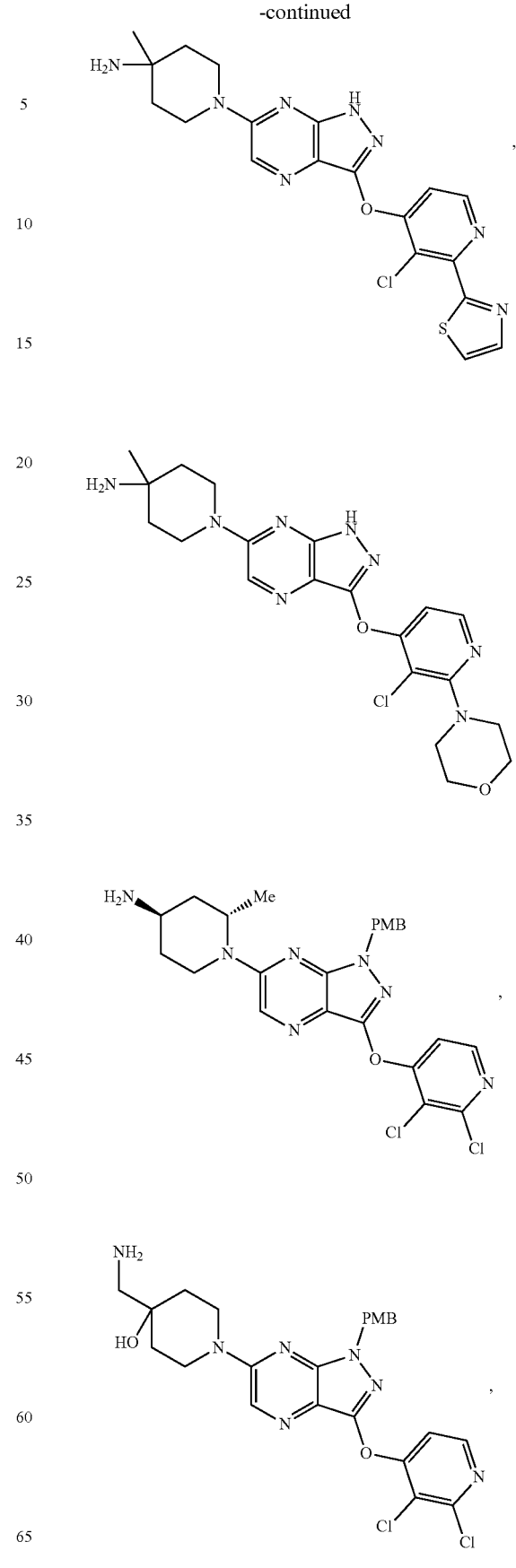

-continued

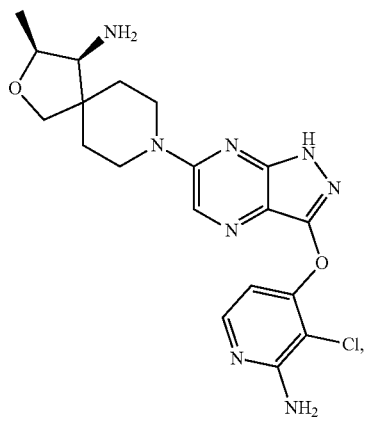

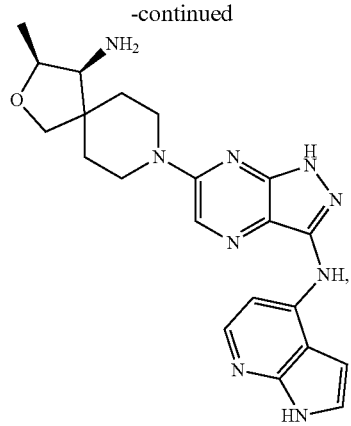

or a pharmaceutically acceptable salt or stereoisomer thereof.

13. A pharmaceutical composition comprising a compound of claim 1, or a pharmaceutically acceptable salt thereof, and a pharmaceutically acceptable carrier.

14. A method of inhibiting Src homology region 2-containing protein tyrosine phosphatase 2 (SHP2) activity in a subject comprising administering a therapeutically effective amount of the compound of claim 1, or a pharmaceutically acceptable salt thereof, to a subject in need thereof, wherein the subject is a human.

15. The method of claim 14, further comprising administering a therapeutically effective amount of an antibody, an antibody-drug conjugate, an immunomodulator, or a histone deacetylase inhibitor.

16. A method of therapeutically treating a disorder related to SHP2 phosphatase activity in a subject comprising administering a therapeutically effective amount of the compound of claim 1, or a pharmaceutically acceptable salt thereof, to a subject in need thereof.

17. The method of claim 16, further comprising administering a therapeutically effective amount of an antibody, an antibody-drug conjugate, an immunomodulator, or a histone deacetylase inhibitor.

18. The method of claim 16, wherein the disorder is selected from the group consisting of Noonan syndrome, neutropenia, diabetes, neuroblastoma, melanoma, acute myeloid leukemia, juvenile leukemia, juvenile myelomonocytic leukemia, breast cancer, lung cancer, and colorectal cancer.

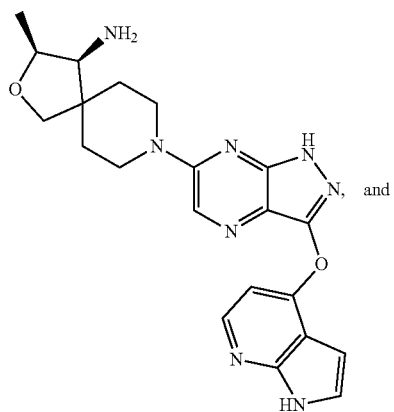

and

* * * * *

UNITED STATES PATENT AND TRADEMARK OFFICE
CERTIFICATE OF CORRECTION

PATENT NO. : 11,629,145 B2
APPLICATION NO. : 16/344061
DATED : April 18, 2023
INVENTOR(S) : Giordanetto et al.

It is certified that error appears in the above-identified patent and that said Letters Patent is hereby corrected as shown below:

In the Claims

Column 159,
Line 61, In Claim 1, "$R^4$ and $R^{11}$" should read --$R^8$ and $R^{11}$--.

Column 160,
Line 40, In Claim 6, "$(C_1-C_3)$alkyl-$N(R^6)_2$, is" should read --$(C_1-C_3)$alkyl-$N(R^6)_2$ is--.

Column 161,
Lines 55 and 66, In Claim 9, "claim 7, a pharmaceutically" should read --claim 7, or a pharmaceutically--.

Signed and Sealed this
Twenty-third Day of January, 2024

Katherine Kelly Vidal
*Director of the United States Patent and Trademark Office*